US007432365B1

(12) United States Patent
O'Donnell et al.

(10) Patent No.: US 7,432,365 B1
(45) Date of Patent: Oct. 7, 2008

(54) DNA MOLECULES ENCODING BETA CLAMP PROTEINS OF GRAM POSITIVE BACTERIA

(76) Inventors: Michael E. O'Donnell, 16 Maple La., Hasting-on-Hudson, NY (US) 10706; Irina Bruck, 1161 York Ave., Apt. 11M, New York, NY (US) 10021; Dan Zhang, 68-37 108th St., #3B, Forest Hills, NY (US) 11375; Richard Whipple, 91 First Ave., Rareton, NJ (US) 08869

( * ) Notice: Subject to any disclaimer, the term of this patent is extended or adjusted under 35 U.S.C. 154(b) by 145 days.

(21) Appl. No.: 10/048,071

(22) PCT Filed: Jul. 28, 2000

(86) PCT No.: PCT/US00/20666

§ 371 (c)(1),
(2), (4) Date: Oct. 23, 2002

(87) PCT Pub. No.: WO01/09164

PCT Pub. Date: Feb. 8, 2001

Related U.S. Application Data

(63) Continuation-in-part of application No. 09/235,245, filed on Jan. 22, 1999, now abandoned.

(60) Provisional application No. 60/146,178, filed on Jul. 29, 1999, provisional application No. 60/093,727, filed on Jul. 22, 1998, provisional application No. 60/074,522, filed on Jan. 22, 1998.

(51) Int. Cl.
*C07H 21/04* (2006.01)
*C07K 1/00* (2006.01)
*C12N 1/20* (2006.01)
*C12N 15/00* (2006.01)

(52) U.S. Cl. .................. 536/23.7; 435/6; 435/199; 435/252.1; 435/253.4; 435/320.1; 530/350

(58) Field of Classification Search .............. 435/320.1, 435/252.1, 199, 6, 253.4; 536/23.7; 530/350
See application file for complete search history.

(56) References Cited

U.S. PATENT DOCUMENTS

| 5,151,350 A | | 9/1992 | Colbert et al. |
|---|---|---|---|
| 5,376,526 A | | 12/1994 | Brown et al. |
| 5,459,039 A | | 10/1995 | Modrich et al. |
| 5,556,750 A | | 9/1996 | Modrich et al. |
| 5,571,676 A | | 11/1996 | Shuber |
| 5,583,026 A | | 12/1996 | O'Donnell |
| 5,587,288 A | | 12/1996 | Cheung et al. |
| 5,635,349 A | | 6/1997 | LaMarco et al. |
| 5,679,522 A | | 10/1997 | Modrich et al. |
| 5,683,877 A | | 11/1997 | Lu-Chang et al. |
| 5,912,143 A | * | 6/1999 | Bandman et al. ............ 435/69.1 |
| 6,077,664 A | | 6/2000 | Slater et al. |
| 6,083,924 A | | 7/2000 | Earnshaw et al. |
| 6,100,030 A | | 8/2000 | McCasky Feazel et al. |
| 6,156,502 A | | 12/2000 | Beattie |
| 6,245,906 B1 | * | 6/2001 | Ueyama et al. ............ 536/24.32 |
| 6,420,161 B1 | | 7/2002 | Earnshaw et al. |
| 6,699,703 B1 | * | 3/2004 | Doucette-Stamm et al. ...... 435/252.3 |
| 2003/0129633 A1 | | 7/2003 | O'Donnell et al. |

FOREIGN PATENT DOCUMENTS

| EP | 0786519 A2 | | 7/1997 |
|---|---|---|---|
| WO | WO96/06614 A1 | | 3/1996 |
| WO | WO9842845 A1 | * | 10/1998 |
| WO | WO99/13060 A1 | | 3/1999 |
| WO | WO99/37661 A1 | | 7/1999 |

OTHER PUBLICATIONS

Nature, 1997, vol. 390, 249-256.*
Rudinger J in Peptide Hormones. Editor Parsons JA. pp. 1-7, 1976, University Park Press, Baltimore.*
Nucleic acids research, 1985 vol. 13, 2251-2265.*
Rudinger et al, in "Peptide Hormones", edited by Parsons, J.A., University Park Press, Jun. 1976.*
Burgess et al., The Journal of Cell Biology, 111:2129 2138, 1990).*
Lazar et al., Molecular and Cellular Biology, 8(3):1247 1252, 1988.*
Jobling et al. (Mol. Microbiol., 1991, 5(7):1755 67.*
Bodnar et al , J Clin Microbiol. 1996.*
Accerssion No. AF000658 see Pestova et al Mol. Microbiol. 21 (4), 853-862 (1996) OR Cheng etal Mol. Microbiol. 23 (4), 683-692 (1997).*
Snyder et al Molecular Genetics of Bacteria, American Society for Microbiology 1997.*
U.S. Appl. No. 09/235,245, O'Donnell.
Biotechnology Industry Organization, "Critical Synergy: The Biotechnology Industry and Intellectual Property Protection," 1-178, 74-95, Presentations of the Intellectual Property Committee of the Biotechnology Industry Organization at the Oct. 17, 1994, Hearing of the U.S. Patent and Trademark Office (Oct. 17, 1994), *available at* http://www.uspto.gov/web/offices/com/hearings/biotech/bioind. html (last accessed Jan. 10, 2005).
Cullmann et al., "Characterization of the Five Replication Factor C Genes of *Saccharomyces cerevisiae*," *Mol. Cell. Biol.* 15(9):4661-71 (1995).
Fraser et al., "The Minimal Gene Complement of *Mycoplasma genitalium*," *Science* 270:397-403 (1995).
Guenther et al., "Crystal Structure of the δ' Subunit of the Clamp-loader Complex of *E. coli* DNA Polymerase III," *Cell* 91:335-45 (1997).
Guenther, "Structural Studies on the DNA Replication Apparatus: X-Ray Crystal Structure of the δ' Subunit of *Escherichia coli* DNA Pol III," at 129-135 (Ph.D. thesis, Rockefeller University) (1996).
Lee & Walker, "*Escherichia coli* DnaX product, the τ Subunit of DNA Polymerase III, Is a Multifunctional Protein with Single-stranded DNA-dependent ATPase Activity," *Proc. Nat'l Acad. Sci. U.S.A.* 84:2713-7 (1987).
McHenry et al., "A DNA Polymerase III Holoenzyme-like Subassembly from an Extreme Thermophilic Eubacterium," *J. Mol. Biol.* 272:178-89 (1997).

(Continued)

*Primary Examiner*—Shanon A. Foley
*Assistant Examiner*—Padma V Baskar
(74) *Attorney, Agent, or Firm*—Nixon Peabody LLP

(57) ABSTRACT

The present invention relates to beta protein-encoding genes from Gram positive bacterium. Expression systems and host cells containing these genes are also disclosed.

5 Claims, 29 Drawing Sheets

OTHER PUBLICATIONS

Morrison et al., "A Third Essential DNA Polymerase in *S. cerevisiae*," *Cell* 62:1143-51 (1990).

Pacitti et al., "Characterization and Overexpression of the Gene Encoding *Staphylococcus aureus* DNA Polymerase III," *Gene* 165:51-6 (1995).

Sauer et al., "Sporulation and Primary Sigma Factor Homologous Genes in *Clostridium acetobutylicum*," *J. Bacterol.* 176(21):6572-82 (1994).

Seville et al., "Fluorometric Assay for DNA Polymerases and Reverse Transcriptase," *BioTechniques* 21:664-72 (1996).

Youmans et al., The Biological and Clinical Basis of Infectious Disease 624, 802 (1985).

Yurieva et al., "*Thermus thermophilis dnaX* Homolog Encoding γ- and τ-like Proteins of the Chromosomal Replicase," *J. Biol. Chem.* 272(43):27131-9 (1997).

GenBank Accession No. AP003130.
GenBank Accession No. AP003359.
GenBank Accession No. AL009126.
GenBank Accession No. BAB41666.
GenBank Accession No. BAB56640.
GenBank Accession No. CAC09993.
GenBank Accession No. P28630.
GenBank Accession No. P43747.
GenBank Accession No. Q9Y5S2.
GenBank Accession No. Z99104.

* cited by examiner

AGAROSE GEL

DNA SYNTHESIS

| ADDITION | DNA SYNTHESIS (PMOl) PEAK | | | |
|---|---|---|---|---|
| | PEAK 1 | PEAK 2 | PEAK 3 | PEAK 4 |
| NONE | 22.7 | 70.6 | 146.1 | 4.7 |
| E. coli β, γ COMPLEX | 72.9 | 61.2 | 71.4 | 25.9 |

```
S.aureus    KIWRATCIWNCDFRSSACKAVAKDVGRIMGFDEVTLNEISSLLIPHKLGITLDEAYQID-D
E.coli      MYGRDAVSQIITFGTMAAKAVIRDVGRVLGHPYGFVDRISKLIPPDPGMTLAKAFEAEPQ
Sal.typ     MYGRDAVSQIITFGTMAAKAVIRDVGRVLGHPYGFVDRISKLVPPDPGMTLAKAFEAEPQ
                  *  ***   ***    .*  **    . *  ** :: * ***.*** **

S.aureus    FKKFVHRNHRHQRWFSICKKLEGLPRHTSTHAAGIIINDHPLYEYAPLTKGDTG--LLTQ
E.coli      LPEIYEADEEVKALIDMARKLEGVTRNAGKHAGGVVIAPTKITDFAPLYCDEEGKHPVTQ
Sal.typ     LPEIYEADEEVRALIDMARKLEGVTRNAGKHAGGVVIAPTKITDFAPLYCDEEGKHPVTQ
             .: :    : :: *  ****   :: *  *  : :   :.:  **        :  *

S.aureus    WTMTEAERIGILLKIDFLGLPNLSIIHQILTRVEKDLGFN----IDIEKIPFDDQKVFELL
E.coli      FDKSDVEYAGLVKFDFLGLRTLTIINWALEMINKRRAKNGEPPLDIAAIPLDDKKSFDML
Sal.typ     FDKSDVEYAGLVKFDFLGLRTLTIINWALEMINKRRAKNGEPPLDIAAIPLDDKKSFDML
              .:    ::*::*****  *:*  : : :.::  :::*    **  ** ** :*: *

S.aureus    SQGDTTGIFQLESDGVRSVLKKLKPEHFEDIVAVTSLYRPGPMEE---IPTYITRRHDPS-
E.coli      QRSETTAVFQLESRGMKDLIKRLQPDCFEDMIALVALFRPGPLQSGMVDNFIDRKHGREE
Sal.typ     QRSETTAVFQLESRGMKDLIKRLQPDCFEDMIALVALFRPGPLQSGMVDNFIDRKHGREE
             : : *.:***** *::.*:*:*:*: ***::*:::*:****::     .* .*:: .

S.aureus    ----KVQYLHPHLEPILLKNTYGVIIYQEQIMQIASTFANFSYGEADILRRAMSKKNRAVL
E.coli      ISYPDVQMQHESLKPVLEPTYGILIYQEQVMQIAQVLSGYTLGGADMLRRAMGKKKKPEEM
Sal.typ     LSYPDVQMQHESLKPVLEPTYGILIYQEQVMQIAQVLSGYTLGGADMLRRAMGKKKKPEEM
                 .** :*. ::*:* .**::****::****.  :.: : ****:****.**:: :

S.aureus    ERDAQHFIEGTKQNGYHEDISKQIFDLI----------------------------------
E.coli      AKQRSVPAEGAEKNGINAELAMKIFDLVEKPAGYGFNKSHSAAYALVSYQTLWLKAHYPA
Sal.typ     AKQRSVPEEGAKKNGIDGELAMKIFDLVEKPAGYGFNKSHSAAYALVSYQTLWLKAHYPA
             :  :    **.::**:: :: :****                                 
```

*FIG. 9*

```
                                                                          ATP site
S.aureus   MKGYCLWRCNLDYQALFVVPTP-KFEDVVGQEHSEDCAMG-------SHAYLFSGPRGTGKT
B.sub.     -------------MSYQALYRVFRPQRFEDVVGQEHITKTLQNALLQKFSHAYLFSGPRGTGKT
E.coli     -------------MSYQVLARKWRPQTFADVVGQEHVLTALANGLSLGRIHHAYLFSGTRGVGKT
                        *  **    *  ******  *       *   ****** ** ***

Zn++ finger
                 |   | |
S.aureus   SIAKVFAKAINCLNSTDGEPCNECHICKGITQGTNSDVIEIDAASNNGVDEIRNIRDKVKYA
B.sub      SAAKIFAKAVNCEHAPVDEPCNECAACKGITNGSISDVIEIDAASNNGVDEIRDIRDKVKFA
E.coli     SIARLLAKGLNCETGITATPCGVCDNCREIEQGRFVDLIEIDAASRTKVEDTRDLLDNVQYA
            *   **    *  .    * *  *    *   .  * *******  .*  *  *..*

S.aureus   PSESKYKVYIIDEVHMLTTGAFNALLKTLEEPPAHAIFILATTEPHKIPPTIISRA
B.sub      PSAVTYKVYIIDEVHMLSIGAFNALLKTLEEPPEHCIFILATTEPHKIPLTIISRC
E.coli     PARGRFKVYLIDEVHMLSRHSFNALLKTLEEPPEHVKFLLATTDPQKLPVTILSRC
            *    ***:******    *************     :****:* * * *:***
```

*FIG. 10*

```
S.aureus   ALNIANKLERMKIYLAVGIFSLEMGADQLTTRMICSSGNVDSNFLRTGTMTEEDWSRFTI
B.sub      ALNIAQNVA-TKTDFSVAIFSLFMGAEQLVMRMLCAEGNINAQNLRTGNLTEEDWGKLTM
E.coli     AMNLVENAA-MLQDKPVLIFSLEMPSEQIMRSLASLSRVDQTKIRTGQLDDEDWARISG
Sal.typ    AMNLCENAA-MLQDKPVLIFSLEMPGEQIMMRMLASLSRVDQTRIRTGQLDDEDWARISG
              *.*.       *****  *  **  ::*  * * ::.  :::** :: :: *

S.aureus   AVGKLS-RTKIFIDDTPGIPINDLRSKCRRLKQEHG-LYVIVIDYLQLIPGVGSRASDNR
B.sub      AMGSLS-NSGIYIDDIPGIRVSEIRAKCRRLKQESG-LGMILIDYLQLIQGSG-RSKDNR
E.coli     TMGILLEKRNIYIDDSSGLTPTEVRSRARRIAREHGGIGLIMIDYLMID--RVPA--LSDNR
Sal.typ    TMGILLEKRNMYIDDSSGLTPTEVRSRARRIFREHGGLSLIMIDYLQLMRVPS--LSDNR
             * :   .: ****  *:  :: *: **:  *.*  :  :****  :       ****

S.aureus   QQEVSEISRTLKALARELECPVIADSQLSPALPPRRATRPDLPRH---------------
B.sub      QQEVSEISRELKSIARELQVPVIALSQLSRGVEQRQDKRPMMSDIRESGSIEQDADIVAF
E.coli     TLEIAEISRSLKALAKELNVPVVALSQLNRSLEQRADKRPVNSDLRESGSIEQDADLIMF
Sal.typ    TLEIAEISRSLKALAKELQVPVVALSQLNRSLEQRADKRPVNSDLRESGSIEQDADLIMF
            :* :****.**::*:**:.**:* ***.   :*   .**  .*
```

FIG. 11

```
B.sub.yqeN   MVFDVWKSLKK--GK-VHPVYCLYGKETYLLQETVSRIRQTVVDQETKDFNLSVFDLEED    59
E.c.delta    MIRLYPEQLRAQLNEGLRAAYLLLGNDPLLLQESQDAVRQVAAAQGFEKHETFSIDPNTD
              *:   :.*:    .*  ::..*  *  *::.  ****: . :**... *  ::.:   :*  :  *

B.s.yqeN     PLDQAIADAETFPFMGERRLVIVKNPYFLTGEKKKEKIEHNVSALESYIQSPAPYTVFVL   117
E.c.delta    -WNAIFSLCQAMSLFASRQTLLLLLP--ENGP--HAAINEQLLTLTQLLHD--DLLLIVR
              :  ::  .:::.::..*: :::     *    .*    :  *:.::  :*  . ::.      ::*

B.s.yqeN     LAPYEKLDERKKLTKALKKHAFNGEAKELNAKETTDFTVNLAKTEQKTIGTEAAEHLVLL   125
E.c.delta    GNKLSKAQEHAAWFTALANRSVQVTCQTPEQAQLPRHVAARAKQLNLELDDAANQVLCYC
              .*  :*.    .**  :::. :  .:   :   :  : ..    **   :  :.   * : *

B.s.yqeN     VEGHLSSIFQEIQKLCTFIGDREEITLDDVKMLVARSLEQNIFELINKIVNRKRTESLQI   235
E.c.delta    YEGMLLALAQALERLSLLWPDGK-LTLPRVEQAVMDAAEFTPFHWVDALLMGKSKRALHI
              :*:*  ::    ::  :**: . :   * : :*.     *:      ..  *: ::  *  ..:*:*

B.s.yqeN     FYDLLKQNEEPIKIMALISHQFRLILQTKYFAEQGYGQKQIASNLKVHPFRVKLAMDQAR   291
E.c.delta    LQQLRLEGSEPVILLRTLQRELLLLVNLKRQSAHTPLR--ALFDKHRVWQNFRGMNGEALN
              :  :*   :..**: ::  :...:: *::      :  :    :  :  : .::*    *    :   :  .

B.s.yqeN     LFSKEELRLIIEQLAVMDYEMKT--GKKDKQLLLLELFLLQLLK--RHEKNDPHY        343
E.c.delta    RLSQTQLRQAVQLLTRTELTLKQDYGQSVWAELEGLSLLLCHKRPLADVFIDG--
              :*:  :**    ::  *:   :  :    *:.     *  **  *    :    *

B.s.yqeN     -MVFDVWKSLKKGEVHPVYCLYGKETYLLQETVSRIR-QTVVDQETKDFNLSVFDLEEDP    59
S.p. delta   MIAIEKIEKLSKEMLGLITLVTGDDIGQYSQLKSRLMEQIAFDKD--DLAYSYFDMSEAA
              :.::   :.*.*  ::   :   :    :  *.:    .:   **:   * ..**::.*  .

Bsub.yqeN    LDQAIADAETFPFMGERRLVIVKNPYFLTGEKKKEKIEHNVSALESYIQSPAPYTVFVLL   117
S.p.delta    YQDAEMDLVSLPFFAEQKVVIFDHLLDITTNKKSFLKEKDLKAFEAYLEMPLETTRLIIF
              ::*    :.. **:.*::. *** ::**:..**..:*..****..*::*::*::.*   *    :::

Bsub.yqeN    APYEKLDERKKLTKALKKHAFNGMEAKELNAKETTDFTVHLAKTEQKTIGTEAAEHLVLLV   125
S.p.delta    AP-GKLDSKRRLVKLLKRDALVLEANPL--KEAELRTYFQKYSHQLGLGFESGAFDQLLL
              **   ***.:::.::*::.*    :**:.   :**:    :  .   :.*.  *:  . .  **:

Bsub.yqeN    NGHLSSIFQEIQKLCTFIGDREE----ITLDDVKMLVARSLEQNIFELINKIVNRKRTESL   235
S.p.delta    KSMDD--FSQIMKRMAFLKAYKKTQNISLTDIEQAIPKSLQDNIFD-VTRLVLRGKIDAA
              :.: .  *.:*  :  :*:  ::  :*  *:::  ::.***.:*** .:*::**.:*  ::

Bsub.yqeN    Q-IFYDLLKQNEEPIKIMALISHQFRLILQTKYFAEQGYGQKQIASNL------KVHPFR   291
S.p.delta    RDLIHDLRLSGEDDIKLIAIMLGQFRLFLQLTILARDVKNEQQLVISLSDILGRRVNPYQ
              :  ::***  ..:*:*::**:*:***:**: : :*.:    :.::**:*    *:*:*:

Bsub.yqeN    VKLAMDQARLFSEEELRLIIEQLAVMDYEMKTGKKDKQLLLLELFLLQLLKRHEKNDPHY   343
S.p.delta    VKYALKDSRTLSLAFLTGAVKTLIETDYQIKTGLYEKSYLVDIALLKIMTHSQK-----
              **  *:.::*  **  :*:  ::  **  :*::**  :*:*.:*:**:**:.:::.*   :*
```

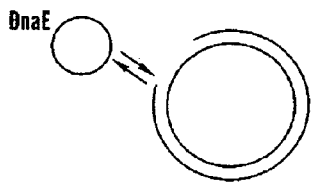
*FIG. 21A*
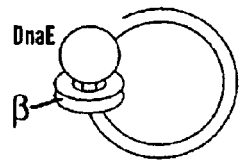
*FIG. 21B*
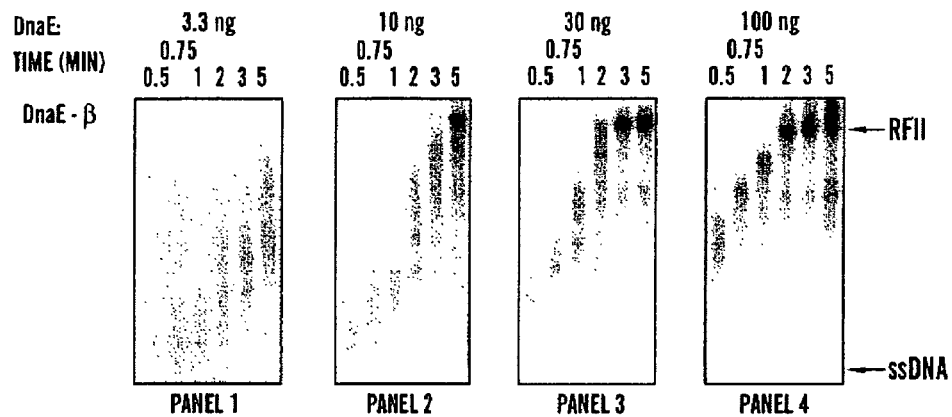
*FIG. 21C*
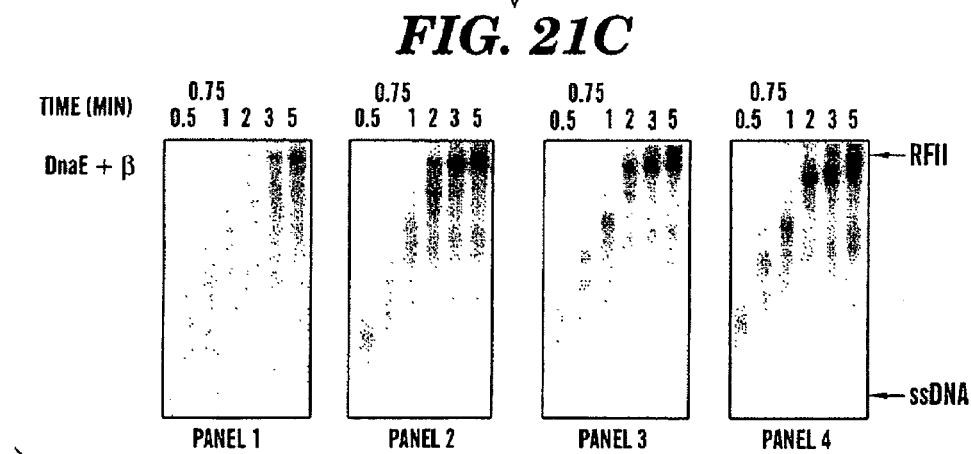
*FIG. 21D*
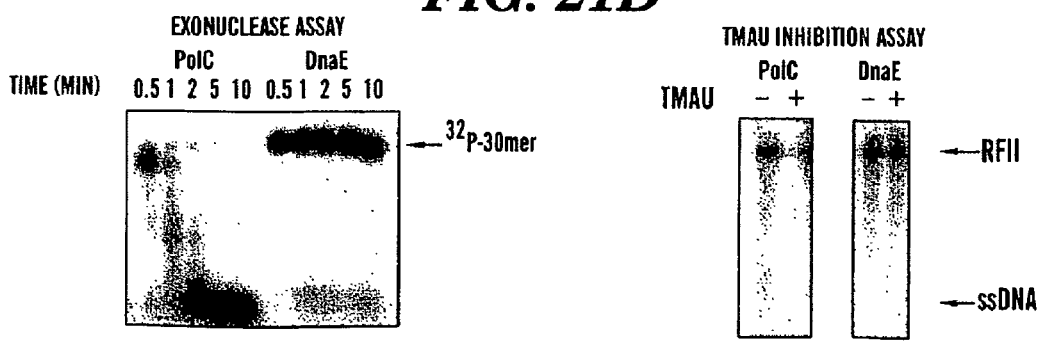
*FIG. 21E*
*FIG. 21F*

DNA MOLECULES ENCODING BETA CLAMP PROTEINS OF GRAM POSITIVE BACTERIA

The present application claims benefit of U.S. Provisional Patent application Ser. No. 60/146,178 filed Jul. 29, 1999, which is hereby incorporated by reference.

The present invention was made with funding from National Institutes of Health Grant No. GM38839. The United States Government may have certain rights in this invention.

FIELD OF THE INVENTION

This invention relates to genes and proteins that replicate the chromosome of Gram positive bacteria. These proteins can be used in sequencing, amplification of DNA, and in drug discovery to screen large libraries of chemicals for identification of compounds with antibiotic activity.

BACKGROUND OF THE INVENTION

All forms of life must duplicate the genetic material to propagate the species. The process by which the DNA in a chromosome is duplicated is called replication. The replication process is performed by numerous proteins that coordinate their actions to duplicate the DNA smoothly. The main protein actors are as follows (reviewed in Kornberg et al., *DNA Replication*, Second Edition, New York: W.H. Freeman and Company, pp. 165-194 (1992)). A helicase uses the energy of ATP hydrolysis to unwind the two DNA strands of the double helix. Two copies of the DNA polymerase use each "daughter" strand as a template to convert them into two new duplexes. The DNA polymerase acts by polymerizing the four monomer unit building blocks of DNA (the 4 dNTPs, or deoxynucleoside triphosphates are: dATP, dCTP, dGTP, dTTP). The polymerase rides along one strand of DNA using it as a template that dictates the sequence in which the monomer blocks are to be polymerized. Sometimes the DNA polymerase makes a mistake and includes an incorrect nucleotide (e.g., A instead of G). A proofreading exonuclease examines the polymer as it is made and excises building blocks that have been improperly inserted in the polymer.

Duplex DNA is composed of two strands that are oriented antiparallel to one another, one being oriented 3'-5' and the other 5' to 3'. As the helicase unwinds the duplex, the DNA polymerase moves continuously forward with the helicase on one strand (called the leading strand). However, due to the fact that DNA polymerases can only extend the DNA forward from a 3' terminus, the polymerase on the other strand extends DNA in the opposite direction of DNA unwinding (called the lagging strand). This necessitates a discontinuous ratcheting motion on the lagging strand in which the DNA is made as a series of Okazaki fragments. DNA polymerases cannot initiate DNA synthesis de novo, but require a primed site (i.e., a short duplex region). This job is fulfilled by primase, a specialized RNA polymerase, that synthesizes short RNA primers on the lagging strand. The primed sites are extended by DNA polymerase. A single-stranded DNA binding protein ("SSB") is also needed; it operates on the lagging strand. The function of SSB is to coat single stranded DNA ("ssDNA"), thereby melting short hairpin duplexes that would otherwise impede DNA synthesis by DNA polymerase.

The replication process is best understood for the Gram negative bacterium *Escherichia coli* and its bacteriophages T4 and T7 (reviewed in Kelman et al., "DNA Polymerase III Holoenzyme: Structure and Function of Chromosomal Replicating Machine," *Annu. Rev. Biochem.*, 64:171-200 (1995); Marians, K. J., "Prokaryotic DNA Replication," *Annu. Rev. Biochem.*, 61:673-719 (1992); McHenry, C. S., "DNA Polymerase III Holoenzyme: Components, Structure, and Mechanism of a True Replicative Complex," *J. Bio. Chem.*, 266: 19127-19130 (1991); Young et al., "Structure and Function of the Bacteriophage T4 DNA Polymerase Holoenzyme," *Am. Chem. Soc.*, 31:8675-8690 (1992)). The eukaryotic systems of yeast (*Saccharomyces cerevisae*) (Morrison et al., "A Third Essential DNA Polymerase in *S. cerevisiae*," *Cell*, 62:1143-51 (1990) and humans (Bambara et al., "Reconstitution of Mammalian DNA Replication, "*Prog. Nuc. Acid Res.,*" 51:93-123 (1995)) have also been characterized in some detail as has herpes virus (Boehmer et al., "Herpes Simplex Virus DNA Replication," *Annu. Rev. Biochem.*, 66:347-384 (1997)) and vaccinia virus (McDonald et al., "Characterization of a Processive Form of the Vaccinia Virus DNA Polymerase," *Virology*, 234:168-175 (1997)). The helicase of *E. coli* is encoded by the dnaB gene and is called the DnaB-helicase. In phage T4, the helicase is the product of the gene 41, and, in T7, it is the product of gene 4. Generally, the helicase contacts the DNA polymerase in *E. coli*. This contact is necessary for the helicase to achieve the catalytic efficiency needed to replicate a chromosome (Kim et al., "Coupling of a Replicative Polymerase and Helicase: A tau-DnaB Interaction Mediates Rapid Replication Fork Movement," *Cell*, 84:643-650 (1996)). The identity of the helicase that acts at the replication fork in a eukaryotic cellular system is still not firm.

The primase of *E. coli* (product of the dnaG gene), phage T4 (product of gene 61), and T7 (gene 4) require the presence of their cognate helicase for activity. The primase of eukaryotes, called DNA polymerase alpha, looks and behaves differently. DNA polymerase alpha is composed of 4 subunits. The primase activity is associated with the two smaller subunits, and the largest subunit is the DNA polymerase which extends the product of the priming subunits. DNA polymerase alpha does not need a helicase for priming activity on single strand DNA that is not coated with binding protein.

The chromosomal replicating DNA polymerase of all these systems, prokaryotic and eukaryotic, share the feature that they are processive, meaning they remain continuously associated with the DNA template as they link monomer units (dNTPs) together. This catalytic efficiency can be manifest in vitro by their ability to extend a single primer around a circular ssDNA of over 5,000 nucleotide units in length. Chromosomal DNA polymerases will be referred to here as replicases to distinguish them from DNA polymerases that function in other DNA metabolic processes and are far less processive.

There are three types of replicases known thus far that differ in how they achieve processivity and how their subunits are organized. These will be referred to here as Types I-III. The Type I is exemplified by the phage T5 replicase, which is composed of only one subunit yet is highly processive (Das et al., "Mechanism of Primer-template Dependent Conversion of dNTP-dNMP by T7 DNA Polymerase," *J. Biol. Chem.*, 255:7149-7154 (1980)). It is possible that the T5 enzyme achieves processivity by having a cavity within it for binding DNA, with a domain of the protein acting as a lid that opens to accept the DNA and closes to trap the DNA inside, thereby keeping the polymerase on DNA during polymerization of dNTPs. Type II is exemplified by the replicases of phage T7, herpes simplex virus, and vaccinia virus. In these systems, the replicase is composed of two subunits, the DNA polymerase and an "accessory protein" which is needed for the polymerase to become highly efficient. It is presumed that the DNA polymerase binds the DNA in a groove and that the accessory protein forms a cap over the groove, trapping the DNA inside for processive action. Type III is exemplified by the replicases of E. coli, phage T4, yeast, and humans in which there are three separate components, a sliding clamp protein, a clamp loader protein complex, and the DNA polymerase. In these systems, the sliding clamp protein is an oligomer in the shape of a ring. The clamp loader is a multiprotein complex which uses ATP to assemble the clamp around DNA. The DNA polymerase then binds the clamp which tethers the polymerase to DNA for high processivity. The replicase of the E. coli system contains a fourth component called tau that acts as a glue to hold two polymerases and one clamp loader together into one structure called Pol III*. In this application, any replicase that uses a minimum of three components (i.e., clamp, clamp loader, and DNA polymerase) will be referred to as either a three component polymerase, a type III enzyme, or a DNA polymerase III-type replicase.

The E. coli replicase is also called DNA polymerase III holoenzyme. The holoenzyme is a single multiprotein particle that contains all the components; it is comprised of ten different proteins. This holoenzyme is suborganized into four functional components called: 1) Pol III core (DNA polymerase); 2) gamma complex or tau/gamma complex (clamp loader); 3) beta subunit (sliding clamp); and 4) tau (glue protein). The DNA polymerase III "core" is a tightly associated complex containing one each of the following three subunits: 1) the alpha subunit is the actual DNA polymerase (129 kDa); 2) the epsilon subunit (28 kDa) contains the proofreading 3'-5' exonuclease activity; and 3) the theta subunit has an unknown function. The gamma complex is the clamp loader and contains the following subunits: gamma, delta, delta prime, chi and psi (U.S. Pat. No. 5,583,026 to O'Donnell). Tau can substitute for gamma, as can a tau/gamma heterooligomer. The beta subunit is a homodimer and forms the ring shaped sliding clamp. These components associate to form the holoenzyme and the entire holoenzyme can be assembled in vitro from 10 isolated pure subunits (U.S. Pat. No. 5,583,026 to O'Donnell; U.S. Pat. No. 5,668,004 to O'Donnell). The E. coli dnaX gene encodes both tau and gamma. Tau is the product of the full gene. Gamma is the product of the first ⅔ of the gene; it is truncated by an efficient translational frameshift that results in incorporation of one unique residue followed by a stop codon.

The tau subunit, encoded by the same gene that encodes gamma (dnaX), also acts as a glue to hold two cores together with one gamma complex. This subassembly is called DNA polymerase III star (Pol III*). One beta ring interacts with each core in Pol III* to form DNA polymerase III holoenzyme.

During replication, the two cores in the holoenzyme act coordinately to synthesize both strands of DNA in a duplex chromosome. At the replication fork, DNA polymerase III holoenzyme physically interacts with the DnaB helicase through the tau subunit to form a yet larger protein complex termed the "replisome" (Kim et al., "Coupling of a Replicative Polymerase and Helicase: A tau-DnaB Interaction Mediates Rapid Replication Fork Movement," Cell, 84:643-650 (1996); Yuzhakov et al., "Replisome Assembly Reveals the Basis for Asymmetric Function in Leading and Lagging Strand Replication," Cell, 86:877-886 (1996)). The primase repeatedly contacts the helicase during replication fork movement to synthesize RNA primers on the lagging strand (Marians, K. J., "Prokaryotic DNA Replication," Annu. Rev. Biochem., 61:673-719 (1992)).

Intensive subtyping of prokaryotic cells has now lead to a taxonomic classification of prokaryotic cells as eubacteria (true bacteria) to distinguish them from archaebacteria. Within eubacteria are many different subcategories of cells, although they can broadly be subdivided into Gram positive- and Gram negative-like cells. Numerous complete and partial genome sequences of prokaryotes have appeared in the public databases.

In the present invention, new genes from the Gram positive bacteria, Streptococcus pyogenes (e.g., S. pyogenes) and Staphylococcus aureus (e.g., S. aureus) are identified. They are assigned names based on their nearest homology to subunits in the E. coli system. The genes encoding E. coli replication proteins are as follows: alpha (dnaE); epsilon (dnaQ); theta (holE); tau (full length dnaX); gamma (frameshift product of dnaX); delta (holA); delta prime (holB); chi (holC); psi (holD); beta (dnaN); DnaB helicase (dnaB); and primase (dnaG).

Study of the organisms for which a complete genome sequence is available reveals that no organism has identifiable homologues to all the subunits of the E. coli three component polymerase, Pol III holoenzyme (see Table 1 below). All other organisms lack the θ subunit (holE), and all except one lack genes encoding the χ and ψ subunits (holC and holD, respectively) as judged by sequence comparison searches. Further, the α and ε subunits are fused into one large a subunit in some organisms (e.g., Gram positive cells) as detailed in (Sanjanwala et al., "DNA Polymerase III Gene of Bacillus subtilis," Proc. Natl. Acad. Sci. USA, 86:4421-4424 (1989)). Although all organisms have homologues to τ, β, δ' and SSB, the δ subunit has diverged significantly (either not recognized or nearly not recognized by gene searching programs), perhaps even to the point where it is no longer involved in DNA replication. The DnaX product also would appear to lack frameshift signals in most organisms. This predicts only one protein (tau) will be produced from this gene, instead of two as in E. coli. Indeed, this has been shown to be true for the Staphylococcus aureus DnaX (U.S. patent application Ser. No. 09/235,245, which is hereby incorporated by reference). Finally, genetic study of Bacillus subtilis identified two genes that do not have counterparts in E. coli (dnaB, not the helicase, and dnaH) as well as one other gene, dnaI, that is only very distantly related to E. coli dnaC (Karamata et al., "Isolation and Genetic Analysis of Temperature-Sensitive Mutants of B. subtilis Defense in DNA Synthesis," Molec. Gen. Genet., 108:277-287 (1970); Braund et al., "Nucleotide Sequence of the Bacillus subtilis dnaD Gene," Microb., 141: 321-322 (1995); Hoshino et al., "Nucleotide Sequence of Bacillus subtilis dnaB: A Gene Essential for DNA Replication Initiation and Membrance Attachment," Proc. Natl. Acad. Sci. USA," 84:653-657 (1987)). Keeping in mind the apparently random, or at least unpredictable process of evolution, it is possible that these apparently new genes perform novel functions that may result in a new type of polymerase for chromosomal replication. Thus, it seems possible that new proteins may have evolved to take the place of χ, ψ, θ, the frameshift product of DnaX, and possibly δ in other eubacteria. These considerations indicate that the three component polymerase of different eubacteria may have different structures. That this may be so would not be surprising as different bacteria are often less related evolutionarily than plants are to humans. For example, the split between Gram positive and Gram negative bacteria occurred about 1.2 billion years ago. This distant split makes Gram positive cells an attractive source to examine how different other eubacterial three component polymerases are from the E. coli Pol III holoenzyme.

TABLE 1

| Organism (Order) | χ | φ | θ | ε | α | β | dnaX | δ' | δ | |
|---|---|---|---|---|---|---|---|---|---|---|
| *Escherichia coli* Proteobacteria | + | + | + | + | + | + | + | + | + | |
| *Haemophilus influenzae* Proteobacteria | + | + | − | + | + | + | + | + | + | |
| *Mycoplasma genitalium* Firmicutes | − | − | − | − | + | + | + | + | + | (weak) |
| *Synichisystis* sp. Cyanobacteria | − | − | − | − | + | + | + | + | + | (weak) |
| *Bacillus subtilis* Firmicutes | − | − | − | − | + | + | + | + | + | (weak) |
| *Borrelia burgdorferi* Spirochaetales | − | − | − | − | + | + | + | + | + | (weak) |
| *Aquifex aeolicus* Aquificales | − | − | − | + | + | + | + | + | + | (weak) |
| *Mycobacterium tuberculosis* Firmicutes & Actinobacteria | − | − | − | + | + | + | + | + | + | (weak) |
| *Treponema pallidum* Spirochaetales | − | − | − | + | + | + | + | + | + | (weak) |
| *Chlamydia trachomatis* Chlamydiales | − | − | − | + | + | + | + | + | + | (weak) |
| *Rickettsia prowazekii* Proteobacteria | − | − | − | + | + | + | + | + | + | (weak) |
| *Helicobacter pylori* Proteobacteria | − | − | − | + | + | + | + | + | + | (weak) |
| *Thermatoga maritima* Thermotogales | − | − | − | − | + | + | + | + | + | (weak) |

The goal of this invention is to learn how to form a functional three component polymerase from an organism that is highly divergent from *E. coli* and whether it is as rapid and processive as the *E. coli* Pol III holoenzyme. Namely, from bacteria lacking χ, ψ, or θ, or having a widely divergent δ subunit, or having only one DnaX product, or an α subunit that encompasses both α and ε activities. All eubacteria for which the entire genome has been sequenced have at least one of these differences from *E. coli*. Many Gram negative bacteria have one or more of these differences (e.g., *Haemophilus influenzae* and *Aquifex aeolicus*). Bacteria of the Gram positive class have all of these different features. Because of the distant evolutionary split between Gram positive and Gram negative bacteria, their mechanisms of replication may have diverged significantly as well. Indeed, purification of the replication polymerase from *B. subtilis*, a Gram positive cell, gives only a single subunit polymerase (Barnes et al., "Purification of DNA Polymerase III of Gram-Positive Bacteria," *Methods Enzy.* 262:35-42 (1995); Barnes et al., "Antibody to *B. subtilis* DNA Polymerase III: Use in Enzyme Purification and Examination of Homology Among Replication-specific DNA Polymerases," *Nucl. Acids Res.*, 6:1203-209 (1979); Barnes et al., "DNA Polymerase III of *Mycoplasma pulmonis*: Isolation and Characterization of the Enzyme and its Structural Gene, polC," *Mol. Microb.*, 13:843-854, (1994); Low et al., "Purification and Characterization of DNA Polymerase III from *Bacillus subtilis*," *J. Biol. Chem.*, 251:1311-1325 (1976)) instead of a 10 subunit assembly containing the three components of a rapidly processive machine as discussed above for Pol III holoenzyme from *E. coli*. This finding suggests a different structural organization of the replicase and possibly different functional characteristics as well.

Although there are many studies of replication mechanisms in eukaryotes and, specifically, the Gram negative bacterium *E. coli* and its bacteriophages, there is very little information about how Gram positive organisms replicate. The Gram positive class of bacteria includes some of the worst human pathogens such as *Staphylococcus aureus*, *Streptococcus pneumoniae*, *Streptococcus pyogenes*, *Enterococcus faecalis*, and *Mycobacterium tuberculosis* (Youmans et al., *The Biological and Clinical Basis of Infectious Disease* (1985)). Until this invention, the best characterized Gram positive organism for chromosomal DNA synthesis was *Bacillus subtilis*. Fractionation of *B. subtilis* has identified three DNA polymerases. (Gass et al., "Further Genetic and Enzymological Characterization of the Three *Bacillus subtilis* Deoxyribonucleic Acid Polymerases," *J. Biol. Chem.*, 248: 7688-7700 (1973); Ganesan et al., "DNA Replication in a Polymerase I Deficient Mutant and the Identification of DNA Polymerases II and III in *Bacillus subtilis*," *Biochem. Biophys. Res. Commun.*, 50:155-163 (1973)). These polymerases are thought to be analogous to the three DNA polymerases of *E. coli* (DNA polymerases I, II, and III). Studies in *B. subtilis* have identified a polymerase that appears to be involved in chromosome replication and is termed Pol III (Ott et al., "Cloning and Characterization of the polC Region of *Bacillus subtilis*," *J. Bacteriol.*, 165:951-957 (1986); Barnes et al., "Localization of the Exonuclease and Polymerase Domains of *Bacillus subtilis* DNA Polymerase III," *Gene*, 111:43-49 (1992); Barnes et al., "The 3'-5' Exonuclease Site of DNA Polymerase III From Gram-positive Bacteria: Definition of a Novel Motif Structure," *Gene*" 165:45-50 (1995) or Barnes et al., "Purification of DNA Polymerase III of Gram-positive Bacteria," *Methods in Enzy.*, 262:35-42 (1995)). The *B. subtilis* Pol III (encoded by polC) is larger (about 165 kDa) than the *E. coli* alpha subunit (about 129 kDa) and exhibits 3'-5' exonuclease activity. The polC gene encoding this Pol III shows weak homology to the genes encoding *E. coli* alpha and the *E. coli* epsilon subunit. Hence, this long form of the *B. subtilis* Pol III (herein referred to as α-large or Pol III-L) essentially comprises both the alpha and epsilon subunits of the *E. coli* core polymerase. The *S. aureus* α-large has also been sequenced, expressed in *E. coli*, and purified; it contains DNA polymerase and 3'-5' exonuclease activity (Pacitti et al., "Characterization and Overexpression of the Gene Encoding *Staphylococcus aureus* DNA Polymerase III," *Gene*, 165:51-56 (1995)). Although α-large is essential to cell growth (Clements et al., "Inhibition of *Bacil-* lus subtilis Deoxyribonucleic Acid Polymerase III by Phenylhydrazinopyrimidines: Demonstration of a Drug-induced Deoxyribonucleic Acid-Enzyme Complex," *J. Biol. Chem.*, 250:522-526 (1975); Cozzarelli et al., "Mutational Alteration of *Bacillus subtilis* DNA Polymerase III to Hydroxyphenylazopyrimidine Resistance: Polymerase III is Necessary for DNA Replication," *Biochem. And Biophy. Res. Commun.*, 51:151-157 (1973); Low et al., "Mechanism of Inhibition of *Bacillus subtilis* DNA Polymerase III by the Arylhydrazinopyrimidine Antimicrobial Agents," *Proc. Natl. Acad. Sci. USA*, 71:2973-2977 (1974)), there could still be another DNA polymerase(s) that is essential to the cell, such as occurs in yeast (Morrison et al., "A Third Essential DNA Polymerase in *S. cerevisiae*," *Cell*, 62:1143-1151 (1990)).

Purification of α-large from *B. subtilis* results in only this single protein without associated proteins (Barnes et al., "Localization of the Exonuclease and Polymerase Domains of *Bacillus subtilis* DNA Polymerase III," *Gene*, 111:43-49 (1992); Barnes et al., "The 3'-5' Exonuclease Site of DNA Polymerase III From Gram-positive Bacteria: Definition of a Novel Motif Structure," Gene" 165:45-50 (1995) or Barnes et al., "Purification of DNA Polymerase III of Gram-positive Bacteria," *Methods in Enzymol.*, 262:35-42 (1995)). Hence, it is possible that α-large is a member of the Type I replicase (like T5) in which it is processive on its own without accessory proteins. *B. subtilis* and *S. aureus* also have a gene encoding a protein that has approximately 30% homology to the beta subunit of *E. coli*; however, the protein product has not been purified or characterized (Alonso et al., "Nucleotide Sequence of the recF Gene Cluster From *Staphylococcus aureus* and Complementation Analysis in *Bacillus subtilis* recF Mutants," *Mol. Gen. Genet.*, 246:680-686 (1995); Alonso et al., "Nucleotide Sequence of the recF Gene Cluster From *Staphylococcus aureus* and Complementation Analysis in *Bacillus subtilis* recF Mutants," *Mol. Gen. Genet.*, 248: 635-636 (1995)). Whether this beta subunit has a function in replication, a ring shape, or functions as a sliding clamp was not known until recently. It was also not known whether it is functional with α-large. Recently, it was shown that *S. aureus* β is functional as a ring, and that it also functions with α-large (U.S. patent application Ser. No. 09/235,245, which is hereby incorporated by reference). Further, a fourth DNA polymerase was identified with greater homology to *E. coli* a than α-large. This polymerase, called herein α-small, is shorter than α-large and lacks the domain homologous to epsilon. This polymerase also functions with the β ring, indicating that it may participate in chromosome replication. Indeed, a recent report indicates that α-small is essential for replication in *Streptomyces coelicolor* A3(2) (Flett et al., "A Gram-negative type" DNA Polymerase III is Essential for Replication of the Linear Chromosome of *Streptomyces Coelicolor* A3(2)," *Mol. Micro.*, 31:949-958, (1999)).

As described earlier, purification of the replicase from the Gram positive *B. subtilis* gives only a single subunit Pol II, instead of a multicomponent complex. Also, *S. aureus* dnaX has been shown to encode only one subunit (U.S. patent application Ser. No. 09/235,245, which is hereby incorporated by reference). Moreover, *S. aureus* and *B. subtilis* lack homologues to χ, ψ, θ, and the δ subunit is only weakly homologous to δ of *E. coli* (only 28%). Further, they lack a homologue to dnaQ encoding E. Instead, they contain this activity (3'-5' exonuclease) in the polC gene product which provides the α-large form of α. The ε subunit is needed for high speed and processivity of the *E. coli* Pol III holoenzyme; the α subunit alone is much less rapid and processive with the β ring compared to the presence of both α and β (Studwell et al., "Processive Replication is Contingent on the Exonuclease Subunit of DNA Polymerase III Holoenzyme," *J. Biol Chem*, 265: 1171-1178 (1990)).

Studies using the *E. coli* β ring (and γ complex) show they confer onto *S. aureus* a quite efficient synthesis (U.S. patent application Ser. No. 09/235,245, which is hereby incorporated by reference), but the efficiency is not equal to that of *E. coli* αε with β (and γ complex). This may be due to use of the heterologous combination of an α subunit from one organism (*S. aureus*) with the β clamp from another (*E. coli*.). However, it is also possible that *S. aureus* α simply does not function with a β clamp to produce speed and processivity comparable to the *E. coli* polymerase. Also, as described earlier, the α-large subunit of *B. subtilis* purifies as a single subunit, rather than associated with accessory subunits assembled into the three components of a rapid, processive machine (i.e., like *E. coli* Pol III holoenzyme). The lack of two DnaX products, lack of a multicomponent structure, and lack of gene homologues encoding several subunits of the three component, Pol III, of *E. coli* brings into question whether other types of bacteria, such as Gram positive cells, even have an enzyme with similar structure or comparable speed and processivity to that found in the Gram negative *E. coli*.

The lack of gene homologues encoding several subunits of the *E. coli* three component polymerase creates uncertainties with respect to reconstructing a rapid and processive polymerase from a Gram positive cell that has characteristics like the Pol III system of *E. coli*.

The γ and δ' proteins are homologous to one another, encoding C-shape proteins Long et al., "DNA Polymerase III Accessory Proteins," *J. Biol. Chem.*, 268:11758-11765, (1993); Guenther et al., "Crystal Structure of the δ' Subunit of the Clamp-loader Complex of *E. coli* DNA Polymerase III," *Cell*, 91:335-345 (1997)). The clamp loaders of yeast and humans are composed of five proteins, all of which are homologous to one another and to γ and δ' (Cullman et al., "Characterization of the Five Replication Factor C Genes of *Saccharomyces Cerevisiae*," *Mol. Cell. Biol.*, 15:4661-4671 (1995)). This provides evidence that a clamp loader can be composed entirely of C-shape proteins. Perhaps the Gram positive DnaX-protein (hereafter referred to as τ) and δ' are sufficient to provide function as a clamp loader. Indeed, the clamp loader of T4 phage is composed of only two different proteins, gp44/62 complex (Young et al., "Structure and Function of the Bacteriophage T4 DNA Polymerase Holoenzyme," *Biochem.*, 31:8675-8690 (1992)). This idea is also supported by the presence of only two RFC genes in archaebacteria, suggesting that they may utilize two C-shaped proteins for clamp loading, in contrast to yeast and humans that use five. With this consideration in mind, genes were identified and isolated and the τ protein (encoded by dnaX) and δ' (encoded by holB) of another Gram positive organism, *Streptococcus pyogenes*, were expressed and purified. As was observed in *S. aureus*, *S. pyogenes* dnaX produces only a single polypeptide. The β, encoded by dnaN of *S. pyogenes*, was also identified, expressed, and purified, as were the α-large subunit encoded by polC and the SSB encoded by the ssb gene. These proteins were studied for interactions and characterized for their effect on α-large. However, the hypothesis was incorrect as T and δ' did not form a τδ' complex, nor did they assemble β onto DNA or provide stimulation of a when using β on primed and SSB coated M13 mp18 ssDNA.

In light of the inability of *S. pyogenes* τ protein and δ' to function as a clamp loader, it seemed reasonable to expect that one or more other proteins are needed. The fact that *E. coli* has some replicase subunits that other bacteria do not, suggests that other bacteria may have some replicase subunits that *E. coli* does not. Indeed, genetic studies of *Bacillus subtilis* demonstrates that it has three genes needed for replication that *E. coli* does not have. Two of these novel genes, called dnaB (not the same as *E. coli* dnaB encoding the helicase) and dnaH, have no significant homology to genes in the *E. coli* genome database (Bruand et al., "Nucleotide Sequence of the *Bacillus subtilis* dnaD gene," *Microbiol.*, 141:321-322 (1995); Hoshino et al., "Nucleotide Sequence of *Bacillus subtilis* dnaB: A gene Essential for DNA replication Initiation and Membrane Attachment," *Proc. Natl. Acad. Sci. USA*, 84:653-657 (1987)). Further, dnaI of *B. subtilis* is important for replication and has, at best, a very limited homology to *E. coli* dnaC (Karamata et al., "Isolation and Genetic Analysis of Temperature-Sensitive Mutants of *B. subtilis* Defective in DNA synthesis," *Molec. Gen. Genetics*, 108:277-287 (1970)). Perhaps one or more of these genes encode the proteins(s) necessary to provide clamp loading activity when combined with τ and δ', or to couple with α to provide it with speed and/or processivity as the *E. coli* epsilon does. The *S. pyogenes* homologues of *B. subtilis* dnaI, dnaH, and dnaB were identified, cloned, and the encoded proteins were expressed and purified. However, these proteins failed to provide activity alone or in combinations with *S. pyogenes* τ and δ' in loading *S. pyogenes* onto DNA, or in stimulating *S. pyogenes* α-large in combination with β, τ, and δ' on SSB coated primed M13 mp18 ssDNA.

Weak homology exists for the holA gene among prokaryotes. This weak homologue of holA was identified in *S. pyogenes* and, then, it was cloned, expressed, and the putative δ was purified. The putative δ formed an isolatable complex with τ and δ'. In fact, the τδδ' complex loaded *S. pyogenes* β onto DNA, and it stimulated *S. pyogenes* α-large in a β dependent reaction on primed SSB coated M13 mp18 ssDNA. Hence, this protein was the only missing component necessary to provide clamp loading activity. Further, a mixture of α with τδδ', followed by ion exchange chromatography on MonoQ, indicated formation of an ατδδ' complex. Consistent with this, τ appeared to bind α in gel filtration analysis.

Whether the *S. pyogenes* three component polymerase can synthesize DNA in as rapid and processive of a fashion as the *E. coli* Pol III holoenzyme three component polymerase is very difficult to predict, because no other DNA polymerase known to date catalyzes synthesis at the rate or processivity of the *E. coli* three component polymerase. For example, the three component T4 phage polymerase travels about 400 nucleotides/s, the yeast DNA polymerase delta three component polymerase travels about 120 nucleotides/s, and the human DNA polymerase delta three component enzyme appears slower and less processive than the yeast enzyme.

The standard test for these speed and processivity characteristics is examination of a time course in extension of a primer on a very long template, such as around the 7.2 kb M13mp18 ssDNA genome coated with SSB and primed with a synthetic DNA oligonucleotide. The results of experiments of this type demonstrate that the three component *S. pyogenes* polymerase is indeed extremely rapid in synthesis. Surprisingly, it is just as fast as the *E. coli* enzyme. Extension proceeds at about 700-800 nucleotides per second, completing the entire template in about 9 seconds. The enzyme was fully processive throughout replication of the M13mp18 genome, as could be determined from the fact that some templates were not extended at all, while others were extended to completion. If the enzyme had not been processive during the entire replication reaction, then when it comes off one partially extended DNA genome it would have reassociated with the unextended DNA that remained and partially replicated it as well (and so on until the entire population of DNA became fully replicated). This did not happen. Instead, the reaction showed a mixture of completely replicated templates and templates that were still untouched starting material. This indicates that the enzyme stays with a template until it completes it before it cycles over to replicate another one (i.e., it is highly processive). Each of the five proteins, α, τ, δ, δ' and β, are needed to obtain this rapid and processive DNA synthesis.

This invention has provided an intellectual template by which the clamp loader component of these three component polymerases can be obtained from any eubacterial prokaryotic cell and how to use it with the other components to produce a rapid and processive polymerase. All prokaryotes in the eubacterial kingdom that have been sequenced to date contain homologues of these genes. As the process of lateral gene transfer appears to be a major force in evolution, it would appear that relatedness of enzymes and enzyme machines is best judged by comparisons of their genes and proteins rather than by phylogeny of which bacteria they are in (Doolittle et al., "Archaeal Genomics: Do Archaea have a Mixed Heritage?," *Curr. Biol.*, 8:R209—R211 (1998)). As pointed out earlier in this application, most bacteria have genetic characteristics of replication genes/proteins of *S. pyogenes* rather than that of *E. coli* (i.e., no genes encoding χ, ψ, or θ, only a weak homolog to δ, or a dnaX gene encoding only a single protein).

The dnaX gene encoding τ and γ in *E. coli* encodes only one protein in some organisms, but, as this application shows, it is still functional in forming a protein complex capable of rapid and processive DNA synthesis. In addition, this application shows that the delta subunit, which is only weakly homologous among different prokaryotic organisms, is an essential functional subunit of the three component polymerase (instead of having diverged so as to fulfill an entirely different function in some other intracellular process). As mentioned earlier, several genes encoding subunits of the *E. coli* clamp loader (γ complex; γ, δ,δ',χ,ψ) are not obviously present in other prokaryotes (holC and holD encoding χ and ψ). Hence, one may anticipate that other genes may have evolved to encode new subunits that replace these, and that these new subunits may have been essential to the activity of the clamp loader. For example, they may have either taken over some of the functionality of another subunit, or structurally (e.g., the physical presence of a subunit could be needed for one subunit to assume its proper and active conformation, or for one or more of the subunits to form a complex together to yield the multisubunit clamp loader assembly). In addition, this application shows that the α subunit (polC gene product) is sufficient for rapid and processive synthesis with the other two components (i.e., *E. coli* requires ε submit to bind to α for rapid and processive synthesis of α with the β clamp). Finally, this application shows that the *S. pyogenes* three component polymerase synthesizes DNA as fast as the *E. coli* Pol III three component polymerase. Up to this point, the *E. coli* Pol III three component polymerase was over twice the speed of the T4 enzyme and over 5 times the speed of others. Hence, it was possible that *E. coli* may have been unique among prokaryotes in having a polymerase that achieves such speed. This invention shows that this is not the case. Instead, this speed in polymerization generalizes to the Gram positive prokaryotic three component DNA polymerases. It may be presumed, now that two examples of three component polymerases in widely divergent bacteria share the characteristics of rapid, processive synthesis, that the three component polymerase of other eubacteria will also be rapid and processive.

These rapid and processive three component DNA polymerases can be applied to several important uses. DNA polymerases currently in use for DNA sequencing and DNA amplification use enzymes that are much slower and thus could be improved upon. This is especially true of amplification as the three component polymerase is capable of speed and high processivity making possible amplification of very long (tens of Kb to Mb) lengths of DNA in a time efficient manner. These three component polymerases also function in conjunction with a replicative helicase (DnaB) and, thus, are capable of amplification at ambient temperature using the helicase to melt the DNA duplex. This property could be useful in amplification reaction procedures such as in polymerase chain reaction (PCR) methodology. Finally, these three component polymerases and their associated helicase (DnaB) and primase (DnaG) are attractive targets for antibiotics due to their essential and central role in cell viability.

This application provides a three component polymerase from two human pathogens in the Gram positive class. It makes possible the production of this three component polymerase from other bacteria of the Gram positive type (e.g., Streptococci, Staphylococci, *Mycoplasma*) and other types of bacteria lacking χ, ψ, or θ, those having only one protein produced by their dnaX gene such as obligate intracellular parasites, Mycoplasmas (possibly evolved from Gram positives), Cyanobacteria (*Synechocystis*), Spirochaetes such as *Borrelia* and *Treponemia* and *Chlamydia*, and distant relatives of *E. coli* in the Gram negative class (e.g., *Rickettsia* and *Helicobacter*). These three component polymerases are useful in manipulation of nucleic acids for research and diagnostic purposes (e.g., sequencing and amplification methods) and for screening chemicals for antibiotic activity (useful in human or animal therapy and agriculture such as animal feed supplements). There are several assays described previously in U.S. patent application Ser. No. 09/235,245 to O'Donnell et al., which is hereby incorporated by reference, that use these three component polymerases (or subassemblies), as well as the DnaB and DnaG homologues, either alone or in various combinations, for the purpose of screening chemicals, such as chemical libraries, for inhibitor activity. Such inhibitors can be developed further (usually by chemical manipulation and alteration) into lead compounds and then into full fledged pharmaceuticals.

There remains a need to understand the molecular details of the process of DNA replication in other cells that are quite different from *E. coli*, such as in Gram positive cells. It is possible that a more detailed understanding of replication proteins will lead to discovery of new antibiotics. Therefore, a deeper understanding of replication proteins of Gram positive bacteria is especially important given the emergence of drug resistant strains of these organisms. For example, *Staphylococcus aureus* has successfully mutated to become resistant to all common antibiotics.

The "target" protein(s) of an antibiotic drug is generally involved in a critical cell function, such that blocking its action with a drug causes the pathogenic cell to die or no longer proliferate. Current antibiotics are directed to very few targets. These include membrane synthesis proteins (e.g., vancomycin, penicillin, and its derivatives such as ampicillin, amoxicillin, and cephalosporin), the ribosome machinery (e.g., tetracycline, chloramphenicol, azithromycin, and the aminoglycosides such as kanamycin, neomycin, gentamicin, streptomycin), RNA polymerase (e.g., rifampimycin), and DNA topoisomerases (e.g., novobiocin, quinolones, and fluoroquinolones). The DNA replication apparatus is a crucial life process and, thus, the proteins involved in this process are good targets for antibiotics.

A powerful approach to discovery of a new drug is to obtain a target protein, characterize it, and develop in vitro assays of its cellular function. Large chemical libraries can then be screened in the functional assays to identify compounds that inhibit the target protein. These candidate pharmaceuticals can then be chemically modified to optimize their potency, breadth of antibiotic spectrum, non-toxicity, performance in animal models and, finally, clinical trials. The screening of large chemical libraries requires a plentiful source of the target protein. An abundant supply of protein generally requires overproduction techniques using the gene encoding the protein. This is especially true for replication proteins as they are present in low abundance in the cell.

Selective and robust assays are needed to screen reliably a large chemical library. The assay should be insensitive to most chemicals in the concentration range normally used in the drug discovery process. These assays should also be selective and not show inhibition by antibiotics known to target proteins in processes outside of replication.

The present invention is directed to overcoming these deficiencies in the art.

SUMMARY OF THE INVENTION

The present invention relates to various isolated DNA molecules from *Staphylococcus aureus* and *Streptococcus pyogenes*, both of which are Gram positive bacteria. These include DNA molecules which include a coding region from the dnaE gene (encoding α-small), dnaX gene (encoding tau), polC gene (encoding Pol III-L or α-large), dnaN gene (encoding beta), holA gene (encoding delta), holB gene (encoding delta prime), ssb gene (encoding SSB), dnaB gene (encoding DnaB), and dnaG gene (encoding DnaG) of *S. aureus* and/or *S. pyogenes*. These DNA molecules can be inserted into an expression system and used to transform host cells. The isolated proteins or polypeptides encoded by these DNA molecules, and their ability to function when used in combination is also disclosed. The resulting actions provide assembling a ring onto DNA via a clamp loader, and polymerase activity dependent on this ring that is rapid and processive.

A further aspect of the present invention relates to a method of identifying compounds which inhibit activity of a polymerase product of polC or dnaE. This method is carried out by forming a reaction mixture comprising a primed DNA molecule, a polymerase product of polC or dnaE, a candidate compound, a dNTP, and optionally either a beta subunit, a tau complex, or both the beta subunit and the tau complex, wherein at least one of the polymerase product of polC or dnaE, the beta subunit, the tau complex, or a subunit or combination of subunits thereof is derived from a Eubacteria other than *Escherichia coli*; subjecting the reaction mixture to conditions effective to achieve nucleic acid polymerization in the absence of the candidate compound; analyzing the reaction mixture for the presence or absence of nucleic acid polymerization extension products; and identifying the candidate compound in the reaction mixture where there is an absence of nucleic acid polymerization extension products.

The present invention deciphers the structure and mechanism of the chromosomal replicase of Gram positive bacteria and other bacteria lacking holC, holD, holE or dnaQ genes, or having a dnaX gene that encodes only one protein. Rather than use a DNA polymerase that attains high efficiency on its own, or with one other subunit, the Gram positive bacteria replicase is a three component type of replicase (class III) that uses a sliding clamp protein. The Gram positive bacteria replicase also uses a clamp loader component that assembles the sliding clamp onto DNA. This knowledge, and the enzymes involved in the replication process, can be used for the purpose of screening for potential antibiotic drugs. Further, information about chromosomal replicases may be useful in DNA sequencing, DNA amplification, polymerase chain reaction, and other DNA polymerase related techniques.

The present invention identifies two DNA polymerases (both of Pol III type) in Gram positive bacteria that utilize the sliding clamp and clamp loader. The present invention also identifies a gene with homology to the alpha subunit of *E. coli* DNA polymerase III holoenzyme, the chromosomal replicase of *E. coli*. These DNA polymerases can extend a primer around a large circular natural template when the beta clamp has been assembled onto the primed ssDNA by the clamp loader or a primer on a linear DNA where the beta clamp may assemble by itself by sliding over an end.

The present invention shows that the clamp and clamp loader components of Gram negative cells can be exchanged for those of Gram positive cells in that the clamp, once assembled onto DNA, will function with Pol III obtained from either Gram positive and Gram negative sources. This result implies that important contacts between the polymerase and clamp have been conserved during evolution. Therefore, these "mixed systems" may provide assays for an inhibitor of this conserved interaction. Such an inhibitor may be expected to shut down replication, and since the interaction is apparently conserved across the evolutionary spectrum from Gram positive and Gram negative cells, the inhibitor may exhibit a broad spectrum of antibiotic activity.

The present invention demonstrates that Gram positive bacteria contain a beta subunit that behaves as a sliding clamp that encircles DNA. A dnaX gene sequence encoding a protein homolog of the gamma/tau subunit of the clamp loader (gamma/tau complex) *E. coli* DNA polymerase III holoenzyme is also identified. The presence of this gene confirms the presence of a clamp loading apparatus in Gram positive bacteria that will assemble beta clamps onto DNA for the DNA polymerases.

This application also outlines methods and assays for use of these replication proteins in drug screening processes.

BRIEF DESCRIPTION OF THE DRAWINGS

FIG. 2A compares *E. coli* cells that contain the pET11PolC expression vector that are either induced or uninduced for protein expression. The gel is stained with Coomassie Blue. The induced band corresponds to the expected molecular weight of the *S. aureus* Pol III-L, and is indicated to the right of the gel. FIG. 2B-C show the results of the MonoQ chromatography of a lysate of *E. coli* (pET$_{11}$PolC-L) induced for Pol III-L. The fractions were analyzed in a Coomassie Blue stained gel (FIG. 2B) and for DNA synthesis (FIG. 2C). Fractions containing Pol III-L are indicated. In FIG. 2D, fractions containing Pol III-L from the MonoQ column were pooled and chromatographed on a phosphocellulose column. This shows an analysis of the column fractions from the phosphocellulose column in a Coomassie Blue stained polyacrylamide gel. The position of Pol III-L is indicated to the right.

FIG. 4A compares *E. coli* cells that contain the pET16beta expression vector that are either induced or uninduced for protein expression. The gel is stained with Coomassie Blue. The induced band corresponds to the expected molecular weight of the *S. aureus* beta, and is indicated to the right of the gel. The migration position of size standards are indicated to the left. FIG. 4B shows the results of MonoQ chromatography of an *E. coli* (pET16beta) lysate induced for beta. The fractions were analyzed in a Coomassie Blue stained gel, and fractions containing beta are indicated. In FIG. 4C, fractions containing beta from the MonoQ column were pooled and chromatographed on a phosphocellulose column. This shows an analysis of the column fractions from the phosphocellulose column in a Coomassie Blue stained polyacrylamide gel. The position of beta is indicated to the right.

In FIG. 5A, the indicated proteins were added to replication reactions containing polydA-oligodT as described in the Examples infra. Amounts of proteins added, when present, were: lanes 1,2: *S. aureus* Pol III-L, 7.5 ng; *S. aureus* beta, 6.2 µg; Lanes 3,4: *E. coli* Pol III core, 45 ng; *S. aureus* beta, 9.3 µg; Lanes 5,6: *E. coli* Pol III core, 45 ng; *E. coli* beta, 5 µg. Total DNA synthesis was: Lanes 1-6: 4.4, 30.3, 5.1, 35.5, 0.97, 28.1 pmol, respectively. In FIG. 5B, Lanes 1-3, the indicated proteins were added to replication reactions containing circular singly primed M13 mp18 ssDNA as described in the Examples infra. *S. aureus* beta, 0.8 µg; *S. aureus* Pol III-L, 300 ng (purified through MonoQ); *E. coli* clamp loader complex, 1.7 µg. Results in the *E. coli* system are shown in Lanes 4-6. Total DNA synthesis was: Lanes 1-6: 0.6, 0.36, 0.99, 2.7, 3.5, 280 pmol, respectively.

FIG. 8A shows the product analysis in an agarose gel.

FIG. 8B shows the extent of DNA synthesis in each assay.

FIG. 9 compares the homology between the polypeptide encoded by dnaE of *S. aureus* and other organisms. An alignment is shown for the amino acid sequence of the *S. aureus* dnaE product (SEQ. ID. No. 85) with the dnaE products (alpha subunits) of *E. coli* (SEQ. ID. No. 86) and *Salmonella typhimurium* (SEQ. ID. No. 87).

FIG. 10 compares the homology between the N-terminal regions of the gamma/tau polypeptides of *S. aureus* (SEQ. ID. No. 88), *B. subtilis* (SEQ. ID. No. 89), and *E. coli* (SEQ. ID. No. 90). The conserved ATP site and the cystines forming the zinc finger are indicated above the sequence. The organisms used in the alignment were: *E. coli* (GenBank); and *B. subtilis*.

FIG. 11 compares the homology between the DnaB polypeptide of *S. aureus* (SEQ. ID. No. 91) and other organisms. The organisms used in the alignment were: *E. coli* (GenBank) (SEQ. ID. No. 92); *B. subtilis* (SEQ. ID. No. 93); *Sal. Typ.*, (*Salmonella typhimurium*) (SEQ. ID. No. 94).

FIGS. 12A-B show the alignment of the delta subunit encoded by holA for *E. coli* (SEQ. ID. No. 95) and *B. subtilis* (SEQ. ID. No. 96) (FIG. 12A) and for the delta subunit of *B. subtilis* (SEQ. ID. No. 96) and *S. pyogenes* (SEQ. ID. No. 97) (FIG. 12B). FIG. 12A shows ClustalW generated alignment of *B. subtilis* (Gram positive) delta (SEQ. ID. No. 96) to *E. coli* (Gram negative) delta (SEQ. ID. No. 95). FIG. 12B shows ClustalW generated alignment of *B. subtilis* (Gram positive) delta (SEQ. ID. No. 96) to *S. pyogenes* (Gram positive) delta (SEQ. ID. No. 97).

FIG. 15A shows a mixture of τδδ'. FIG. 15B shows a mixture of τδ. FIG. 15C shows a mixture of τδ'.

FIG. 16A demonstrates the ability of τδδ' complex to load the beta dimer onto a nicked pBSK circular plasmid. FIGS. 16B-E show the results of using either: beta alone (FIG. 16B); δδ' plus β (FIG. 16C); τ, δ and β (FIG. 16D); τ, δ' and β (FIG. 16E).

FIG. 17A shows the result of gel filtration analysis of a mixture of τ with alpha-large. Gel filtration fractions are analyzed in a SDS polyacrylamide gel. FIGS. 17B and 17C show the results using only τ or only alpha-large, respectively. Comparison of the elution positions of proteins shows that the positions of alpha and tau are shifted toward a higher molecular weight complex when they are present together. The fact they do not exactly comigrate may indicate that they initially are together in a complex, but that the complex dissociates during the time of the gel filtration experiment (over one half hour).

FIG. 21A-F are images illustrating that the *S. pyogenes* DnaE (alpha-small) polymerase functions with β. FIGS. 21A-B illustrate the relationship between DnaE and β for association with ssDNA. Different amounts of DnaE polymerase were added to a SSB coated M13mp18 ssDNA circle primed with a single DNA oligonucleotide, and products were analyzed in a native agarose gel. Reactions were performed in the presence of τδδ' and either the absence (FIG. 21C, panels 1-4) or presence (FIG. 21D, panels 1-4) of β. Positions of completed duplex (RFII) and initial primed template (ssDNA) are indicated. FIG. 21E shows an analysis of exonuclease activity by PolC and DnaE on a 5'-32P-DNA 30-mer. Aliquots were removed at the indicated times and analyzed in a sequencing gel. FIG. 21F shows the effect of TMAU on PolC and DnaE in the presence of τδδ' and β. DNA products were analyzed in a native agarose gel. Positions of initial primed M13mp18 (ssDNA) and completed circular duplex (RFII) are indicated.

DETAILED DESCRIPTION OF THE INVENTION

Figure 1:
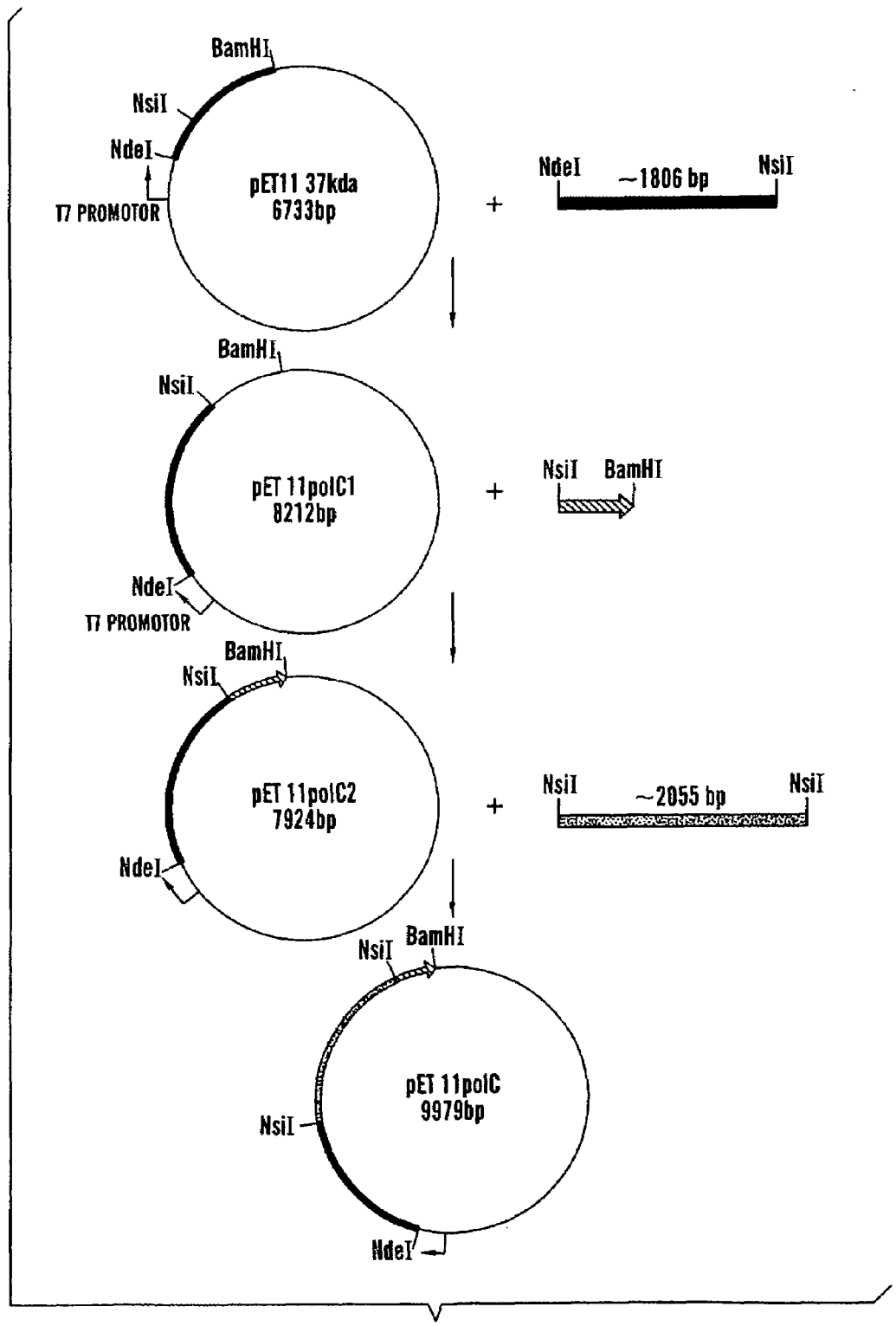
FIG. 1 shows the construction of the *S. aureus* Pol III-L expression vector. The gene encoding Pol III-L was cloned into a pET11 expression vector in a three step cloning scheme as illustrated.

The present invention relates to various isolated nucleic acid molecules from Gram positive bacteria and other bacteria lacking holC, holD, or holE genes or having a dnaX gene encoding only one subunit. These include DNA molecules which correspond to the coding regions of the dnaE, dnaX, holA, holB, polC, dnaN, SSB, dnaB, and dnaG genes. These DNA molecules can be inserted into an expression system or used to transform host cells. The isolated proteins or polypeptides encoded by these DNA molecules and their use to form a three component polymerase are also disclosed. Also encompassed by the present invention are corresponding RNA molecules transcribed from the DNA molecules.

These DNA molecules and proteins can be derived from numerous bacteria, including *Staphylococcus, Streptococcus, Enterococcus, Mycoplasma, Mycobacterium, Borrelia, Treponema, Rickettsia, Chlamydia, Helicobacter*, and *Thermatoga*. It is particularly directed to such DNA molecules and proteins derived from *Streptococcus* and *Staphylococcus* bacteria, particularly *Streptococcus pyogenes* and *Staphylococcus aureus* (see U.S. patent application Ser. No. 09/235,245, which is hereby incorporated by reference).

The gene sequences used to obtain DNA molecules of the present invention were obtained by sequence comparisons with the *E. coli* counterparts, followed by detailed analysis of the raw sequence data in the contigs from the *S. pyogenes* database (http://dna1.chem.ou.edu/strep.html) or the *S. aureus* database (http://www.genome.ou.edu/staph.html) to identify the open reading frames. In many instances, nucleotide errors were observed causing frameshifts in the open reading frame thus truncating it. Therefore, upon cloning the genes via PCR, the genes were sequenced to obtain correct information. Also, the full nucleotide sequence of the ssb gene was not present in the data base. This was cloned by circular PCR and the full sequence is reported below.

The *S. aureus* dnaX and dnaE genes were identified by aligning genes of several organisms and designing primers for use in PCR to obtain a gene fragment, followed by steps to identify the entire gene.

One aspect of the present invention relates to a newly discovered Pol III gene (herein identified as dnaE) of *S. aureus* whose encoded protein is homologous to *E. coli* alpha (product of dnaE gene). The partial nucleotide sequence of the *S. aureus* dnaE gene corresponds to SEQ. ID. No. 1 as follows:

```
atggtggcat atttaaatat tcatacggct tatgatttgt taaattcaag cttaaaaata   60
gaagatgccg taagacttgc tgtgtctgaa aatgttgatg cacttgccat aactgacacc  120
aatgtattgt atggttttcc taaattttat gatgcatgta tagcaaataa cattaaaccg  180
atttttggta tgacaatata tgtgacaaat ggattaaata cagtcgaaac agttgttcta  240
gctaaaaata atgatggatt aaaagatttg tatcaactat catcggaaat aaaaatgaat  300
gcattagaac atgtgtcgtt tgaattatta aaacgatttt ctaacaatat gattatcatt  360
tttaaaaaag tcggtgatca acatcgtgat attgtacaag tgtttgaaac ccataatgac  420
acatatatgg accaccttag tatttcgatt caaggtagaa aacatgtttg gattcaaaat  480
gtttgttacc aaacacgtca agatgccgat acgatttctg cattagcagc tattagagac  540
aatacaaaat tagacttaat tcatgatcaa gaagattttg gtgcacattt tttaactgaa  600
aaggaaatta atcaattaga tattaaccaa gaatatttaa cgcaggttga tgttatagct  660
caaaagtgtg atgcagaatt aaaatatcat caatctctac ttcctcaata tgagacacct  720
aatgatgaat cagctaaaaa atatttgtgg cgtgtcttag ttacacaatt gaaaaaatta  780
gaacttaatt atgacgtcta tttagagcga ttgaaatatg agtataaagt tattactaat  840
atgggttttg aagattattt cttaatagta agtgatttaa tccattatgc gaaaacgaat  900
gatgtgatgg taggtcctgg tcgtggttct tcagctggct cactggtcag ttatttattg  960
ggaattacaa cgattgatcc tattaaattc aatctattat ttgaacgttt tttaaaccca 1020
gaacgtgtaa caatgcctga tattgatatt gactttgaag atacacgccg agaaagggtc 1080
attcagtacg tccaagaaaa atatggcgag ctacatgtat ctggaattgt gactttcggt 1140
catctgcttg caagagcagt tgctagagat gttggaagaa ttatggggtt tgatgaagtt 1200
acattaaatg aaatttcaag tttaatccca cataaattag gaattacact tgatgaagca 1260
tatcaaattg acgattttaa agagtttgta catcgaaacc atcgacatga acgctggttc 1320
agtatttgta aaaagttaga aggtttacca agacatacat ctacacatgc ggcaggaatt 1380
attattaatg accatccatt atatgaatat gcccctttaa cgaaagggga tacaggatta 1440
ttaacgcaat ggacaatgac tgaagccgaa cgtattgggt tattaaaaat agattttcta 1500
gggttgagaa acttatcgat tattcatcaa atcttaacac aagtcaaaaa agatttaggt 1560
attaatattg atatcgaaaa gattccgttt gatgatcaaa aagtgtttga attgttgtcg 1620
caaggagata cgactggcat attccaatta gagtctgacg gtgtaagaag tgtattaaaa 1680
```

```
                                -continued
aaattaaagc cggaacactt tgaagatatt gttgctgtaa cttctttgta tagaccaggt 1740
ccaatggaag aaattccaac ttacattaca agaagacatg atccaagcaa agttcaatat 1800
ttacatccgc atttagaacc tatattaaaa aatacttacg gtgttattat ttatcaagag 1860
caaattatgc aaatagcgag cacatttgca aacttcagtt atggtgaagc ggatatttta 1920
agaagagcaa tgagtaaaaa aaatagagct gttcttgaaa gtgagcgtca acattttata 1980
gaaggtgcaa agcaaaatgg ttatcacgaa gacattagta agcaaatatt tgatttgatt 2040
ctgaaacttg ctgattatgg ttttcctaga gcacatgctg tcagctattc taaaattgca 2100
tacattacga gcttttttaaa agtccattat ccaaattatt tttacgcaaa tattttaagt 2160
aatgttattg gaagtgagaa gaaaactgct caaatgatag aagaagcaaa aaaacaaggt 2220
atcactatat tgccaccgaa cattaacgaa agtcattggt tttataaacc ttcccaagaa 2280
ggcatttatt tatcaattgg tacaattaaa ggtgttggtt atcaaagtgt gaaagtgatt 2340
gttgatgaac gttatcagaa cggcaaattt aaagatttct ttgattttgc tagacgtata 2400
ccgaagagag tcaaaacgag aaagttactt gaagcactga ttttagtggg agcgtttgat 2460
gcttttggta aaacacgttc aacgttgttg caagctattg atcaagtgtt ggatggcgat 2520
ttaaacactg aacaagatgg tttttttattt gatatttttaa cgccaaaaca gatgtatgaa 2580
gataaagaag aattgcctga tgcacttatt agtcagtacg aaaaagaata tttaggattt 2640
tatgtttcgc aacacccagt agataaaaag tttgttgcca acaatatttt aacgatattt 2700
aaattgagta acgcgcagaa ttataaacct atattagtac agtttgataa agttaaacaa 2760
attcgaacta aaaatggtca aaatatggca ttcgtcacat taaatgatgg cattgaaact 2820
ttagatggtg tgattttccc taatcagttt aaaaagtacg aagagttgtt atcacataat 2880
gacttgttta tagttagcgg gaaatttgac catagaaagc aacaacgtca actaattata 2940
aatgagattc agacattago cactttgaa gaacaaaat tagcatttgc caaacaaatt 3000
ataattagaa ataaatcaca aatagatatg tttgaagaga tgattaaagc tacgaaagag 3060
aatgctaatg atgttgtgtt atcctttat gatgaaacga ttaaacaaat gactacttta 3120
ggctatatta atcaaaaaga tagtatgttt aataatttta tacaatcctt taaccctagt 3180
gatattaggc ttata                                                 3195
```

The *S. aureus* dnaE encoded protein, called α-small, has an amino acid sequence corresponding to SEQ. ID. No. 2 as follows:

```
Met Val Ala Tyr Leu Asn Ile His Thr Ala Tyr Asp Leu Leu Asn Ser
 1               5                  10                  15

Ser Leu Lys Ile Glu Asp Ala Val Arg Leu Ala Val Ser Glu Asn Val
            20                  25                  30

Asp Ala Leu Ala Ile Thr Asp Thr Asn Val Leu Tyr Gly Phe Pro Lys
        35                  40                  45

Phe Tyr Asp Ala Cys Ile Ala Asn Asn Ile Lys Pro Ile Phe Gly Met
    50                  55                  60

Thr Ile Tyr Val Thr Asn Gly Leu Asn Thr Val Glu Thr Val Val Leu
65                  70                  75                  80

Ala Lys Asn Asn Asp Gly Leu Lys Asp Leu Tyr Gln Leu Ser Ser Glu
                85                  90                  95

Ile Lys Met Asn Ala Leu Glu His Val Ser Phe Glu Leu Leu Lys Arg
            100                 105                 110
```

-continued

```
Phe Ser Asn Asn Met Ile Ile Ile Phe Lys Lys Val Gly Asp Gln His
        115                 120                 125

Arg Asp Ile Val Gln Val Phe Glu Thr His Asn Asp Thr Tyr Met Asp
    130                 135                 140

His Leu Ser Ile Ser Ile Gln Gly Arg Lys His Val Trp Ile Gln Asn
145                 150                 155                 160

Val Cys Tyr Gln Thr Arg Gln Asp Ala Asp Thr Ile Ser Ala Leu Ala
                165                 170                 175

Ala Ile Arg Asp Asn Thr Lys Leu Asp Leu Ile His Asp Gln Glu Asp
            180                 185                 190

Phe Gly Ala His Phe Leu Thr Glu Lys Glu Ile Asn Gln Leu Asp Ile
        195                 200                 205

Asn Gln Glu Tyr Leu Thr Gln Val Asp Val Ile Ala Gln Lys Cys Asp
    210                 215                 220

Ala Glu Leu Lys Tyr His Gln Ser Leu Leu Pro Gln Tyr Glu Thr Pro
225                 230                 235                 240

Asn Asp Glu Ser Ala Lys Lys Tyr Leu Trp Arg Val Leu Val Thr Gln
                245                 250                 255

Leu Lys Lys Leu Glu Leu Asn Tyr Asp Val Tyr Leu Glu Arg Leu Lys
            260                 265                 270

Tyr Glu Tyr Lys Val Ile Thr Asn Met Gly Phe Glu Asp Tyr Phe Leu
        275                 280                 285

Ile Val Ser Asp Leu Ile His Tyr Ala Lys Thr Asn Asp Val Met Val
        290                 295                 300

Gly Pro Gly Arg Gly Ser Ser Ala Gly Ser Leu Val Ser Tyr Leu Leu
305                 310                 315                 320

Gly Ile Thr Thr Ile Asp Pro Ile Lys Phe Asn Leu Leu Phe Glu Arg
                325                 330                 335

Phe Leu Asn Pro Glu Arg Val Thr Met Pro Asp Ile Asp Ile Asp Phe
            340                 345                 350

Glu Asp Thr Arg Arg Glu Arg Val Ile Gln Tyr Val Gln Glu Lys Tyr
        355                 360                 365

Gly Glu Leu His Val Ser Gly Ile Val Thr Phe Gly His Leu Leu Ala
        370                 375                 380

Arg Ala Val Ala Arg Asp Val Gly Arg Ile Met Gly Phe Asp Glu Val
385                 390                 395                 400

Thr Leu Asn Glu Ile Ser Ser Leu Ile Pro His Lys Leu Gly Ile Thr
                405                 410                 415

Leu Asp Glu Ala Tyr Gln Ile Asp Asp Phe Lys Glu Phe Val His Arg
            420                 425                 430

Asn His Arg His Gln Arg Trp Phe Ser Ile Cys Lys Lys Leu Glu Gly
        435                 440                 445

Leu Pro Arg His Thr Ser Thr His Ala Ala Gly Ile Ile Asn Asp
        450                 455                 450

His Pro Leu Tyr Glu Tyr Ala Pro Leu Thr Lys Gly Asp Thr Gly Leu
465                 470                 475                 480

Leu Thr Gln Trp Thr Met Thr Glu Ala Glu Arg Ile Gly Leu Leu Lys
                485                 490                 495

Ile Asp Phe Leu Gly Leu Arg Asn Leu Ser Ile Ile His Gln Ile Leu
            500                 505                 510

Thr Gln Val Lys Lys Asp Leu Gly Ile Asn Ile Asp Ile Glu Lys Ile
        515                 520                 525
```

-continued

```
Pro Phe Asp Asp Gln Lys Val Phe Glu Leu Leu Ser Gln Gly Asp Thr
    530                 535                 540

Thr Gly Ile Phe Gln Leu Glu Ser Asp Gly Val Arg Ser Val Leu Lys
545                 550                 555                 560

Lys Leu Lys Pro Glu His Phe Glu Asp Ile Val Ala Val Thr Ser Leu
                565                 570                 575

Tyr Arg Pro Gly Pro Met Glu Glu Ile Pro Thr Tyr Ile Thr Arg Arg
            580                 585                 590

His Asp Pro Ser Lys Val Gln Tyr Leu His Pro His Leu Glu Pro Ile
        595                 600                 605

Leu Lys Asn Thr Tyr Gly Val Ile Ile Tyr Gln Glu Gln Ile Met Gln
    610                 615                 620

Ile Ala Ser Thr Phe Ala Asn Phe Ser Tyr Gly Glu Ala Asp Ile Leu
625                 630                 635                 640

Arg Arg Ala Met Ser Lys Lys Asn Arg Ala Val Leu Glu Ser Glu Arg
                645                 650                 655

Gln His Phe Ile Glu Gly Ala Lys Gln Asn Gly Tyr His Glu Asp Ile
            660                 665                 670

Ser Lys Gln Ile Phe Asp Leu Ile Leu Lys Phe Ala Asp Tyr Gly Phe
        675                 680                 685

Pro Arg Ala His Ala Val Ser Tyr Ser Lys Ile Ala Tyr Ile Met Ser
    690                 695                 700

Phe Leu Lys Val His Tyr Pro Asn Tyr Phe Tyr Ala Asn Ile Leu Ser
705                 710                 715                 720

Asn Val Ile Gly Ser Glu Lys Lys Thr Ala Gln Met Ile Glu Glu Ala
                725                 730                 735

Lys Lys Gln Gly Ile Thr Ile Leu Pro Pro Asn Ile Asn Glu Ser His
            740                 745                 750

Trp Phe Tyr Lys Pro Ser Gln Glu Gly Ile Tyr Leu Ser Ile Gly Thr
        755                 760                 765

Ile Lys Gly Val Gly Tyr Gln Ser Val Lys Val Ile Val Asp Glu Arg
    770                 775                 780

Tyr Gln Asn Gly Lys Phe Lys Asp Phe Asp Phe Ala Arg Arg Ile
785                 790                 795                 800

Pro Lys Arg Val Lys Thr Arg Lys Leu Leu Glu Ala Leu Ile Leu Val
                805                 810                 815

Gly Ala Phe Asp Ala Phe Gly Lys Thr Arg Ser Thr Leu Leu Gln Ala
            820                 825                 830

Ile Asp Gln Val Leu Asp Gly Asp Leu Asn Ile Glu Gln Asp Gly Phe
        835                 840                 845

Leu Phe Asp Ile Leu Thr Pro Lys Gln Met Tyr Glu Asp Lys Glu Glu
    850                 855                 860

Leu Pro Asp Ala Leu Ile Ser Gln Tyr Glu Lys Glu Tyr Leu Gly Phe
865                 870                 875                 880

Tyr Val Ser Gln His Pro Val Asp Lys Lys Phe Val Ala Lys Gln Tyr
                885                 890                 895

Leu Thr Ile Phe Lys Leu Ser Asn Ala Gln Asn Tyr Lys Pro Ile Leu
            900                 905                 910

Val Gln Phe Asp Lys Val Lys Gln Ile Arg Thr Lys Asn Gly Gln Asn
        915                 920                 925

Met Ala Phe Val Thr Leu Asn Asp Gly Ile Glu Thr Leu Asp Gly Val
    930                 935                 940
```

```
Ile Phe Pro Asn Gln Phe Lys Lys Tyr Glu Glu Leu Leu Ser His Asn
945                 950                 955                 960

Asp Leu Phe Ile Val Ser Gly Lys Phe Asp His Arg Lys Gln Gln Arg
                965                 970                 975

Gln Leu Ile Ile Asn Glu Ile Gln Thr Leu Ala Thr Phe Glu Glu Gln
            980                 985                 990

Lys Leu Ala Phe Ala Lys Gln Ile Ile Arg Asn Lys Ser Gln Ile
        995                1000                1005

Asp Met Phe Glu Glu Met Ile Lys Ala Thr Lys Glu Asn Ala Asn Asp
    1010                1015                1020

Val Val Leu Ser Phe Tyr Asp Glu Thr Ile Lys Gln Met Thr Thr Leu
1025                1030                1035                1040

Gly Tyr Ile Asn Gln Lys Asp Ser Met Phe Asn Asn Phe Ile Gln Ser
                1045                1050                1055

Phe Asn Pro Ser Asp Ile Arg Leu Ile
            1060                1065
```

The present invention also relates to the *S. aureus* dnaX gene. This *S. aureus* dnaX gene has a partial nucleotide sequence corresponding to SEQ. ID. No. 3 as follows:

```
ttgaattatc aagccttata tcgtatgtac agaccccaaa gtttcgagga tgtcgtcgga   60
caagaacatg tcacgaagac attgcgcaat gcgatttcga aagaaaaaca gtcgcatgca  120
tatattttta gtggtccgag aggtacgggg aaaacgagta ttgccaaagt gtttgctaaa  180
gcaatcaact gtttaaatag cactgatgga gaaccttgta tgaatgtca  tatttgtaaa  240 ggcattacgc aggggactaa ttcagatgtg atagaaattg atgctgctag taataatggc  300
gttgatgaaa taagaaatat tagagacaaa gttaaatatg caccaagtga atcgaaatat  360
aaagtttata ttatagatga ggtgcacatg ctaacaacag gtgcttttaa tgcccttttta 420 aagacgttag aagaacctcc agcacacgct atttttatat tggcaacgac agaaccacat  480
aaaatccctc aacaatcat  ttctagggca caacgtttg  attttaaagc aattagccta  540
gatcaaattg ttgaacgttt aaaatttgta gcagatgcac aacaaattga atgtgaagat  600
gaagccttgg catttatcgc taaagcgtct gaaggggta  tgcgtgatgc attaagtatt  660
atggatcagg ctattgcttt cggcgatggc acattgacat tacaagatgc cctaaatgtt  720
acgggtagcg ttcatgatga agcgttggat cacttgtttg atgatattgt acaaggtgac  780
gtacaagcat cttttaaaaa ataccatcag tttataacag aaggtaaaga agtgaatcgc  840
ctaataaatg atatgattta ttttgtcaga gatacgatta tgaataaaac atctgagaaa  900
gatactgagt atcgagcact gatgaactta gaattagata tgttatatca atgattgat  960 cttattaatg atacattagt gtcgattcgt tttagtgtga atcaaaacgt tcattttgaa 1020
gtattgttag taaaattagc tgagcagatt aagggtcaac cacaagtgat tgcgaatgta 1080
gctgaaccag cacaaattgc ttcatcgcca aacacagatg tattgttgca acgtatggaa 1140
cagttagagc aagaactaaa aacactaaaa gcacaaggag tgagtgttgc tcctactcaa 1200
aaatcttcga aaaagcctgc gagaggtata caaaaatcta aaaatgcatt ttcaatgcaa 1260
caaattgcaa aagtgctaga taaagcgaat aaggcagata tcaaattgtt gaaagatcat 1320
tggcaagaag tgattgacca tgcccaaaac aatgataaaa aatcactcgt tagtttattg 1380
caaaattcgg aacctgtggc ggcaagtgaa gatcacgtcc ttgtgaaatt tgaggaagag 1440
```

-continued

```
atccattgtg aaatcgtcaa taaagacgac gagaaacgta gtagtataga aagtgttgta 1500
tgtaatatcg ttaataaaaa cgttaaagtt gttggtgtac catcagatca atggcaaaga 1560
gttcgaacgg agtatttaca aaatcgtaaa aacgaaggcg atgatatgcc aaagcaacaa 1620
gcacaacaaa cagatattgc tcaaaaagca aagatctttt cggtgaaga aactgtacat 1680 gtgatagatg aagagtga                                                1698
```

The *S. aureus* dnaX encoded protein (i.e., the tau subunit) has a partial amino acid sequence corresponding to SEQ. ID. No. 4 as follows:

```
Leu Asn Tyr Gln Ala Leu Tyr Arg Met Tyr Arg Pro Gln Ser Phe Glu
1               5                   10                  15

Asp Val Val Gly Gln Glu His Val Thr Lys Thr Leu Arg Asn Ala Ile
            20                  25                  30

Ser Lys Glu Lys Gln Ser His Ala Tyr Ile Phe Ser Gly Pro Arg Gly
        35                  40                  45

Thr Gly Lys Thr Ser Ile Ala Lys Val Phe Ala Lys Ala Ile Asn Cys
    50                  55                  60

Leu Asn Ser Thr Asp Gly Glu Pro Cys Asn Glu Cys His Ile Cys Lys
65                  70                  75                  80

Gly Ile Thr Gln Gly Thr Asn Ser Asp Val Ile Glu Ile Asp Ala Ala
                85                  90                  95

Ser Asn Asn Gly Val Asp Glu Ile Arg Asn Ile Arg Asp Lys Val Lys
            100                 105                 110

Tyr Ala Pro Ser Glu Ser Lys Tyr Lys Val Tyr Ile Ile Asp Glu Val
        115                 120                 125

His Met Leu Thr Thr Gly Ala Phe Asn Ala Leu Leu Lys Thr Leu Glu
    130                 135                 140

Glu Pro Pro Ala His Ala Ile Phe Ile Leu Ala Thr Thr Glu Pro His
145                 150                 155                 160

Lys Ile Pro Pro Thr Ile Ile Ser Arg Ala Gln Arg Phe Asp Phe Lys
                165                 170                 175

Ala Ile Ser Leu Asp Gln Ile Val Glu Arg Leu Lys Phe Val Ala Asp
            180                 185                 190

Ala Gln Gln Ile Glu Cys Glu Asp Glu Ala Leu Ala Phe Ile Ala Lys
        195                 200                 205

Ala Ser Glu Gly Gly Met Arg Asp Ala Leu Ser Ile Met Asp Gln Ala
    210                 215                 220

Ile Ala Phe Gly Asp Gly Thr Leu Thr Leu Gln Asp Ala Leu Asn Val
225                 230                 235                 240

Thr Gly Ser Val His Asp Glu Ala Leu Asp His Leu Phe Asp Asp Ile
                245                 250                 255

Val Gln Gly Asp Val Gln Ala Ser Phe Lys Lys Tyr His Gln Phe Ile
            260                 265                 270

Thr Glu Gly Lys Glu Val Asn Arg Leu Ile Asn Asp Met Ile Tyr Phe
        275                 280                 285

Val Arg Asp Thr Ile Met Asn Lys Thr Ser Glu Lys Asp Thr Glu Tyr
    290                 295                 300

Arg Ala Leu Met Asn Leu Glu Leu Asp Met Leu Tyr Gln Met Ile Asp
305                 310                 315                 320
```

```
Leu Ile Asn Asp Thr Leu Val Ser Ile Arg Phe Ser Val Asn Gln Asn
                325                 330                 335

Val His Phe Glu Val Leu Leu Val Lys Leu Ala Glu Gln Ile Lys Gly
            340                 345                 350

Gln Pro Gln Val Ile Ala Asn Val Ala Glu Pro Ala Gln Ile Ala Ser
            355                 360                 365

Ser Pro Asn Thr Asp Val Leu Leu Gln Arg Met Glu Gln Leu Glu Gln
        370                 375                 380

Glu Leu Lys Thr Leu Lys Ala Gln Gly Val Ser Val Ala Pro Thr Gln
385                 390                 395                 400

Lys Ser Ser Lys Lys Pro Ala Arg Gly Ile Gln Lys Ser Lys Asn Ala
                405                 410                 415

Phe Ser Met Gln Gln Ile Ala Lys Val Leu Asp Lys Ala Asn Lys Ala
            420                 425                 430

Asp Ile Lys Leu Leu Lys Asp His Trp Gln Glu Val Ile Asp His Ala
            435                 440                 445

Gln Asn Asn Asp Lys Lys Ser Leu Val Ser Leu Leu Gln Asn Ser Glu
        450                 455                 460

Pro Val Ala Ala Ser Glu Asp His Val Leu Val Lys Phe Glu Glu Glu
465                 470                 475                 480

Ile His Cys Glu Ile Val Asn Lys Asp Asp Glu Lys Arg Set Ser Ile
            485                 490                 495

Glu Ser Val Val Cys Asn Ile Val Asn Lys Asn Val Lys Val Val Gly
            500                 505                 510

Val Pro Ser Asp Gln Trp Gln Arg Val Arg Thr Glu Tyr Leu Gln Asn
            515                 520                 525

Arg Lys Asn Glu Gly Asp Asp Met Pro Lys Gln Gln Ala Gln Gln Thr
        530                 535                 540

Asp Ile Ala Gln Lys Ala Lys Asp Leu Phe Gly Glu Glu Thr Val His
545                 550                 555                 560

Val Ile Asp Glu Glu Glx
                565
```

The tau subunit of *S. aureus* functions as does both the tau subunit and the gamma subunit of *E. coli*.

This invention also relates to the partial nucleotide sequence of the *S. aureus* dnaB gene. The partial nucleotide sequence of this dnaB gene corresponds to SEQ. ID. No. 5 as follows:

```
atggatagaa tgtatgagca aaatcaaatg ccgcataaca atgaagctga acagtctgtc   60
ttaggttcaa ttattataga tccagaattg attaatacta ctcaggaagt tttgcttcct  120
gagtcgtttt ataggggtgc ccatcaacat attttccgtg caatgatgca cttaaatgaa  180
gataataaag aaattgatgt tgtaacattg atggatcaat tatcgacgga aggtacgttg  240
aatgaagcgg gtggcccgca atatcttgca gagttatcta caaatgtacc aacgacgcga  300
aatgttcagt attatactga tatcgtttct aagcatgcat taaaacgtag attgattcaa  360
actgcagata gtattgccaa tgatggatat aatgatgaac ttgaactaga tgcgatttta  420
agtgatgcag aacgtcgaat tttagagcta tcatcttctc gtgaaagcga tggctttaaa  480
gacattcgag acgtcttagg acaagtgtat gaaacagctg aagagcttga tcaaaatagt  540
ggtcaaacac caggtatacc tacaggatat cgagatttag accaaatgac agcagggttc  600
```

-continued

```
aaccgaaatg atttaattat ccttgcagcg cgtccatctg taggtaagac tgcgttcgca  660
cttaatattg cacaaaaagt tgcaacgcat gaagatatgt atacagttgg tattttctcg  720
ctagagatgg gtgctgatca gttagccaca cgtatgattt gtagttctgg aaatgttgac  780
tcaaaccgct taagaacggg tactatgact gaggaagatt ggagtcgttt tactatagcg  840
gtaggtaaat tatcacgtac gaagattttt attgatgata caccgggtat tcgaattaat  900
gatttacgtt ctaaatgtcg tcgattaaag caagaacatg gcttagacat gattgtgatt  960
gactacttac agttgattca aggtagtggt tcacgtgcgt ccgataacag acaacaggaa 1020
gtttctgaaa tctctcgtac attaaaagca ttagcccgtg aattaaaatg tccagttatc 1080
gcattaagtc agttatctcg tggtgttgaa caacgacaag ataaacgtcc aatgatgagt 1140
gatattcgtg aatctggttc gattgagcaa gatgccgata tcgttgcatt cttataccgt 1200
gatgattact ataaccgtgg cggcgatgaa gatgatgacg atgatggtgg tttcgagcca 1260
caaacgaatg atgaaaacgg tgaaattgaa attatcattg ctaagcaacg taacggtcca 1320
acaggcacag ttaagttaca ttttatgaaa caatataata aatttaccga tatcgattat 1380
gcacatgcag atatgatg                                                1398
```

The amino acid sequence of *S. aureus* DnaB encoded by the dnaB gene corresponds to SEQ. ID. No. 6 as follows:

```
Met Asp Arg Met Tyr Glu Gln Asn Gln Met Pro His Asn Asn Glu Ala
 1               5                  10                  15

Glu Gln Ser Val Leu Gly Ser Ile Ile Ile Asp Pro Glu Leu Ile Asn
            20                  25                  30

Thr Thr Gln Glu Val Leu Leu Pro Glu Ser Phe Tyr Arg Gly Ala His
        35                  40                  45

Gln His Ile Phe Arg Ala Met Met His Leu Asn Glu Asp Asn Lys Glu
    50                  55                  60

Ile Asp Val Val Thr Leu Met Asp Gln Leu Ser Thr Glu Gly Thr Leu
65                  70                  75                  80

Asn Glu Ala Gly Gly Pro Gln Tyr Leu Ala Glu Leu Ser Thr Asn Val
                85                  90                  95

Pro Thr Thr Arg Asn Val Gln Tyr Tyr Thr Asp Ile Val Ser Lys His
            100                 105                 110

Ala Leu Lys Arg Arg Leu Ile Gln Thr Ala Asp Ser Ile Ala Asn Asp
        115                 120                 125

Gly Tyr Asn Asp Glu Leu Glu Leu Asp Ala Ile Leu Ser Asp Ala Glu
    130                 135                 140

Arg Arg Ile Leu Glu Leu Ser Ser Ser Arg Glu Ser Asp Gly Phe Lys
145                 150                 155                 160

Asp Ile Arg Asp Val Leu Gly Gln Val Tyr Glu Thr Ala Glu Glu Leu
                165                 170                 175

Asp Gln Asn Ser Gly Gln Thr Pro Gly Ile Pro Thr Gly Tyr Arg Asp
            180                 185                 190

Leu Asp Gln Met Thr Ala Gly Phe Asn Arg Asn Asp Leu Ile Ile Leu
        195                 200                 205

Ala Ala Arg Pro Ser Val Gly Lys Thr Ala Phe Ala Leu Asn Ile Ala
    210                 215                 220

Gln Lys Val Ala Thr His Glu Asp Met Tyr Thr Val Gly Ile Phe Ser
225                 230                 235                 240
```

```
Leu Glu Met Gly Ala Asp Gln Leu Ala Thr Arg Met Ile Cys Ser Ser
            245                 250                 255
Gly Asn Val Asp Ser Asn Arg Leu Arg Thr Gly Thr Met Thr Glu Glu
            260                 265                 270
Asp Trp Ser Arg Phe Thr Ile Ala Val Gly Lys Leu Ser Arg Thr Lys
            275                 280                 285
Ile Phe Ile Asp Asp Thr Pro Gly Ile Arg Ile Asn Asp Leu Arg Ser
            290                 295                 300
Lys Cys Arg Arg Leu Lys Gln Glu His Gly Leu Asp Met Ile Val Ile
305                 310                 315                 320
Asp Tyr Leu Gln Leu Ile Gln Gly Ser Gly Ser Arg Ala Ser Asp Asn
            325                 330                 335
Arg Gln Gln Glu Val Ser Glu Ile Ser Arg Thr Leu Lys Ala Leu Ala
            340                 345                 350
Arg Glu Leu Lys Cys Pro Val Ile Ala Leu Ser Gln Leu Ser Arg Gly
            355                 360                 365
Val Glu Gln Arg Gln Asp Lys Arg Pro Met Met Ser Asp Ile Arg Glu
            370                 375                 380
Ser Gly Ser Ile Glu Gln Asp Ala Asp Ile Val Ala Phe Leu Tyr Arg
385                 390                 395                 400
Asp Asp Tyr Tyr Asn Arg Gly Gly Asp Glu Asp Asp Asp Asp Asp Gly
            405                 410                 415
Gly Phe Glu Pro Gln Thr Asn Asp Glu Asn Gly Glu Ile Glu Ile Ile
            420                 425                 430
Ile Ala Lys Gln Arg Asn Gly Pro Thr Gly Thr Val Lys Leu His Phe
            435                 440                 445
Met Lys Gln Tyr Asn Lys Phe Thr Asp Ile Asp Tyr Ala His Ala Asp
450                 455                 460
Met Met
465
```

The present invention also relates to the *S. aureus* polC gene (encoding Pol III-L or α-large). The partial nucleotide sequence of this polC gene corresponds to SEQ. ID. No. 7 as follows:

```
atgacagagc aacaaaaatt taaagcgctt gctgatcaaa ttaaaatttc aaatcaatta    60
gatgctgaaa ttttaaattc aggtgaactg acacgtatag atgtttctaa caaaaacaga   120
acatgggaat ttcatattac attaccacaa ttcttagctc atgaagatta tttattattt   180
ataaatgcaa tagagcaaga gtttaaagat atcgccaacg ttacatgtcg ttttacggta   240
acaaatggca cgaatcaaga tgaacatgca attaaatact ttgggcactg tattgaccaa   300
acagctttat ctccaaaagt taaggtcaa ttgaaacaga aaaagcttat tatgtctgga   360
aaagtattaa aagtaatggt atcaaatgac actgaacgta atcattttga taaggcatgt   420
aatggaagtc ttatcaaagc gtttagaaat tgtggttttg atatcgataa aatcatattc   480
gaaacaaatg ataatgatca agaacaaaac ttagcttctt tagaagcaca tattcaagaa   540
gaagacgaac aaagtgcacg attggcaaca gagaaacttg aaaaaatgaa agctgaaaaa   600
gcgaaacaac aagataacaa cgaaagtgct gtcgataagt gtcaaattgg taagccgatt   660
caaattgaaa atattaaacc aattgaatct attattgagg aagagtttaa agttgcaata   720
gagggtgtca ttttttgatat aaacttaaaa gaacttaaaa gtggtcgcca tatcgtagaa   780
```

-continued

```
attaaagtga ctgactatac ggactcttta gttttaaaaa tgtttactcg taaaaacaaa   840
gatgatttag aacattttaa agcgctaagt gttggtaaat gggttagggc tcaaggtcgt   900
attgaagaag atacatttat tagagattta gttatgatga tgtctgatat tgaagagatt   960
aaaaaagcga caaaaaaaga taaggctgaa gaaaagcgtg tagaactcca cttgcatact  1020
gcaatgagcc aaatggatgg tatacccaat attggtgcgt atgttaaaca ggcagcagac  1080
tggggacatc cagccattgc ggttacagac cataatgttg tgcaagcatt tccagatgct  2140
cacgcagcag cggaaaaaca tggcattaaa atgatatacg gtatggaagg tatgttagtt  1200
gatgatggtt ttccgattgc atacaaacca caagatgtcg tattaaaaga tgctacttat  1260
gttgtgttcg acgttgagac aactggttta tcaaatcagt atgataaaat catcgagctt  1320
gcagctgtga aagttcataa cggtgaaatc atcgataagt ttgaaaggtt tagtaatccg  1380
catgaacgat tatcggaaac gattatcaat ttgacgcata ttactgarga tatgttagta  1440
gatgcccctg agattgaaga agtacttaca gagtttaaag aatgggttgg cgatgcgata  1500
ttcgtagcgc acaatgcttc gtttgatatg ggcttcatcg atacgggata tgaacgtctt  1560
gggttcggac caccaacgaa tggtgttatc gatactttag aattatcccg tacgattaat  1620
actgaatatg gtaaacatgg tttgaatttc ttggctaaaa aatatggcgt agaattaacg  1680
caacatcacc gcgccattta tgatacagaa gcaacagctt acatttttcac aaaaatggtt  1740
caacaaatga aagaatcagg cgtattaaat cataacgaaa tcaacaaaaa actcagtaat  1800
gaagatgcat ataaacgtgc aagacctagt catgtcacat taattgtaca aaaccaacaa  1860
ggtcttaaaa atctattcaa aattgtaagt gcatcattgg tgaagtactc ctaccgtaca  1920
cctcgaattc cacgttcacc gttagatgaa tatcgcgagg gattattggc aggtacagcg  1980
cgtgatgaag gtgaattatt tacggcagtt atgcagaagg accagagtca agttgaaaaa  2040
attgccaaat attatgattt tattgaaatt caaccaccgg cactttatca agatttaatt  2100
gatagagagc ttattagaga tactgaaaca ttacatgaaa tttatcaacg tttaatacat  2160
gcaggtgaca cagcgggtat acctgttatt gcgacaggaa atgcacacta tttgtttgaa  2220
catgatggta tcgcacgtaa aattttaata gcatcacaac ccggcaatcc acttaatcgc  2280
tcaactttac cggaagcaca ttttagaact acagatgaaa tgttaaacga gtttcatttt  2340
ttaggtgaag aaaaagcgca tgaaattgtt gtgaaaaata caaacgaatt agcagatcga  2400
attgaacgtg ttgttcctat taaagatgaa ttatacacac cgcgtatgga aggtgctaac  2460
gaagaaatta gagaactaag ttatgcaaat gcgcgtaaac tgtatggtga agacctgcct  2520
caaatcgtaa ttgatcgatt agaaaaagaa ttaaaaagta ttatcggtaa tggatttgcg  2580
gtaatttact taatttcgca acgtttagtt aaaaaatcat tagatgatgg atacttagtt  2640
ggttcccgtg gttcagtagg ttctagtttt gtagcgacaa tgactgagat cactgaagta  2700
aacccgttac cgccacacta tatttgtccg aactgtaaaa cgagtgaatt tttcaatgat  2760
ggttcagtag gatcaggatt tgatttacct gataagacgt gtgaaacttg tggagcgcca  2820
cttattaaag aaggacaaga tattccgttt gaaacatttt taggatttaa gggagataaa  2880
gttcctgata tcgacttaaa ctttagtggt gaatatcaac cgaatgccca taactacaca  2940
aaagtattat ttggtgagga taaagtattc cgtgcaggta caattggtac tgttgctgaa  3000
aagactgctt ttggttatgt taaaggttat ttgaatgatc aaggtatcca caaagaggt   3060
gctgaaatag atcgactcgt taaaggatgt acaggtgtta aacgtacaac tggacagcat  3120
ccaggggggta ttattgtagt acctgattac atggatattt atgattttac gccgatacaa  3180
```

-continued

```
tatcctgccg atgatcaaaa ttcagcatgg atgacgacac attttgattt ccattctatt 3240
catgataatg tattaaaact tgatatactt ggacacgatg atccaacaat gattcgtatg 3300
cttcaagatt tatcaggaat tgatccaaaa acaatacctg tagatgataa agaagttatg 3360
cagatattta gtacacctga aagtttgggt gttactgaag atgaaatttt atgtaaaaca 3420
ggtacatttg gggtaccaga attcggtaca ggattcgtgc gtcaaatgtt agaagataca 3480
aagccaacaa cattttctga attagttcaa atctcaggat tatctcatgg tacagatgtg 3540
tggttaggca atgctcaaga attaattaaa accggtatat gtgatttatc aagtgtaatt 3600
ggttgtcgtg atgatatcat ggtttattta atgtatgctg gtttagaacc atcaatggct 3660
tttaaaataa tggagtcagt acgtaaaggt aaaggtttaa ctgaagaaat gattgaaacg 3720
atgaaagaaa atgaagtgcc agattggtat ttagattcat gtcttaaaat taagtacatg 3780
ttccctaaag cccatgcagc agcatacgtt ttaatggcag tacgtatcgc atatttcaaa 3840
gtacatcatc cactttatta ctatgcatct tactttacaa ttcgtgcgtc agactttgat 3900
ttaatcacga tgattaaaga taaaacaagc attcgaaata ctgtaaaaga catgtattct 3960
cgctatatgg atctaggtaa aaaagaaaaa gacgtattaa cagtcttgga aattatgaat 4020
gaaatggcgc atcgaggtta tcgaatgcaa ccgattagtt tagaaaagag tcaggcgttc 4080
gaatttatca ttgaaggcga tacacttatt ccgccgttca tatcagtgcc tgggcttggc 4140
gaaaacgttg cgaaacgaat tgttgaagct cgtgacgatg gcccattttt atcaaaagaa 4200
gatttaaaca aaaagctgg attatctcag aaaattattg agtatttaga tgagttaggc 4260
tcattaccga atttaccaga taaagctcaa ctttcgatat ttgatatg             4308
```

The amino acid sequence of the *S. aureus* polC gene product, a-large, corresponds to SEQ. ID. No. 8 as follows:

```
Met Thr Glu Gln Gln Lys Phe Lys Val Leu Ala Asp Gln Ile Lys Ile
 1               5                  10                  15

Ser Asn Gln Leu Asp Ala Glu Ile Leu Asn Ser Gly Glu Leu Thr Arg
                 20                  25                  30

Ile Asp Val Ser Asn Lys Asn Arg Thr Trp Glu Phe His Ile Thr Leu
            35                  40                  45

Pro Gln Phe Leu Ala His Glu Asp Tyr Leu Leu Phe Ile Asn Ala Ile
        50                  55                  60

Glu Gln Glu Phe Lys Asp Ile Ala Asn Val Thr Cys Arg Phe Thr Val
65                  70                  75                  80

Thr Asn Gly Thr Asn Gln Asp Glu His Ala Ile Lys Tyr Phe Gly His
                85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
        115                 120                 125

Asn Asp Ile Glu Arg Asn His Phe Asp Lys Ala Cys Asn Gly Ser Leu
    130                 135                 140

Ile Lys Ala Phe Arg Asn Cys Gly Phe Asp Ile Asp Lys Ile Ile Phe
145                 150                 155                 160

Glu Thr Asn Asp Asn Asp Gln Glu Gln Asn Leu Ala Ser Leu Glu Ala
                165                 170                 175

His Ile Gln Glu Glu Asp Glu Gln Ser Ala Arg Leu Ala Thr Glu Lys
            180                 185                 190
```

-continued

```
Leu Glu Lys Met Lys Ala Glu Lys Ala Lys Gln Gln Asp Asn Lys Gln
        195                 200                 205

Ser Ala Val Asp Lys Cys Gln Ile Gly Lys Pro Ile Gln Ile Glu Asn
        210                 215                 220

Ile Lys Pro Ile Glu Ser Ile Ile Glu Glu Phe Lys Val Ala Ile
225                 230                 235                 240

Glu Gly Val Ile Phe Asp Ile Asn Leu Lys Glu Leu Lys Ser Gly Arg
                    245                 250                 255

His Ile Val Glu Ile Lys Val Thr Asp Tyr Thr Asp Ser Leu Val Leu
        260                 265                 270

Lys Met Phe Thr Arg Lys Asn Lys Asp Asp Leu Glu His Phe Lys Ala
        275                 280                 285

Leu Ser Val Gly Lys Trp Val Arg Ala Gln Gly Arg Ile Glu Glu Asp
        290                 295                 300

Thr Phe Ile Arg Asp Leu Val Met Met Met Ser Asp Ile Glu Glu Ile
305                 310                 315                 320

Lys Lys Ala Thr Lys Asp Lys Ala Glu Glu Lys Arg Val Glu Phe
                    325                 330                 335

His Leu His Thr Ala Met Ser Gln Met Asp Gly Ile Pro Asn Ile Gly
        340                 345                 350

Ala Tyr Val Lys Gln Ala Ala Asp Trp Gly His Pro Ala Ile Ala Val
        355                 360                 365

Thr Asp His Asn Val Val Gln Ala Phe Pro Asp Ala His Ala Ala Ala
        370                 375                 380

Glu Lys His Gly Ile Lys Met Ile Tyr Gly Met Glu Gly Met Leu Val
385                 390                 395                 400

Asp Asp Gly Val Pro Ile Ala Tyr Lys Pro Gln Asp Val Val Leu Lys
                    405                 410                 415

Asp Ala Thr Tyr Val Val Phe Asp Val Glu Thr Thr Gly Leu Ser Asn
                    420                 425                 430

Gln Tyr Asp Lys Ile Ile Glu Leu Ala Ala Val Lys Val His Asn Gly
        435                 440                 445

Glu Ile Ile Asp Lys Phe Glu Arg Phe Ser Asn Pro His Glu Arg Leu
        450                 455                 460

Ser Glu Thr Ile Ile Asn Leu Thr His Ile Thr Asp Asp Met Leu Val
465                 470                 475                 480

Asp Ala Pro Glu Ile Glu Glu Val Leu Thr Glu Phe Lys Glu Trp Val
                    485                 490                 495

Gly Asp Ala Ile Phe Val Ala His Asn Ala Ser Phe Asp Met Gly Phe
                    500                 505                 510

Ile Asp Thr Gly Tyr Glu Arg Leu Gly Phe Gly Pro Ser Thr Asn Gly
        515                 520                 525

Val Ile Asp Thr Leu Glu Leu Ser Arg Thr Ile Asn Thr Glu Tyr Gly
        530                 535                 540

Lys His Gly Leu Asn Phe Leu Ala Lys Lys Tyr Gly Val Glu Leu Thr
545                 550                 555                 560

Gln His His Arg Ala Ile Tyr Asp Thr Glu Ala Thr Ala Tyr Ile Phe
                    565                 570                 575

Ile Lys Met Val Gln Gln Met Lys Glu Leu Gly Val Leu Asn His Asn
                580                 585                 590

Glu Ile Asn Lys Lys Leu Ser Asn Glu Asp Ala Tyr Lys Arg Ala Arg
        595                 600                 605
```

-continued

Pro Ser His Val Thr Leu Ile Val Gln Asn Gln Gly Leu Lys Asn
610                 615                 620

Leu Phe Lys Ile Val Ser Ala Ser Leu Val Lys Tyr Phe Tyr Arg Thr
625                 630                 635                 640

Pro Arg Ile Pro Arg Ser Leu Leu Asp Glu Tyr Arg Glu Gly Leu Leu
                645                 650                 655

Val Gly Thr Ala Cys Asp Glu Gly Leu Phe Thr Ala Val Met Gln
                660                 665                 670

Lys Asp Gln Ser Gln Val Glu Lys Ile Ala Lys Tyr Tyr Asp Phe Ile
                675                 680                 685

Glu Ile Gln Pro Pro Ala Leu Tyr Gln Asp Leu Ile Asp Arg Glu Leu
690                 695                 700

Ile Arg Asp Thr Glu Thr Leu His Glu Ile Tyr Gln Arg Leu Ile His
705                 710                 715                 720

Ala Gly Asp Thr Ala Gly Ile Pro Val Ile Ala Thr Gly Asn Ala His
                725                 730                 735

Tyr Leu Phe Glu His Asp Gly Ile Ala Arg Lys Ile Leu Ile Ala Ser
                740                 745                 750

Gln Pro Gly Asn Pro Leu Asn Arg Ser Thr Leu Pro Glu Ala His Phe
                755                 760                 765

Arg Thr Thr Asp Glu Met Leu Asn Glu Phe His Phe Leu Gly Glu Glu
770                 775                 780

Lys Ala His Glu Ile Val Val Lys Asn Thr Asn Glu Leu Ala Asp Arg
785                 790                 795                 800

Ile Glu Arg Val Val Pro Ile Lys Asp Glu Leu Tyr Thr Pro Arg Met
                805                 810                 815

Glu Gly Ala Asn Glu Glu Ile Arg Glu Leu Ser Tyr Ala Asn Ala Arg
                820                 825                 830

Lys Leu Tyr Gly Glu Asp Leu Pro Gln Ile Val Ile Asp Arg Leu Glu
                835                 840                 845

Lys Glu Leu Lys Ser Ile Ile Gly Asn Gly Phe Ala Val Ile Tyr Leu
850                 855                 860

Ile Ser Gln Arg Leu Val Lys Lys Ser Leu Asp Asp Gly Tyr Leu Val
865                 870                 875                 880

Gly Ser Arg Gly Ser Val Gly Ser Ser Phe Val Ala Thr Met Thr Glu
                885                 890                 895

Ile Thr Glu Val Asn Pro Leu Pro His Tyr Ile Cys Pro Asn Cys
                900                 905                 910

Lys Thr Ser Glu Phe Phe Asn Asp Gly Ser Val Gly Ser Gly Phe Asp
                915                 920                 925

Leu Pro Asp Lys Thr Cys Glu Thr Cys Gly Ala Pro Leu Ile Lys Glu
                930                 935                 940

Gly Gln Asp Ile Pro Phe Glu Lys Phe Leu Gly Phe Lys Gly Asp Lys
945                 950                 955                 960

Val Pro Asp Ile Asp Leu Asn Phe Ser Gly Glu Tyr Gln Pro Asn Ala
                965                 970                 975

His Asn Tyr Thr Lys Val Leu Phe Gly Glu Asp Lys Val Phe Arg Ala
                980                 985                 990

Gly Thr Ile Gly Thr Val Ala Glu Lys Thr Ala Phe Gly Tyr Val Lys
                995                 1000                1005

Gly Tyr Leu Asn Asp Gln Gly Ile His Lys Arg Gly Ala Glu Ile Asp
        1010                1015                1020

-continued

Arg Leu Val Lys Gly Cys Thr Gly Val Lys Ala Thr Thr Gly Gln His
1025                1030                1035                1040

Pro Gly Gly Ile Ile Val Val Pro Asp Tyr Met Asp Ile Tyr Asp Phe
            1045                1050                1055

Thr Pro Ile Gln Tyr Pro Ala Asp Asp Gln Asn Ser Ala Trp Met Thr
        1060                1065                1070

Thr His Phe Asp Phe His Ser Ile His Asp Asn Val Leu Lys Leu Asp
        1075                1080                1085

Ile Leu Gly His Asp Asp Pro Thr Met Ile Arg Met Leu Gln Asp Leu
    1090                1095                1100

Ser Gly Ile Asp Pro Lys Thr Ile Pro Val Asp Asp Lys Glu Val Met
1105                1110                1115                1120

Gln Ile Phe Ser Thr Pro Glu Ser Leu Gly Val Thr Glu Asp Glu Ile
            1125                1130                1135

Leu Cys Lys Thr Gly Thr Phe Gly Val Pro Asn Ser Asp Arg Ile Arg
            1140                1145                1150

Arg Gln Met Leu Glu Asp Thr Lys Pro Thr Thr Phe Ser Glu Leu Val
        1155                1160                1165

Gln Ile Ser Gly Leu Ser His Gly Thr Asp Val Trp Leu Gly Asn Ala
    1170                1175                1180

Gln Gln Leu Ile Lys Thr Gly Ile Cys Asp Leu Ser Ser Val Ile Gly
1185                1190                1195                1200

Cys Arg Asp Asp Ile Met Val Tyr Leu Met Tyr Ala Gly Leu Glu Pro
                1205                1210                1215

Ser Met Ala Phe Lys Ile Met Gln Ser Val Arg Lys Gly Lys Gly Leu
            1220                1225                1230

Thr Glu Gln Met Ile Glu Thr Met Lys Gln Asn Glu Val Pro Asp Trp
        1235                1240                1245

Tyr Leu Asp Ser Cys Leu Lys Ile Lys Tyr Ile Phe Pro Lys Ala His
    1250                1255                1260

Ala Ala Ala Tyr Val Leu Met Ala Val Arg Ile Ala Tyr Phe Lys Val
1265                1270                1275                1280

His His Pro Leu Tyr Tyr Tyr Ala Ser Tyr Phe Thr Ile Arg Ala Ser
            1285                1290                1295

Asp Phe Asp Leu Ile Thr Met Ile Lys Asp Lys Thr Ser Ile Arg Asn
            1300                1305                1310

Thr Val Lys Asp Met Tyr Ser Arg Tyr Met Asp Leu Gly Lys Lys Glu
        1315                1320                1325

Lys Asp Val Leu Thr Val Leu Gln Ile Met Asn Glu Met Ala His Arg
    1330                1335                1340

Gly Tyr Arg Met Gln Pro Ile Ser Leu Glu Lys Ser Gln Ala Phe Glu
1345                1350                1355                1360

Phe Ile Ile Glu Gly Asp Thr Leu Ile Pro Pro Phe Ile Ser Val Pro
            1365                1370                1375

Gly Leu Gly Glu Asn Val Ala Lys Arg Ile Val Gln Ala Arg Asp Asp
            1380                1385                1390

Gly Pro Phe Leu Ser Lys Glu Asp Leu Asn Lys Ala Gly Leu Tyr
            1395                1400                1405

Gln Lys Ile Ile Gln Tyr Leu Asp Glu Leu Gly Ser Leu Pro Asn Leu
    1410                1415                1420

Pro Asp Lys Ala Gln Leu Ser Ile Phe Asp Met
1425                1430                1435

This invention also relates to the *S. aureus* dnaN gene encoding the beta subunit. The partial nucleotide sequence of this dnaN gene corresponds to SEQ. ID. No. 9 as follows:

```
atgatggaat tcactattaa aagagattat tttattacac aattaaatga cacattaaaa   60
gctatttcac caagaacaac attacctata ttaactggta tcaaaatcga tgcgaaagaa  120
catgaagtta tattaactgg ttcagactct gaaatttcaa tagaaatcac tattcctaaa  180
actgtagatg gcgaagatat tgtcaatatt tcagaaacag gctcagtagt acttcctgga  240
cgattctttg ttgatattat aaaaaaatta cctggtaaag atgttaaatt atctacaaat  300
gaaeaattcc agacattaat tacatcaggt cattctgaat ttaatttgag tggcttagat  360
ccagatcaat atcctttatt acctcaagtt tctagagatg acgcaattca attgtcggta  420
aaagtactta aaaacgtgat tgcacaaacg aatttttgcag tgtccacctc agaaacacgc  480
ccagtactaa ctggtgtgaa ctggcttata caagaaaatg aattaatatg cacagcgact  540
gattcacacc gcttggctgt aagaaagttg cagttagaag atgtttctga aaacaaaaat  600
gtcatcattc caggtaaggc tttagctgaa ttaaataaaa ttatgtctga caatgaagaa  660
gacattgata tcttctttgc ttcaaaccaa gttttattta agttggaaa tgtgaacttt  720
atttctcgat tattagaagg acattatcct gatacaacac gtttattccc tgaaaactat  780
gaaattaaat taagtataga caatggggag ttttatcatg cgattgatcg tgcctcttta  840
ttagcacgtg aaggtggtaa taacgttatt aaattaagta caggtgatga cgttgttgaa  900
ttatcttcta catcaccaga aattggtact gtaaaagaag aagttgatgc aaacgatgtt  960
gaaggtggta gcctgaaaat ttcattcaac tctaaatata tgatggatgc tttaaaagca 1020
atcgataatg atgaggttga agttgaattc ttcggtacaa tgaaaccatt tattctaaaa 1080
ccaaaaggtg acgactcggt aacgcaatta attttaccaa tcagaactta ctaa        1134
```

This amino acid sequence of *S. aureus* beta subunit is as follows (SEQ. ID. No. 10):

```
Met Met Glu Phe Thr Ile Lys Arg Asp Tyr Phe Ile Thr Gln Leu Asn
1               5                   10                  15

Asp Thr Leu Lys Ala Ile Ser Pro Arg Thr Thr Leu Pro Ile Leu Thr
                20                  25                  30

Gly Ile Lys Ile Asp Ala Lys Glu His Glu Val Ile Leu Thr Gly Ser
            35                  40                  45

Asp Ser Glu Ile Ser Ile Glu Ile Thr Ile Pro Lys Thr Val Asp Gly
        50                  55                  60

Glu Asp Ile Val Asn Ile Ser Glu Thr Gly Ser Val Val Leu Pro Gly
65                  70                  75                  80

Arg Phe Phe Val Asp Ile Ile Lys Lys Leu Pro Gly Lys Asp Val Lys
                85                  90                  95

Leu Ser Thr Asn Glu Gln Phe Gln Thr Leu Ile Thr Ser Gly His Ser
            100                 105                 110

Glu Phe Asn Leu Ser Gly Leu Asp Pro Asp Gln Tyr Pro Leu Leu Pro
        115                 120                 125

Gln Val Ser Arg Asp Asp Ala Ile Gln Leu Ser Val Lys Val Leu Lys
    130                 135                 140

Asn Val Ile Ala Gln Thr Asn Phe Ala Val Ser Thr Ser Glu Thr Arg
145                 150                 155                 160
```

-continued

```
Pro Val Leu Thr Gly Val Asn Trp Leu Ile Gln Glu Asn Glu Leu Ile
            165                 170                 175
Cys Thr Ala Thr Asp Ser His Arg Leu Ala Val Arg Lys Leu Gln Leu
            180                 185                 190
Glu Asp Val Ser Glu Asn Lys Asn Val Ile Ile Pro Gly Lys Ala Leu
            195                 200                 205
Ala Glu Leu Asn Lys Ile Met Ser Asp Asn Glu Glu Asp Ile Asp Ile
    210                 215                 220
Phe Phe Ala Ser Asn Gln Val Leu Phe Lys Val Gly Asn Val Asn Phe
225                 230                 235                 240
Ile Ser Arg Leu Leu Glu Gly His Tyr Pro Asp Thr Thr Arg Leu Phe
            245                 250                 255
Pro Glu Asn Tyr Glu Ile Lys Leu Ser Ile Asp Asn Gly Glu Phe Tyr
            260                 265                 270
His Ala Ile Asp Arg Ala Ser Leu Leu Ala Arg Glu Gly Gly Asn Asn
            275                 280                 285
Val Ile Lys Leu Ser Thr Gly Asp Asp Val Val Glu Leu Ser Ser Thr
    290                 295                 300
Ser Pro Glu Ile Gly Thr Val Lys Glu Glu Val Asp Ala Asn Asp Val
305                 310                 315                 320
Glu Gly Gly Ser Leu Lys Ile Ser Phe Asn Ser Lys Tyr Met Met Asp
            325                 330                 335
Ala Leu Lys Ala Ile Asp Asn Asp Glu Val Glu Val Glu Phe Phe Gly
            340                 345                 350
Thr Met Lys Pro Phe Ile Leu Lys Pro Lys Gly Asp Asp Ser Val Thr
            355                 360                 365
Gln Leu Ile Leu Pro Ile Arg Thr Tyr
    370                 375
```

This invention also relates to the *S. aureus* holA gene encoding the delta subunit. The partial nucleotide sequence of this holA gene corresponds to SEQ. ID. No. 11 as follows:

```
atggatgaac agcaacaatt gacgaatgca tatcattcaa ataaattatc gcatgcctat   60
ttatttgaag gtgatgatgc acaaacgatg aaacaagttg cgattaattt tgcaaagctt  120
attttatgtc aaacagatag tcaatgtgaa acaaaggtta gtacatataa tcatccagac  180
tttatgtata tcaacaac tgagaatgca attaagaaag aacaagttga acaacttgtg   240
cgtcatatga tcaacttcc tatagaaagc acaaataaag tgtacatcat cgaagacttt  300
gaagactttg aaaagttaac tgttcaaggg gaaaacagta tcttgaaatt tcttgaagaa  360
ccaccggaca atacgattgc tattttattg tctacaaaac ctgagcaaat tttagacaca  420
atccattcaa ggtgtcagca tgtatatttc aagcctattg ataaagaaaa gtttataaat  480
agattagttg aacaaaacat gtctaagcca gtagctgaaa tgattagtac ttatactacg  540
caaatagata atgcaatggc tttaaatgaa gaatttgatt tattagcatt aaggaaatca  600
gttatacgtt gggaattgtt gcttactaat aagccaatgg cacttatagg tattattgat  660
ttattgaaac aggctaaaaa taaaaaactg caatctttaa ctattgcagc tgtgaatggt  720
ttcttcgaag atatccataca tacaaaggta aatgtagagg ataaacaaat atatagtgat  780
ttaaaaaatg atattgatca atatgcgcaa aagttgtcgt ttaatcaatt aattttgatg  840
tttgatcaac tgacggaagc acataagaaa ttgaatcaaa atgtaaatcc aacgcttgta  900
tttgaacaaa tcgtaattaa gggtgtgagt                                   930
```

The amino acid sequence of the delta subunit encoded by *S. aureus* holA corresponds to SEQ. ID. No. 12 as follows:

```
Met Asp Glu Gln Gln Gln Leu Thr Asn Ala Tyr His Ser Asn Lys Leu
 1               5                  10                  15

Ser His Ala Tyr Leu Phe Glu Gly Asp Asp Ala Gln Thr Met Lys Gln
                20                  25                  30

Val Ala Ile Asn Phe Ala Lys Leu Ile Leu Cys Gln Thr Asp Ser Gln
            35                  40                  45

Cys Glu Thr Lys Val Ser Thr Tyr Asn His Pro Asp Phe Met Tyr Ile
     50                  55                  60

Ser Thr Thr Glu Asn Ala Ile Lys Lys Glu Gln Val Glu Gln Leu Val
 65                  70                  75                  80

Arg His Met Asn Gln Leu Pro Ile Glu Ser Thr Asn Lys Val Tyr Ile
                85                  90                  95

Ile Glu Asp Phe Glu Asp Phe Glu Lys Leu Thr Val Gln Gly Glu Asn
                100                 105                 110

Ser Ile Leu Lys Phe Leu Glu Glu Pro Pro Asp Asn Thr Ile Ala Ile
            115                 120                 125

Leu Leu Ser Thr Lys Pro Glu Gln Ile Leu Asp Thr Ile His Ser Arg
    130                 135                 140

Cys Gln His Val Tyr Phe Lys Pro Ile Asp Lys Glu Lys Phe Ile Asn
145                 150                 155                 160

Arg Leu Val Glu Gln Asn Met Ser Lys Pro Val Ala Glu Met Ile Ser
                165                 170                 175

Thr Tyr Thr Thr Gln Ile Asp Asn Ala Met Ala Leu Asn Glu Glu Phe
                180                 185                 190

Asp Leu Leu Ala Leu Arg Lys Ser Val Ile Arg Trp Glu Leu Leu Leu
            195                 200                 205

Thr Asn Lys Pro Met Ala Leu Ile Gly Ile Ile Asp Leu Leu Lys Gln
    210                 215                 220

Ala Lys Asn Lys Lys Leu Gln Ser Leu Thr Ile Ala Ala Val Asn Gly
225                 230                 235                 240

Phe Phe Glu Asp Ile Ile His Thr Lys Val Asn Val Glu Asp Lys Gln
                245                 250                 255

Ile Tyr Ser Asp Leu Lys Asn Asp Ile Asp Gln Tyr Ala Gln Lys Leu
                260                 265                 270

Ser Phe Asn Gln Leu Ile Leu Met Phe Asp Gln Leu Thr Glu Ala His
            275                 280                 285

Lys Lys Leu Asn Gln Asn Val Asn Pro Thr Leu Val Phe Glu Gln Ile
    290                 295                 300

Val Ile Lys Gly Val Ser
305                 310
```

This invention also relates to the *S. aureus* holB gene encoding the delta prime subunit. The partial nucleotide sequence of this holB gene corresponds to SEQ. ID. No. 13 as follows:

```
atgagcgaca atattgtagc tatttatgga gatgtgcctg aattggttga aaaacaaagt  60
gcagaaatca tatcacaatt tttgaaaagt gatagagatg actttaactt tgtgaaatat 120
aatttatacg aaacagagat tgcaccaatt gttgaagaaa cattaacatt gcctttcttt 180
tcagataaaa aagcaatttt ggttaaaaat gcatatatat ttacaggtga aaaagcgcca 240
```

-continued

```
aaagatatgg ctcataatgt agaccaatta atagaattta ttgaaaaata tgatggcgaa    300
aatttgattg tctttgagat atatcaaaat aaacttgatg aaagaaaaaa gttaactaaa    360
actctaaaaa agcatgcaag gcttaaaaaa atagagcaga tgtcggagga gatcaagtgg    420
attcaaaaaa aagaacaagc gattgatttt gtaaaagatc ttataacaat gaaagaagaa    480
ccaattaaac ttcttgcact tacatcaaat tatagacttt tttatcaatg taaaattctt    540
tcacaaaaag gttatagtgg tcaacaaatt gcaaaaacaa taggtgttca tccatataga    600
gtgaaacttg cacttggtca agtgagacat tatcaacttg atgaacttct taatattatt    660
gatgcatgtg cagaaacaga ttataaactt aaatcatcat atatggataa acaacttatt    720
cttgaacttt ttattctttc actt                                          744
```

The amino acid sequence of the delta prime subunit encoded by *S. aureus* holB corresponds to SEQ. ID. No. 14 as follows:

```
Met Ser Asp Asn Ile Val Ala Ile Tyr Gly Asp Val Pro Glu Leu Val
 1               5                  10                  15

Glu Lys Gln Ser Ala Glu Ile Ile Ser Gln Phe Leu Lys Ser Asp Arg
                20                  25                  30

Asp Asp Phe Asn Phe Val Lys Tyr Asn Leu Tyr Glu Thr Glu Ile Ala
            35                  40                  45

Pro Ile Val Glu Glu Thr Leu Thr Leu Pro Phe Phe Ser Asp Lys Lys
        50                  55                  60

Ala Ile Leu Val Lys Asn Ala Tyr Ile Phe Thr Gly Glu Lys Ala Pro
 65                 70                  75                  80

Lys Asp Met Ala His Asn Val Asp Gln Leu Ile Glu Phe Ile Glu Lys
                85                  90                  95

Tyr Asp Gly Glu Asn Leu Ile Val Phe Glu Ile Tyr Gln Asn Lys Leu
               100                 105                 110

Asp Glu Arg Lys Lys Leu Thr Lys Thr Leu Lys Lys His Ala Arg Leu
           115                 120                 125

Lys Lys Ile Glu Gln Met Ser Glu Glu Ile Lys Trp Ile Gln Lys Lys
       130                 135                 140

Glu Gln Ala Ile Asp Phe Val Lys Asp Leu Ile Thr Met Lys Glu Glu
145                 150                 155                 160

Pro Ile Lys Leu Leu Ala Leu Thr Ser Asn Tyr Arg Leu Phe Tyr Gln
               165                 170                 175

Cys Lys Ile Leu Ser Gln Lys Gly Tyr Ser Gly Gln Gln Ile Ala Lys
           180                 185                 190

Thr Ile Gly Val His Pro Tyr Arg Val Lys Leu Ala Leu Gly Gln Val
       195                 200                 205

Arg His Tyr Gln Leu Asp Glu Leu Leu Asn Ile Ile Asp Ala Cys Ala
   210                 215                 220

Glu Thr Asp Tyr Lys Leu Lys Ser Ser Tyr Met Asp Lys Gln Leu Ile
225                 230                 235                 240

Leu Glu Leu Phe Ile Leu Ser Leu
               245
```

This invention also relates to the *S. aureus* dnaG gene encoding a primase. The partial nucleotide sequence of this dnaG gene corresponds to SEQ. ID. No. 15 as follows:

```
atgataggtt tgtgtccttt tcatgatgaa aagacacctt catttacagt ttctgaagat   60
aaacaaatct gtcattgttt tggttgtaaa aaggtggca atgtttttca atttactcaa  120
gaaattaaag acatatcatt tgttgaagcg gttaaagaat taggtgatag agttaatgtt  180
gctgtagata ttgaggcaac acaatctaac tcaaatgttc aaattgcttc tgatgattta  240
caaatgattg aaatgcatga gttaatacaa gaattttatt attacgcttt aacaaagaca  300
gtcgaaggcg aacaagcatt aacatactta caagaacgtg gttttacaga tgcgcttatt  360
aaagagcgag gcattggctt tgcacccgat agctcacatt tttgtcatga ttttcttcaa  420
aaaaagggtt acgatattga attagcatat gaagccggac tattatcacg taacgaagaa  480
aatttcagtt attacgatag atttcgaaat cgtattatgt ttcctttgaa aaatgcgcaa  540
ggaagaattg ttggatattc aggtcgaaca tataccggtc aagaaccaaa atacctaaat  600
agtcctgaaa cgcctatctt tcaaaaaaga agttgttat ataacttaga taaagcacgt  660
aaatcaatta gaaaattaga tgaaattgta ttactagaag gttttatgga tgttataaaa  720
tctgatactg ctggcttgaa aaacgttgtt gcaacaatgg gtacacagtt gtcagatgaa  780
catattacct ttatacgaaa gttaacatca aatataacat taatgtttga tggggatttt  840
gcgggtagtg aagcaacact taaaacaggt caacatttgt tacagcaagg gctaaatgta  900
tttgttatac aattgccatc tggcatggat ccggatgaat acattggtaa gtatggcaac  960
gacgcattta ctactttgt aaaaaatgac aaaaagtcat ttgcacatta taagtaagt 1020
atattaaaag atgaaattgc acataatgac ctttcatatg aacgttattt gaaagaactg 1080
agtcatgaca tttcacttat gaagtcatca attctgcaac aaaaggctat aaatgatgtt 1140
gcgccatttt tcaatgttag tcctgagcag ttagctaacg aaatacaatt caatcaagca 1200
ccagccaatt attatccaga agatgagtat ggcggttatg atgagtatgg cggttatatt 1260
gaacctgagc caattggtat ggcacaattt gacaatttga gccgtcgaga aaaagcggag 1320
cgagcatttt taaacatttt aatgagagat aaagatacat ttttaaatta ttatgaaagt 1380
gttgataagg ataacttcac aaatcagcat tttaaatatg tattcgaagt cttacatgat 1440
ttttatgcgg aaaatgatca atataatatc agtgatgctg tgcagtatgt taattcaaat 1500
gagttgagag aaacactaat tagcttagaa caatataatt tgaatggcga accatatgaa 1560
aatgaaattg atgattatgt caatgttatt aatgaaaaag gacaagaaac aattgagtca 1620
ttgaatcata aattaaggga agctacaagg attggcgatg tagaattaca aaaatactat 1680
ttacagcaaa ttgttgctaa gaataaagaa cgcatgtag                        1719
```

The amino acid sequence of primase encoded by *S. aureus* dnaG corresponds to SEQ. ID. No. 16 as follows:

```
Met Ile Gly Leu Cys Pro Phe His Asp Glu Lys Thr Pro Ser Phe Thr
1               5                   10                  15

Val Ser Glu Asp Lys Gln Ile Cys His Cys Phe Gly Cys Lys Lys Gly
            20                  25                  30

Gly Asn Val Phe Gln Phe Thr Gln Glu Ile Lys Asp Ile Ser Phe Val
        35                  40                  45

Glu Ala Val Lys Glu Leu Gly Asp Arg Val Asn Val Ala Val Asp Ile
    50                  55                  60

Glu Ala Thr Gln Ser Asn Ser Asn Val Gln Ile Ala Ser Asp Asp Leu
65                  70                  75                  80
```

-continued

```
Gln Met Ile Glu Met His Glu Leu Ile Gln Glu Phe Tyr Tyr Tyr Ala
                85                  90                  95
Leu Thr Lys Thr Val Glu Gly Gln Ala Leu Thr Tyr Leu Gln Glu
            100                 105                 110
Arg Gly Phe Thr Asp Ala Leu Ile Lys Glu Arg Gly Ile Gly Phe Ala
            115                 120                 125
Pro Asp Ser Ser His Phe Cys His Asp Phe Leu Gln Lys Lys Gly Tyr
    130                 135                 140
Asp Ile Glu Leu Ala Tyr Glu Ala Gly Leu Leu Ser Arg Asn Glu Glu
145                 150                 155                 160
Asn Phe Ser Tyr Tyr Asp Arg Phe Arg Asn Arg Ile Met Phe Pro Leu
                165                 170                 175
Lys Asn Ala Gln Gly Arg Ile Val Gly Tyr Ser Gly Arg Thr Tyr Thr
            180                 185                 190
Gly Gln Glu Pro Lys Tyr Leu Asn Ser Pro Glu Thr Pro Ile Phe Gln
            195                 200                 205
Lys Arg Lys Leu Leu Tyr Asn Leu Asp Lys Ala Arg Lys Ser Ile Arg
    210                 215                 220
Lys Leu Asp Glu Ile Val Leu Leu Glu Gly Phe Met Asp Val Ile Lys
225                 230                 235                 240
Ser Asp Thr Ala Gly Leu Lys Asn Val Val Ala Thr Met Gly Thr Gln
                245                 250                 255
Leu Ser Asp Glu His Ile Thr Phe Ile Arg Lys Leu Thr Ser Asn Ile
            260                 265                 270
Thr Leu Met Phe Asp Gly Asp Phe Ala Gly Ser Glu Ala Thr Leu Lys
            275                 280                 285
Thr Gly Gln His Leu Leu Gln Gln Gly Leu Asn Val Phe Val Ile Gln
    290                 295                 300
Leu Pro Ser Gly Met Asp Pro Asp Glu Tyr Ile Gly Lys Tyr Gly Asn
305                 310                 315                 320
Asp Ala Phe Thr Thr Phe Val Lys Asn Asp Lys Lys Ser Phe Ala His
                325                 330                 335
Tyr Lys Val Ser Ile Leu Lys Asp Glu Ile Ala His Asn Asp Leu Ser
            340                 345                 350
Tyr Glu Arg Tyr Leu Lys Glu Leu Ser His Asp Ile Ser Leu Met Lys
            355                 360                 365
Ser Ser Ile Leu Gln Gln Lys Ala Ile Asn Asp Val Ala Pro Phe Phe
    370                 375                 380
Asn Val Ser Pro Glu Gln Leu Ala Asn Glu Ile Gln Phe Asn Gln Ala
385                 390                 395                 400
Pro Ala Asn Tyr Tyr Pro Glu Asp Glu Tyr Gly Gly Tyr Asp Glu Tyr
                405                 410                 415
Gly Gly Tyr Ile Glu Pro Glu Pro Ile Gly Met Ala Gln Phe Asp Asn
            420                 425                 430
Leu Ser Arg Arg Glu Lys Ala Glu Arg Ala Phe Leu Lys His Leu Met
            435                 440                 445
Arg Asp Lys Asp Thr Phe Leu Asn Tyr Glu Ser Val Asp Lys Asp
    450                 455                 460
Asn Phe Thr Asn Gln His Phe Lys Tyr Val Phe Glu Val Leu His Asp
465                 470                 475                 480
Phe Tyr Ala Glu Asn Asp Gln Tyr Asn Ile Ser Asp Ala Val Gln Tyr
                485                 490                 495
Val Asn Ser Asn Gln Leu Arg Glu Thr Len Ile Ser Leu Glu Gln Tyr
            500                 505                 510
```

```
Asn Leu Asn Gly Glu Pro Tyr Glu Ann Glu Ile Asp Asp Tyr Val Asn
        515                 520                 525

Val Ile Asn Glu Lys Gly Gln Glu Thr Ile Glu Ser Leu Asn His Lys
        530                 535                 540

Leu Arg Glu Ala Thr Arg Ile Gly Asp Val Glu Len Gln Lys Tyr Tyr
545                 550                 555                 560

Leu Gln Gln Ile Val Ala Lys Ann Lys Glu Arg Met
                565                 570
```

This invention also relates to the polC gene of *Streptococcus pyogenes* encoding the α-large subunit. The partial nucleotide sequence of polC (α-large) corresponds to SEQ. ID. No. 17 as follows:

```
atgtcagatt tattcgctaa attgatggac cagatagaaa tgccacttga catgagacgt    60
tcaagtgcct tttcatctgc tgatattatc gaggtaaagg tacattcggt gtcacgcttg   120
tgggaatttc attttgcctt tgcagcggtc ttaccgattg caacttatcg tgaattgcat   180
gatcgtttga taagaacttt tgaggcggct gacattaagg taacctttga catccaagct   240
gctcaggtgg attattcaga tgatctgctt caagcttatt accaagaagc ttttgagcat   300
gcaccgtgta atagtgctag ttttaaatct tctttctcaa agctcaaagt gacttatgag   360
gatgacaaac tcattattgc agcgccaggt tttgtgaata cgatcatttt tagaaacaat   420
catctgccta atctggtcaa gcaattagaa gcctttggct ttggcatctt gaccatagat   480
atggtgtcag atcaggaaat gactgagcat ttgaccaaga attttgtttc cagtcgtcag   540
gctcttgtga aaaaggctgt gcaggataat ttggaagccc aaaaatctct tgaagccatg   600
atgccaccag ttgaggaagc cacacctgct cctaagtttg actacaagga acgagcagct   660
aagcgtcagg cagggtttga aaaagcaacc atcacaccaa tgattgagat tgagaccgaa   720
gaaaaccgga ttgtctttga gggtatggtt tttgacgtgg agcgtaaaac gactaggaca   780
ggtcgccata tcatcaactt taaaatgaca gactatacct cctcgtttgc tctccaaaaa   840
tgggctaaag acgatgagga gctccgtaaa tttgatatga ttgctaaggg agcttggtta   900
cgggtacaag ggaatattga gaccaatcct tttacgaaga gtctcaccat gaatgtccag   960
caggtcaaag aaattgtccg tcatgagcgc aaagacctga tgccagaagg gcaaaagcgg  1020
gtcgaacttc atgcccacac caatatgtct accatggatg ccttaccgac agtagaaagc  1080
ttgattgata cggcagccaa gtggggacac aaggcgattg ctatcaccga ccatgctaat  1140
gtgcaaagtt ttcctcatgg ctaccatagg gctcgcaaag ctgggattaa ggctattttt  1200
ggcctagaag ccaatattgt tgaggacaag gtgcctattt cttatgaacc tgttgatatg  1260
gatttgcacg aagccaccta tgtggtcttt gacgtggaaa ccacaggtct atctgctatg  1320
aataatgacc tgattcagat tgcggcttcc aaaatgttta aaggaaatat tgtagagcag  1380
tttgatgaat ccatcgatcc tgggcatccc ctttcagcct ttaccaccga attgacagga  1440
attaccgata agcatttgca gggcgccaag ccattggtta ctgtcctaaa gcttttcag   1500
gacttttgca aagatagtac cttggttgcc cacaacgcca gttttgacgt gggctttatg  1560
aacgccaatt atgaacgcca cgacttgccc aaaatcacac agcctgtgat tgataccta   1620
gaatttgcta gaaacttgta tcctgagtac aagcgtcacg gtttgggacc gctcaccaag  1680
cgtttccaag tgagtctaga ccaccatcat atggccaatt acgacgcgga agccacagga  1740
```

```
                              -continued
cgtcttttgt ttattttttct aaaagatgcc agagaaaagc atggcatcaa aaatcttttg    1800
caactcaata cagatttggt ggctgaggat tcttacaaaa aagcgcggat taagcatgcg    1860
actatctatg tgcaaaatca ggttggtctt aaaaatatgt ttaagttggt cagccttttcc   1920 aatatcaaat attttgaagg ggtgccgcgt attccaagaa ccgtcttaga tgctcacaga    1980
gagggtttgt tacttggtac agcttgttct gacggcgagg ttttttgatgc cgttctgact   2040 aaaggaattg atgcagcggt tgatttggct aggtattatg attttatcga aatcatgcca    2100
ccagccattt accagccatt ggttgtccgt gaattaatca agatcaagc aggtattgag     2160 caggtgattc gtgacctcat tgaagtaggg aaacgagcta agaaacctgt gcttgccact    2220
gggaatgtgc attatctaga gcctgaagaa gagatttacc gtgaaattat tgtgcgtagt    2280
cttggtcagg gtgccatgat taatagaaca atcggccgtg gggaagggc  acagcctgct    2340 cctctaccta aagcgcactt tagaacaacc aatgaaatgc tggatgagtt tgccttctt    2400 ggaaaagacc tcgcttatca agtagttgtg caaaatactc aggattttgc ggaccgtatt    2460
gaggaagtgg aagtggttaa gggcgacctt tacacccgt  atattgataa ggccgaagag    2520
acggttgccg aattaaccta tcaaaaagcc tttgaaattt atggtaatcc tctcccagat    2580
attattgatt tacgcattga aaaagagtta acctctatct tggggaacgg ttttgctgtg    2640
atttatctcg cttcccaaat gcttgttaac cggtcaaatg agcgaggcta cctagttggt    2700 tctagggat  ctgtagggtc tagctttgtc gccaccatga ttgggattac tgaggttaat    2760
cctatgccgc ctcactacgt ttgcccgtcc tgccaacatt ctgaatttat cacagatggg    2820
tcagttggat ctggctatga tttgcctaat aaaccctgtc cgaaatgtgg caccccttat    2880
caaaaagatg ggcaagacat tcccttgag  acctttcttg ggtttgatgg ggataaggtg    2940
cccgatattg atttgaactt ctctggtgat gaccagccca gtgcccattt ggatgtccga    3000
gatatttttg gtgacgaata cgcctttcgt gctggaacag ttggtaccgt agcagaaaaa    3060
acagcttatg gatttgtcaa aggctatgaa cgcgactatg caagttcta  tcgtgatgct    3120 gaggtggatc gtctagcagc aggtgctgct ggtgtgaaac gaacgactgg gcagcaccct    3180 gggggattg  ttgttattcc taattacatg gatgtttatg attttacccc cgtgcaatat    3240
ccagccgatg atgtaacggc ttcttggcag acaactcact ttaacttcca tgatattgat    3300
gaaaacgtct tgaaacttga tatcctaggg catgatgatc cgaccatgat tcgtaaactt    3360
caggatttat cgggcattga tcctattact attcctgctg atgatccggg agttatggct    3420 ctctttttctg gacagaggt  tttgggcgtt accccggaac aaattgggac accgactggt    3480
atgctaggca ttccagaatt tggaaccaac tttgttcgcg gcatggttaa tgagacgcat    3540
ccgaccactt ttgcggagct tttgcagctg tctggactat ctcatggaac cgatgttttgg   3600 cttggtaatg cacaagattc gattaaagaa ggcattgcaa ccctaaaaac cgttatcggc    3660
tgtcgtgacg acatcatggt ttacctcatg cacgcaggct tagaaccaaa aatgccttt    3720 accattatgg agcgtgtgcg taagggatta tggctaaaaa tttctgagga agaacgtaat    3780
ggctatattg atgccatgcg agaaaacaat gtgcccgact ggtacattga atcgtgtgga    3840
aaaatcaagt acatgttccc taaagcccat gcggcagctt atgtttttgat ggcccttcgg    3900 gtggcttatt tcaaggtgca ccaccccatt atgtattatt gtgcttatt  ctctattcgt    3960 gcgaaggctt ttgaattaaa aaccatgagt ggtggtttag atgctgttaa agcaagaatg    4020
gaagatatta ctataaaacg taaaaataat gaagccacca atgtgaaaa  tgacctcttt    4080 acaaccttgg agattgtcaa cgaaatgtta gaacgcggct ttaagtttgg caaattagac    4140
```

-continued

```
ctttacaaaa gtgatgctat agaattccaa atcaaaggag ataccctttat ccctccatttt  4200 atagcgctag aaggtctggg tgaaaacgtg gccaagcaaa tcgttaaagc tcgtcaagaa  4260
ggcgaattcc tctctaaaat ggaattgcgt aaacgaggcg gggcatcgtc aacgctcgtt  4320
gagaaaatgg atgagacggg tattttagga aatatgccag aagataatca attaagtctt  4380
tttgatgact ttttc                                                    4395
```

The encoded α-large subunit has an amino acid sequence corresponding to SEQ. ID. No. 18 as follows:

```
Met Ser Asp Leu Phe Ala Lys Leu Met Asp Gln Ile Glu Met Pro Leu
 1               5                  10                  15

Asp Met Arg Arg Ser Ser Ala Phe Ser Ser Ala Asp Ile Ile Glu Val
                20                  25                  30

Lys Val His Ser Val Ser Arg Leu Trp Glu Phe His Phe Ala Phe Ala
            35                  40                  45

Ala Val Leu Pro Ile Ala Thr Tyr Arg Glu Leu His Asp Arg Leu Ile
    50                  55                  60

Arg Thr Phe Glu Ala Ala Asp Ile Lys Val Thr Phe Asp Ile Gln Ala
65                  70                  75                  80

Ala Gln Val Asp Tyr Ser Asp Asp Leu Leu Gln Ala Tyr Tyr Gln Glu
                85                  90                  95

Ala Phe Glu His Ala Pro Cys Asn Ser Ala Ser Phe Lys Ser Ser Phe
            100                 105                 110

Ser Lys Leu Lys Val Thr Tyr Glu Asp Asp Lys Leu Ile Ile Ala Ala
        115                 120                 125

Pro Gly Phe Val Asn Asn Asp His Phe Arg Asn Asn His Leu Pro Asn
    130                 135                 140

Leu Val Lys Gln Leu Glu Ala Phe Gly Phe Gly Ile Leu Thr Ile Asp
145                 150                 155                 160

Met Val Ser Asp Gln Glu Met Thr Glu His Leu Thr Lys Asn Phe Val
                165                 170                 175

Ser Ser Arg Gln Ala Leu Val Lys Lys Ala Val Gln Asp Asn Leu Glu
            180                 185                 190

Ala Gln Lys Ser Leu Glu Ala Met Met Pro Val Glu Glu Ala Thr
        195                 200                 205

Pro Ala Pro Lys Phe Asp Tyr Lys Glu Arg Ala Ala Lys Arg Gln Ala
    210                 215                 220

Gly Phe Glu Lys Ala Thr Ile Thr Pro Met Ile Glu Ile Glu Thr Glu
225                 230                 235                 240

Glu Asn Arg Ile Val Phe Glu Gly Met Val Phe Asp Val Glu Arg Lys
                245                 250                 255

Thr Thr Arg Thr Gly Arg His Ile Ile Asn Phe Lys Met Thr Asp Tyr
            260                 265                 270

Thr Ser Ser Phe Ala Leu Gln Lys Trp Ala Lys Asp Asp Glu Glu Leu
        275                 280                 285

Arg Lys Phe Asp Met Ile Ala Lys Gly Ala Trp Leu Arg Val Gln Gly
    290                 295                 300

Asn Ile Glu Thr Asn Pro Phe Thr Lys Ser Leu Thr Met Asn Val Gln
305                 310                 315                 320

Gln Val Lys Glu Ile Val Arg His Glu Arg Lys Asp Leu Met Pro Glu
                325                 330                 335
```

-continued

```
Gly Gln Lys Arg Val Glu Leu His Ala His Thr Asn Met Ser Thr Met
            340                 345                 350

Asp Ala Leu Pro Thr Val Glu Ser Leu Ile Asp Thr Ala Ala Lys Trp
            355                 360                 365

Gly His Lys Ala Ile Ala Ile Thr Asp His Ala Asn Val Gln Ser Phe
        370                 375                 380

Pro His Gly Tyr His Arg Ala Arg Lys Ala Gly Ile Lys Ala Ile Phe
385                 390                 395                 400

Gly Leu Glu Ala Asn Ile Val Glu Asp Lys Val Pro Ile Ser Tyr Glu
                405                 410                 415

Pro Val Asp Met Asp Leu His Glu Ala Thr Tyr Val Val Phe Asp Val
            420                 425                 430

Glu Thr Thr Gly Leu Ser Ala Met Asn Asn Asp Leu Ile Gln Ile Ala
            435                 440                 445

Ala Ser Lys Met Phe Lys Gly Asn Ile Val Glu Gln Phe Asp Glu Phe
        450                 455                 460

Ile Asp Pro Gly His Pro Leu Ser Ala Phe Thr Thr Glu Leu Thr Gly
465                 470                 475                 480

Ile Thr Asp Lys His Leu Gln Gly Ala Lys Pro Leu Val Thr Val Leu
                485                 490                 495

Lys Ala Phe Gln Asp Phe Cys Lys Asp Ser Ile Leu Val Ala His Asn
            500                 505                 510

Ala Ser Phe Asp Val Gly Phe Met Asn Ala Asn Tyr Glu Arg His Asp
        515                 520                 525

Leu Pro Lys Ile Thr Gln Pro Val Ile Asp Thr Leu Glu Phe Ala Arg
            530                 535                 540

Asn Leu Tyr Pro Glu Tyr Lys Arg His Gly Leu Gly Pro Leu Thr Lys
545                 550                 555                 560

Arg Phe Gln Val Ser Leu Asp His His Met Ala Asn Tyr Asp Ala
                565                 570                 575

Glu Ala Thr Gly Arg Leu Leu Phe Ile Phe Leu Lys Asp Ala Arg Glu
            580                 585                 590

Lys His Gly Ile Lys Asn Leu Leu Gln Leu Asn Thr Asp Leu Val Ala
        595                 600                 605

Glu Asp Ser Tyr Lys Lys Ala Arg Ile Lys His Ala Thr Ile Tyr Val
610                 615                 620

Gln Asn Gln Val Gly Leu Lys Asn Met Phe Lys Leu Val Ser Leu Ser
625                 630                 635                 640

Asn Ile Lys Tyr Phe Glu Gly Val Pro Arg Ile Pro Arg Thr Val Leu
                645                 650                 655

Asp Ala His Arg Glu Gly Leu Leu Gly Thr Ala Cys Ser Asp Gly
            660                 665                 670

Glu Val Phe Asp Ala Val Leu Thr Lys Gly Ile Asp Ala Ala Val Asp
        675                 680                 685

Leu Ala Arg Tyr Tyr Asp Phe Ile Glu Ile Met Pro Pro Ala Ile Tyr
            690                 695                 700

Gln Pro Leu Val Val Arg Glu Leu Ile Lys Asp Gln Ala Gly Ile Glu
705                 710                 715                 720

Gln Val Ile Arg Asp Leu Ile Glu Val Gly Lys Arg Ala Lys Lys Pro
                725                 730                 735

Val Leu Ala Thr Gly Asn Val His Tyr Leu Glu Pro Glu Glu Glu Ile
            740                 745                 750

Tyr Arg Glu Ile Ile Val Arg Ser Leu Gly Gln Gly Ala Met Ile Asn
        755                 760                 765
```

-continued

```
Arg Thr Ile Gly Arg Gly Glu Gly Ala Gln Pro Ala Pro Leu Pro Lys
770                 775                 780

Ala His Phe Arg Thr Thr Asn Glu Met Leu Asp Glu Phe Ala Phe Leu
785                 790                 795                 800

Gly Lys Asp Leu Ala Tyr Gln Val Val Gln Asn Thr Gln Asp Phe
                805                 810                 815

Ala Asp Arg Ile Glu Glu Val Val Val Lys Gly Asp Leu Tyr Thr
            820                 825                 830

Pro Tyr Ile Asp Lys Ala Glu Glu Thr Val Ala Glu Leu Thr Tyr Gln
                835                 840                 845

Lys Ala Phe Glu Ile Tyr Gly Asn Pro Leu Pro Asp Ile Ile Asp Leu
850                 855                 860

Arg Ile Glu Lys Glu Leu Thr Ser Ile Leu Gly Asn Gly Phe Ala Val
865                 870                 875                 880

Ile Tyr Leu Ala Ser Gln Met Leu Val Asn Arg Ser Asn Glu Arg Gly
                885                 890                 895

Tyr Leu Val Gly Ser Arg Gly Ser Val Gly Ser Ser Phe Val Ala Thr
                900                 905                 910

Met Ile Gly Ile Thr Glu Val Asn Pro Met Pro His Tyr Val Cys
            915                 920                 925

Pro Ser Cys Gln His Ser Glu Phe Ile Thr Asp Gly Ser Val Gly Ser
    930                 935                 940

Gly Tyr Asp Leu Pro Asn Lys Pro Cys Pro Lys Cys Gly Thr Pro Tyr
945                 950                 955                 960

Gln Lys Asp Gly Gln Asp Ile Pro Phe Glu Thr Phe Leu Gly Phe Asp
                965                 970                 975

Gly Asp Lys Val Pro Asp Ile Asp Leu Asn Phe Ser Gly Asp Asp Gln
            980                 985                 990

Pro Ser Ala His Leu Asp Val Arg Asp Ile Phe Gly Asp Glu Tyr Ala
                995                 1000                1005

Phe Arg Ala Gly Thr Val Gly Thr Val Ala Glu Lys Thr Ala Tyr Gly
    1010                1015                1020

Phe Val Lys Gly Tyr Glu Arg Asp Tyr Gly Lys Phe Tyr Arg Asp Ala
1025                1030                1035                1040

Glu Val Asp Arg Leu Ala Ala Gly Ala Ala Gly Val Lys Arg Thr Thr
                1045                1050                1055

Gly Gln His Pro Gly Gly Ile Val Val Ile Pro Asn Tyr Met Asp Val
            1060                1065                1070

Tyr Asp Phe Thr Pro Val Gln Tyr Pro Ala Asp Asp Val Thr Ala Ser
    1075                1080                1085

Trp Gln Thr Thr His Phe Asn Phe His Asp Ile Asp Glu Asn Val Leu
    1090                1095                1100

Lys Leu Asp Ile Leu Gly His Asp Asp Pro Thr Met Ile Arg Lys Leu
1105                1110                1115                1120

Gln Asp Leu Ser Gly Ile Asp Pro Ile Thr Ile Pro Ala Asp Asp Pro
                1125                1130                1135

Gly Val Met Ala Leu Phe Ser Gly Thr Glu Val Leu Gly Val Thr Pro
            1140                1145                1150

Glu Gln Ile Gly Thr Pro Thr Gly Met Leu Gly Ile Pro Glu Phe Gly
    1155                1160                1165

Thr Asn Phe Val Arg Gly Met Val Asn Glu Thr His Pro Thr Thr Phe
    1170                1175                1180
```

-continued

```
Ala Glu Leu Leu Gln Leu Ser Gly Leu Ser His Gly Thr Asp Val Trp
1185                1190                1195                1200

Leu Gly Asn Ala Gln Asp Leu Ile Lys Glu Gly Ile Ala Thr Leu Lys
            1205                1210                1215

Thr Val Ile Gly Cys Arg Asp Asp Ile Met Val Tyr Leu Met His Ala
            1220                1225                1230

Gly Leu Glu Pro Lys Met Ala Phe Thr Ile Met Glu Arg Val Arg Lys
        1235                1240                1245

Gly Leu Trp Leu Lys Ile Ser Glu Glu Glu Arg Asn Gly Tyr Ile Asp
    1250                1255                1260

Ala Met Arg Glu Asn Asn Val Pro Asp Trp Tyr Ile Glu Ser Cys Gly
1265                1270                1275                1280

Lys Ile Lys Tyr Met Phe Pro Lys Ala His Ala Ala Ala Tyr Val Leu
                1285                1290                1295

Met Ala Leu Arg Val Ala Tyr Phe Lys Val His His Pro Ile Met Tyr
            1300                1305                1310

Tyr Cys Ala Tyr Phe Ser Ile Arg Ala Lys Ala Phe Glu Leu Lys Thr
        1315                1320                1325

Met Ser Gly Gly Leu Asp Ala Val Lys Ala Arg Met Glu Asp Ile Thr
    1330                1335                1340

Ile Lys Arg Lys Asn Asn Glu Ala Thr Asn Val Glu Asn Asp Leu Phe
1345                1350                1355                1360

Thr Thr Leu Glu Ile Val Asn Glu Met Leu Glu Arg Gly Phe Lys Phe
                1365                1370                1375

Gly Lys Leu Asp Leu Tyr Lys Ser Asp Ala Ile Glu Phe Gln Ile Lys
            1380                1385                1390

Gly Asp Thr Leu Ile Pro Pro Phe Ile Ala Leu Glu Gly Leu Gly Glu
        1395                1400                1405

Asn Val Ala Lys Gln Ile Val Lys Ala Arg Gln Glu Gly Glu Phe Leu
    1410                1415                1420

Ser Lys Met Glu Leu Arg Lys Arg Gly Gly Ala Ser Ser Thr Leu Val
1425                1430                1435                1440

Glu Lys Met Asp Glu Met Gly Ile Leu Gly Asn Met Pro Glu Asp Asn
                1445                1450                1455

Gln Leu Ser Leu Phe Asp Asp Phe Phe
            1460                1465
```

The present invention also relates to the dnaE gene of *Streptococcus pyogenes* encoding the α-small subunit. The partial nucleotide sequence of the dnaE gene corresponds to SEQ. ID. No. 19 as follows:

```
atgtttgctc aacttgatac taaaactgta tactcattta tggatagttt aattgactta    60
aatcattatt ttgaacgagc aaagcaattt ggttaccaca ccataggaat catggataag   120
gataatcttt atggtgctta ccatttatt aaaggttgtc aaaaaaatgg actgcagcca   180
gttttaggtt tggaaataga gattctctat caagagcggc aggtgctcct taacttaatc   240
gcccagaata cacaaggcta tcatcagctt ttaaaaattt ccacggcaaa aatgtctggc   300
aagcttcata tggattactt ctgccaacat ttggaaggga tagcggttat tattcctagt   360
aagggttgga gcgatacatt agtggtccct tttgactact atatgggtgt tgatcagtat   420
actgatttat ctcatatgga ttctaagagg cagcttatac ccctaaggac agttcgttat   480
```

-continued

```
tttgcgcaag atgatatgga aaccctgcac atgttgcatg ccattcgaga taacctcagt   540
ctggcagaga cccctgtggt agaaagtgat caagagttag cagattgtca acaactaacc   600
gccttctatc aaacacactg ccctcaagct ctacagaatt tagaagactt agtgtcagga   660
atctattatg atttcgatac aaatttaaaa ttgcctcatt ttaatagaga taagtctgcc   720
aagcaagaat tgcaagactt gactgaggct ggtttgaagg aaaaaggatt gtggaaagag   780
ccttatcaat cgcgcttact acatgaactg gtcattattt ctgacatggg ctttgatgat   840
tattttttga ttgtgtggga tttacttcgc tttggacgca gtaaaggcta ttatatggga   900
atgggacgtg gctcggcggc aggtagtcta gtggcttatg ctctgaacat tacagggatt   960
gatccagttc aacatgattt gctatttgag cgcttttttaa acaaagaacg ttatagcatg  1020
cctgatattg atatcgatct tccagatatt taccgttcag aatttctacg gtatgtccga  1080
aatcgttatg gtagcgacca ttcggcgcaa attgtgacct tttcaacctt tggccaggct  1140
attcgtgatg ttttcaaacg gttcggggtt ccagaatacg aactgactaa tctcactaaa  1200
aaaattggtt ttaaagatag cttggctact gtctatgaaa agtcaatctc ttttaggcag  1260
gttattaata gtagaactga atttcaaaag gcttttgcca ttgccaagcg tatcgaagga  1320
aatccaagac aaacgtccat tcacgcagct ggtattgtga tgagtgatga tgccttgacc  1380
aatcatattc ctctaaaatc gggcgatgac atgatgatca cccagtatga tgctcatgcg  1440
gtcgaagcta atggcctgtt aaaaatggat tttttggggt taagaaattt gacctttgtt  1500
caaaaaatgc aagagaaggt tgctaaagac tacgggtgtc agattgatat tacagccatt  1560
gatttagaag acccgcaaac gttggcactt tttgctaaag gggataccaa gggaattttc  1620
caatttgaac aaaatggtgc tattaatctt ttaaaacgga ttaagccaca acgttttgaa  1680
gaaattgttg ccactaccag tctaaataga ccaggggcaa gtgactatac cactaatttc  1740
attaaacgaa gagaaggaca agaaaaaatt gatttgattg atcctgtgat tgctcccatt  1800
ttagagccaa cttacggtat tatgctttat caagaacaag ttatgcagat tgcacaggtt  1860
tatgctggtt ttacgttagg caaggccgac ttgttaaggc gtgccatgtc taaaaaaaat  1920
ctacaagaaa tgcaaaaaat ggaagaagac tttattgctt ctgctaagca cctagggaga  1980
gctgaagaaa cagctagagg actttttaaa cggatggaaa aatttgcagg ttatggtttt  2040
aaccgcagcc atgcctttgc ctattcagct ttagcttttc aattggctta tttcaaagcc  2100
cattacccgg ctgttttttta cgatatcatg atgaattatt ctagcagtga ctatatcaca  2160
gatgctctag aatcagattt tcaagtagcg caagttacca ttaatagtat tccttacact  2220
gataaaattg aagctagcaa gatttacatg gggctgaaaa atattaaggg gttgccaagg  2280
gattttgctt attggattat cgagcaaaga ccatttaata gcgtagagga ttttctcact  2340
agaactccag aaaaatatca aaaaaaggtt ttccttgagc ctctgataaa aataggtctg  2400
tttgattgct ttgagcctaa ccgtaaaaaa attctggaca atttggatgg tttactggta  2460
tttgttaacg agcttggttc tcttttttca gattcttcct ttagttgggt agatacgaaa  2520
gattactcag taactgaaaa atattctttg gaacaggaga tcgttggagt tggcatgagc  2580
aagcatcctt taattgatat tgctgagaaa agtacccaaa cttttactcc tatttcacag  2640
ttagtcaaag aaagcgaagc agtcgtactg attcaaatag atagcattag gatcattaga  2700
accaaaacaa gtgggcagca aatggctttt ttaagtgtga atgacactaa gaaaaagctc  2760
gatgtcacac ttttttccaca agagtatgcc atttataaag accaattaaa agaaggagaa  2820
ttctattact taaaaggtag aataaaagaa agagaccatc gactgcagat ggtgtgtcag  2880
```

-continued

```
caagtgcaaa tggctattag tcaaaaatat tggttattag ttgaaaacca tcagtttgat 2940
tcccaaattt ctgagatttt aggtgccttt ccaggaacga ctccagttgt tattcactat 3000
caaaaaaata aggaaacaat tgcattaact aagattcagg ttcatgtaac agagaattta 3060
aaggaaaaac ttcgtccttt tgttctgaaa acggttttc ga                     3102
```

The encoded α-small subunit has an amino acid sequence corresponding to SEQ. ID. No. 20 as follows:

```
Met Phe Ala Gln Leu Asp Thr Lys Thr Val Tyr Ser Phe Met Asp Ser
 1               5                  10                  15

Leu Ile Asp Leu Asn His Tyr Phe Glu Arg Ala Lys Gln Phe Gly Tyr
                 20                  25                  30

His Thr Ile Gly Ile Met Asp Lys Asp Asn Leu Tyr Gly Ala Tyr His
             35                  40                  45

Phe Ile Lys Gly Cys Gln Lys Asn Gly Leu Gln Pro Val Leu Gly Leu
         50                  55                  60

Glu Ile Glu Ile Leu Tyr Gln Glu Arg Gln Val Leu Leu Asn Leu Ile
 65                  70                  75                  80

Ala Gln Asn Thr Gln Gly Tyr His Gln Leu Leu Lys Ile Ser Thr Ala
                 85                  90                  95

Lys Met Ser Gly Lys Leu His Met Asp Tyr Phe Cys Gln His Leu Glu
                100                 105                 110

Gly Ile Ala Val Ile Ile Pro Ser Lys Gly Trp Ser Asp Thr Leu Val
            115                 120                 125

Val Pro Phe Asp Tyr Tyr Met Gly Val Asp Gln Tyr Thr Asp Leu Ser
        130                 135                 140

His Met Asp Ser Lys Arg Gln Leu Ile Pro Leu Arg Thr Val Arg Tyr
145                 150                 155                 160

Phe Ala Gln Asp Asp Met Glu Thr Leu His Met Leu His Ala Ile Arg
                165                 170                 175

Asp Asn Leu Ser Leu Ala Glu Thr Pro Val Val Glu Ser Asp Gln Glu
            180                 185                 190

Leu Ala Asp Cys Gln Gln Leu Thr Ala Phe Tyr Gln Thr His Cys Pro
        195                 200                 205

Gln Ala Leu Gln Asn Leu Glu Asp Leu Val Ser Gly Ile Tyr Tyr Asp
    210                 215                 220

Phe Asp Thr Asn Leu Lys Leu Pro His Phe Asn Arg Asp Lys Ser Ala
225                 230                 235                 240

Lys Gln Glu Leu Gln Asp Leu Thr Glu Ala Gly Leu Lys Glu Lys Gly
                245                 250                 255

Leu Trp Lys Glu Pro Tyr Gln Ser Arg Leu Leu His Glu Leu Val Ile
            260                 265                 270

Ile Ser Asp Met Gly Phe Asp Asp Tyr Phe Leu Ile Val Trp Asp Leu
        275                 280                 285

Leu Arg Phe Gly Arg Ser Lys Gly Tyr Tyr Met Gly Met Gly Arg Gly
    290                 295                 300

Ser Ala Ala Gly Ser Leu Val Ala Tyr Ala Leu Asn Ile Thr Gly Ile
305                 310                 315                 320

Asp Pro Val Gln His Asp Leu Leu Phe Glu Arg Phe Leu Asn Lys Glu
                325                 330                 335

Arg Tyr Ser Met Pro Asp Ile Asp Ile Asp Leu Pro Asp Ile Tyr Arg
            340                 345                 350
```

```
Ser Glu Phe Leu Arg Tyr Val Arg Asn Arg Tyr Gly Ser Asp His Ser
        355                 360                 365

Ala Gln Ile Val Thr Phe Ser Thr Phe Gly Pro Lys Gln Ala Ile Arg
        370                 375                 380

Asp Val Phe Lys Arg Phe Gly Val Pro Glu Tyr Glu Leu Thr Asn Leu
385                 390                 395                 400

Thr Lys Lys Ile Gly Phe Lys Asp Ser Leu Ala Thr Val Tyr Glu Lys
                405                 410                 415

Ser Ile Ser Phe Arg Gln Val Ile Asn Ser Arg Thr Glu Phe Gln Lys
        420                 425                 430

Ala Phe Ala Ile Ala Lys Arg Ile Glu Gly Asn Pro Arg Gln Thr Ser
        435                 440                 445

Ile His Ala Ala Gly Ile Val Met Ser Asp Asp Ala Leu Thr Asn His
        450                 455                 460

Ile Pro Leu Lys Ser Gly Asp Met Met Ile Thr Gln Tyr Asp Ala
465                 470                 475                 480

His Ala Val Glu Ala Asn Gly Leu Leu Lys Met Asp Phe Leu Gly Leu
                485                 490                 495

Arg Asn Leu Thr Phe Val Gln Lys Met Gln Glu Lys Val Ala Lys Asp
        500                 505                 510

Tyr Gly Cys Gln Ile Asp Ile Thr Ala Ile Asp Leu Glu Asp Pro Gln
        515                 520                 525

Thr Leu Ala Leu Phe Ala Lys Gly Asp Thr Lys Gly Ile Phe Gln Phe
        530                 535                 540

Glu Gln Asn Gly Ala Ile Asn Leu Leu Lys Arg Ile Lys Pro Gln Arg
545                 550                 555                 560

Phe Glu Glu Ile Val Ala Thr Thr Ser Leu Asn Arg Pro Gly Ala Ser
                565                 570                 575

Asp Tyr Thr Thr Asn Phe Ile Lys Arg Arg Glu Gly Gln Glu Lys Ile
        580                 585                 590

Asp Leu Ile Asp Pro Val Ile Ala Pro Ile Leu Glu Pro Thr Tyr Gly
        595                 600                 605

Ile Met Leu Tyr Gln Glu Gln Val Met Gln Ile Ala Gln Val Tyr Ala
        610                 615                 620

Gly Phe Thr Leu Gly Lys Ala Asp Leu Leu Arg Arg Ala Met Ser Lys
625                 630                 635                 640

Lys Asn Leu Gln Glu Met Gln Lys Met Glu Glu Asp Phe Ile Ala Ser
                645                 650                 655

Ala Lys His Leu Gly Arg Ala Glu Glu Thr Ala Arg Gly Leu Phe Lys
        660                 665                 670

Arg Met Glu Lys Phe Ala Gly Tyr Gly Phe Asn Arg Ser His Ala Phe
        675                 680                 685

Ala Tyr Ser Ala Leu Ala Phe Gln Leu Ala Tyr Phe Lys Ala His Tyr
        690                 695                 700

Pro Ala Val Phe Tyr Asp Ile Met Met Asn Tyr Ser Ser Ser Asp Tyr
705                 710                 715                 720

Ile Thr Asp Ala Leu Glu Ser Asp Phe Gln Val Ala Gln Val Thr Ile
                725                 730                 735

Asn Ser Ile Pro Tyr Thr Asp Lys Ile Glu Ala Ser Lys Ile Tyr Met
        740                 745                 750

Gly Leu Lys Asn Ile Lys Gly Leu Pro Arg Asp Phe Ala Tyr Trp Ile
        755                 760                 765
```

-continued

```
Ile Glu Gln Arg Pro Phe Asn Ser Val Glu Asp Phe Leu Thr Arg Thr
    770                 775                 780
Pro Glu Lys Tyr Gln Lys Lys Val Phe Leu Glu Pro Leu Ile Lys Ile
785                 790                 795                 800
Gly Leu Phe Asp Cys Phe Glu Pro Asn Arg Lys Lys Ile Leu Asp Asn
                805                 810                 815
Leu Asp Gly Leu Leu Val Phe Val Asn Glu Leu Gly Ser Leu Phe Ser
            820                 825                 830
Asp Ser Ser Phe Ser Trp Val Asp Thr Lys Asp Tyr Ser Val Thr Glu
        835                 840                 845
Lys Tyr Ser Leu Glu Gln Glu Ile Val Gly Val Gly Met Ser Lys His
    850                 855                 860
Pro Leu Ile Asp Ile Ala Glu Lys Ser Thr Gln Thr Phe Thr Pro Ile
865                 870                 875                 880
Ser Gln Leu Val Lys Glu Ser Glu Ala Val Val Leu Ile Gln Ile Asp
                885                 890                 895
Ser Ile Arg Ile Ile Arg Thr Lys Thr Ser Gly Gln Gln Met Ala Phe
            900                 905                 910
Leu Ser Val Asn Asp Thr Lys Lys Lys Leu Asp Val Thr Leu Phe Pro
        915                 920                 925
Gln Glu Tyr Ala Ile Tyr Lys Asp Gln Leu Lys Glu Gly Glu Phe Tyr
    930                 935                 940
Tyr Leu Lys Gly Arg Ile Lys Glu Arg Asp His Arg Leu Gln Met Val
945                 950                 955                 960
Cys Gln Gln Val Gln Met Ala Ile Ser Gln Lys Tyr Trp Leu Leu Val
                965                 970                 975
Glu Asn His Gln Phe Asp Ser Gln Ile Ser Glu Ile Leu Gly Ala Phe
            980                 985                 990
Pro Gly Thr Thr Pro Val Val Ile His Tyr Gln Lys Asn Lys Glu Thr
        995                 1000                1005
Ile Ala Leu Thr Lys Ile Gln Val Thr Glu Asn Leu Lys Glu Lys Leu
    1010                1015                1020
Arg Pro Phe Val Leu Lys Thr Val Phe Arg
1025                1030
```

The present invention also relates to the holA gene of *Streptococcus pyogenes* encoding the δ subunit. The holA gene has a nucleotide sequence which corresponds to SEQ. ID. No. 21 as follows:

```
atgattgcga tagaaaagat tgaaaaactg agtaaagaaa atttgggtct tataacccttt    60
gtcacaggag atgacattgg tcagtatagc cagttgaaat cccgcttaat ggagcagatt   120
gcttttgata aggatgattt ggcctattct tactttgata tgtctgaggc cgcttatcag   180
gatgcagaaa tggatctagt gagcctaccc ttctttgctg agcagaaggt ggttattttt   240
gaccatttgt tagatatcac gaccaataaa aaaagtttct taaagaaaaa agacctaaag   300
gcctttgaag cctatttaga aaatccctta gagactactc gactaattat ctttgctcca   360
ggtaaattgg atagtaagag acggcttgtt aagcttttga acgtgatgc ccttgtttta   420
gaagccaacc ctctgaaaga agcagagcta agaacttatt ttcaaaaata cagtcatcaa   480
ctgggtttag gttcgagag tggtgccttt gaccaattac ttttgaaatc aaacgatgat   540
tttagtcaaa tcatgaaaaa catggccttt ttaaaagcct ataaaaaaac gggaaatatt   600
```

-continued

```
agcctaactg atattgagca agccattcct aaaagtttac aagataatat tttcgatctg  660
actagacttg tcctaggagg taaaattgat gcggctagag atttgattca tgatttacgg  720
ttatctggag aagatgacat taaattaatc gctatcatgc taggceaatt tcgcttattt  780 ttgcagctga ctattcttgc tagagatgta aaaaacgagc aacaactagt gattagttta  840
tcagatattc ttgggcggcg ggttaatcct taccaggtca agtatgcgtt aaaggattct  900
aggaccttat ctcttgcctt tctaacagga gcggtgaaaa ccttgattga gacagattac  960
cagataaaaa caggacttta tgagaagagt tatctagttg atattgctct cttaaaaatc 1020
atgactcact ctcaaaaa                                               1038
```

The encoded δ subunit has an amino acid sequence corresponding to SEQ. ID. No. 22 as follows:

```
Met Ile Ala Ile Glu Lys Ile Glu Lys Leu Ser Lys Glu Asn Leu Gly
  1               5                  10                  15

Leu Ile Thr Leu Val Thr Gly Asp Asp Ile Gly Gln Tyr Ser Gln Leu
                 20                  25                  30

Lys Ser Arg Leu Met Glu Gln Ile Ala Phe Asp Lys Asp Asp Leu Ala
             35                  40                  45

Tyr Ser Tyr Phe Asp Met Ser Glu Ala Ala Tyr Gln Asp Ala Glu Met
         50                  55                  60

Asp Leu Val Ser Leu Pro Phe Phe Ala Glu Gln Lys Val Val Ile Phe
 65                  70                  75                  80

Asp His Leu Leu Asp Ile Thr Thr Asn Lys Lys Ser Phe Leu Lys Glu
                 85                  90                  95

Lys Asp Leu Lys Ala Phe Glu Ala Tyr Leu Glu Asn Pro Leu Glu Thr
            100                 105                 110

Thr Arg Leu Ile Ile Phe Ala Pro Gly Lys Leu Asp Ser Lys Arg Arg
            115                 120                 125

Leu Val Lys Leu Leu Lys Arg Asp Ala Leu Val Leu Glu Ala Asn Pro
130                 135                 140

Leu Lys Glu Ala Glu Leu Arg Thr Tyr Phe Gln Lys Tyr Ser His Gln
145                 150                 155                 160

Leu Gly Leu Gly Phe Glu Ser Gly Ala Phe Asp Gln Leu Leu Leu Lys
                165                 170                 175

Ser Asn Asp Asp Phe Ser Gln Ile Met Lys Asn Met Ala Phe Leu Lys
                180                 185                 190

Ala Tyr Lys Lys Thr Gly Asn Ile Ser Leu Thr Asp Ile Glu Gln Ala
            195                 200                 205

Ile Pro Lys Ser Leu Gln Asp Asn Ile Phe Asp Leu Thr Arg Leu Val
210                 215                 220

Leu Gly Gly Lys Ile Asp Ala Ala Arg Asp Leu Ile His Asp Leu Arg
225                 230                 235                 240

Leu Ser Gly Glu Asp Asp Ile Lys Leu Ile Ala Ile Met Leu Gly Gln
                245                 250                 255

Phe Arg Leu Phe Leu Gln Leu Thr Ile Leu Ala Arg Asp Val Lys Asn
            260                 265                 270

Glu Gln Gln Leu Val Ile Ser Leu Ser Asp Ile Leu Gly Arg Arg Val
            275                 280                 285

Asn Pro Tyr Gln Val Lys Tyr Ala Leu Lys Asp Ser Arg Thr Leu Ser
        290                 295                 300
```

-continued

```
Leu Ala Phe Leu Thr Gly Ala Val Lys Thr Leu Ile Glu Thr Asp Tyr
305                 310                 315                 320

Gln Ile Lys Thr Gly Leu Tyr Glu Lys Ser Tyr Leu Val Asp Ile Ala
                325                 330                 335

Leu Leu Lys Ile Met Thr His Ser Gln Lys
            340                 345
```

The present invention also relates to the holB gene of *Streptococcus pyogenes* encoding the δ' subunit. The holB gene has a nucleotide sequence which corresponds to SEQ. ID. No. 23 as follows:

```
atggatttag cgcaaaaagc tcctaacgtt tatcaagctt ttcagacaat tttaaagaaa  60
gaccgtctga atcatgctta tcttttttcg ggtgattttg ctaatgaaga aatggctctt 120
tttttagcta aggtcatctt ttgtgaacag aaaaaggatc agacgccctg cgggcattgt 180
cgctcttgtc aattgattga acaaggagat tttgccgatg tgacggtatt ggaaccaaca 240
gggcaagtga ttaaaacgga tgtggtcaaa gaaatgatgg ctaacttttc tcagacagga 300
tatgaaaaca aacgacaagt ttttattatc aaagattgtg acaaaatgca tatcaatgcc 360
gctaatagct tgctaaaata cattgaggag cctcagggag aagcttacat attttttattg 420
accaatgatg ataacaaagt gcttccgacc attaaaagtc ggacacaggt ttttcagttt 480
cctaaaaacg aagcctatct ttaccaattg gcacaagaaa agggattatt aaaccatcag 540
gctaagctag tagccaaact tgccacaaac accagtcatc tagaacgtct gttgcaaacg 600
agcaagcttt tagaactgat aactcaagca gagcgttttg tatctatttg gctgaaagat 660
cagttgcagg catatttagc gttgaaccgt ctggtacagt tagcaactga aaagaagaa 720
caagatttag ttttgacccct tttgaccttg ctcttggcaa gagagcgtgc gcaaacgcct 780
ttgacacaat tggaggctgt ctatcaggct aggctcatgt ggcagagcaa tgttaatttt 840
caaaacacat tagaatatat ggtgatgtca gaa                             873
```

The encoded δ' subunit has an amino acid sequence corresponding to SEQ. ID. No. 24 as follows:

```
Met Asp Leu Ala Gln Lys Ala Pro Asn Val Tyr Gln Ala Phe Gln Thr
  1               5                  10                  15

Ile Leu Lys Lys Asp Arg Leu Asn His Ala Tyr Leu Phe Ser Gly Asp
                20                  25                  30

Phe Ala Asn Glu Glu Met Ala Leu Phe Leu Ala Lys Val Ile Phe Cys
            35                  40                  45

Glu Gln Lys Lys Asp Gln Thr Pro Cys Gly His Cys Arg Ser Cys Gln
        50                  55                  60

Leu Ile Glu Gln Gly Asp Phe Ala Asp Val Thr Val Leu Glu Pro Thr
 65                  70                  75                  80

Gly Gln Val Ile Lys Thr Asp Val Val Lys Glu Met Met Ala Asn Phe
                85                  90                  95

Ser Gln Thr Gly Tyr Glu Asn Lys Arg Gln Val Phe Ile Ile Lys Asp
            100                 105                 110

Cys Asp Lys Met His Ile Asn Ala Ala Asn Ser Leu Leu Lys Tyr Ile
        115                 120                 125
```

```
Glu Glu Pro Gln Gly Glu Ala Tyr Ile Phe Leu Leu Thr Asn Asp Asp
    130                 135                 140

Asn Lys Val Leu Pro Thr Ile Lys Ser Arg Thr Gln Val Phe Gln Phe
145                 150                 155                 160

Pro Lys Asn Glu Ala Tyr Leu Tyr Gln Leu Ala Gln Glu Lys Gly Leu
                165                 170                 175

Leu Asn His Gln Ala Lys Leu Val Ala Lys Leu Ala Thr Asn Thr Ser
            180                 185                 190

His Leu Glu Arg Leu Leu Gln Thr Ser Lys Leu Leu Glu Leu Ile Thr
        195                 200                 205

Gln Ala Glu Arg Phe Val Ser Ile Trp Leu Lys Asp Gln Leu Gln Ala
    210                 215                 220

Tyr Leu Ala Leu Asn Arg Leu Val Gln Leu Ala Thr Glu Lys Glu Glu
225                 230                 235                 240

Gln Asp Leu Val Leu Thr Leu Thr Leu Leu Ala Arg Glu Arg
                245                 250                 255

Ala Gln Thr Pro Leu Thr Gln Leu Glu Ala Val Tyr Gln Ala Arg Leu
                260                 265                 270

Met Trp Gln Ser Asn Val Asn Phe Gln Asn Thr Leu Glu Tyr Met Val
        275                 280                 285

Met Ser Glu
    290
```

The present invention also relates to the dnaX gene of *Streptococcus pyogenes* encoding the τ subunit. The dnaX gene has a nucleotide sequence which corresponds to SEQ. ID. No. 25 as follows:

```
atgtatcaag ctctttatcg gaaataccgg agccaaacgt ttgaegaaat ggtgggacaa   60
tcggttattt ccacaacttt aaagcaggca gttgaatctg gcaagattag ccatgcttat  120
cttttttcag gtcctagagg gactgggaaa acaagtgcgg caaagatttt tgcaaaggcc  180
atgaattgtc ctaaccaagt cgatggtgaa ccctgtaatc aatgcgatat tgccgagat   240
atcacgaatg gaagcttgga agatgtgatt gaaattgatg ctgcctcgaa taatggtgtt  300
gatgaaattc gtgacattcg agacaaatca acctatgcgc caagtcgtgc gacttacaag  360
gtttatatta ttgatgaggt tcacatgtta tcaacagggg cttttaatgc gcttttgaaa  420
actttggaag aaccgacaga atgttgtctt tatcttggca acaacggaat gcataaaatt  480
ccagccacta ttttatctcg tgtgcaacgc tttgaattca aagctattaa gcaaaaagct  540
attcgagagc atttagcctg ggttttggac aaagaaggta ttgcctatga ggtggatgct  600
ttaaatctca ttgcaaggcg agcagaagga ggcatgcgtg atgctttatc tattttagat  660
caggctttga gcttgtcacc agataatcag gtcgccattg caattgccga agaaattaca  720
ggttctattt ccatacttgc tctgggtgac tatgttcgat atgtctccca agaacaggct  780
acgcaagctc tggcagcctt agagaccatt tatgatagtg ggaagagcat gagccgcttt  840
gcgacagatt tattgaccta tctgcgtgat ttattggtgg ttaaagctgg cggcgacaat  900
caacgtcagt cagctgtttt tgataccaat ttgtctctct cgatagatcg tatattccaa  960
atgataacag ttgttactag tcatctccct gaaatcaaaa agggaaccca tcctcggatt 1020
tatgccgaaa tgatgactat ccaattagct cagaaagagc agattttgtc ccaagtaaac 1080
ttgtcaggag agttaatctc agagattgaa acgctcaaaa atgagttggc acaacttaaa 1140
```

-continued

```
caacaattgt cgcagctcca atcgcgtcct gattcactgg caagatctga taaaacgaaa 1200
cctaaaacca caagctacag ggttgatcgg gttaccattt tgaaaatcat ggaagaaacg 1260
gttcgaaata gccaacaatc tcgacaatat ctagatgctc taaaaaatgc ttggaatgaa 1320
attctagata acatttctgc ccaagacaga gccttattga tgggctctga gcctgtctta 1380
gcaaatagtg agaatgcgat tttggctttc gaggctgcct ttaatgcaga acaagtcatg 1440
agccgaaata atcttaatga tatgtttggt aacattatga gtaaagctgc tggtttttct 1500
cccaatattc tggcagtacc aaggacagat tttcagcata ttcgtaagga atttgctcag 1560
caaatgaaat cgcaaaaaga cagtgttcaa gaagaacaag aagtagcgct tgatattcca 1620
gaagggtttg attttttgct cgataaaata aatactattg acgac            1665
```

The encoded τ subunit has an amino acid sequence corresponding to SEQ. ID. No. 26 as follows:

```
Met Tyr Gln Ala Leu Tyr Arg Lys Tyr Arg Ser Gln Thr Phe Asp Glu
 1               5                  10                  15

Met Val Gly Gln Ser Val Ile Ser Thr Thr Leu Lys Gln Ala Val Glu
                20                  25                  30

Ser Gly Lys Ile Ser His Ala Tyr Leu Phe Ser Gly Pro Arg Gly Thr
            35                  40                  45

Gly Lys Thr Ser Ala Ala Lys Ile Phe Ala Lys Ala Met Asn Cys Pro
        50                  55                  60

Asn Gln Val Asp Gly Glu Pro Cys Asn Gln Cys Asp Ile Cys Arg Asp
 65                 70                  75                  80

Ile Thr Asn Gly Set Leu Glu Asp Val Ile Glu Ile Asp Ala Ala Ser
                85                  90                  95

Asn Asn Gly Val Asp Glu Ile Arg Asp Ile Arg Asp Lys Ser Thr Tyr
            100                 105                 110

Ala Pro Ser Arg Ala Thr Tyr Lys Val Tyr Ile Ile Asp Glu Val His
        115                 120                 125

Met Leu Ser Thr Gly Ala Phe Asn Ala Leu Leu Lys Thr Leu Glu Glu
    130                 135                 140

Pro Thr Glu Asn Val Phe Ile Leu Ala Thr Thr Glu Leu His Lys Ile
145                 150                 155                 160

Pro Ala Thr Ile Leu Set Arg Val Gln Arg Phe Glu Phe Lys Ala Ile
                165                 170                 175

Lys Gln Lys Ala Ile Arg Glu His Leu Ala Trp Val Leu Asp Lys Glu
            180                 185                 190

Gly Ile Ala Tyr Glu Val Asp Ala Leu Asn Leu Ile Ala Arg Arg Ala
        195                 200                 205

Glu Gly Gly Met Arg Asp Ala Leu Set Ile Leu Asp Gln Ala Leu Set
    210                 215                 220

Leu Ser Pro Asp Asn Gln Val Ala Ile Ala Ile Ala Glu Glu Ile Thr
225                 230                 235                 240

Gly Ser Ile Set Ile Leu Ala Leu Gly Asp Tyr Val Arg Tyr Val Ser
                245                 250                 255

Gln Glu Gln Ala Thr Gln Ala Leu Ala Ala Leu Glu Thr Ile Tyr Asp
            260                 265                 270

Ser Gly Lys Set Met Set Arg Phe Ala Thr Asp Leu Leu Thr Tyr Leu
        275                 280                 285
```

-continued

```
Arg Asp Leu Leu Val Val Lys Ala Gly Gly Asp Asn Gln Arg Gln Ser
    290                 295                 300

Ala Val Phe Asp Thr Asn Leu Ser Leu Ser Ile Asp Arg Ile Phe Gln
305                 310                 315                 320

Met Ile Thr Val Val Thr Set His Leu Pro Glu Ile Lys Lys Gly Thr
                325                 330                 335

His Pro Arg Ile Tyr Ala Glu Met Met Thr Ile Gln Leu Ala Gln Lys
            340                 345                 350

Glu Gln Ile Leu Ser Gln Val Asn Leu Ser Gly Glu Leu Ile Ser Glu
        355                 360                 365

Ile Glu Thr Leu Lys Asn Glu Leu Ala Gln Leu Lys Gln Gln Leu Ser
    370                 375                 380

Gln Leu Gln Ser Arg Pro Asp Ser Leu Ala Arg Ser Asp Lys Thr Lys
385                 390                 395                 400

Pro Lys Thr Thr Ser Tyr Arg Val Asp Arg Val Thr Ile Leu Lys Ile
                405                 410                 415

Met Glu Glu Thr Val Arg Asn Ser Gln Gln Ser Arg Gln Tyr Leu Asp
                420                 425                 430

Ala Leu Lys Asn Ala Trp Asn Glu Ile Leu Asp Asn Ile Ser Ala Gln
            435                 440                 445

Asp Arg Ala Leu Leu Met Gly Ser Glu Pro Val Leu Ala Asn Ser Glu
        450                 455                 460

Asn Ala Ile Leu Ala Phe Glu Ala Ala Phe Asn Ala Glu Gln Val Met
465                 470                 475                 480

Ser Arg Asn Asn Leu Asn Asp Met Phe Gly Asn Ile Met Ser Lys Ala
                485                 490                 495

Ala Gly Phe Ser Pro Asn Ile Leu Ala Val Pro Arg Thr Asp Phe Gln
            500                 505                 510

His Ile Arg Lys Glu Phe Ala Gln Gln Met Lys Ser Gln Lys Asp Ser
        515                 520                 525

Val Gln Glu Glu Gln Glu Val Ala Leu Asp Ile Pro Glu Gly Phe Asp
    530                 535                 540

Phe Leu Leu Asp Lys Ile Asn Thr Ile Asp Asp
545                 550                 555
```

The present invention also relates to the dnaN gene of *Streptococcus pyogenes* encoding the β subunit. The dnaN gene has a nucleotide sequence which corresponds to SEQ. ID. No. 27 as follows:

```
atgattcaat tttcaattaa tcgcacatta tttattcatg ctttaaatac aactaaacgt    60
gctattagca ctaaaaatgc cattcctatt ctttcatcaa taaaaattga agtcacttct   120
acaggagtaa ctttaacagg gtctaacggt caaatatcaa ttgaaaacac tattcctgta   180
agtaatgaaa atgctggttt gctaattacc tctccaggag ctattttatt agaagctagt   240
tttttttatta atattatttc aagtttgcca gatattagta taaatgttaa agaaattgaa   300
caacaccaag ttgttttaac cagtggtaaa tcagagatta ccttaaaagg aaaagatgtt   360
gaccagtatc ctcgtctaca agaagtatca acagaaaatc ctttgatttt aaaaacaaaa   420
ttattgaagt ctattattgc tgaaacagct tttgcagcca gtttacaaga aagtcgtcct   480
attttaacag gagttcatat tgtattaagt aatcataaag attttaaagc agtagcgact   540
gactctcatc gtatgagcca acgtttaatc actttggaca atacttcagc agatttgatg   600
```

-continued

```
gtagttcttc caagtaaatc tttgagagaa ttttcagcag tatttacaga tgatattgag   660
accgttgagg tattttctc accaagccaa atcttgttca gaagtgaaca catttctttt   720
tatacacgcc tcttagaagg aaattatccc gatacagacc gtttattaat gacagaattt   780
gagacggagg ttgttttcaa tacccaatcc cttcgccacg ctatgaacg tgccttcttg   840 acttccaatg ctactcaaaa tggtactgtt aagcttgaga ttactcaaaa tcatatttca   900
gctcatgtta actcacctga ggttggtaag gtaaacgagg atttagatac tgttagtcag   960
tctggtagtg atttaactat cagcttcaat ccaacttacc ttattgagtc tttaaaagcc  1020
attaaaagtg aaacagtaaa aattcatttc ttatcaccag ttcgaccatt caccctaaca  1080
ccaggcgatg aggaagaaag ttttatccaa ttaattacac cagtacgaac aaac        1134
```

The encoded β subunit has all amino acid sequence corresponding to SEQ. ID. No. 28 as follows:

```
Met Ile Gln Phe Ser Ile Asn Arg Thr Leu Phe Ile His Ala Leu Asn
 1               5                  10                  15

Thr Thr Lys Arg Ala Ile Ser Thr Lys Asn Ala Ile Pro Ile Leu Ser
                20                  25                  30

Ser Ile Lys Ile Glu Val Thr Ser Thr Gly Val Thr Leu Thr Gly Ser
                35                  40                  45

Asn Gly Gln Ile Ser Ile Glu Asn Thr Ile Pro Val Ser Asn Glu Asn
        50                  55                  60

Ala Gly Leu Leu Ile Thr Ser Pro Gly Ala Ile Leu Leu Glu Ala Ser
 65                  70                  75                  80

Phe Phe Ile Asn Ile Ile Ser Ser Leu Pro Asp Ile Ser Ile Asn Val
                85                  90                  95

Lys Gln Ile Gln Gln His Gln Val Val Leu Thr Ser Gly Lys Ser Glu
                100                 105                 110

Ile Thr Leu Lys Gly Lys Asp Val Asp Gln Tyr Pro Arg Leu Gln Glu
                115                 120                 125

Val Ser Thr Glu Asn Pro Leu Ile Leu Lys Thr Lys Leu Leu Lys Ser
        130                 135                 140

Ile Ile Ala Glu Thr Ala Phe Ala Ala Ser Leu Gln Glu Ser Arg Pro
145                 150                 155                 160

Ile Leu Thr Gly Val His Ile Val Leu Ser Asn His Lys Asp Phe Lys
                165                 170                 175

Ala Val Ala Thr Asp Ser His Arg Met Ser Gln Arg Leu Ile Thr Leu
                180                 185                 190

Asp Asn Thr Ser Ala Asp Leu Met Val Val Leu Pro Ser Lys Ser Leu
        195                 200                 205

Arg Glu Phe Ser Ala Val Phe Thr Asp Asp Ile Glu Thr Val Glu Val
        210                 215                 220

Phe Phe Ser Pro Ser Gln Ile Leu Phe Arg Ser Glu His Ile Ser Phe
225                 230                 235                 240

Tyr Thr Arg Leu Leu Glu Gly Asn Tyr Pro Asp Thr Asp Arg Leu Leu
                245                 250                 255

Met Thr Glu Phe Glu Thr Glu Val Val Phe Asn Thr Glu Ser Leu Arg
                260                 265                 270

His Ala Met Glu Arg Ala Phe Leu Ile Ser Asn Ala Thr Gln Asn Gly
                275                 280                 285
```

```
                            -continued
Thr Val Lys Leu Glu Ile Thr Gln Asn His Ile Ser Ala His Val Asn
    290                 295                 300

Ser Pro Glu Val Gly Lys Val Asn Glu Asp Leu Asp Ile Val Ser Gln
305                 310                 315                 320

Ser Gly Ser Asp Leu Thr Ile Ser Phe Asn Pro Thr Tyr Leu Ile Glu
                325                 330                 335

Ser Leu Lys Ala Ile Lys Ser Glu Thr Val Lys Ile His Phe Leu Ser
            340                 345                 350

Pro Val Arg Pro Phe Thr Leu Thr Pro Gly Asp Glu Glu Ser Phe
        355                 360                 365

Ile Gln Leu Ile Thr Pro Val Arg Thr Asn
    370                 375
```

The present invention also relates to the ssb gene of *Streptococcus pyogenes* encoding the single strand-binding protein (SSB). The ssb gene has a nucleotide sequence which corresponds to SEQ. ID. No. 29 as follows:

```
atgattaata atgtagtact agttggtcgc atgaccaagg atgcagaact tcgttacaca  60
ccaagtcaag tagctgtggc taccttcaca cttgctgtta accgtacctt taaaagccaa 120
aatggtgaac gcgaggcaga tttcattaac tgtgtgatct ggcgtcaacc ggctgaaaat 180
ttagcgaact gggctaaaaa aggtgctttg atcggagtta cgggtcgtat tcatacacgt 240
aactacgaaa accaacaagg acaacgtgtc tatgtaacag aagttgttgc agataatttc 300
caaatgttgg aaagtcgtgc tacacgtgaa ggtggctcaa ctggctcatt taatggtggt 360
tttaacaata acacttcatc atcaaacagt tactcagcgc ctgcacaaca aacgcctaac 420
tttggaagag atgatagccc atttgggaac tcaaacccga tggatatctc agatgacgat 480
cttccattct ag                                                    492
```

The encoded SSB protein has an amino acid sequence corresponding to SEQ. ID. No. 30 as follows:

```
Met Ile Asn Asn Val Val Leu Val Gly Arg Met Thr Lys Asp Ala Glu
  1               5                  10                  15

Leu Arg Tyr Thr Pro Ser Gln Val Ala Val Ala Thr Phe Thr Leu Ala
                20                  25                  30

Val Asn Arg Thr Phe Lys Ser Gln Asn Gly Glu Arg Glu Ala Asp Phe
            35                  40                  45

Ile Asn Cys Val Ile Trp Arg Gln Pro Ala Glu Asn Leu Ala Asn Trp
        50                  55                  60

Ala Lys Lys Gly Ala Leu Ile Gly Val Thr Gly Arg Ile Gln Thr Arg
 65                  70                  75                  80

Asn Tyr Glu Asn Gln Gln Gly Gln Arg Val Tyr Val Thr Glu Val Val
                85                  90                  95

Ala Asp Asn Phe Gln Met Leu Glu Ser Arg Ala Thr Arg Glu Gly Gly
            100                 105                 110

Ser Thr Gly Ser Phe Asn Gly Gly Phe Asn Asn Asn Thr Ser Ser Ser
            115                 120                 125

Asn Ser Tyr Ser Ala Pro Ala Gln Gln Thr Pro Asn Phe Gly Arg Asp
            130                 135                 140
```

Asp Ser Pro Phe Gly Asn Ser Asn Pro Met Asp Ile Ser Asp Asp Asp
145                 150                 155                 160

Leu Pro Phe

The present invention also relates to the dnaG gene of *Streptococcus pyogenes* encoding the primase. The dnaG gene has a nucleotide sequence which corresponds to SEQ. ID. No. 31 as follows:

```
atgggatttt tatggggagg tgacgatttg gcaattgaca aagaaatgat ttcccaagta     60
aaaaatagcg ttaatattgt cgatgtcatt ggagaagtgg tcaaactttc ccgatcaggg    120
cggcattacc tcgggctttg cccatttcat aaggaaaaga caccctcttt taatgttgtt    180
gaagacagac aatttttca ctgctttggc tgtggaaaat caggggatgt ttttaaattt     240
attgaggaat accgccaagt cccttctta gaaagtgttc agattattgc cgataagact    300
ggtatgtcgc ttaatatacc gccaagtcag gcagtacttg ctagccaaca caagcaccct    360
aatcacgctt tgatgacact tcatgaggat gctgctaaat tttaccatgc agttttgatg    420
accactacca ttggtcaaga agctaggaag tacctttacc agagaggctt ggatgaccaa    480
ttaattgagc atttcaatat tggtttagcc ccagatgagt cagattatct ttatcaagct    540
ctttctaaaa aatacgagga aggtcaattg gttgcttcag gattgtttca cttgtccgat    600
caatccaata ccatttacga cgcctttcga aatcgtatca tgtttccctt atcagatgac    660
cgagggcata ttattgcctt ttcaggacgt atctggacgg cagctgatat ggaaaagaga    720
caggcaaagt ataaaaattc aagaggaaca gttcttttta acaaatctta tgaattgtat    780
catctggaca aggcaaggcc tgttattgcc aaaacccatg aagtgtttct aatggaaggg    840
tttatggacg tgattgccgc ttaccgttcc ggctatgaaa atgctgttgc ttcaatgggg    900
acggcattga ctcaagaaca tgtcaatcac cttaagcaag tcactaaaaa agttgttttg    960
atttatgatg gtgacgatgc tggacaacat gctattgcaa atcactaga attgcttaaa   1020
gattttgtcg tcgaaattgt cagaatcccc aataaaatgg atcctgacga atttgtacaa   1080
cggcattccc cagaagcatt tgcagatttg cttaagcagt cacggatcag tagtgttgaa   1140
ttttttattg attacctaaa acctactaat gtagacaatt tgcaatcaca aattgtttat   1200
gtggagaaaa tggcaccatt gattgctcaa tcaccatcca tcacagctca acattcgtat   1260
attaacaaga ttgctgattt gttgccaaac tttgactatt tcaagtaga acaatcagta    1320
aatgcattaa ggattcaaga taggcaaaaa catcaaggtc aaatagctca agccgtcagc   1380
aatcttgtga ccttaccaat gccaaaaagt ttgacagcta ttgctaagac agaaagtcat   1440
ctcatgcatc ggctcttaca tcatgactat ttattaaatg aatttcgaca tcgtgatgat   1500
ttttatttg atacctctac cttagaatta ctttatcaac ggctgaagca acaaggacac   1560
attacatctt atgatttgtc agagatgtca gaggaagtta accgtgctta ttacaatgtt   1620
ttagaagaaa accttcccaa agaagtagct cttggtgaga ttgatgatat tttatccaaa   1680
cgtgccaaac ttttagcaga gcgcgatctt cacaaacaag ggaaaaaagt tagagaatct   1740
agtaacaaag gcgatcatca agcggctcta gaagtactag aacatttat tgcgcagaaa   1800
cgaaaaatgg aatag                                                    1815
```

The encoded primase has an amino acid sequence corresponding to SEQ. ID. No. 32 as follows:

```
Met Gly Phe Leu Trp Gly Gly Asp Asp Leu Ala Ile Asp Lys Glu Met
 1               5                  10                  15

Ile Ser Gln Val Lys Asn Ser Val Asn Ile Val Asp Val Ile Gly Glu
             20                  25                  30

Val Val Lys Leu Ser Arg Ser Gly Arg His Tyr Leu Gly Leu Cys Pro
             35                  40                  45

Phe His Lys Glu Lys Thr Pro Ser Phe Asn Val Val Glu Asp Arg Gln
             50                  55                  60

Phe Phe His Cys Phe Gly Cys Gly Lys Ser Gly Asp Val Phe Lys Phe
 65              70                  75                  80

Ile Glu Glu Tyr Arg Gln Val Pro Phe Leu Glu Ser Val Gln Ile Ile
             85                  90                  95

Ala Asp Lys Thr Gly Met Ser Leu Asn Ile Pro Pro Ser Gln Ala Val
             100                 105                 110

Leu Ala Ser Gln His Lys His Pro Asn His Ala Leu Met Thr Leu His
             115                 120                 125

Glu Asp Ala Ala Lys Phe Tyr His Ala Val Leu Met Thr Thr Thr Ile
 130                 135                 140

Gly Gln Glu Ala Arg Lys Tyr Leu Tyr Gln Arg Gly Leu Asp Asp Gln
 145                 150                 155                 160

Leu Ile Glu His Phe Asn Ile Gly Leu Ala Pro Asp Glu Ser Asp Tyr
             165                 170                 175

Leu Tyr Gln Ala Leu Ser Lys Lys Tyr Glu Glu Gly Gln Leu Val Ala
             180                 185                 190

Ser Gly Leu Phe His Leu Ser Asp Gln Ser Asn Thr Ile Tyr Asp Ala
             195                 200                 205

Phe Arg Asn Arg Ile Met Phe Pro Leu Ser Asp Arg Gly His Ile
 210                 215                 220

Ile Ala Phe Ser Gly Arg Ile Trp Thr Ala Ala Asp Met Glu Lys Arg
 225                 230                 235                 240

Gln Ala Lys Tyr Lys Asn Ser Arg Gly Thr Val Leu Phe Asn Lys Ser
             245                 250                 255

Tyr Glu Leu Tyr His Leu Asp Lys Ala Arg Pro Val Ile Ala Lys Thr
             260                 265                 270

His Glu Val Phe Leu Met Glu Gly Phe Met Asp Val Ile Ala Ala Tyr
             275                 280                 285

Arg Ser Gly Tyr Glu Asn Ala Val Ala Ser Met Gly Thr Ala Leu Thr
 290                 295                 300

Gln Glu His Val Asn His Leu Lys Gln Val Thr Lys Lys Val Val Leu
 305                 310                 315                 320

Ile Tyr Asp Gly Asp Ala Gly Gln His Ala Ile Ala Lys Ser Leu
             325                 330                 335

Glu Leu Leu Lys Asp Phe Val Val Glu Ile Val Arg Ile Pro Asn Lys
             340                 345                 350

Met Asp Pro Asp Glu Phe Val Gln Arg His Ser Pro Glu Ala Phe Ala
             355                 360                 365

Asp Leu Leu Lys Gln Ser Arg Ile Ser Ser Val Glu Phe Phe Ile Asp
             370                 375                 380

Tyr Leu Lys Pro Thr Asn Val Asp Asn Leu Gln Ser Gln Ile Val Tyr
 385                 390                 395                 400

Val Glu Lys Met Ala Pro Leu Ile Ala Gln Ser Pro Ser Ile Thr Ala
             405                 410                 415

Gln His Ser Tyr Ile Asn Lys Ile Ala Asp Leu Leu Pro Asn Phe Asp
             420                 425                 430
```

```
Tyr Phe Gln Val Glu Gln Ser Val Asn Ala Leu Arg Ile Gln Asp Arg
        435                 440                 445

Gln Lys His Gln Gly Gln Ile Ala Gln Ala Val Ser Asn Leu Val Thr
    450                 455                 460

Leu Pro Met Pro Lys Ser Leu Thr Ala Ile Ala Lys Thr Glu Ser His
465                 470                 475                 480

Leu Met His Arg Leu Leu His His Asp Tyr Leu Leu Asn Glu Phe Arg
                485                 490                 495

His Arg Asp Asp Phe Tyr Phe Asp Thr Ser Thr Leu Glu Leu Leu Tyr
            500                 505                 510

Gln Arg Leu Lys Gln Gln Gly His Ile Thr Ser Tyr Asp Leu Ser Glu
        515                 520                 525

Met Ser Glu Glu Val Asn Arg Ala Tyr Tyr Asn Val Leu Glu Glu Asn
    530                 535                 540

Leu Pro Lys Glu Val Ala Leu Gly Glu Ile Asp Asp Ile Leu Ser Lys
545                 550                 555                 560

Arg Ala Lys Leu Leu Ala Glu Arg Asp Leu His Lys Gln Gly Lys Lys
                565                 570                 575

Val Arg Glu Ser Ser Asn Lys Gly Asp His Gln Ala Ala Leu Glu Val
            580                 585                 590

Leu Glu His Phe Ile Ala Gln Lys
        595                 600
```

The present invention also relates to the dnaB gene of *Streptococcus pyogenes* encoding DnaB. The dnaB gene has a nucleotide sequence which corresponds to SEQ. ID. No. 33 as follows:

```
atgaggttgc ctgaagtagc tgaattacga gttcaacccc aagatttact agcagagcaa   60
tctgttcttg ggtcaatctt tatctcacct gataagctga ttgcagtgag agaatttatc  120
agtccagacg attttttataa gtacgctcat aaaattatct tcgggcaat gattaccctc  180
agcgatcgta atgatgccat tgatgcaacc actataagaa caatcctaga tgatcaagat  240
gatctgcaaa gtattggtgg cttatcctat attgttgaac tagttaatag tgtcccaact  300
agtgctaatg cagaatatta tgctaaaatt gtagctgaga aagctatgtt gcgtgatatt  360
attgctaggt tgacagaatc tgtcaaccta gcttatgatg aaattttaaa accagaagag  420
gttatcgctg gagttgagag agctttaatt gaactcaatg aacatagtaa tcgtagtggg  480
tttcgcaaaa tttcagatgt gctaaaagtt aattacgagg ctttagaagc acgttctaag  540
cagacttcaa atgttacagg tttaccaact ggttttagag accttgacaa gattacaaca  600
ggtttacacc cagatcaatt agttatttta gctgctcggc cagcagtggg gaagactgcc  660
tttgttctta atattgcgca aaatgtgggg actaagcaaa aaagactgt tgctattttt  720
tctttggaaa tgggtgctga agtttagta gatcgtatgc ttgcagcaga aggaatggtt  780
gattcgcaca gttaagaac agggcaactc acagatcagg attggaataa tgtaacaatt  840
gctcagggag ctttggcaga agcaccgatt tatattgacg atacgcccgg gattaaaatt  900
actgaaatcc gcgcaagatc acggaaattg tctcaagaag tggatggtgg tttaggtctc  960
attgtaattg actacttaca gttgattaca ggaactaaac ccgaaaatcg tcagcaagag 1020
gtttcagata tttcaagaca gcttaaaatc ctagctaaag aattgaaagt accagttatt 1080
gccctaagtc agctttctcg tggcgttgag caaaggcaag ataaacgacc agttttatca 1140
```

```
gatattcgtg aatcaggatc tattgagcag gatgccgata ttgtagcctt cttataccgg 1200
gacgattatt accgtaaaga atgtgatgat gctgaagaag ctgttgaaga taacacaatt 1260
gaagttatcc tcgagaaaaa tagagctggg gcgcgtggaa cagtcaaact gatgttccaa 1320
aaagaataca acaaattctc aagtatagcc cagtttgaag aaagataa                1368
```

The encoded DnaB has an amino acid sequence corresponding to SEQ. ID. No. 34 as follows:

```
Met Arg Leu Pro Glu Val Ala Glu Leu Arg Val Gln Pro Gln Asp Leu
 1               5                  10                  15

Leu Ala Glu Gln Ser Val Leu Gly Ser Ile Phe Ile Ser Pro Asp Lys
            20                  25                  30

Leu Ile Ala Val Arg Glu Phe Ile Ser Pro Asp Asp Phe Tyr Lys Tyr
        35                  40                  45

Ala His Lys Ile Ile Phe Arg Ala Met Ile Thr Leu Ser Asp Arg Asn
    50                  55                  60

Asp Ala Ile Asp Ala Thr Thr Ile Arg Thr Ile Leu Asp Asp Gln Asp
65                  70                  75                  80

Asp Leu Gln Ser Ile Gly Gly Leu Ser Tyr Ile Val Glu Leu Val Asn
            85                  90                  95

Ser Val Pro Thr Ser Ala Asn Ala Glu Tyr Tyr Ala Lys Ile Val Ala
            100                 105                 110

Glu Lys Ala Met Leu Arg Asp Ile Ile Ala Arg Leu Thr Glu Ser Val
            115                 120                 125

Asn Leu Ala Tyr Asp Glu Ile Leu Lys Pro Glu Glu Val Ile Ala Gly
            130                 135                 140

Val Glu Arg Ala Gln Gly Ala Leu Ala Glu Ala Pro Ile Tyr Ile Asp
145                 150                 155                 160

Asp Thr Pro Gly Ile Lys Ile Ala Leu Ile Glu Leu Asn Glu His Ser
                165                 170                 175

Asn Arg Ser Gly Phe Arg Lys Ile Ser Asp Val Leu Lys Val Asn Tyr
            180                 185                 190

Glu Ala Leu Glu Ala Arg Ser Lys Gln Thr Ser Asn Val Thr Gly Leu
            195                 200                 205

Pro Thr Gly Phe Arg Asp Leu Asp Lys Ile Thr Thr Gly Leu His Pro
            210                 215                 220

Asp Gln Leu Val Ile Leu Ala Ala Arg Pro Ala Val Gly Lys Thr Ala
225                 230                 235                 240

Phe Val Leu Asn Ile Ala Gln Asn Val Gly Thr Lys Gln Lys Lys Thr
                245                 250                 255

Val Ala Ile Phe Ser Leu Gln Met Gly Ala Gln Ser Leu Val Asp Arg
            260                 265                 270

Met Leu Ala Ala Gln Gly Met Val Asp Ser His Ser Leu Arg Thr Gly
            275                 280                 285

Gln Leu Thr Asp Gln Asp Trp Asn Asn Val Thr Ile Thr Glu Ile Arg
            290                 295                 300

Ala Arg Ser Arg Lys Leu Ser Gln Gln Val Asp Gly Gly Leu Gly Leu
305                 310                 315                 320

Ile Val Ile Asp Tyr Leu Gln Leu Ile Thr Gly Thr Lys Pro Gln Asn
                325                 330                 335
```

-continued

```
Arg Gln Gln Glu Val Ser Asp Ile Ser Arg Gln Leu Lys Ile Leu Ala
            340             345                 350

Lys Gln Leu Lys Val Pro Val Ile Ala Leu Ser Gln Leu Ser Arg Gly
        355             360             365

Val Gln Gln Arg Gln Asp Lys Arg Pro Val Leu Ser Asp Ile Arg Glu
    370             375             380

Ser Gly Ser Ile Glu Gln Asp Ala Asp Ile Val Ala Phe Leu Tyr Arg
385             390             395             400

Asp Asp Tyr Tyr Arg Lys Glu Cys Asp Asp Ala Glu Glu Ala Val Glu
            405             410             415

Asp Asn Thr Ile Glu Val Ile Leu Glu Lys Asn Arg Ala Gly Ala Arg
            420             425             430

Gly Thr Val Lys Leu Met Phe Gln Lys Glu Tyr Asn Lys Phe Ser Ser
        435             440             445

Ile Ala Gln Phe Glu Glu Arg
    450             455
```

Fragments of the above polypeptides or proteins are also encompassed by the present invention.

Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for activity according to the procedures described below.

As an alternative, fragments of replication proteins can be produced by digestion of a full-length replication protein with proteolytic enzymes like chymotrypsin or *Staphylococcus* proteinase A, or trypsin. Different proteolytic enzymes are likely to cleave replication proteins at different sites based on the amino acid sequence of the protein. Some of the fragments that result from proteolysis may be active and can be tested for activity as described below.

In another approach, based on knowledge of the primary structure of the protein, fragments of a replication protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences of replication proteins being produced. Alternatively, subjecting a full length replication protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which cotranslationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of at least about 20, more preferably at least about 30 to about 50, continuous bases of either SEQ. ID. Nos. 1, 3, 5, 7, 9, 11, 13, 15, 17, 19, 21, 23, 25, 27, 29, 31, or 33 under stringent conditions such as those characterized by a hybridization buffer comprising 0.9 M sodium citrate ("SSC") buffer at a temperature of about 37° C. and remaining bound when subject to washing the SSC buffer at a temperature of about 37° C.; and preferably in a hybridization buffer comprising 20% formamide in 0.9 M SSC buffer at a temperature of about 42° C. and remaining bound when subject to washing at about 42° C. with 0.2×SSC buffer. Stringency conditions can be further varied by modifying the temperature and/or salt content of the buffer, or by modifying the length of the hybridization probe.

The proteins or polypeptides of the present invention are preferably produced in purified form (preferably at least 80%, more preferably 90%, pure) by conventional techniques. Typically, the proteins or polypeptides of the present invention is secreted into the growth medium of recombinant host cells. Alternatively, the proteins or polypeptides of the present invention are produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to purification procedures such as ammonium sulfate precipitation, gel filtration, ion exchange chromatography, FPLC, and HPLC.

The DNA molecule encoding replication polypeptides or proteins derived from Gram positive bacteria can be incorporated in cells using conventional recombinant DNA technology. Generally, this involved inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/(see "Stratagene Cloning Systems" Catalog (1993) from Stratagene, La Jolla, Calif, which is hereby incorporated by reference), pQE, pIH821, pGEX, pET series (see F. W. Studier et al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further procaryotic promoters are not recognized and do not function in eucaryotic cells.

Similarly, translation of mRNA in procaryotes depends upon the presence of the proper procaryotic signals which differ from those of eukaryotes. Efficient translation of mRNA in procaryotes requires a ribosome binding site called the Shine-Dalgarno ("SD") sequence on the mRNA. This sequence is a short nucleotide sequence of mRNA that is located before the same codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited to, lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls. Additionally, the cell may carry the gene for a heterologous RNA polymerase such as from phage T7. Thus, a promoter specific for T7 RNA polymerase is used. The T7 RNA polymerase may be under inducible control.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, an SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding a replication polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, viruses, yeast, mammalian cells, insects, plants, and the like.

The invention provides efficient methods of identifying pharmacological agents or lead compounds for agents active at the level of a replication protein function, particularly DNA replication. Generally, these screening methods involve assaying for compounds which interfere with the replication activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of a replication activity or the formation of a complex comprising a replication protein and one or more natural intracellular binding targets. Target indications may include arresting cell growth or causing cell death resulting in recovery from the bacterial infection in animal studies.

A wide variety of assays for activity and binding agents are provided, including DNA synthesis, ATPase, clamp loading onto DNA, protein-protein binding assays, immunoassays, cell based assays, etc. The replication protein compositions, used to identify pharmacological agents, are in isolated, partially pure or pure form and are typically recombinantly produced. The replication protein may be part of a fusion product with another peptide or polypeptide (e.g., a polypeptide that is capable of providing or enhancing protein-protein binding, stability under assay conditions (e.g., a tag for detection or anchoring), etc.). The assay mixtures comprise a natural intracellular replication protein binding target such as DNA, another protein, NTP, or dNTP. For binding assays, while native binding targets may be used, it is frequently preferred to use portions (e.g., peptides, nucleic acid fragments) thereof so long as the portion provides binding affinity and avidity to the subject replication protein conveniently measurable in the assay. The assay mixture also comprises a candidate pharmacological agent. Generally, a plurality of assay mixtures are run in parallel with different agent concentrations to obtain a differential response to the various concentrations. Typically, one of these concentrations serves as a negative control (i.e., at zero concentration or below the limits of assay detection). Additional controls are often present such as a positive control, a dose response curve, use of known inhibitors, use of control heterologous proteins, etc. Candidate agents encompass numerous chemical classes, though typically they are organic compounds; preferably they are small organic compounds and are obtained from a wide variety of sources, including libraries of synthetic or natural compounds. A variety of other reagents may also be included in the mixture. These include reagents like salts, buffers, neutral proteins (e.g., albumin, detergents, etc.), which may be used to facilitate optimal binding and/or reduce nonspecific or background interactions, etc. Also reagents that otherwise improve the efficiency of the assay (e.g., protease inhibitors, nuclease inhibitors, antimicrobial agents, etc.) may be used.

The invention provides replication protein specific assays and the binding agents including natural intracellular binding targets such as other replication proteins, etc., and methods of identifying and making such agents, and their use in a variety of diagnostic and therapeutic applications, especially where disease is associated with excessive cell growth. Novel replication protein-specific binding agents include replication protein-specific antibodies and other natural intracellular binding agents identified with assays such as one- and two-hybrid screens, non-natural intracellular binding agents identified in screens of chemical libraries, etc.

Generally, replication protein-specificity of the binding agent is shown by binding equilibrium constants. Such agents are capable of selectively binding a replication protein (i.e., with an equilibrium constant at least about $10^7$ $M^{-1}$, preferably, at least about $10^8$ $M^{-1}$, more preferably, at least about $10^9$ $M^{-1}$). A wide variety of cell-based and cell-free assays may be used to demonstrate replication protein-specific activity, binding, gel shift assays, immunoassays, etc.

The resultant mixture is incubated under conditions whereby, but for the presence of the candidate pharmacological agent, the replication protein specifically binds the cellular binding target, portion, or analog. The mixture of components can be added in any order that provides for the requisite bindings. Incubations may be performed at any temperature which facilitates optimal binding, typically between 4° C. and 40° C., more commonly between 15° C. and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of activity or specific binding between the replication protein and one or more binding targets is detected by any convenient way. For cell-free activity and binding type assays, a separation step may be used to separate the activity product or the bound from unbound components. Separation may be effected by precipitation (e.g., immunoprecipitation), immobilization (e.g., on a solid substrate such as a microtiter plate), etc., followed by washing. Many assays that do not require separation are also possible such as use of europium conjugation in proximity assays or a detection system that is dependent on a product or loss of substrate.

Detection may be effected in any convenient way. For cell-free activity and binding assays, one of the components usually comprises or is coupled to a label. A wide variety of labels may be employed—essentially any label that provides for detection of DNA product, loss of DNA substrate, conversion of a nucleotide substrate, or bound protein is useful. The label may provide for direct detection such as radioactivity, fluorescence, luminescence, optical, or electron density, etc. or indirect detection such as an epitope tag, an enzyme, etc. The label may be appended to the protein (e.g., a phosphate group comprising a radioactive isotope of phosphorous), or incorporated into the DNA substrate or the protein structure (e.g., a methionine residue comprising a radioactive isotope of sulfur.) A variety of methods may be used to detect the label depending on the nature of the label and other assay components. For example, the label may be detected bound to the solid substrate, or a portion of the bound complex containing the label may be separated from the solid substrate, and thereafter the label detected. Labels may be directly detected through optical or electron density, radioactive emissions, nonradiative energy transfer, fluorescence emission, etc. or indirectly detected with antibody conjugates, etc. For example, in the case of radioactive labels, emissions may be detected directly (e.g., with particle counters) or indirectly (e.g., with scintillation cocktails and counters).

The present invention identifies the set of proteins that together result in a three component polymerase from bacteria that are distantly related to E. coli, such as Gram positive bacteria. Specifically, these bacteria lack several genes that E. coli DNA polymerase III has, such as holD, holD or holE. Further, dnaX is believed to encode only one protein, tau. Also, holA is quite divergent in homology suggesting it may function in another process in these organisms. Gram positive cells even have replication genes that E. coli does not, implying that they may not utilize the replication strategies exemplified by E. coli.

The present invention identifies genes and proteins that form a three component polymerase in Gram positive organisms, such as S. pyogenes and S. aureus. In S. pyogenes and S. aureus, the polymerase α-large, functions with a β clamp and a clamp loader component of τδδ'. They display high speed and processivity in synthesis of ssDNA coated with SSB and primed with a DNA oligonucleotide.

This invention also expresses and purifies a protein from a Gram positive bacteria that is homologous to the E. coli beta subunit. The invention demonstrates that it behaves like a circular protein. Further, this invention shows that a beta subunit from a Gram positive bacteria is functional with both Pol III-L α-large) from a Gram positive bacteria and with DNA polymerase III from a Gram negative bacteria. This result can be explained by an interaction between the clamp and the polymerase that has been conserved during the evolutionary divergence of Gram positive and Gram negative cells. A chemical inhibitor that would disrupt this interaction would be predicted to have a broad spectrum of antibiotic activity, shutting down replication in gram negative and gram positive cells alike. This assay, and others based on this interaction, can be devised to screen chemicals for such inhibition. Further, since all the proteins in this assay are highly overexpressed through recombinant techniques, sufficient quantities of the protein reagents can be obtained for screening hundreds of thousands of compounds.

This invention also shows that the DnaE polymerase (α-small), encoded by the dnaE gene, functions with the beta clamp and τδδ' complex. The speed of DnaE is not significantly increased by τδδ' and β, but the processivity of DnaE is greatly increased by τδδ' and β. Hence, the DnaE polymerase, coupled with its β clamp on DNA (loaded by τδδ') may also be an important target for a candidate pharmaceutical drug.

The present invention provides methods by which replication proteins from a Gram positive bacteria are used to discover new pharmaceutical agents. The function of replication proteins is quantified in the presence of different chemical compounds. A chemical compound that inhibits the function is a candidate antibiotic. Some replication proteins from a Gram positive bacteria and from a Gram negative bacteria can be interchanged for one another. Hence, they can function as mixtures. Reactions that assay for the function of enzyme mixtures consisting of proteins from Gram positive bacteria and from Gram negative bacteria can also be used to discover drugs. Suitable *E. coli* replication proteins are the subunits of its Pol III holoenzyme which are described in U.S. Pat. Nos. 5,583,026 and 5,668,004 to O'Donnell, which are hereby incorporated by reference.

The methods described herein to obtain genes, and the assays demonstrating activity behavior of *S. pyogenes* and *S. aureus* replication proteins are likely to generalize to all members of the *Streptococcus* and *Staphylococcus* genuses, as well as to all Gram positive bacteria. Such assays are also likely to generalize to other cells besides Gram positive bacteria which also share features in common with *S. pyogenes* and *S. aureus* that are different from *E. coli* (i.e., lacking holC, holD, or holE; having a dnaX gene encoding a single protein; or having a weak homology to holA encoding delta).

The present invention describes a method of identifying compounds which inhibit the activity of a polymerase product of polC or dnaE. This method is carried out by forming a reaction mixture that includes a primed DNA molecule, a polymerase product of polC or dnaE, a candidate compound, a dNTP, and optionally either a beta subunit, a tau complex, or both the beta subunit and the tau complex, wherein at least one of the polymerase product of polC or dnaE, the beta subunit, the tau complex, or a subunit or combination of subunits thereof is derived from a Eubacteria other than *Escherichia coli*; subjecting the reaction mixture to conditions effective to achieve nucleic acid polymerization in the absence of the candidate compound; analyzing the reaction mixture for the presence or absence of nucleic acid polymerization extension products; and identifying the candidate compound in the reaction mixture where there is an absence of nucleic acid polymerization extension products. Preferably, the polymerase product of polC or dnaE, the beta subunit, the tau complex, or the subunit or combination of subunits thereof is derived from a Gram positive bacterium, more preferably a *Streptococcus* bacterium such as *S. pyogenes* or a *Staphylococcus* bacterium such as *S. aureus*.

The present invention describes a method to identify chemicals that inhibit the activity of the three component polymerase. This method involves contacting primed DNA with the DNA polymerase in the presence of the candidate pharmaceutical, and dNTPs (or modified dNTPs) to form a reaction mixture. The reaction mixture is subjected to conditions effective to achieve nucleic acid polymerization in the absence of the candidate pharmaceutical and the presence or absence of the extension product in the reaction mixture is analyzed. The candidate pharmaceutical is detected by the absence of product.

The present invention describes a method to identify candidate pharmaceuticals that inhibit the activity of a clamp loader complex and a beta subunit in stimulating the DNA polymerase. The method includes contacting a primed DNA (which may be coated with SSB) with a DNA polymerase, a beta subunit, and a tau complex (or subunit or subassembly of the tau complex) in the presence of the candidate pharmaceutical, and dNTPs (or modified dNTPs) to form a reaction mixture. The reaction mixture is subjected to conditions which, in the absence of the candidate pharmaceutical, would effect nucleic acid polymerization and the presence or absence of the extension product in the reaction mixture is analyzed. The candidate pharmaceutical is detected by the absence of product. The DNA polymerase, the beta subunit, and/or the tau complex or subunit(s) thereof are derived from a Gram positive bacterium.

The present invention describes a method to identify chemicals that inhibit the ability of a beta subunit and a DNA polymerase to interact physically. This method involves contacting the beta subunit with the DNA polymerase in the presence of the candidate pharmaceutical to form a reaction mixture. The reaction mixture is subjected to conditions under which the DNA polymerase and the beta subunit would interact in the absence of the candidate pharmaceutical. The reaction mixture is then analyzed for interaction between the beta unit and the DNA polymerase. The candidate pharmaceutical is detected by the absence of interaction between the beta subunit and the DNA polymerase. The DNA polymerase and/or the beta subunit are derived from a Gram positive bacterium.

The present invention describes a method to identify chemicals that inhibit the ability of a beta subunit and a tau complex (or a subunit or subassembly of the tau complex) to interact. This method includes contacting the beta subunit with the tau complex (or subunit or subassembly of the tau complex) in the presence of the candidate pharmaceutical to form a reaction mixture. The reaction mixture is subjected to conditions under which the tau complex (or the subunit or subassembly of the tau complex) and the beta subunit would interact in the absence of the candidate pharmaceutical. The reaction mixture is then analyzed for interaction between the beta subunit and the tau complex (or the subunit or subassembly of the tau complex). The candidate pharmaceutical is detected by the absence of interaction between the beta subunit and the tau complex (or the subunit or subassembly of the tau complex). The beta subunit and/or the tau complex or subunit thereof is derived from a Gram positive bacterium.

The present invention describes a method to identify chemicals that inhibit the ability of a tau complex (or a subassembly of the tau complex) to assemble a beta subunit onto a DNA molecule. This method involves contacting a circular primed DNA molecule (which may be coated with SSB) with the tau complex (or the subassembly thereof) and the beta subunit in the presence of the candidate pharmaceutical, and ATP or dATP to form a reaction mixture. The reaction mixture is subjected to conditions under which the tau complex (or subassembly) assembles the beta subunit on the DNA molecule absent the candidate pharmaceutical. The presence or absence of the beta subunit on the DNA molecule in the reaction mixture is analyzed. The candidate pharmaceutical is detected by the absence of the beta subunit on the DNA molecule. The beta subunit and/or the tau complex are derived from a Gram positive bacterium.

The present invention describes a method to identify chemicals that inhibit the ability of a tau complex (or a subunit(s) of the tau complex) to disassemble a beta subunit from a DNA molecule. This method comprises contacting a DNA molecule onto which the beta subunit has been assembled in the presence of the candidate pharmaceutical, to form a reaction mixture. The reaction mixture is subjected to conditions under which the tau complex (or a subunit(s) or subassembly of the tau complex) disassembles the beta subunit from the DNA molecule absent the candidate pharmaceutical. The presence or absence of the beta subunit on the DNA molecule in the reaction mixture is analyzed. The candidate pharmaceutical is detected by the presence of the beta subunit on the DNA molecule. The beta subunit and/or the tau complex are derived from a Gram positive bacterium.

The present invention describes a method to identify chemicals that disassemble a beta subunit from a DNA molecule. This method involves contacting a circular primed DNA molecule (which may be coated with SSB) upon which the beta subunit has been assembled (e.g. by action of the tau complex) with the candidate pharmaceutical. The presence or absence of the beta subunit on the DNA molecule in the reaction mixture is analyzed. The candidate pharmaceutical is detected by the absence of the beta subunit on the DNA molecule. The beta subunit is derived from a Gram positive bacterium.

The present invention describes a method to identify chemicals that inhibit the dATP/ATP binding activity of a tau complex or a tau complex subunit (e.g. tau subunit). This method includes contacting the tau complex (or the tau complex subunit) with dATP/ATP either in the presence or absence of a DNA molecule and/or the beta subunit in the presence of the candidate pharmaceutical to form a reaction. The reaction mixture is subjected to conditions in which the tau complex (or the subunit of tau complex) interacts with dATP/ATP in the absence of the candidate pharmaceutical. The reaction is analyzed to determine if dATP/ATP is bound to the tau complex (or the subunit of tau complex) in the presence of the candidate pharmaceutical. The candidate pharmaceutical is detected by the absence of hydrolysis. The tau complex and/or the beta subunit is derived from a Gram positive bacterium.

The present invention describes a method to identify chemicals that inhibit the dATP/ATPase activity of a tau complex or a tau complex subunit (e.g., the tau subunit). This method involves contacting the tau complex (or the tau complex subunit) with dATP/ATP either in the presence or absence of a DNA molecule and/or a beta subunit in the presence of the candidate pharmaceutical to form a reaction mixture. The reaction mixture is subjected to conditions in which the tau subunit (or complex) hydrolyzes dATP/ATP in the absence of the candidate pharmaceutical. The reaction is analyzed to determine if dATP/ATP was hydrolyzed. Suitable candidate pharmaceuticals are identified by the absence of hydrolysis. The tau complex and/or the beta subunit is derived from a Gram positive bacterium.

Further methods for identifying chemicals that inhibit the activity of a DNA polymerase encoded by either the dnaE gene, polC gene, or their accessory proteins (i.e., clamp loader, clamp, etc.), are as follows:

1) Contacting a primed DNA molecule with the encoded product of the dnaE gene or polC gene in the presence of the candidate pharmaceutical, and dNTPs (or modified dNTPs) to form a reaction mixture. The reaction mixture is subjected to conditions, which in the absence of the candidate pharmaceutical, affect nucleic acid polymerization and the presence or absence of the extension product in the reaction mixture is analyzed. The candidate pharmaceutical is detected by the absence of extension product. The protein encoded by the dnaE gene and PolC gene is derived from a Gram positive bacterium.

2) Contacting a linear primed DNA molecule with a beta subunit and the encoded product of dnaE or PolC in the presence of the candidate pharmaceutical, and dNTPs (or modified dNTPs) to form a reaction mixture. The reaction mixture is subjected to conditions, which in the absence of the candidate pharmaceutical, affect nucleic acid polymerization, and the presence or absence of the extension product in the reaction mixture is analyzed. The candidate pharmaceutical is detected by the absence of extension product. The protein encoded by the dnaE gene and PolC gene is derived from a Gram positive bacterium.

3) Contacting a circular primed DNA molecule (may be coated with SSB) with a tau complex, a beta subunit and the encoded product of a dnaE gene or PolC gene in the presence of the candidate pharmaceutical, and dNTPs (or modified dNTPs) to form a reaction mixture. The reaction mixture is subjected to conditions, which in the absence of the candidate pharmaceutical, affect nucleic acid polymerization, and the presence or absence of the extension product in the reaction mixture is analyzed. The candidate pharmaceutical is detected by the absence of product. The protein encoded by the dnaE gene and PolC gene, the beta subunit, and/or the tau complex are derived from a Gram positive bacterium.

4) Contacting a beta subunit with the product encoded by a dnaE gene or PolC gene in the presence of the candidate pharmaceutical to form a reaction mixture. The reaction mixture is then analyzed for interaction between the beta subunit and the product encoded by the dnaE gene or PolC gene. The candidate pharmaceutical is detected by the absence of interaction between the beta subunit and the product encoded by the dnaE gene or PolC gene. The beta subunit and/or the protein encoded by the dnaE gene and PolC gene is derived from a Gram positive bacterium.

5) The present invention discloses a method to identify chemicals that inhibit a DnaB helicase. The method includes contacting the DnaB helicase with a DNA molecule substrate that has a duplex region in the presence of a nucleoside or deoxynucleoside triphosphate energy source and a candidate pharmaceutical to form a reaction mixture. The reaction mixture is subjected to conditions that support helicase activity in the absence of the candidate pharmaceutical. The DNA duplex molecule in the reaction mixture is analyzed for whether it is converted to ssDNA. The candidate pharmaceutical is detected by the absence of conversion of the duplex DNA molecule to the ssDNA molecule. The DnaB helicase is derived from a Gram positive bacterium.

6) The present invention describes a method to identify chemicals that inhibit the nucleoside or deoxynucleoside triphosphatase activity of a DnaB helicase. The method includes contacting the DnaB helicase with a DNA molecule substrate that has a duplex region in the presence of a nucleoside or deoxynucleoside triphosphate energy source and the candidate pharmaceutical to form a reaction mixture. The reaction mixture is subjected to conditions that support nucleoside or deoxynucleoside triphosphatase activity of the DnaB helicase in the absence of the candidate pharmaceutical. The candidate pharmaceutical is detected by the absence of conversion of nucleoside or deoxynucleoside triphosphate to nucleoside or deoxynucleoside diphosphate. The DnaB helicase is derived from a Gram positive bacterium.

7) The present invention describes a method to identify chemicals that inhibit a primase. The method includes contacting primase with a ssDNA molecule in the presence of a candidate pharmaceutical to form a reaction mixture. The reaction mixture is subjected to conditions that support primase activity (e.g., the presence of nucleoside or deoxynucleoside triphosphates, appropriate buffer, presence or absence of DnaB helicase) in the absence of the candidate pharmaceutical. Suitable candidate pharmaceuticals are identified by the absence of primer formation detected either directly or indirectly. The primase is derived from a Gram positive bacterium.

8) The present invention describes a method to identify chemicals that inhibit the ability of a primase and the protein encoded by a dnaB gene to interact. This method includes contacting the primase with the protein encoded by the dnaB gene in the presence of the candidate pharmaceutical to form a reaction mixture. The reaction mixture is subjected to conditions under which the primase and the protein encoded by the dnaB gene interact in the absence of the candidate pharmaceutical. The reaction mixture is then analyzed for interaction between the primase and the protein encoded by the dnaB gene. The candidate pharmaceutical is detected by the absence of interaction between the primase and the protein encoded by the dnaB gene. The primase and/or the dnaB gene are derived from a Gram positive bacterium.

9) The present invention describes a method to identify chemicals that inhibit the ability of a protein encoded by a dnaB gene to interact with a DNA molecule. This method includes contacting the protein encoded by the dnaB gene with the DNA molecule in the presence of the candidate pharmaceutical to form a reaction mixture. The reaction mixture is subjected to conditions under which the DNA molecule and the protein encoded by the dnaB gene interact in the absence of the candidate pharmaceutical. The reaction mixture is then analyzed for interaction between the protein encoded by the dnaB gene and the DNA molecule. The candidate pharmaceutical is detected by the absence of interaction between the DNA molecule and the protein encoded by the dnaB gene. The dnaB gene is derived from a Gram positive bacterium.

EXAMPLES

The following examples are provided to illustrate embodiments of the present invention, but they are by no means intended to limit its scope.

Example 1

Materials

Labeled deoxy- and ribonucleoside triphosphates were from Dupont-New England Nuclear; unlabelled deoxy- and ribonucleoside triphosphates were from Pharmacia-LKB; *E. coli* replication proteins were purified as described, alpha, epsilon, gamma, and tau (Studwell et al., "Processive Replication is Contingent on the Exonuclease Subunit of DNA Polymerase III Holoenzyme," *J. Biol. Chem.*, 265:1171-1178 (1990), which is hereby incorporated by reference), beta (Kong et al., "Three Dimensional Structure of the Beta Subunit of *Escherichia coli* DNA Polymerase III Holoenzyme: A Sliding DNA Clamp," *Cell*, 69:425-437 (1992), which is hereby incorporated by reference), delta and delta prime (Dong et al., "DNA Polymerase III Accessory Proteins. I. HolA and holB Encoding δ and δ'," *J. Biol. Chem.*, 268: 11758-11765 (1993), which is hereby incorporated by reference), chi and psi (Xiao et al., "DNA Polymerase III Accessory Proteins. III. HolC and holD Encoding chi and psi," *J. Biol. Chem.*, 268:11773-11778 (1993), which is hereby incorporated by reference), theta (Studwell-Vaughan et al., "DNA Polymerase III Accessory Proteins. V. Theta Encoded by holE," *J. Biol. Chem.*, 268:11785-11791 (1993), which is hereby incorporated by reference), and SSB (Weiner et al., "The Deoxyribonucleic Acid Unwinding Protein of *Escherichia coli*," *J. Biol. Chem.*, 250:1972-1980 (1975), which is hereby incorporated by reference). *E. coli* Pol III core and clamp loader complex (composed of subunits gamma, delta, delta prime, chi, and psi) were reconstituted as described in Onrust et al., "Assembly of a Chromosomal Replication Machine: Two DNA Polymerases, a Clamp Loader and Sliding Clamps in One Holoenzyme Particle. I. Organization of the Clamp Loader," *J. Biol. Chem.*, 270:13348-13357 (1995), which is hereby incorporated by reference. Pol III* was reconstituted and purified as described in Onrust et al., "Assembly of a Chromosomal Replication Machine Two DNA Polymerases, a Clamp Loader and Sliding Clamps in One Holoenzyme Particle. III. Interface Between Two Polymerases and the Clamp Loader," *J. Biol. Chem.*, 270:13366-13377 (1995), which is hereby incorporated by reference. Protein concentrations were quantitated by the Protein Assay (Bio-Rad) method using bovine serum albumin (BSA) as a standard. DNA oligonucleotides were synthesized by Oligos etc. Calf thymus DNA was from Sigma. Buffer A is 20 mM Tris-HCl (pH=7.5), 0.5 mM EDTA, 2 mM DTT, and 20% glycerol. Replication buffer is 20 mM Tris-Cl (pH 7.5), 8 mM $MgCl_2$, 5 mM DTT, 0.5 mM EDTA, 40 µg/ml BSA, 4% glycerol, 0.5 mM ATP, 3 mM each dCTP, dGTP, dATP, and 20 µM [$\alpha$-$^{32}$P]dTTP. P-cell buffer is 50 mM potassium phosphate (pH 7.6), 5 mM DTT, 0.3 mM EDTA, 20% glycerol. T.E. buffer is 10 mM Tris-HCl (pH 7.5), 1 mM EDTA. Cell lysis buffer is 50 mM Tris-HCl (pH 8.0) 10% sucrose, 1 M NaCl, 0.3 mM spermidine.

Example 2

Calf Thymus DNA Replication Assays

These assays were used in the purification of DNA polymerases from *S. aureus* cell extracts. Assays contained 2.5 µg activated calf thymus DNA in a final volume of 25 µl replication buffer. An aliquot of the fraction to be assayed was added to the assay mixture on ice followed by incubation at 37° C. for 5 min. DNA synthesis was quantitated using DE81 paper as described in Rowen et al., "Primase, the DnaG Protein of *Escherichia coli*. An Enzyme Which Starts DNA Chains," *J. Biol. Chem.*, 253:758-764 (1979), which is hereby incorporated by reference.

Example 3

PolydA-oligodT Replication Assays

PolydA-oligodT was prepared as follows. PolydA of average length 4500 nucleotides was purchased from SuperTecs. OligodT35 was synthesized by Oligos etc. 145 ul of 5.2 mM (as nucleotide) polydA and 22 µl of 1.75 mM (as nucleotide) oligodT were mixed in a final volume of 2100 µl T.E. buffer (ratio as nucleotide was 21:1 polydA to oligodT). The mixture was heated to boiling in a 1 ml eppendorf tube, then removed and allowed to cool to room temperature. Assays were performed in a final volume of 25 µl 20 mM Tris-Cl (pH 7.5), 8 mM MgCl$_2$, 5 mM DTT, 0.5 mM EDTA, 40 µg/ml BSA, 4% glycerol, containing 20 µM [α-$^{32}$P]dTTP and 0.36 µg polydA-oligodT. Proteins were added to the reaction on ice, then shifted to 37° C. for 5 min. DNA synthesis was quantitated using DE81 paper as described in Rowen et al., "Primase, the DnaG Protein of *Escherichia coli*. An Enzyme Which Starts DNA Chains," *J. Biol. Chem.*, 253:758-764 (1979), which is hereby incorporated by reference.

Example 4

Singly Primed M13mp18 ssDNA Replication Assays

M13mp18 was phenol extracted from phage and purified by two successive bandings (one downward and one upward) in cesium chloride gradients. M13mp18 ssDNA was singly primed with a DNA 30mer (map position 6817-6846) as described in Studwell et al. "Processive Replication is Contingent on the Exonuclease Subunit of DNA Polymerase III Holoenzyme," *J. Biol. Chem.*, 265:1171-1178 (1990), which is hereby incorporated by reference. Replication assays contained 72 ng of singly primed M13mp18 ssDNA in a final volume of 25 µl of replication buffer. Other proteins added to the assay, and their amounts, are indicated in the Brief Description of the Drawings. Reactions were incubated for 5 min. at 37° C. and then were quenched upon adding an equal volume of 1% SDS and 40 mM EDTA. DNA synthesis was quantitated using DE81 paper as described in Rowen et al., "Primase, the DnaG Protein of *Escherichia coli*. An Enzyme Which Starts DNA Chains," *J. Biol. Chem.*, 253:758-764 (1979), which is hereby incorporated by reference, and product analysis was performed in a 0.8% native agarose gel followed by autoradiography.

Example 5

Genomic *Staphylococcus aureus* DNA

Two strains of *S. aureus* were used. For PCR of the first fragment of the dnaX gene sequence, the strain was ATCC 25923. For all other work the strain was strain 4220 (a gift of Dr. Pat Schlievert, University of Minnesota). This strain lacks a gene needed for producing toxic shock (Kreiswirth et al., "The Toxic Shock Syndrome Exotoxin Structural Gene is Not Detectably Transmitted by a Prophage," *Nature*, 305:709-712 (1996) and Balan et al., "Autocrine Regulation of Toxin Synthesis by *Staphylococcus aureus*," *Proc. Natl. Acad. Sci. USA*, 92:1619-1623 (1995), which are hereby incorporated by reference). *S. aureus* cells were grown overnight at 37° C. in LB containing 0.5% glucose. Cells were collected by centrifugation (24 g wet weight). Cells were resuspended in 80 ml solution I (50 mM glucose, 10 mM EDTA, 25 mM Tris-HCL (pH 8.0)). SDS and NaOH were then added to 1% and 0.2 N, respectively, followed by incubation at 65° C. for 30 min. to lyse the cells. 68.5 ml of 3 M sodium acetate (pH 5.0) was added followed by centrifugation at 12,000 rpm for 30 min. The supernatant was discarded and the pellet was washed twice with 50 ml of 6 M urea, 10 mM Tris-HCL (pH 7.5), 1 mM EDTA using a dounce homogenizer. After each wash, the resuspended pellet was collected by centrifugation (12,000 rpm for 20 min.). After the second wash, the pellet was resuspended in 50 ml 10 mM T.E. buffer using a dounce homogenizer and then incubated for 30 min. at 65° C. The solution was centrifuged at 12,000 rpm for 20 min., and the viscous supernatant was collected. 43.46 g CsCl$_2$ was added to the 50 ml of supernatant (density between 1.395-1.398) and poured into two 35 ml quick seal ultracentrifuge tubes (tubes were completely filled using the same density of CsCl$_2$ in T.E.). To each tube was added 0.5 ml of a 10 mg/ml stock of ethidium bromide. Tubes were spun at 55,000 rpm for 18 h at 18° C. in a Sorvall TV860 rotor. The band of genomic DNA was extracted using a syringe and needle. Ethidium bromide was removed using two butanol extractions and then dialyzed against 4 l of T.E. at pH 8.0 overnight. The DNA was recovered by ethanol precipitation and then resuspended in T.E. buffer (1.7 mg total) and stored at −20° C.

Example 6

Cloning and Purification of *S. aureus* Pol III-L

To further characterize the mechanism of DNA replication in *S. aureus*, large amounts of its replication proteins were produced through use of the genes. The polC gene encoding *S. aureus* Pol III-L (alpha-large) subunit has been sequenced and expressed in *E. coli* (Pacitti et al., "Characterization and Overexpression of the Gene Encoding *Staphylococcus aureus* DNA Polymerase III," *Gene*, 165:51-56 (1995), which is hereby incorporated by reference). The previous work utilized a pBS[KS] vector for expression in which the *E. coli* RNA polymerase is used for gene transcription. In the earlier study, the *S. aureus* polC gene was precisely cloned at the 5' end encoding the N-terminus, but the amount of the gene that remained past the 3' end was not disclosed and the procedure for subcloning the gene into the expression vector was only briefly summarized. Furthermore, the previous study does not show the level of expression of the *S. aureus* Pol III-L, nor the amount of *S. aureus* Pol III-L that is obtained from the induced cells. Since the previously published procedure could not be repeated and the efficiency of the expression vector could not be assessed, another strategy outlined below had to be developed.

The isolated polC gene was cloned into a vector that utilizes T7 RNA polymerase for transcription as this process generally expresses a large amount of protein. Hence, the *S. aureus* polC gene was cloned precisely into the start codon at the NdeI site downstream of the T7 promotor in a pET vector. As the polC gene contains an internal NdeI site, the entire gene could not be amplified and placed it into the NdeI site of a pET vector. Hence, a three step cloning strategy that yielded the desired clone was devised (FIG. 1). These attempts were quite frustrating initially as no products of cloning in standard *E. coli* strains such as DH5α, a typical laboratory strain for preparation of DNA, could be obtained. Finally, a cell that was mutated in several genes affecting DNA stability was useful in obtaining the desired products of cloning.

In brief, the cloning strategy required use of another expression vector (called pET1137 kDa) in which the 37 kDa subunit of human RFC, the clamp loader of the human replication system, had been cloned into the pET11 vector. The gene encoding the 37 kDa subunit contains an internal NsiI site, which was needed for the precise cloning of the isolated polC gene. This three step strategy is shown in FIG. 1. In the first step, an approximately 2.3 kb section of the 5' section of the gene (encoding the N-terminus of Pol III-L) was amplified using the polymerase chain reaction (PCR). Primers were as follows:

Upstream (SEQ. ID. No. 35)

ggtggtaatt gtcttgcata tgacagagc     29

Downstream (SEQ. ID. No. 36)

agcgattaag tggattgccg ggttgtgatg c     31

Amplification was performed using 500 ng genomic DNA, 0.5 mM EDTA, 1 μM of each primer, 1 mM MgSO$_4$, 2 units vent DNA polymerase (New England Biolabs) in 100 μl of vent buffer (New England Biolabs). Forty cycles were performed using the following cycling scheme: 94° C., 1 min; 60° C., 1 min.; 72° C., 2.5 min. The product was digested with NdeI (underlined in the upstream primer) and NsiI (an internal site in the product) and the approximately 1.8 kb fragment was gel purified. A pET11 vector containing as an insert the 37 kDa subunit of human replication factor C (pET1137 kDa) was digested with NdeI and NsiI and gel purified. The PCR fragment was ligated into the digested pET1137 kDa vector and the ligation reaction was transformed into Epicurean coli supercompetent SURE 2 cells (Stratagene) and colonies were screened for the correct chimera (pET11PolC1) by examining minipreps for proper length and correct digestion products using NdeI and NsiI. In the second step, an approximately 2076 bp fragment containing the DNA encoding the C-terminus of Pol III-L subunit was amplified using the following sequences as primers:

Upstream (SEQ. ID. No. 37)

agcatcacaa cccggcaatc cacttaatcg c                31

Downstream (SEQ. ID. No. 38)

gactacgcca tgggcattaa ataaatacc                   29

The amplification cycling scheme was as described above except the elongation step at 72° C. was for 2 min. The product was digested with BamHI (underlined in the downstream primer) and NsiI (internal to the product) and the approximately 480 bp product was gel purified and ligated into the pET11PolC1 that had been digested with NsiI/BamHI and gel purified (ligated product is pET11PolC2). To complete the expression vector, an approximately 2080 bp PCR product was amplified over the two NsiI sites internal to the gene using the following primers:

Upstream (SEQ. ID. No. 39)

gaagatgcat ataaacgtgc aagacctagt                  30

Downstream (SEQ. ID. No. 40)

gtctgacgca cgaattgtaa agtaagatgc atag             34

The amplification cycling scheme was as described above except the 72° C. elongation step was 2 min. The PCR product, and the pET11PolC2 vector, were digested with NsiI and gel purified. The ligation mixture was transformed as described above and colonies were screened for the correct chimera (pET11PolC).

Figure 2A:
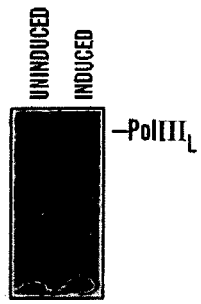
FIGS. 2A-D describe the expression and purification of *S. aureus* Pol III-L (alpha-large).

To express Pol III-L polymerase, the pET11PolC plasmid was transformed into *E. coli* strain BL21 (DE3). 24 L of *E. coli* BL21(DE3)pET11PolC were grown in LB media containing 50 pg/ml ampicillin at 37° C. to an OD of 0.7 and then the temperature was lowered to 15° C. Cells were then induced for Pol III-L expression upon addition of 1 mM IPTG to produce the T7 RNA polymerase needed to transcribe polC. This step was followed by further incubation at 15° C. for 18 h. Expression of *S. aureus* Pol III-L polymerase was so high that it could easily be visualized by Coomassie staining of a SDS polyacrylamide, gel of whole cells (FIG. 2A). The expressed protein migrated in the SDS polyacrylamide gel in a position expected for a 165 kDa polypeptide. In this procedure, it is important that cells are induced at 15° C., as induction at 37° C. produces a truncated version of Pol III-L polymerase, of approximately 130 kDa.

Figure 2B:
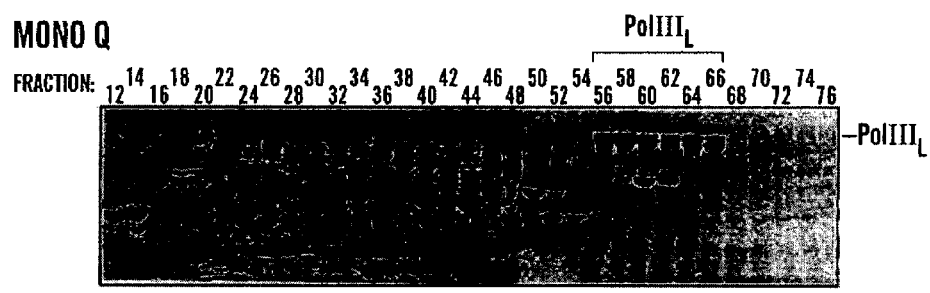
Figure 2C:
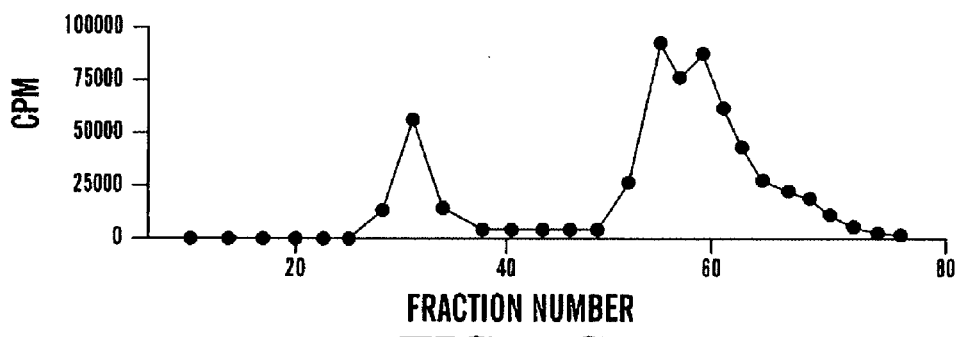
Figure 2D:
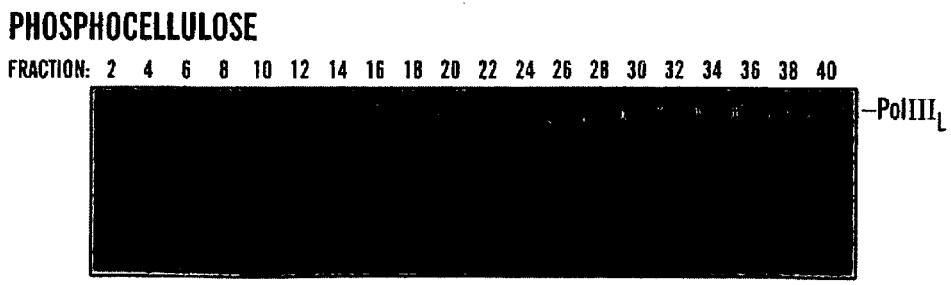

Cells were collected by centrifugation at 5° C. Cells (12 g wet weight) were stored at −70° C. The following steps were performed at 4° C. Cells were thawed and lysed in cell lysis buffer as described (final volume=50 ml) and were passed through a French Press (Amico) at a minimum of 20,000 psi. PMSF (2 mM) was added to the lysate as the lysate was collected from the French Press. DNA was removed and the lysate was clarified by centrifugation. The supernatent was dialyzed for 1 h against Buffer A containing 50 mM NaCl. The final conductivity was equivalent to 190 mM NaCl. Supernatent (24 ml, 208 mg) was diluted to 50 ml using Buffer A to bring the conductivity to 96 mM MgCl$_2$, and then was loaded onto an 8 ml MonoQ column equilibrated in Buffer A containing 50 mM NaCl. The column was eluted with a 160 ml linear gradient of Buffer A from 50 mM NaCl to 500 mM NaCl. Seventy five fractions (1.3 ml each) were collected (FIG. 2B-C). Aliquots were analyzed for their ability to synthesize DNA, and 20 μl of each fraction was analyzed by Coomassie staining of an SDS polyacrylamide gel. Based on the DNA synthetic capability, and the correct size band in the gel, fractions 56-65 containing Pol III-L polymerase were pooled (22 ml, 31 mg). The pooled fractions were dialyzed overnight at 4° C. against 50 mM phosphate (pH 7.6), 5 mM DTT, 0.1 mM EDTA, 2 mM PMSF, and 20% glycerol (P-cell buffer). The dialyzed pool was loaded onto a 4.5 ml phosphocellulose column equilibrated in P-cell buffer, and then eluted with a 25 ml linear gradient of P-cell buffer from 0 M NaCl to 0.5 M NaCl. Fractions of 1 ml were collected and analyzed in a SDS polyacrylamide gel stained with Coomassie Blue (FIG. 2D). Fractions 20-36 contained the majority of the Pol III-large at a purity of greater than 90% (5 mg).

Example 7

*S. aureus* Pol III-L is not Processive on its Own

The Pol III-L polymerase purifies from *B. subtilis* as a single subunit without accessory factors (Barnes et al., "Purification of DNA Polymerase III of Gram-positive Bacteria," *Methods in Enzy.*, 262:35-42 (1995), which is hereby incorporated by reference). Hence, it seemed possible that it may be a Type I replicase (e.g., like T5 polymerase) and, thus, be capable of extending a single primer full length around a long singly primed template. To perform this experiment, a template M13 mp18 ssDNA primed with a single DNA oligonucleotide either in the presence or absence of SSB was used. DNA products were analyzed in a neutral agarose gel which resolved products by size. The results showed that Pol III-L polymerase was incapable of extending the primer around the DNA (to form a completed duplex circle referred to as replicative form II ("RFII")) whether SSB was present or not. This experiment has been repeated using more enzyme and longer times, but no full length RFII products are produced. Hence, Pol III-L would appear not to follow the paradigm of the T5 system (Type I replicase) in which the polymerase is efficient in synthesis in the absence of any other protein(s).

Example 8

Cloning and Purification of *S. aureus* Beta Subunit

The sequence of an *S. aureus* homolog of the *E. coli* dnaN gene (encoding the beta subunit) was obtained in a study in which the large recF region of DNA was sequenced (Alonso et al., "Nucleotide Sequence of the recF Gene Cluster From *Staphylococcus aureus* and Complementation Analysis in *Bacillus subtilis* recF Mutants," *Mol. Gen. Genet.*, 246:680-686 (1995), Alonso et al., "Nucleotide Sequence of the recF Gene Cluster From *Staphylococcus aureus* and Complementation Analysis in *Bacillus subtilis* recF Mutants," *Mol. Gen. Genet.*, 248:635-636 (1995), which are hereby incorporated by reference). Sequence alignment of the *S. aureus* beta and *E. coli* beta show approximately 30% identity. Overall this level of homology is low and makes it uncertain that *S. aureus* beta will have the same shape and function as the *E. coli* beta subunit.

To obtain *S. aureus* beta protein, the dnaN gene was isolated and precisely cloned into a pET vector for expression in *E. coli*. *S. aureus* genomic DNA was used as template to amplify the homolog of the dnaN gene (encoding the putative beta). The upstream and downstream primers were designed to isolate the dnaN gene by PCR amplification from genomic DNA. Primers were:

Upstream (SEQ. ID. No. 41)

cgactggaag gagttttaac atatgatgga attcac    36

Downstream (SEQ. ID. No. 42)

ttatatggat ccttagtaag ttctgattgg    30

Figure 3:
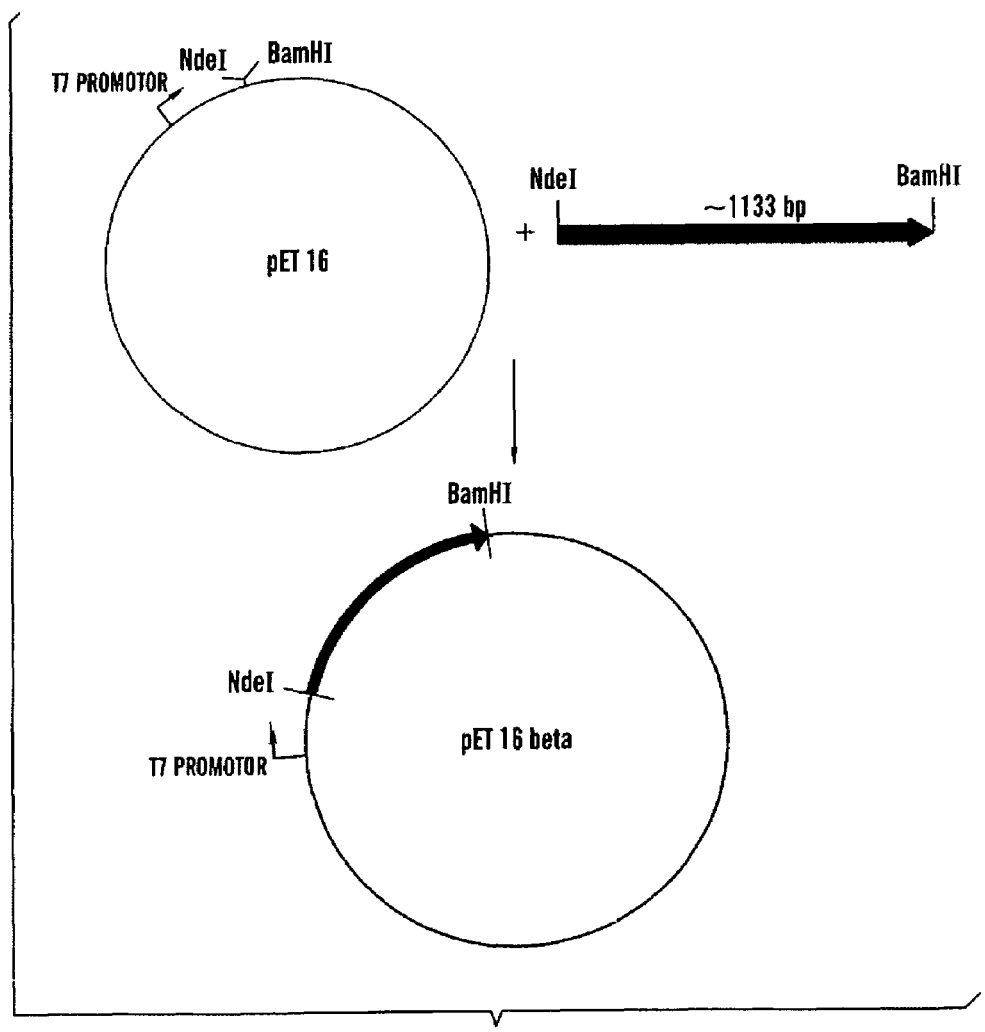
FIG. 3 shows the *S. aureus* beta expression vector. The dnaN gene was amplified from *S. aureus* genomic DNA and cloned into the pET16 expression vector.

The NdeI site used for cloning into pET16b (Novagen) is underlined in the Upstream primer and the BamHI site used for cloning into pET16b is underlined in the Downstream primer. The NdeI and BamHI sites were used for directional cloning into pET16 (FIG. 3). Amplification was performed using 500 ng genomic DNA, 0.5 mM dNTPs, 1 µM of each primer, 1 mM MgSO₄, 2 units vent DNA polymerase in 100 ul of vent buffer. Forty cycles were performed using the following cycling scheme: 94° C., 1 min; 60° C., 1 min.; 72° C., 1 min. 10s. The 1167 bp product was digested with NdeI and BamHI and purified in a 0.7% agarose gel. The pure digested fragment was ligated into the pET16b vector which had been digested with NdeI and BamHI and gel purified in a 0.7% agarose gel. Ligated products were transformed into *E. coli* competent SURE II cells (Stratagene) and colonies were screened for the correct chimera by examining minipreps for proper length and correct digestion products using NdeI and BamHI.

Figure 4A:
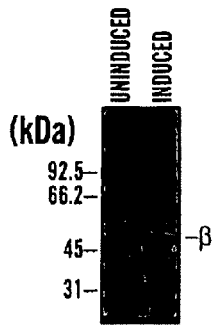
FIGS. 4A-C illustrate the expression and purification of *S. aureus* beta.

24 L of BL21(DE3)pETbeta cells were grown in LB containing 50 pg/ml ampicillin at 37° C. to an O.D. of 0.7, and, then, the temperature was lowered to 15C. IPTG was added to a concentration of 2 mM and after a further 18 h at 15° C. to induce expression of *S. aureus* beta (FIG. 4A). It is interesting to note that the beta subunit, when induced at 37° C., was completely insoluble. However, induction of cells at 15° C. provided strong expression of beta and, upon cell lysis, over 50% of the beta was present in the soluble fraction.

Figure 4B:
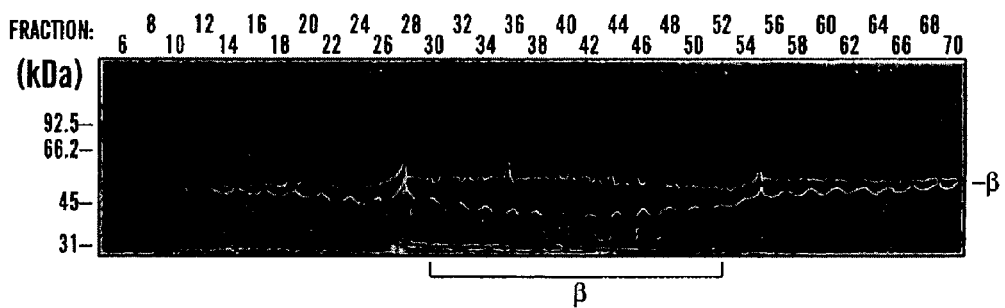
Figure 4C:
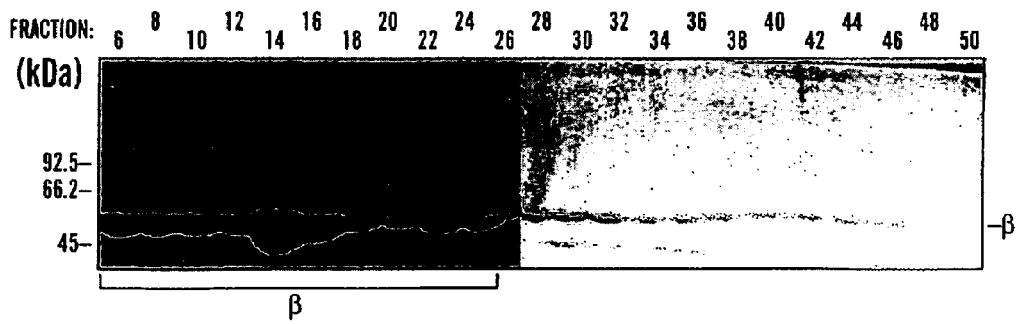

Cells were harvested by centrifugation (44 g wet weight) and stored at −70° C. The following steps were performed at 4° C. Cells (44 g wet weight) were thawed and resuspended in 45 ml 1× binding buffer (5 mM imidizole, 0.5 M NaCl, 20 mM Tris HCl (final pH 7.5)) using a dounce homogenizer. Cells were lysed using a French Pressure cell (Aminco) at 20,000 psi, and then 4.5 ml of 10% polyamine P (Sigma) was added. Cell debris and DNA was removed by centrifugation at 13,000 rpm for 30 min. at 4° C. The pET16beta vector places a 20 residue leader containing 10 histidine residues at the N-terminus of beta. Hence, upon lysing the cells, the *S. aureus* beta was greatly purified by chromatography on a nickel chelate resin (FIG. 4B). The supernatant (890 mg protein) was applied to a 10 ml HiTrap Chelating Separose column (Pharmacia-LKB) equilibrated in binding buffer. The column was washed with binding buffer, then eluted with a 100 ml linear gradient of 60 mM imidazole to 1 M imidazole in binding buffer. Fractions of 1.35 ml were collected. Fractions were analyzed for the presence of beta in an SDS polyacrylamide gel stained with Coomassie Blue. Fractions 28-52, containing most of the beta subunit, were pooled (35 ml, 82 mg). Remaining contaminating protein was removed by chromatography on MonoQ. The *S. aureus* beta becomes insoluble as the ionic strength is lowered and, thus, the pool of beta was dialyzed overnight against Buffer A containing 400 mM NaCl. The dialyzed pool became slightly turbid indicating it was at its solubility limit at these concentrations of protein and NaCl. The insoluble material was removed by centrifugation (64 mg remaining) and, then, diluted 2-fold with Buffer A to bring the conductivity to 256. The protein was then applied to an 8 ml MonoQ column equilibrated in Buffer A plus 250 mM NaCl and then eluted with a 100 ml linear gradient of Buffer A from 0.25 M NaCl to 0.75 M NaCl; fractions of 1.25 ml were collected (FIG. 4C). Under these conditions, approximately 27 mg of the beta flowed through the column and the remainder eluted in fractions 1-18 (24 mg).

Example 9

Figure 5A:
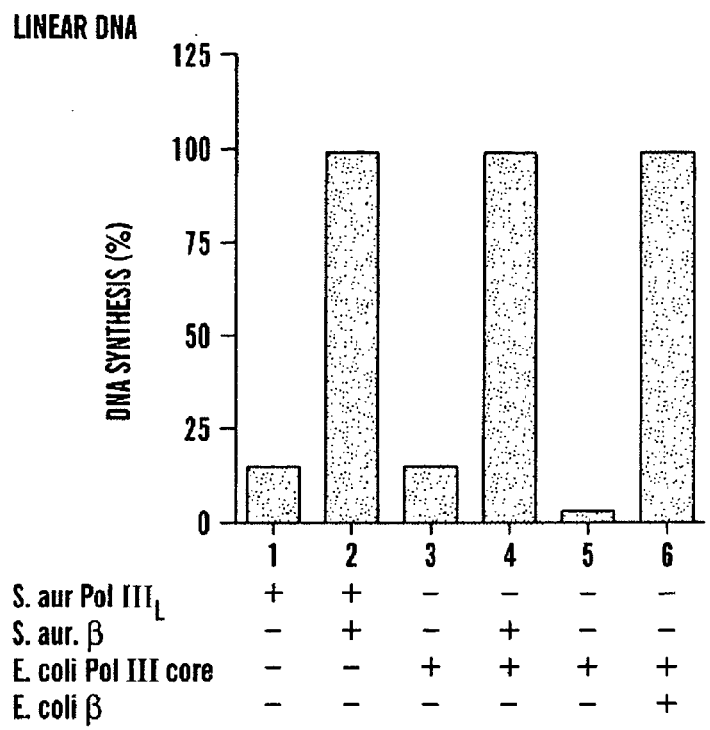
FIGS. 5A-B demonstrate that the *S. aureus* beta stimulates *S. aureus* Pol III-L and *E. coli* Pol III core on linear DNA, but not circular DNA.

The *S. aureus* Beta Subunit Protein Stimulates *S. aureus* Pol III-L and *E. coli* Core The experiment of FIG. 5A, tests the ability of *S. aureus* beta to stimulate *S. aureus* Pol III-L on a linear polydA-oligodT template. Reactions are also performed with *E. coli* beta and Pol III core. The linear template was polydA of average length of 4500 nucleotides primed with a 30mer oligonucleotide of T residues. The first two lanes show the activity of Pol III-L either without (lane 1) or with *S. aureus* beta (lane 2). The result shows that the *S. aureus* beta stimulates Pol III-L approximately 5-6 fold. Lanes 5 and 6 show the corresponding experiment using *E. coli* core with (lane 6) or without (lane 5) *E. coli* beta. The core is stimulated over 10-fold by the *E. coli* beta subunit under the conditions used.

Although Gram positive and Gram negative cells diverged from one another long ago and components of one polymerase machinery would not be expected to be interchangable, it was decided to test the activity of the *S. aureus* beta with *E. coli* Pol III core. Lanes 3 and 4 shows that the *S. aureus* beta also stimulates *E. coli* core about 5-fold. This result can be explained by an interaction between the clamp and the polymerase that has been conserved during the evolutionary divergence of gram positive and gram negative cells. A chemical inhibitor that would disrupt this interaction would be predicted to have a broad spectrum of antibiotic activity, shutting down replication in Gram negative and Gram positive cells alike. This assay, and others based on this interaction, can be devised to screen chemicals for such inhibition. Further, since all the proteins in this assay are highly overexpressed through recombinant techniques, sufficient quantities of the protein reagents can be obtained for screening hundreds of thousands of compounds.

In summary, the results show that *S. aureus* beta, produced in *E. coli*, is indeed an active protein (i.e., it stimulates polymerase activity). Furthermore, the results shows that Pol III-L functions with a second protein (i.e., *S. aureus* beta). Before this experiment, there was no assurance that Pol III-L, which is significantly different in structure from *E. coli* alpha, would function with another protein. For example, unlike *E. coli* alpha, which copurifies with several accessory proteins, Pol III-L purified from *B. subtilis* as a single protein with no other subunits attached (Barnes et al., "Purification of DNA Polymerase III of Gram-positive Bacteria," *Methods in Enzy.*, 262:35-42 (1995), which is hereby incorporated by reference). Finally, if one were to assume that *S. aureus* beta would function with a polymerase, the logical candidate would have been the product of the dnaE gene (alpha-small) instead of polC (Pol III-L) since the dnaE product is more homologous to *E. coli* alpha subunit than Pol III-L.

Example 10

The *S. aureus* Beta Subunit Behaves as a Circular Sliding Clamp

The ability of *S. aureus* beta to stimulate Pol III-L could be explained by formation of a 2-protein complex between Pol III-L and beta to form a processive replicase similar to the Type II class (e.g., T7 type). Alternatively, the *S. aureus* replicase is organized as the Type III replicase which operates with a circular sliding clamp and a clamp loader. In this case, the *S. aureus* beta would be a circular protein and would require a clamp loading apparatus to load it onto DNA. The ability of the beta subunit to stimulate Pol III-L in FIG. 5A could be explained by the fact that the polydA-oligodT template is a linear DNA and a circular protein could thread itself onto the DNA over an end. Such "end threading" has been observed with PCNA and explains its ability to stimulate DNA polymerase delta in the absence of the RFC clamp loader (Burgers et al., "ATP-Independent Loading of the Proliferating Cell Nuclear Antigen Requires DNA Ends," *J. Biol. Chem.*, 268:19923-19926 (1993), which is hereby incorporated by reference).

Figure 5B:
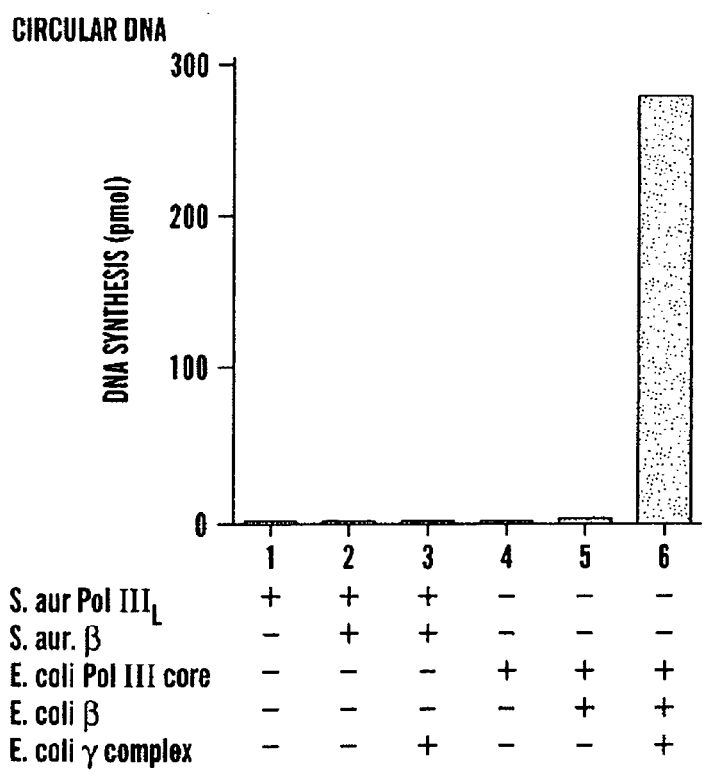

To distinguish between these possibilities, *S. aureus* beta was examined for ability to stimulate Pol III-L on a circular primed template. In FIG. 5B, assays were performed using circular M13 mp18 ssDNA coated with *E. coli* SSB and primed with a single oligonucleotide to test the activity of beta on circular DNA. Lane 1 shows the extent of DNA synthesis using Pol III-L alone. In lane 2, Pol III-L was supplemented with *S. aureus* beta. The *S. aureus* beta did not stimulate the activity of Pol III-L on this circular DNA (nor in the absence of SSB). Inability of *S. aureus* beta to stimulate Pol III-L is supported by the results of FIG. 6, lane 1 that analyzes the product of Pol III-L action on the circular DNA in an agarose gel in the presence of *S. aureus* beta. In summary, these results show that *S. aureus* beta only stimulates Pol III-L on linear DNA, not circular DNA. Hence, the *S. aureus* beta subunit behaves as a circular protein.

Lane 3 shows the result of adding both *S. aureus* beta and *E. coli* gamma complex to Pol III-L. Again, no stimulation was observed (compare with lane 1). This result indicates that the functional contacts between the clamp and clamp loader were not conserved during evolution of Gram positive and Gram negative cells.

Controls for these reactions on circular DNA are shown for the *E. coli* system in Lanes 4-6. Addition of only beta to *E. coli* Pol III core did not result in stimulating the polymerase (compare lanes 4 and 5). However, when clamp loader complex was included with beta and core, a large stimulation of synthesis was observed (lane 6). In summary, stimulation of synthesis is only observed when both beta and clamp loader complex were present, consistent with inability of the circular beta ring to assemble onto circular DNA by itself.

Example 11

Figure 6:
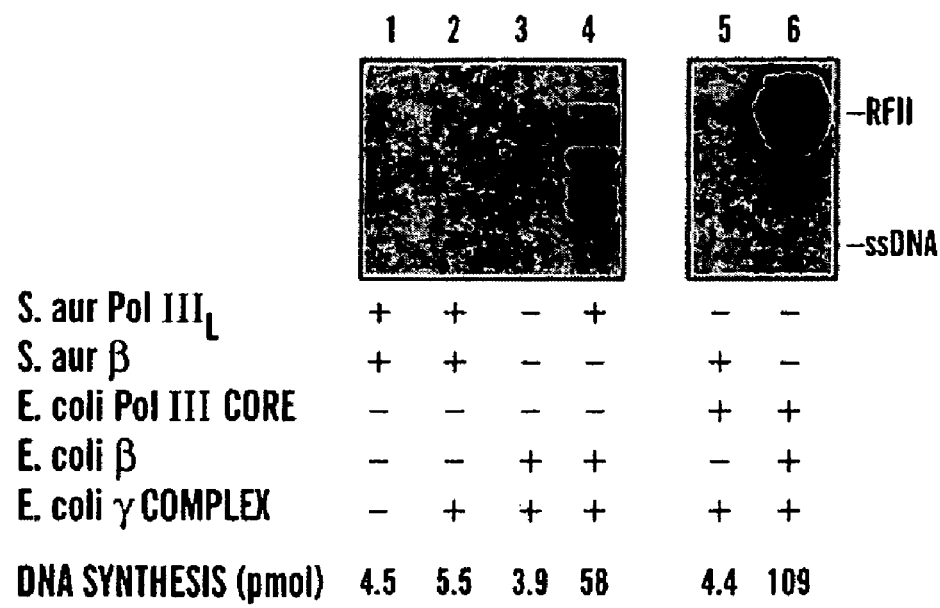
FIG. 6 shows that *S. aureus* Pol III-L functions with *E. coli* beta and clamp loader complex on circular primed DNA. It also shows that *S. aureus* beta does not convert Pol III-L with sufficient processivity to extend the primer all the way around a circular DNA. Replication reactions were performed on the circular singly primed M13mp18 ssDNA. Proteins added to the assay are as indicated in this figure. The amount of each protein, when present, is: *S. aureus* beta, 800 ng; *S. aureus* Pol III-L, 1500 ng (MonoQ fraction 64); *E. coli* Pol III core, 450 ng; *E. coli* beta, 100 ng; *E. coli* gamma complex, 1720 ng. Total DNA synthesis in each assay is indicated at the bottom of the figure.

Pol III-L Functions as a Pol III-Type Replicase with Beta and a Clamp Loader Complex to Become Processive Next, it was determined whether *S. aureus* Pol III-L requires two components (a beta clamp and a clamp loader) to extend a primer full length around a circular primed template. In FIG. 6, a template circular M13 mp18 ssDNA primed with a single DNA oligonucleotide was used. DNA products were analyzed in a neutral agarose gel which resolves starting materials (labeled ssDNA in FIG. 6) from completed duplex circles (labelled RFII for replicative form II). The first two lanes show, as demonstrated in other examples, that Pol III-L is incapable of extending the primer around the circular DNA in the presence of only *S. aureus* beta. In lane 4 of FIG. 6, *E. coli* clamp loader complex (also known as gamma complex) and beta subunit were mixed with *S. aureus* Pol III-L in the assay containing singly primed M13mp18 ssDNA coated with SSB. If the beta clamp, assembled on DNA by clamp loader complex, provides processivity to *S. aureus* Pol III-L, the ssDNA circle should be converted into a fully duplex circle (RFII) which would be visible in an agarose gel analysis. The results of the experiment showed that the *E. coli* beta and clamp loader complex did indeed provide Pol III-L with ability to fully extend the primer around the circular DNA to form the RFII (lane 4). The negative control using only *E. coli* clamp loader complex and beta is shown in lane 3. For comparison, lane 6 shows the result of mixing the three components of the *E. coli* system (Pol III core, beta, and clamp loader complex). This reaction gives almost exclusively full length RFII product. The qualitatively different product profile that Pol III-L gives in the agarose gel analysis compared to *E. coli* Pol III core with beta and clamp loader complex shows that the products observed using Pol III-L is not due to a contaminant of *E. coli* Pol III core in the *S. aureus* Pol III-L preparation (compare lanes 4 and 6).

It is generally thought that the polymerase of one system is specific for its SSB. However, these reactions are performed on ssDNA coated with the *E. coli* SSB protein. Hence, the *S. aureus* Pol III-L appears capable of utilizing *E. coli* SSB and the *E. coli* beta. It would appear that the only component that is not interchangeable between the Gram positive and Gram negative systems is the clamp loader complex.

Thus, the *S. aureus* Pol III-L functions as a Pol III type replicase with the *E. coli* beta clamp assembled onto DNA by a clamp loader complex.

Example 12

Purification of Two DNA Polymerase III-Type Enzymes from *S. aureus* Cells

The MonoQ resin by Pharmacia has very high resolution which would resolve the three DNA polymerases of *S. aureus*. Hence, *S. aureus* cells were lysed, DNA was removed from the lysate, and the clarified lysate was applied onto a MonoQ column. The details of this procedure are: 300 L of *S. aureus* (strain 4220, a gift of Dr. Pat Schlievert, University of Minnesota) was grown in 2×LB media at 37° C. to an O.D. of approximately 1.5 and then were collected by centrifugation. Approximately 2 kg of wet cell paste was obtained and stored at −70° C. 122 g of cell paste was thawed and resuspended in 192 ml of cell lysis buffer followed by passage through a French Press cell (Aminco) at 40,000 psi. The resultant lysate was clarified by high speed centrifugation (1.3 g protein in 120 ml). A 20 ml aliquot of the supernatant was dialyzed 2 h against 2 L of buffer A containing 50 mM NaCl. The dialyzed material (148 mg, conductivity =101 mM NaCl) was diluted 2-fold with Buffer A containing 50 mM NaCl and then loaded onto an 8 ml MonoQ column equilibrated in Buffer A containing 50 mM NaCl. The column was washed with Buffer A containing 50 mM NaCl, and then eluted with a 160 ml linear gradient of 0.05 M NaCl to 0.5 M NaCl in Buffer A. Fractions of 2.5 ml (64 total) were collected, followed by analysis in an SDS polyacrylamide gel for their replication activity in assays using calf thymus DNA.

Figure 7A:
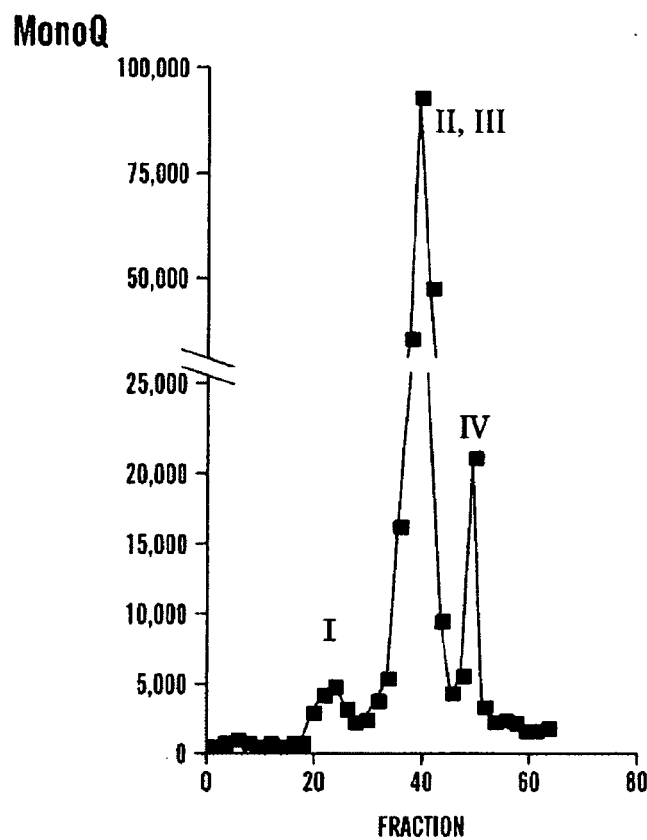
FIGS. 7A-B show that *S. aureus* contains four distinct DNA polymerases. Four different DNA polymerases were partially purified from *S. aureus* cells. *S. aureus* cell lysate was separated from DNA and, then, chromatographed on a MonoQ column. Fractions were analyzed for DNA polymerase activity. Three peaks of activity were observed. The second peak was the largest and was expected to be a mixture of two DNA polymerases based on early studies in *B. subtilis*. Chromatography of the second peak on phosphocellulose (FIG. 7B) resolved two DNA polymerases from one another.
Figure 7B:
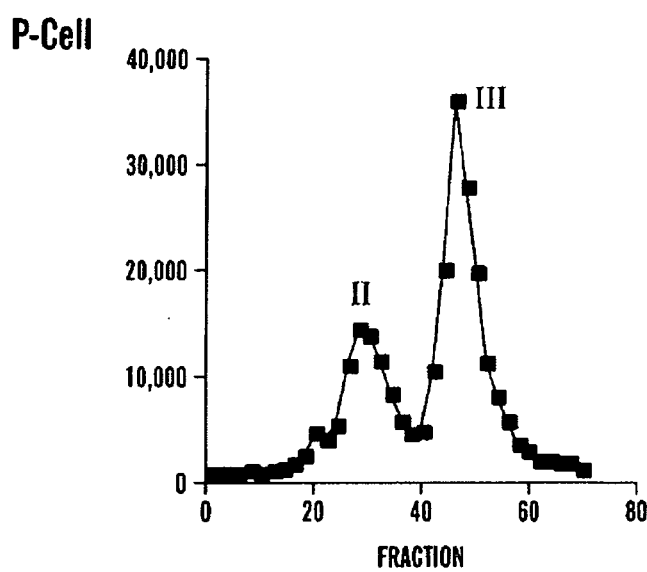

Three peaks of DNA polymerase activity were identified (FIG. 7). Previous studies of cell extracts prepared from the Gram positive organism *Bacillus subtilis* identified only two peaks of activity off a DEAE column (similar charged resin to MonoQ). The first peak was Pol II, and the second peak was a combination of DNA polymerases I and III. The DNA polymerases I and III were then separated on a subsequent phosphocellulose column. The middle peak in FIG. 7 is much larger than the other two peaks and, thus, it was decided to chromatograph this peak on a phosphocellulose column. The second peak of DNA synthetic activity was pooled (fractions 37-43; 28 mg in 14 ml) and dialyzed against 1.5 L P-cell buffer for 2.5 h. Then, the sample (ionic strength equal to 99 mM NaCl) was applied to a 5 ml phosphocellulose column equilibrated in P-cell buffer. After washing the column in 10 ml P-cell buffer, the column was eluted with a 60 ml gradient of 0-0.5 M NaCl in P-cell buffer. Seventy fractions were collected and then analyzed for DNA synthesis using calf thymus DNA as template. This column resolved the polymerase activity into two distinct peaks (FIG. 7B).

Hence, there appear to be four DNA polymerases in *Staphylococcus aureus*. They were designated here as peak 1 (first peak off MonoQ), peak 2 (first peak off phosphocellulose), peak 3 (second peak of phosphocellulose), and peak 4 (last peak off Mono Q) (see FIG. 7). Peak 4 was presumably Pol III-L, as it elutes from MonoQ in a similar position as the Pol III-L expressed in *E. coli* (compare FIG. 7A with FIG. 2).

Example 13

Figures 8A, 8B:
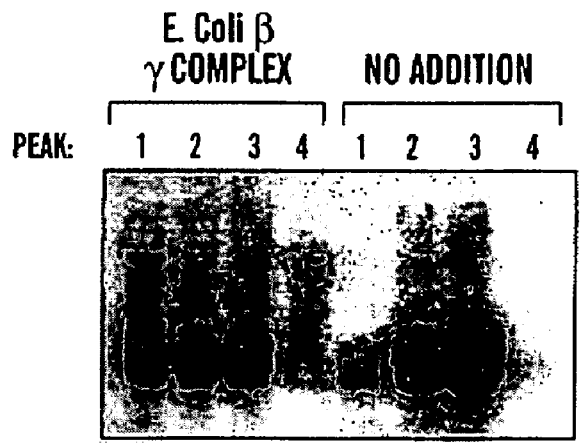
FIGS. 8A-B show that *S. aureus* has two DNA Pol III's. The four DNA polymerases partially purified from *S. aureus* extract, designated peaks I-IV in FIG. 7, were assayed on circular singly primed M13mp18 ssDNA coated with *E. coli* SSB either in the presence or absence of *E. coli* beta (Song) and clamp loader complex (50 ng). Each reaction contained 2 µl of the partially pure polymerase (Peak I was Mono Q fraction 24 (1.4 µg), Peak 2 was phosphocellulose fraction 26 (0.016 mg/ml), Peak 3 was phosphocellulose fraction 46 (0.18 mg/ml), and Peak 4 was MonoQ fraction 50 (1 pg).

Demonstration That Peak 1 (Pol III-2) Functions as a Pol III-Type Replicase with *E. coli* Beta Assembled on DNA by *E. coli* Clamp Loader Complex To test which peak contained a Pol III-type of polymerase, an assay was used in which the *E. coli* clamp loader complex and beta support formation of full length RFII product starting from *E. coli* SSB coated circular M13mp18 ssDNA primed with a single oligonucleotide. In FIG. 8, both Peaks 1 and 2 are stimulated by the *E. coli* clamp loader complex and beta subunit and, in fact, Peaks 2 and 3 are inhibited by these proteins (the quantitation is shown below the gel in the figure). Further, the product analysis in the agarose gel shows full length RFII duplex DNA circles only for peaks 1 and 4. These results, combined with the NEM, pCMB, and KC1 characteristics in Tables 2 and 3 below, suggest that there are two Pol III-type DNA polymerases in *S. aureus* and that these are partially purified in peaks 1 and 4.

Next, it was determined which of these peaks of DNA polymerase activity correspond to DNA polymerases 1, I, and III, and which peak is the unidentified DNA polymerase. In the Gram positive bacterium *B. subtilis*, Pol III is inhibited by pCMB, NEM, and 0.15 M NaCl, Pol II is inhibited by KCl, but not NEM or 0.15 M KCL, and Pol I is not inhibited by any of these treatments (Gass et al., "Further Genetic and Enzymological Characterization of the Three *Bacillus subtilis* Deoxyribonucleic Acid Polymerases," *J. Biol. Chem.*, 248: 7688-7700 (1973), which is hereby incorporated by reference). Hence, assays were performed in the presence or absence of pCMB, NEM, and 0.15 M KCl (see Tables 2 and 3 below). Peak 3 clearly corresponded to Pol I, because it was not inhibited by NEM, pCMB, or 0.15 M NaCl. Peak 2 correspond to Pol II, because it was not inhibited by NEM, but was inhibited by pCMB and 0.15 M NaCl. Peaks 1 and 4 both had characteristics that mimic Pol III; however, peak 4 elutes on MonoQ at a similar position as Pol III-L expressed in *E. coli* (see FIG. 2B). Hence, peak 4 is likely Pol III-L, and peak 1 is likely the unknown polymerase.

TABLE 2

Expected Characteristics of Polymerases

| Polymerase | pCMB | NEM | 0.15 M KCl |
|---|---|---|---|
| Pol I | not inhibited* | not inhibited | not inhibited |
| Pol II | inhibited** | not inhibited | not inhibited |
| Pol III-L | inhibited | inhibited | not inhibited |

*Not inhibited is defined as greater than 75% remaining activity
**Inhibited is defined as less than 40% remaining activity

TABLE 3

Observed Characteristics

| Peak | pCMB | NEM | 0.15 M KCL | assignment |
|---|---|---|---|---|
| Peak1 | inhibited | inhibited | | new polymerase |
| Peak2 | inhibited | not inhibited | | Pol II |
| Peak3 | not inhibited | not inhibited | | Pol I |
| Peak4 | inhibited | inhibited | | Pol III-L |

Example 14

Identification and Cloning of *S. aureus* dnaE

This invention describes the finding of two DNA polymerases that function with a sliding clamp assembled onto DNA by a clamp loader. One of these DNA polymerases is likely Pol III-L, but the other has not been identified previously. Presumably, the chromatographic resins used in earlier studies did not have the resolving power to separate the enzyme from other polymerases. This would be compounded by the low activity of Pol III-2. To identify a gene encoding the second Pol III, the amino acid sequences of the Pol III alpha subunit of *Escherichia coli, Salmonella typhimurium, Vibrio cholerae, Haemophilus influenzae*, and *Helicobacter pylori* were aligned using Clustal W (1.5). Two regions about 400 residues apart were conserved and primers were designed for the following amino acid sequences:

Upstream, corresponding in *E. coli* to residues 385-399 (SEQ. ID. No. 43)

```
Leu Leu Phe Glu Arg Phe Leu Asn Pro Glu Arg Val
 1               5                      10

Ser Met Pro
         15
```

Downstream, corresponding in E. coli to residues 750-764 (SEQ. ID. No. 44)

```
Lys Phe Ala Gly Tyr Gly Phe Asn Lys Ser His Ser
 1               5                  10
Ala Ala Tyr
         15
```

The following primers were designed to these two peptide regions using codon preferences for S. aureus:

Upstream (SEQ. ID. No. 45)

cttcttttg aaagatttct aaataaagaa cgttattcaa tgcc    44

Downstream (SEQ. ID. No. 46)

ataagctgca gcatgactttt tattaaaacc ataacctgca aattt    45

Amplification was performed using 2.5 units of Taq DNA Polymerase (Gibco, BRL), 100 ng S. aureus genomic DNA, 1 mM of each of the four dNTPs, 1 µM of each primer, and 3 mM MgCl$_2$ in 100 µl of Taq buffer. Thirty-five cycles of the following scheme were repeated: 94° C., 1 min; 55° C., 1 min; 72° C., 90 sec. The PCR product (approximately 1.1 kb) was electrophoresed in a 0.8% agarose gel and purified using a Geneclean III kit (Bio 101). The product was then divided equally into ten separate aliquots and used as a template for PCR reactions, according to the above protocol, to reamplify the fragment for sequencing. The final PCR product was purified using a Quiagen Quiaquick PCR Purification kit, quantitated via optical density at 260 nM, and sequenced by the Protein/DNA Technology Center at Rockefeller University. The same primers used for PCR were used to prime the sequencing reactions.

Next, the following additional PCR primers were designed to obtain more sequence information 3' to the first amplified section.

Upstream (SEQ. ID. No. 47)

agttaaaaat gccatatttt gacgtgtttt agttctaat    39

Downstream (SEQ. ID. No. 48)

cttgcaaaag cggttgctaa agatgttgga cgaattatgg gg    42

These primers were used in a PCR reaction using 2.5 units of Taq DNA Polymerase (Gibco, BRL) with 100 ng S. aureus genomic DNA as a template, 1 mM dNTP's, 1 µM of each primer, and 3 mM MgCl$_2$ in 100 1 of Taq buffer. Thirty-five cycles of the following scheme were repeated: 94° C., 1 min; 55° C., 1 min; 72° C., 2 min 30 seconds. The 1.6 Kb product was then divided into 5 aliquots, and used as a template in a set of 5 PCR reactions, as described above, to amplify the product for sequencing. The products of these reactions were purified using a Qiagen Qiaquick PCR Purification kit, quantitated via optical density at 260 nm, and sequenced by the Protein/DNA Technology Center at Rockefeller University. The sequence of this product yielded about 740 bp of new sequence 3' of the first sequence.

As this gene shows better homology to the Gram negative Pol III α subunit compared to Gram positive Pol III-L, it will be designated the dnaE gene.

Example 15

Identification and Cloning of S. aureus dnaX

The fact that the S. aureus beta stimulates Pol III-L and has a ring shape suggests that the Gram positive replication machinery is of the three component type. This implies the presence of a clamp loader complex. This is not a simple determination to make as the B. subtilis genome shows homologs to only two of the five subunits of the E. coli clamp loader (dnaX encoding gamma, and holB encoding delta prime). On the basis of the experiments in this application, which suggests that there is a clamp loader, it was believed that these two subunit homologues are part of the clamp loader for the S. aureus beta.

As a start in obtaining the clamp loading apparatus, a strategy was devised to obtain the gene encoding the tau subunit of S. aureus. In E. coli, the tau and gamma subunits are derived from the same gene. Tau is the full length product, and gamma is about ⅔ the length of tau. Gamma is derived from the dnaX gene by what was originally believed to be an efficient translational frameshift mechanism that, after it occurs, incorporates only one unique C-terminal residue before encountering a stop codon. To identify the dnaX gene of S. aureus by PCR analysis, the dnaX genes of B. subtilis, E. coli, and H. influenzae were aligned. Upon comparison of the amino acid sequence encoded by these dnaX genes, two areas of high homology were used to predict the amino acid sequence of the S. aureus dnaX gene product. PCR primers were designed to these sequences, and a PCR product of the expected size was indeed produced. DNA primers were designed to two regions of high similarity for use in PCR that were about 100 residues apart. The amino acid sequences of these regions were:

Upstream, corresponding to residues 39-48 of E. coli (SEQ. ID. No. 49)

```
His Ala Tyr Leu Phe Ser Gly Pro Arg Gly
 1               5                  10
```

Downstream, corresponding to residues 138-148 of E. coli (SEQ. ID. No. 50)

```
His Ala Tyr Leu Phe Ser Gly Pro Arg Gly
 1               5                  10
```

The DNA sequence of the PCR primers was based upon the codon usage of S. aureus. The primers are as follows:

Upstream (SEQ. ID. No. 51)

cgc<u>ggatcc</u>c atgcatattt attttcaggt ccaagagg    38

Downstream (SEQ. ID. No. 52)

ccg<u>gaattc</u>t ggtggttctt ctaatgtttt taataatgc    39

The first 9 nucleotides of the upstream primer (SEQ. ID. No. 51) contain a BamHI site, which is underlined, and do not correspond to amino acid codons; the 3' 29 nucleotides correspond to the amino acid sequence of SEQ. ID. No. 49. The EcoRI site of the downstream primer (SEQ. ID. No. 52) is underlined and the 3' 33 nucleotides correspond to the amino acid sequence of SEQ. ID. No. 50.

The expected PCR product, based on the alignment, is approximately 268 bp between the primer sequences. Amplification was performed using 500 ng genomic DNA, 0.5 mM dNTPs, 1 µM of each primer, 1 mM MgSO$_4$, 2 units vent DNA polymerase in 100 µl of vent buffer. Forty cycles were performed using the following cycling scheme: 94° C., 1 min; 60° C., 1 min.; 72° C., 30s. The approximately 300 bp product was digested with EcoRI and BamHI and purified in a 0.7% agarose gel. The pure digested fragment was ligated into pUC18 which had been digested with EcoRI and BamHI and gel purified in a 0.7% agarose gel. Ligated products were transformed into *E. coli* competent DH5a cells (Stratagene), and colonies were screened for the correct chimera by examining minipreps for proper length and correct digestion products using EcoRI and BamHI. The sequence of the insert was determined and was found to have high homology to the dnaX genes of several bacteria. This sequence was used to design circular PCR primers. Two new primers were designed for circular PCR based on this sequence.

A circular PCR product of approximately 1.6 kb was obtained from a HincII digest of chromosomal DNA that was recircularized with ligase. This first circular PCR yielded most of the remaining dnaX gene. The two primers were as follows:

Rightward (SEQ. ID. No. 53)

tttgtaaagg cattacgcag gggactaatt cagatgtg     38

Leftward (SEQ. ID. No. 54)

tatgacattc attacaaggt tctccatcag tgc     33

Genomic DNA (3 µg) was digested with HincII, purified with phenol/chloroform extraction, ethanol precipitated and redissolved in 70 µl T.E. buffer. The genomic DNA was recircularized upon adding 4000 units T4 ligase (New England Biolabs) in a final volume of 100 µl T4 ligase buffer (New England Biolabs) at 16° C. overnight. The PCR reaction consisted of 90 ng recircularized genomic DNA, 0.5 mM each dNTP, 100 µmol of each primer, 1.4 mM magnesium sulfate, and 1 unit of elongase (GIBCO) in a final volume of 100 µl elongase buffer (GIBCO). 40 cycles were performed using the following scheme: 94° C., 1 min.; 55° C., 1 min.; and 68° C., 2 min. The resulting PCR product was approximately 1.6 kb. The PCR product was purified from a 0.7% agarose gel and sequenced directly. A stretch of approximately 750 nucleotides was obtained using the rightward primer used in the circular PCR reaction. To obtain the rest of the sequence, other sequencing primers were designed in succession based on the information of each new sequencing run.

This sequence, when spliced together with the previous 300 bp PCR sequence, contained the complete N-terminus of the gene product (stop codons are present upstream) and possibly lacked only about 50 residues of the C-terminus. The amino terminal region of *E. coli* tau shares what appears to be the most conserved region of the gene as this area shares homology with RFC subunit of the human clamp loader and with the gene 44 protein of the phage T4 clamp loader. An alignment of the N-terminal region of the *S. aureus* tau protein with that of *B. subtilis* and *E. coli* is shown in FIG. 10. Among the highly conserved residues are the ATP binding site consensus sequence and the four cystine residues that form a Zn$^{2+}$ finger.

After obtaining 1 kb of sequence in the 5' region of dnaX, it was sought to determine the remaining 3' end of the gene. Circular PCR products of approximately 800 bps, 600 bps, and 1600 bps were obtained from Apo I, or Nsi I or Ssp I digest of chromosomal DNA that were recircularized with ligase.

Rightward (SEQ. ID). No. 55)

gagcactgat gaacttagaa ttagatatg     29

Leftward (SEQ. ID. No. 56)

gatactcagt atctttctca gatgttttat tc     32

Genomic DNA (3 g) was digested with, Apo I, or Nsi I or Ssp I, purified with phenol/chloroform extraction, ethanol precipitated, and redissolved in 70 1 T.E. buffer. The genomic DNA was recircularized upon adding 4000 units of T4 ligase (New England Biolabs) in a final volume of 100 1 T4 ligase buffer (New England Biolabs) at 16° C. overnight. The PCR reaction consisted of 90 ng recircularized genomic DNA, 0.5 mM each dNTP, 100 µmol of each primer, 1.4 mM magnesium sulfate, and I unit of elongase (GIBCO) in a final volume of 100 1 elongase buffer (GIBCO). 40 cycles were performed using the following scheme: 94° C., 1 min.; 55° C., 1 min.; 68° C., 2 min. The PCR products were directly cloned into pCR II TOPO vector using the TOPO TA cloning kit (Invitrogen Corporation) for obtaining the rest of the C terminal sequence of *S. aureus* dnaX. DNA sequencing was performed by the Rockefeller University sequencing facility.

Example 16

Identification and Cloning of *S. aureus* dnaB

In *E. coli*, the DnaB helicase assembles with the DNA polymerase III holoenzyme to form a replisome assembly. The DnaB helicase also interacts directly with the primase to complete the machinery needed to duplicate a double helix. As a first step in studying how the *S. aureus* helicase acts with the replicase and primase, *S. aureus* was examined for presence of a dnaB gene.

The amino acid sequences of the DnaB helicase of *Escherichia coli, Salmonella typhimurium, Haemophilus influenzae*, and *Helicobacter pylori* were aligned using Clustal W (1.5). Two regions about 200 residues apart showed good homology. These peptide sequences were:

Upstream, corresponding to residues 225-238 of *E. coli* DnaB (SEQ. ID. No. 57)

```
Asp Leu Ile Ile Val Ala Ala Arg Pro Ser Met Gly
 1               5                  10
Lys Thr
```

Downstream, corresponding to residues 435-449 of *E. coli* DnaB (SEQ. ID. No. 58)

```
Glu Ile Ile Ile Gly Lys Gln Arg Asn Gly Pro Ile
 1               5                  10
Gly Thr Val
      15
```

The following primers were designed from regions which contained conserved sequences using codon preferences for *S. aureus*:

Upstream (SEQ. ID. No. 59)

gaccttataa ttgtagctgc acgtccttct atgggaaaaa c     41

Downstream (SEQ. ID. No. 60)

aacattatta agtcagcatc ttgttctatt gatccagatt caacgaag     48

A PCR reaction was carried out using 2.5 units of Taq DNA Polymerase (Gibco, BRL) with 100 ng. *S. aureus* genomic DNA as template, 1 mM dNTP's, 1 µM of each primer, 3 mM MgCl$_2$ in 100 µl of Taq buffer. Thirty-five cycles of the following scheme were repeated: 94° C., 1 min.; 55° C., 1 min.; and 72° C., 1 min. Two PCR products were produced, one was about 1.1 kb, and another was 0.6 kb. The smaller one was the size expected. The 0.6 kb product was gel purified and used as a template for a second round of PCR as follows. The 0.6 kb PCR product was purified from a 0.8% agarose gel using a Geneclean III kit (Bio 101) and then divided equally into five separate aliquots, as a template for PCR reactions. The final PCR product was purified using a Quiagen Quiaquick PCR Purification kit, quantitated via optical density at 260 nM, and sequenced by the Protein/DNA Technology Center at Rockefeller University. The same primers used for PCR were used to prime the sequencing reaction. The amino acid sequence was determined by translation of the DNA sequence in all three reading frames, and selecting the longest open reading frame. The PCR product contained an open reading frame over its entire length. The predicted amino acid sequence shares homology to the amino acid sequences encoded by dnaB gene of other organisms.

Additional sequence information was determined using the circular PCR technique. Briefly, *S. aureus* genomic DNA was digested with various endonucleases, then religated with T4 DNA ligase to form circular templates. To perform PCR, two primers were designed from the initial sequence.

First primer (SEQ. ID. No. 61)

gatttgtagt tctggtaatg ttgactcaaa ccgcttaaga accgg     45

Second primer (SEQ. ID. No. 62)

atacgtgtgg ttaactgatc agcaacccat ctctagtgag aaaatacc     48

The first primer matches the sequence of the coding strand and the second primer matches the sequence of the complementary strand. These two primers are directed outwards from a central point, and allow determination of new sequence information up to the ligated endonuclease site. A PCR product of approximately 900 bases in length was produced using the above primers and template derived from the ligation of *S. aureus* genomic DNA which had been cut with the restriction endonuclease Apo I. This PCR product was electrophoresed in a 0.8% agarose gel, eluted with a Qiagen gel elution kit, divided into five separate aliquots, and used as a template for reamplification by PCR using the same primers as described above. The final product was electrophoresed in an 0.8% agarose gel, visualized via staining with ethidium bromide under ultraviolet light, and excised from the gel. The excised gel slice was frozen, and centrifuged at 12,000 rpm for 15 minutes. The supernatant was extracted with phenol/chloroform to remove ethidium bromide, and was then cleaned using a Qiagen PCR purification kit. The material was then quantitated from its optical density at 260 nm and sequenced by the Protein/DNA Technology Center at the Rockefeller University.

The nucleotide sequence contained an open reading frame over its length, up to a sequence which corresponded to the consensus sequence of a cleavage site of the enzyme Apo I. Following this point, a second open reading frame encoded a different reading frame up to the end of the product. The initial sequence information was found to match the initial sequence and to extend it yet further towards the C-terminus of the protein. The second reading frame was found to end in a sequence which matched the 5'-terminus of the previously determined sequence and, thus, represents an extension of the sequence towards the N-terminus of the protein.

Additional sequence information was obtained using the above primers and a template generated using *S. aureus* genomic DNA circularized via ligation with T4 ligase following digestion with Cla I. The PCR product was generated using 35 cycles of the following program: denaturation at 94° C. for 1 min.; annealing at 55° C. for 1 min.; and extension at 68° C. for 3 minutes and 30 s. The PCR products were electrophoresed in a 0.8% agarose gel, eluted with a Qiagen gel elution kit, divided into five separate aliquots, and used as a template reamplification via PCR with the same primers described above. The final product was electrophoresed in an 0.8% agarose gel, visualized via staining with ethidium bromide under ultraviolet light, and excised from the gel. The excised gel slice was frozen, and centrifuged at 12,000 rpm for 15 min. The supernatant was cleaned using a Qiagen PCR purification kit. The material was then quantitated via optical density at 260 nm and sequenced by the Protein/DNA Technology Center at Rockefeller University. The open reading frames continued past 500 bases. Therefore, the following additional sequencing primers were designed from the sequence to obtain further information:

First primer (SEQ. ID. No. 63)

cgttttaatg catgcttaga aacgatatca g     31

Second primer (SEQ. ID. No. 64)

cattgctaag caacgttacg gtccaacagg c     31

The N-terminal and C-terminal nucleotide sequence extensions generated using this circular PCR product completed the 5' region of the gene (encoding the N-terminus of DnaB); however, a stop codon was not reached in the 3' region and, thus, a small amount of sequence is still needed to complete this gene.

The alignment of the *S. aureus* dnaB with *E. coli* dnaB and the dnaB genes of *B. subtilis* and *S. typhimurium* is shown in FIG. 11.

Example 17

Identification and Cloning of *S. aureus* holB

The *S. aureus* holB was identified by searching the *S. aureus* database with the sequences of *S. pyogenes* δ' subunit. The *S. aureus* holB encodes a 253 residue protein of about 28 kDa. The holB gene was amplified by PCR using an upstream 69-mer primer as follows:

Upstream Primer (SEQ. ID. No. 65):

ggataacaat tccccgctag caataatttt gtttaactt aagaaggaga
   tataccatg     60 gatgaacag     69 which contains an NcoI site (underlined), and a downstream 39-mer primer as follows:

Downstream Primer (SEQ. ID. No. 66):

aattttaaag gatccgtgta taatattcta attttcccg     39 which contains a BamHI site (underlined). The PCR product was digested with NcoI and BamHI, purified, and ligated into the NcoI and BamHI sites of pET11a to produce plasmid pETSaholB.

Example 18

Purification of S. aureus δ'

The pETSaholB plasmid of Example 17 was transformed into E. coli BL21(DE3)recA. A single colony was used to innoculate 2 L of LB media supplemented with 200 µg/ml ampicillin. Cells (2 L) were grown at 37° C. to $OD_{600}$=0.5 at which point the temperature was lowered to 15° C. and 0.5 mM IPTG was added. After 16 hr of induction, cells were collected by centrifugation, resuspended in 50 mM Tris-HCl (pH 7.5), 10% sucrose, 1 M NaCl, 30 mM spermidine, 5 mM DTT, and 2 mM EDTA. Cells were lysed by two passages through a French press (15,000 psi), followed by centrifugation at 13,000 rpm for 30 min at 4° C. Ammonium sulfate (0.3 g/ml) was added to the clarified lysate. The pellet was back-washed in 30 ml buffer A containing 0.1 M NaCl and 0.24 g/ml ammonium sulfate using a Dounce homogenizer, then the pellet was recovered by centrifugation. The resulting pellet was resuspended in 20 ml of buffer A and dialyzed against buffer A. The dialyzed protein was applied to a 20 ml FFQ Sepharose column equilibrated in buffer A and eluted with a 200 ml linear gradient of 0-500 mM NaCl in buffer A; 80 fractions were collected. Peak fractions (54-75) were combined (72 mg) and dialyzed against buffer A. The 6' preparation was aliquoted and stored frozen at −80° C.

Example 19

Identification and Cloning of S. aureus holA

The S. aureus holA gene was identified by searching the S. aureus database with the sequences of E. coli and S. pyogenes 6 subunits. The S. aureus holA gene encodes a 288 residue protein of about 32 kDa. The holA gene was amplified by PCR using an upstream 28-mer primer as follows:

Upstream Primer (SEQ. ID. No. 67):

gggagtttgt aatccatgga tgaacagc                28 which contains a NcoI site (underlined), and a downstream 37-mer primer as follows:

Downstream Primer (SEQ. ID. No. 68):

ctgaacacct attaccctag gcatctaact cacaccc      37 which contains a BamHI site (underlined). The PCR product was digested with NcoI and BamHI, purified, and ligated into the NcoI and BamHI sites of pET11a to produce plasmid pETSaholA.

Example 20

Purification of S. aureus δ

The pETSaholA plasmid of Example 19 was transformed into E. coli NovaBlue (recA1 lac[F'proA⁺B⁺lac$^q$ZΔJM15:: Tn10(Tc$^R$)) (Novagen). A single colony was used to innoculate 12 L of LB media supplemented with 200 µg/ml ampicillin. Cells (12 L) were grown at 37° C. to $OD_{600}$=0.5 at which point the temperature was lowered to 15° C. and 0.5 mM IPTG was added. After 16 hr of induction, cells were collected by centrifugation, resuspended in 50 mM Tris-HCl (pH 7.5), 10% sucrose, 1 M NaCl, 30 mM spermidine, 5 mM DTT, and 2 mM EDTA. Cells were lysed by two passages through a French press (15,000 psi), followed by centrifugation at 13,000 rpm for 30 min at 4° C. Ammonium sulfate (0.3 g/ml) was added to the clarified lysate. The resulting pellet was resuspended in 250 ml of buffer A. The dialyzed protein was applied to a 100 ml FFQ Sepharose column equilibrated in buffer A and eluted with a 1000 ml linear gradient of 0-500 mM NaCl in buffer A; 80 fractions were collected. Peak fractions (40-49) were combined (65 mg) and dialyzed against buffer A. The dialyzed protein was applied to a 8 ml MonoQ Sepharose column equilibrated in buffer A and eluted with a 80 ml linear gradient of 0-500 mM NaCl in buffer A; 80 fractions were collected. Peak fractions of the 6 preparation were stored frozen at −80° C.

Example 21

Constitution of a Processive S. aureus DNA Polymerase III Enzyme from Three Components The PolC (alpha-large) requires the β clamp for processivity, which in turn requires the clamp loader (τδδ') for assembly onto DNA. The S. aureus clamp loader, τδδ' complex, was assembled by mixing the three proteins as follows: 400 µg of r and 80 µg each of 6 and 6' were mixed in buffer A containing no NaCl and preincubated at 15° C. for 10 min. The mixture was injected onto a 1 ml MonoQ column equilibrated in buffer A, and then eluted with a 30 ml linear gradient of 0-500 mM NaCl in buffer A; 60 fractions were collected. Fractions were analyzed in a 10% SDS-polyacrylamide gel stained with Coomassie Blue. Peak fractions (40-50) were combined and concentrated using a Centricon 30 concentrator.

Figure 13:
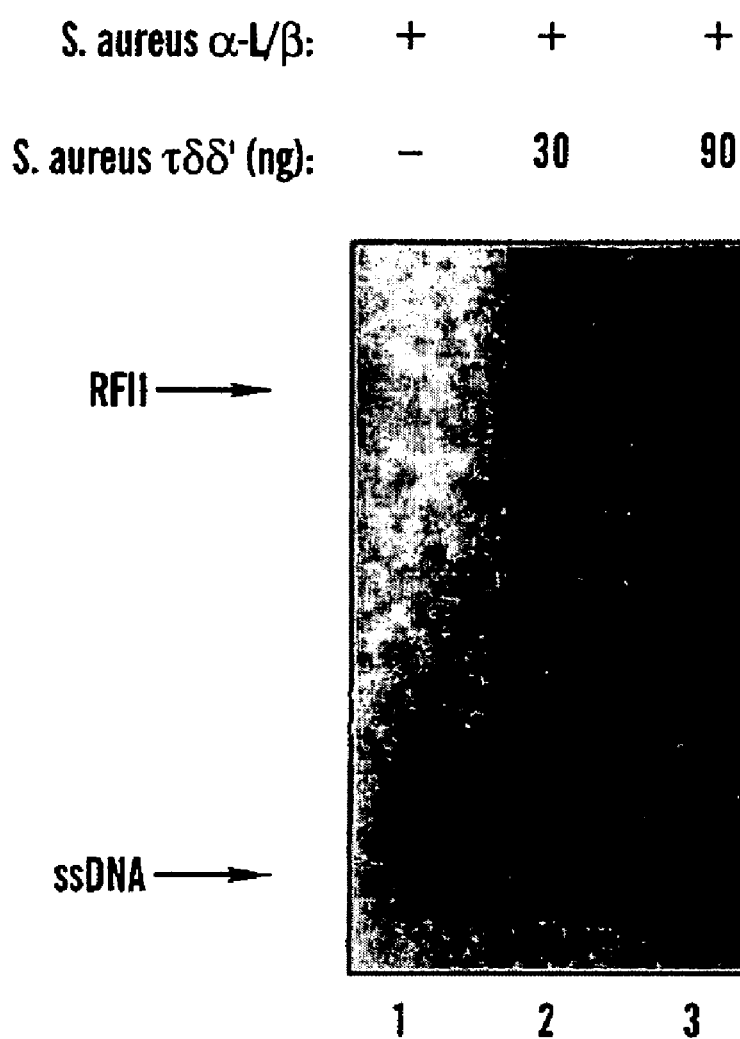
FIG. 13 is an image of an autoradiograph of an agarose gel analysis of replication products from singly primed, SSB coated M13mp18 ssDNA using the reconstituted *S. aureus* Pol III holozyme. Only in the presence of the τδδ' complex does α-large (PolC) function with β to replicate a full circular duplex DNA (RFII).

The ability of the three components to work together to form the processive Pol III was tested by determining whether τδδ' and β clamp could confer the ability of PolC to completely extend a single primer full circle around a large 7.2 kb circular M13mp18 ssDNA genome. Replication reaction contained 70 ng (25 fmol) on singly primed M13 mp18 ssDNA, 20 ng S. aureusβ, 50 ng S. aureus PolC, either 30 ng or 90 ng of S. aureus τδδ' (when indicated), and 0.82 µg of S. pyogenes SSB in 24 µl of 20 mM Tris-HCl (pH 7.5), 4% glycerol, 0.1 mM EDTA, 5 mM DTT, 2 mM ATP, 8 mM $MgCl_2$, 40 µg/ml BSA, and 60 mM each of dGTP and dCTP. Reactions were pre-incubated for 2 min at 37° C. to assemble protein complexes on the primer terminus. DNA synthesis was initiated upon addition of 1.5 µl dATP and $^{32}$P-TTP (specific activity 2,000-4,000 cpm/µmol) and synthesis was allowed to proceed for 1 min before being quenched with an equal volume (25 µl) of a solution of 1% SDS and 40 mM EDTA. One-half of the quenched reaction was analyzed for total DNA synthesis using DE81 paper as described, and the other half was analyzed by agarose gel phoresis. An autoradiogram of the agarose gel analysis of the replication products is depicted in FIG. 13, which shows that the presence of PolC and β, but absence of τδδ' (lane 1) gives no full length circular duplex (RFII). However, in the presence of τδδ' (lanes 2 and 3), full length circular duplex DNA (RFII) is produced, as expected for the action of a processive Pol III holozyme.

Example 22

General Induction/Purification Conditions for S. pyogenes

The purification protocols for S. pyogenes proteins were performed using following standardized conditions. Cells were grown from a single colony, freshly transformed overnight. Cells were grown in 200 µg/ml Ampicillin to OD600=0.3-0.4, at which point cultures were chilled prior to addition of IPTG (to a final concentration of 0.5 mM) and were allowed to incubate for 16 hrs at 15° C. Following this, all procedures were performed at 4° C. Cell paste (1-2 g/liter of culture) was resuspended (10 ml/g cell paste) in 50 mM Tris-HCl (pH 7.5)/10% Sucrose/1 M NaCl/5 mM DTT/30 mM Spermidine/1×Heat lysis buffer (50 mM Tris-HCl (pH 7.5), 1% Sucrose, 100 mM NaCl, 2 mM EDTA). Cells were lysed by two passages through the French Press (15,000 psi) followed by centrifugation at 14,000 rpm at 4° C. Ammonium sulfate, when added to the cleared lysate, was added gradually. Precipitate was allowed to settle on ice for a minimum of 30 min prior to collection by centrifugation. Protein pellets were resuspended in buffer A (50 mM Tris-HCl pH 7.5, 1 mM EDTA, 5 mM DTT, 10% glycerol) and dialyzed for over 3 hours in the same buffer. Column design is based on the manufacturer's suggested capacities: Fast Flow Q (FFQ) and MonoQ are 20 mg protein/ml resin, Heparin-Affigel agarose is 1.2 mg protein/ml resin. Elution was performed using 10 column volume (c.v.) gradients, and the entire gradient elution profile was collected in 80 fractions. Unless mentioned otherwise all columns were equilibrated and eluted with buffer A.

Example 23

Identification of a S. pyogenes holA gene Encoding a Functional Delta Subunit and Purification of the Delta Subunit Alignment of E. coli delta subunit with 10 other putative holA products from unfinished genome databases of Gram negative bacteria indicates a region of conserved amino acid sequence. Amino acids Q140 to L230 of E. coli delta were used to search the B. subtilis genome database for a Gram positive delta homolog. This search revealed yqeN, a potential reading frame of unknown function, as the highest scoring sequence. Although the score was low, it was treated as a candidate for Gram positive delta. The alignment with E. coli delta is shown in FIG. 12A. A Streptococcus pyogenes genome database was searched with yqeN. Two contigs which represent N- (contig 206) and C- (contig 264) termini of S. pyogenes delta subunit were identified. The alignment of the putative S. pyogenes holA with B. subtilis yqeN is shown in FIG. 12B. The following primers were used to obtain PCR products for delta subunit:

holA Upstream (SEQ. ID No. 69)

ggagcagatt gcttttgata catatgattg gcctattc    38 holA Downstream (SEQ. ID No. 70)

ttgtctccgc atcaaactgg gatccaagag catcatacgc gtatgg    46

These primers were used to amplify the holA gene from S. pyogenes genomic DNA. The PCR product was digested with NdeI and BamHI, purified and ligated into the pET11a vector to produce pET11a.S.p. holA.

Figure 14:
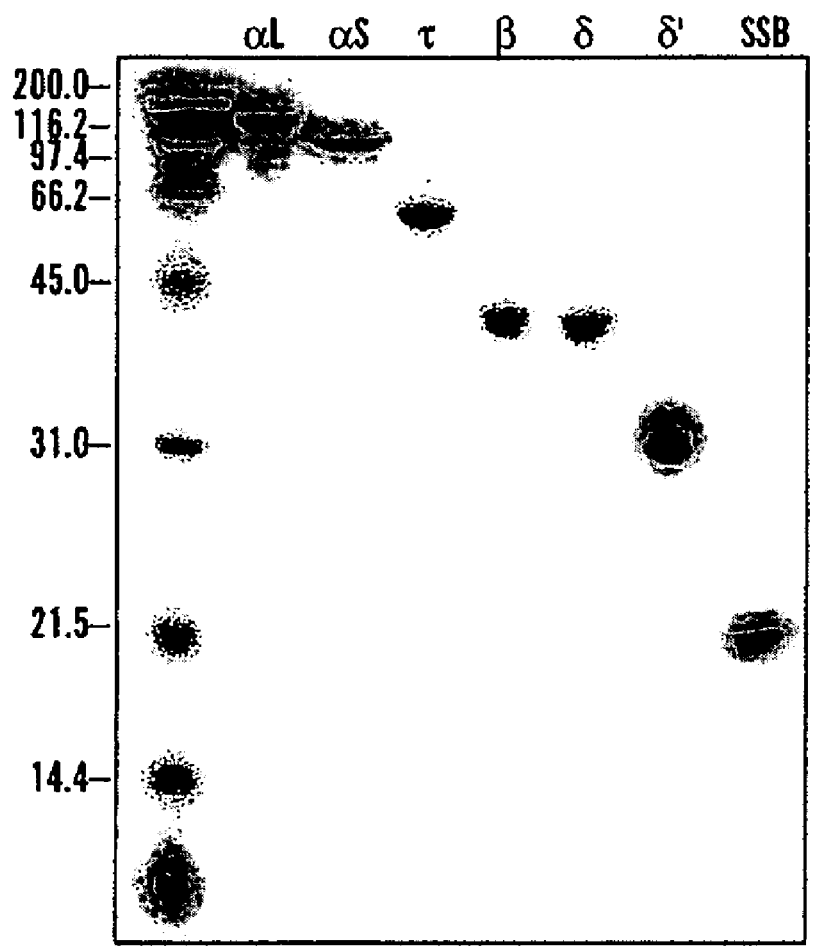
FIG. 14 shows a Comassie Blue stained SDS polyacrylamide gel of the pure *S. pyogenes* subunits corresponding to alpha-large, alpha-small, dnaX gene product (called tau), beta, delta, delta prime, and SSB. The first lane shows the position of molecular weight markers. Purified proteins were separated on a 15% SDS-PAGE and stained with Coommassie Brilliant Blue R-250. Each lane contains 5 microgram of each protein. Lane 1, markers; lane 2, alpha-large; lane 3, alpha-small, lane 4, tau subunit; lane 5, beta subunit; lane 6, delta subunit; lane 7, delta prime subunit; lane 8, single strand DNA binding protein.

The pET11a.S.p.holA plasmid was transformed into the BL21(DE3)RecA-strain of E. coli. A single colony from an overnight transformation was used to innoculate 12 L LB broth supplemented with 200 µg/ml Ampicillin. Cells were grown at 37° C. to OD600=0.5, at which point the temperature was lowered to 15° C. and 0.5 mM IPTG was added. Induction proceeded for 16 hrs. In the morning, cells were collected by centrifugation and resuspended in 50 mM Tris-HCl (pH 7.5)/10% Sucrose/1×Heat Lysis Buffer/1 M NaCl/30 mM Spermidine/5 mM DTT. Cells were lysed by two passages through the French press (15,000 psi), followed by centrifugation at 13,000 rpm for 30 min. The supernatant was decanted and ammonium sulfate was added to a final concentration of 0.226 g/ml. The resulting pellet was collected by centrifugation and resuspended in 20 ml of buffer A. The resuspended pellet was dialyzed against buffer A containing no salt. The dialyzed protein (500 mg) was loaded onto a FFQ- Sepharose (35 ml) column and eluted with a linear gradient from 0-500 mM NaCl (10 c.v.). The peak fractions (21-45) were combined and dialyzed against buffer A (0 NaCl) for 3 hrs, then diluted to a conductivity of 50 mM NaCl and loaded (160 mg) onto a 120 ml Heparin-Affigel column. Protein was eluted with a linear gradient of 0-500 mM NaCl (10 c.v.). The fractions containing the least contaminants (39-51) were precipitated with ammonium sulfate (0.226 g), collected by centrifugation, resuspended 5 ml of buffer A, and dialyzed in buffer A containing 200 mM NaCl. The delta subunit was stored at −80° C. The final delta subunit preparation is shown in the lane marked δ of the Coomassie Blue stained SDS-polyacrylamide gel of FIG. 14. Yield=65 mg.

Example 24

Identification of S. pyogenes holB Encoding Delta Prime and Purification of the Delta Prime Subunit A search of the S. pyogenes genome database with the predicted B. subtilis delta prime amino acid sequence revealed a DNA sequence in contig #209 (previously known as contig #210) that predicted a high scoring match for a gene encoding a delta prime protein. The following primers were used to obtain PCR products for holB:

holB Upstream (SEQ. ID. No. 71)

gcctaggata agggagggta catatggatt tagcgc    36 holB Downstream (SEQ. ID. No. 72)

cgggcaagtc ttttgacaag cttcggatcc ccataacgaa ttcc    44

The PCR product obtained from these primers was digested with NdeI and BamHI, purified and ligated into the pET11a vector to produce pET11a.S.p. holB.

The pET11a.S.p.holB plasmid was transformed into the BL21 (DE3)RecA-strain of E. coli. A single colony from an overnight transformation was used to innoculate 12L LB broth supplemented with 200 µg/ml Ampicillin. Cells were grown at 37° C. to O.D. 600=0.4, at which point the temperature was lowered to 15° C. and 0.5 mM IPTG was added. Induction proceeded for 16 hrs. In the morning, cells were collected by centrifugation and resuspended in 100 ml 50 mM Tris-HCl (pH 7.5)/10% Sucrose/1×Heat Lysis Buffer. Lysis was initiated upon addition of 0.4 mg/ml lysozyme followed by a 1 hr incubation on ice. Lysate was clarified by centrifugation at 13,000 rpm for 30 min. Ammonium sulfate was added to the supernatant to a final concentration of 0.3 g/ml. The protein pellet was resuspended in buffer A(0.1 M NaCl)+ 0.24 g/ml ammonium sulfate and clarified by centrifugation. The resulting protein pellet was resuspended in 20 ml of buffer A and dialyzed against buffer A. The dialyzed protein (450 mg) was loaded onto a 30 ml FFQ- Sepharose column and eluted with a linear gradient from 0-500 mM NaCl. The peak fractions were combined (fr#20-30 containing 130 mg) and dialyzed against buffer A and loaded (70 mg) onto a 50 ml Heparin-Affigel column. Protein was eluted with a linear gradient of 0-500 mM NaCl. Delta prime binds weakly to both resins and elutes in the beginning of the gradient. This delta prime subunit was stored frozen at −80° C. The final delta prime subunit preparation is shown in lane marked δ' of the Coomassie Blue stained SDS-polyacrylamide gel of FIG. 14. Yield=40 mg.

Example 25

Identification of the *S. pyogenes* dnaX Gene and Purification of the Tau Subunit A search of the *S. pyogenes* genome database with the putative *B. subtilis* tau amino acid sequence revealed a DNA sequence in contig #284 (previously known as contig #289) with a high scoring match which predicted a gene encoding for a tau subunit protein. A set of PCR primers to 5'- and 3'-termini of the putative gene sequence were designed to include restriction enzyme recognition sequences for NdeI and BamHI sites, respectively. These primers are:

dnaX Upstream (SEQ. ID. No. 73)

ggagttaaaa acatatgtat caagctcttt atc         33 dnaX Downstream (SEQ. ID. No. 74)

cgtgggtaag ggcaaaacgg atcccttatg tatttcag         38

A PCR product obtained with the above primers was digested with NdeI and BamHI, purified and ligated into pET11a vector to produce pET11a.S.p.dnaX.

The pET11a.S.p.dnaX plasmid was transformed into the BL21(DE3)RecA-strain of *E. coli*. A single colony from an overnight transformation was used to innoculate 24L LB broth supplemented with 200 µg/ml Ampicillin. Cells were grown at 37° C. to O.D.600=0.5, at which point the temperature was lowered to 15° C. and 0.5 mM IPTG was added. Induction proceeded for 16 hrs. In the morning, cells were collected by centrifugation and resuspended in 200 mls of 50 mM Tris-HCl (pH 7.5)/10% Sucrose/1×Heat Lysis Buffer/1 M NaCl/30 mM Spermidine/5 mM DTT/5 mM EDTA. Cells were lysed by two passages through the French press (15,000 psi), followed by centrifugation at 13,000 rpm for 30 min. The supernatant (2.4 gm) was dialyzed against buffer A containing 50 mM NaCl, loaded onto a 120 ml FFQ column (without ammonium sulfate precipitation) and eluted with a linear gradient of 100-700 mM NaCl. The peak fractions (fr#41-55) were combined, diluted with buffer A containing no salt (a dilution of 1/5) to a conductivity of 100 mM NaCl, loaded (310 mg) onto a 300 ml Heparin-Affigel column, and eluted with a linear gradient of 100-500 mM NaCl. The peak fractions (fr#21-36) were combined, dialyzed against buffer A, loaded (87 mg) onto 10 ml FFQ column, and eluted as described for the first FFQ column. The peak fractions (fr#27-41) were concentrated by centrifugation in Centriprep 30 filtration unit and frozen at −80° C. The final tau subunit preparation is shown in the lane marked T of the Coomassie Blue stained SDS-polyacrylamide gel of FIG. 14. Yield=103 mg.

Example 26

Identification of the *S. pyogenes* dnaN Gene and Purification of the Beta Subunit A search of the *S. pyogenes* genome database with the putative *B. subtilis* beta subunit amino acid sequence revealed a DNA sequence (contig #266) with a high scoring match which predicted a gene encoding for a beta subunit protein. A set of PCR primers to 5'- and 3'-termini of the putative gene sequence were designed to include restriction enzyme recognition sequences for NdeI and BamHI, respectively. The primers were:

dnaN Upstream (SEQ. ID. No. 75)

ggagttcata tgattcaatt ttcaaattaa tcgc         34 dnaN Downstream (SEQ. ID. No. 76)

tatcagctcc tggatccagt accttccatt gattagcc         38

A PCR product obtained with these primers was digested with NdeI and BamHI, purified and ligated into pET16b vector to produce pET16b.S.p.dnaN.

The pET16b.S.p.dnaN plasmid was transformed into the BL21(DE3)RecA- strain of *E. coli*. A single colony from an overnight transformation was used to innoculate 15L LB broth supplemented with 200 µg/ml Ampicillin. Cells were grown at 37° C. to O.D.600=0.4, at which the point temperature was lowered to 15° C. and 0.5 mM IPTG was added. Induction proceeded for 16 hrs. In the morning, cells were collected by centrifugation and resuspended in 100 ml 50 mM Tris-HCl (pH 7.5)/10% Sucrose/1×Heat Lysis Buffer/1 M NaCl/5 mM DTT/30 mM Spermidine/5 mM EDTA. Cells were lysed by two passages through the French press (15,000 psi), followed by centrifugation at 13,000 rpm for 30 min. Ammonium sulfate was added to the supernatant to a final concentration of 0.3 g/ml. The resulting protein pellet was resuspended and dialyzed against buffer A containing 50 mM NaCl. The dialyzed protein (300 mg) was loaded onto a 45 ml FFQ- Sepharose column and eluted with a linear gradient from 50-500 mM NaCl. The peak fractions (16-30) were combined, dialyzed against buffer A containing 50 mM NaCl, loaded onto a 25 ml EAH-Sepharose column, and eluted with a linear gradient of 50-500 mM NaCl. The fractions containing the least contaminants were combined into two pools (pool I 10-17, pool II 19-27). Each pool was further purified on a 8 ml MonoQ column (performed under conditions described for the FFQ column above). The final beta subunit preparation is shown in the lane marked β of the Coomassie Blue stained SDS-polyacrylamide gel of FIG. 14. Yield=48 mg.

Example 27

Identification of the *S. pyogenes* polC Gene and Purification of the Alpha-Large Polymerase Subunit A search of the *B. subtilis* genome database with the *E. coli* alpha subunit amino acid sequence revealed two DNA sequences with a high scoring match which predicted two genes encoding alpha-like polymerase subunits. The DNA sequence with the second highest scoring match which encoded the largest of the two polymerase subunits also appeared to encode for the epsilon exonuclease domain at the N-terminus of the putative alpha subunit. A search of the *B. subtilis* genome database with *S. pyogenes* DNA sequence confirmed this nucleotide sequence to encode the Gram positive homolog of the *E. coli* replicative polymerase subunit (alpha). This Gram negative alpha-like subunit lacked homology to epsilon. The gene encoding the large alpha polypeptide sequence (alpha-large) will be referred to as the product of the polC gene and the gene encoding the smaller Gram-negative alpha-like polymerase (alpha-small) will be referred to as the product of the polE or dnaE gene (see Example 28).

The alpha-large polymerase polypeptide is a product of two overlapping contigs; contig #197 (renamed #193) encodes the N-terminal 630 amino acids, and contig #278 (renamed #273) encodes the C-terminal 1392 amino acids. The putative Open Reading Frame generates a 1464 amino acid polypeptide (SEQ. ID. No. 18). Since the polC nucleotide sequence contained several NdeI sites, a primer was designed to mutate two restriction endonuclease sites in the pET11a nucleotide sequence upstream of the N-terminus of the gene; an XbaI restriction site was mutated to an NheI restriction site and an NdeI restriction site at the starting ATG was removed. A 74mer primer which spans from mutated XbaI site upstream of T7 promoter includes NheI site, rbs site (ribosome binding site), mutated NdeI site and first 10 amino acid codons of polC gene sequence. The following primers were used in a PCR reaction to amplify polC gene from *S. pyogenes* genomic DNA:

polC Upstream (SEQ. ID. No. 77)

ggataacaat tccccgctag caataatttt gtttaactt aagaaggaga tatacccatg  60
tcagatttat tcgc  74 polC Downstream (SEQ. ID. No. 78)

cggtgtctct atctaaatga ctcatttggg atcctcgctt tatacggtat gtcacag  57

Elongase (BRL) produced the best amplification results. PCR reaction conditions were: 5 pg genomic DNA, 20 ng of each primer, 1 ml Elongase, 60 µM each dNTP, in 100 ml Elongase reaction buffer for 1 min at 94° C., 1 min at 55° C., and 6 min at 60° C. repeated for 40 cycles. The resulting 4000 bp PCR fragment was digested with NheI and BamHI, purified and ligated into the pET11a vector (digested with XbaI and BamHI) to produce pET11a.S.p.polC.

The pET11a.S.p.polC plasmid was transformed into the BL21(DE3)RecA-strain of *E. coli*. A single colony from an overnight transformation was used to innoculate 24L LB broth supplemented with 200 µg/ml Ampicillin. Cells were grown at 37° C. to OD600=0.4 at which point temperature was lowered to 15° C. and 0.5 mM IPTG was added. Induction proceeded for 16 hrs. In the morning, cells (12g) were collected by centrifugation and resuspended in 100 ml 50 mM Tris-HCl (pH 7.5)/10% Sucrose/1×Heat Lysis Buffer/1 M NaCl/5 mM DTT/30 mM Spermidine/5 mM EDTA. Cells were lysed by two passages through the French press (15,000 psi), followed by centrifugation at 13,000 rpm for 30 min. Ammonium sulfate was added to the supernatant to a final concentration of 0.226 g/ml. The precipitate was collected by centrifugation. The protein pellet (220 mg resuspended in buffer A) was dialyzed against buffer A containing 150 mM NaCl, loaded onto an 8 ml FFQ column equilibrated with buffer A containing 150 mM NaCl, and eluted with a linear gradient of buffer A containing 150-600 mM NaCl. The fractions containing the least contaminants (fr#42-64) were combined and precipitated with ammonium sulfate (0.226 g/ml). The precipitate was collected by centrifugation and resuspended in buffer A (10 mg/ml in 5 ml). A fraction (1 ml=10 mgs) of the concentrated protein was dialyzed, loaded onto 10 ml ssDNA-agarose column, and eluted with a linear gradient of 50-500 mM NaCl. The peak fractions (fr#30-50) were combined and concentrated with ammonium sulfate (as above). The final alpha-large subunit preparation is shown in lane marked $\alpha_L$ of the Coomassie Blue stained SDS-polyacrylamide gel of FIG. 14. Yield=4 mgs.

Example 28

Identification of the *S. pyogenes* dnaE Gene and Purification of the Alpha-Small Polymerase A search of the *B. subtilis* genome database using the *E. coli* alpha subunit amino acid sequence revealed two DNA sequences with a high scoring match which predicted two genes encoding for alpha-like polymerase subunits. The DNA sequence with the highest scoring match encodes a smaller alpha polymerase which does not contain an exonuclease domain. The putative short alpha DNA sequence is a product of the open reading frame in contig #253 of the *S. pyogenes* genome database. A set of PCR primers to 5'- and 3'-termini of the putative gene sequence were designed to include restriction enzyme recognition sequences for NdeI and BamHI, respectively. The primers were:

α-Short Upstream (SEQ. ID. No. 79)

gggaacaaga taaccaagga ggaacccatg gttgctcaac ttg  43

α-Short Downstream (SEQ. ID. No. 80)

cgaatagcag cgttcatacc aggatcctcg ccgccactgg  40

A PCR product obtained with these primers was digested with NdeI and BamHI, purified and ligated into pET11a vector to produce pET11a.S.p.dnaE.

The pET 11a.S.p.dnaE plasmid was transformed into the BL21 (DE3)RecA- strain of *E. coli*. A single colony from an overnight transformation was used to innoculate 12L LB broth supplimented with 200 µg/ml Ampicillin. Cells were grown at 37° C. to OD600=0.4, at which point temperature was lowered to 15° C. and 0.5 mM IPTG was added. Induction proceeded for 16 hrs. In the morning, cells were collected by centrifugation and resuspended in 100 mls 50 mM Tris-HCl (pH 7.5)/10% Sucrose/1×Heat Lysis Buffer/5 mM DTT/30 mM Spermidine/1 M NaCl/5 mM EDTA. Cells were lysed by two passages through the French press (15,000 psi), followed by centrifugation at 13,000 rpm for 30 min. Ammonium sulfate was added to the supernatant to a final concentration of 0.226 g/ml. The precipitate was collected by centrifugation. The protein pellet (resuspended in buffer A) was then dialyzed against buffer A. The dialyzed protein (600 mg) was loaded onto a 30 ml FFQ and eluted with a linear gradient of buffer A containing 50-500 mM NaCl. The peak fractions (200 mg in fr#70-79) were dialyzed and loaded onto a 100 ml Heparin-Affigel column. The fractions containing the least contaminants (100 mg from fr#18-30) were pooled and dialyzed against buffer A containing 300 mM NaCl. The dialysate (50 mg) was loaded onto a 50 ml ssDNA-agarose column and eluted with a linear gradient of 300 mM-1 M NaCl. The final alpha-small subunit preparation is shown in lane marked as of the Coomassie Blue stained SDS-polyacrylamide gel of FIG. 14. Yield=25 mg.

Example 29

Identification of the *S. pyogenes* ssb Gene and Purification of the Single Strand DNA-Binding Protein Search of the *S. pyogenes* genome using the *B. subtilis* SSB amino acid sequence identified a polypeptide in contig #230 (212) as having highest homology to single strand binding protein of several Gram negative bacteria. This contig lacked the first 26 amino acids at the N-terminus. Circular PCR was employed to identify the DNA encoding the N-terminus of the putative SSB protein. *S. pyogenes* genomic DNA was digested overnight with ApoI (5 µg chromosomal DNA in a 50µl reaction). The DNA was extracted with phenol and pre-cipitated with ethanol. The ApoI digested chromosomal DNA was self-ligated to generate circular template for future use in the circular PCR. A circular PCR was performed with primers designed to anneal back-to-back to amplify circularized ApoI reaction fragments. The primers were:

ssb.circ Upstream (SEQ. ID. No. 81)

accattttgg cttttaaagg tacggttaac agcaagtgtg aaggtagcc    49 ssb.circ Downstream (SEQ. ID. No. 82)

gaacgcgagg cagatttcat taactgtgtg atctggcg    38

The PCR reaction conditions were as follows: 100 ng circularized S. pyogenes genomic DNA, 20 ng each primer, 1 ml Elongase, 60 µM each dNTP, 100 1 Elongase reaction buffer. Amplification was performed for 40 cycles as follows: denature, 1 min at 94° C.; anneal, 1 min at 55° C.; and extend, 5 min at 68° C. PCR products were cloned into the Topo TA vector following instructions of the manufacturer (Promega). Several positive clones were sequenced to obtain N-terminal nucleotide sequence. This information lead to design of the following primers with which the use of a standard PCR reaction generated whole ssb gene products. The primers were:

ssb Upstream (SEQ. ID. No. 83)

tttaaaagag ggtagcatat gattaataat gtagtactag ttggtcgc    48 ssb Downstream (SEQ. ID. No. 84)

tttaaattta aacctaggtt caatccattc tgactagaat ggaagatcgt c    51

The resulting PCR product was digested with NdeI and BamHI, purified and ligated into pET11a vector to produce pET11a.S.p. ssb.

The pET11a.S.p.ssb plasmid was transformed into the BL21 (DE3)RecA- strain of E. coli. A single colony from an overnight transformation was used to inoculate 12L LB broth supplemented with 200 µg/ml Ampicillin. Cells were grown at 37° C. to OD600=0.5, at which point 0.5 mM IPTG was added. At the end of the 3 hr induction, cells were collected by centrifugation and resuspended in 100 ml of 50 mM Tris-HCl (pH 7.5)/10% Sucrose/1×Heat Lysis Buffer/5 mM DTT/5 mM EDTA. The cell lysis was initiated upon addition of 0.4 mg/ml lysozyme followed by a 1 hr incubation on ice. The lysate was clarified by centrifugation at 13,000 rpm for 30 min. The SSB protein was significantly purified by sequential fractionation with ammonium sulfate in the following manner. Solid ammonium sulfate was added to the clarified lysate to a final concentration of 0.24 g/ml and the precipitated protein was collected by centrifugation at 13,000 rpm for 30 min. The resulting pellet was homogenized in buffer A(0.1 M NaCl)+0.24 g/ml ammonium sulfate and the precipitate was collected by centrifugation. This procedure was repeated with buffer A(0.1 M NaCl)+0.2 g/ml ammonium sulfate, buffer A(0.1 M NaCl)+0.15 g/ml ammonium sulfate, and buffer A(0.1 M NaCl)+0.13 g/ml ammonium sulfate. The final pellet was resuspended in buffer A +0.15 M NaCl and dialyzed against the same buffer. The resulting pellet was resuspended in buffer A and dialyzed against buffer A containing 500 mM NaCl. The dialysate (300 mg) was diluted to 0.15 M NaCl before it was loaded onto a 20 ml MonoQ column and eluted with a linear gradient of 0.15 M-0.5 M NaCl in buffer A. The SSB protein elutes in the very beginning of the gradient. The peak fractions were combined (150 mg in fractions 16-30), diluted to 0.05 M NaCl, loaded onto a 10 ml ssDNA-agarose column, and eluted with 0.5 M NaCl. The peak fractions (32-62) were combined and frozen. The SSB was further purified over a MonoQ column to remove contaminating polymerase activity. The final single strand DNA binding protein preparation is shown in lane marked ssb of the Coomassie Blue stained SDS-polyacrylamide gel of FIG. 14. Yield=120 mg.

Example 30

First Demonstration that S. pyogene holA Encodes a Delta Subunit Involved In Replication: Assembly of τδδ' Complex Gel filtration is a standard analytical technique to demonstrate direct protein-protein interaction. Purified τ, δ, δ' proteins were used to examine whether they form a protein complex assembly. Gel filtration of t mixed with either δ, δ', or both δ and δ' was performed using an HR 10/30 Superose 6 column equilibrated with buffer A containing 100 mM NaCl. Either δ (200 µg), δ' (200 µg), or a mixture of δ and δ' (200 µg each) was incubated for 30 min at 15° C. in 100 µl of buffer A containing 100 mM NaCl, and the entire mixture was injected onto the column. The mixture was resolved on the column by collection of 170 µl fractions after the initial void (6.6 µl) volume was collected. Fractions were analyzed by 10% SDS-polyacrylamide gels (301/lane) stained with Coomassie Blue.

Figure 15A:
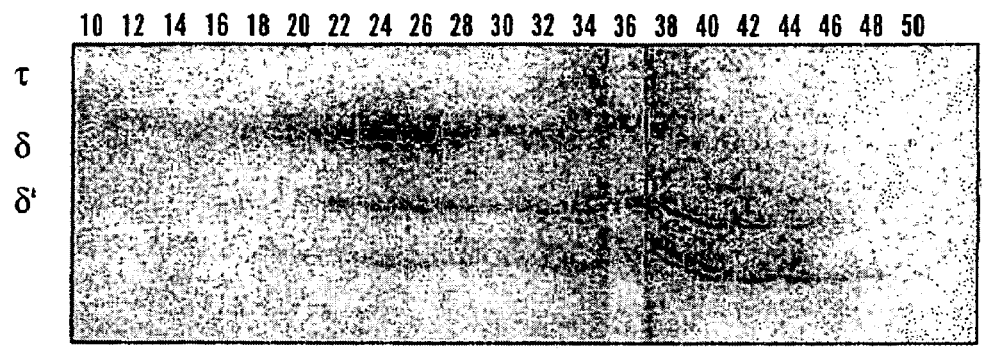
FIGS. 15A-C document the ability to reconstitute the τδδ' complex of *S. pyogenes*. Proteins were mixed and gel filtered on Superose 6, followed by analysis of the column fractions in a SDS polyacrylamide gel.
Figure 15B:
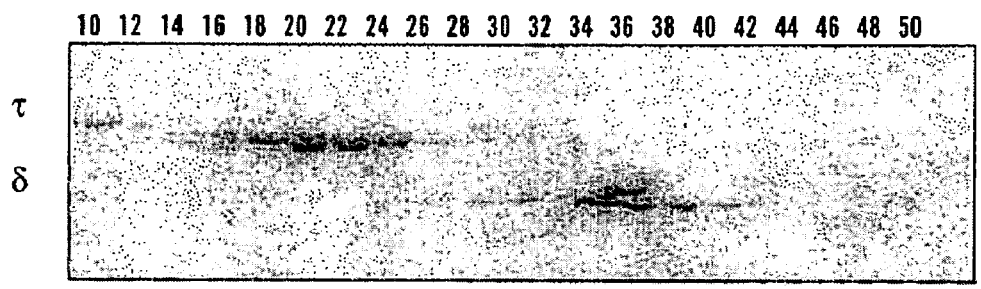
Figure 15C:
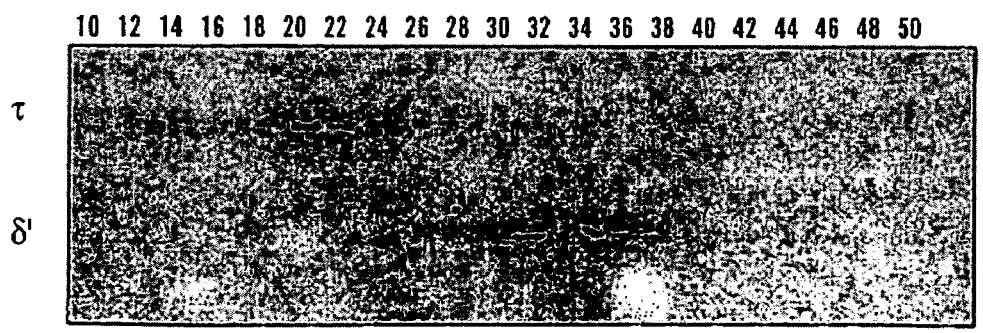

The results, in FIG. 15, demonstrate that under these conditions the τ protein exhibits no (weak) interaction with the delta (FIG. 15B) and the delta prime subunits (FIG. 15C) individually, and yet assembles readily into a complex when all the subunits are mixed in the reaction (FIG. 15A). The τ protein was mixed with a 2-fold molar excess of each δ and δ', then gel filtered. A complex of τδδ' was formed as demonstrated by coelution of δ and δ' with τ (fr#22-30) whereas excess δδ' complex elutes in later fractions (fr#38-46). To determine whether individual δ or δ' subunits interact with t, the τ subunit was mixed with either δ or δ' and then gel filtered. The results demonstrate that a gel filterable complex does not form when τ is mixed with δ (FIG. 15B) or δ' (FIG. 15C) subunits individually, as indicated by the absence of these subunits in the T containing fractions (fr#20-26). Therefore, it appears that the presence of both δ and δ' subunits is essential for the formation of the τδδ' complex.

Example 31

Second Demonstration that S. pyogenes holA Encodes Delta: Functional Assembly of δ on DNA Gel filtration was used to demonstrate that the τ, δ, δ' proteins form a functional clamp loading complex which is able to load the β clamp onto a circular DNA molecule The reaction contained 0.5 µmol of gp2 nicked pBluescript plasmid (a circular double strand plasmid with a single nick produced by M13 gp2 protein), 1 pmol [$^{32}$P]β, 0.5 pmol τδδ' complex, 0.25 pmol of either δ, δ', τ were used in individual experiments when a subassembly of the complex was tested (τδ, τδ', δδ') in 75 µl buffer B (20 mM Tris-HCl (pH 7.5), 20% glycerol, 0.1 mM EDTA, 5 mM DTT, 2 mM ATP, 8 mM MgCl$_2$). β was incubated with nicked DNA for 10 min at 37° C. either alone, or in combination with various assemblies of the τ complex. All gel filtration experiments were performed at 4° C. The reaction mixtures were applied to a 5 ml column of Bio-Gel 15 M (Bio-Rad) equilibrated in buffer B containing 100 mM NaCl. Fractions of 170 µl were collected and quantitated in the Scintillation counter.

Figure 16A:
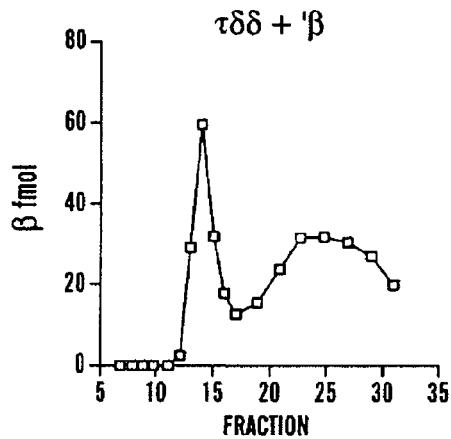
FIGS. 16A-E show that the *S. pyogenes* τδδ' complex can load the *S. pyogenes* beta clamp onto (circular) DNA. Loading reactions contained 500 fm nicked pBSK plasmid, 500 fin either τδδ' complex, tau, delta, or delta prime, 1 pm $^{32}$P-labelled beta dimer, 8 mM MgCl$_2$, 1 mM ATP. Reaction components were preincubated for 10 min at 37° C. prior to loading onto 5 ml Biogel A15M column equilibrated with buffer A containing 100 mM NaCl.
Figure 16B:
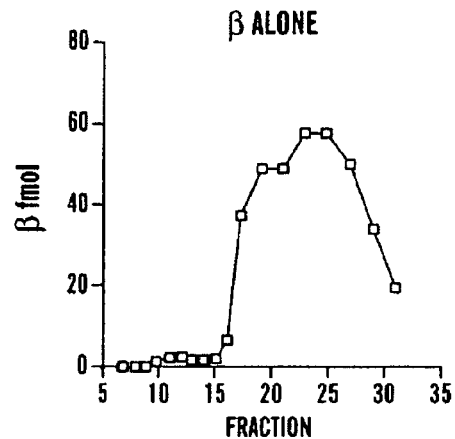
Figure 16C:
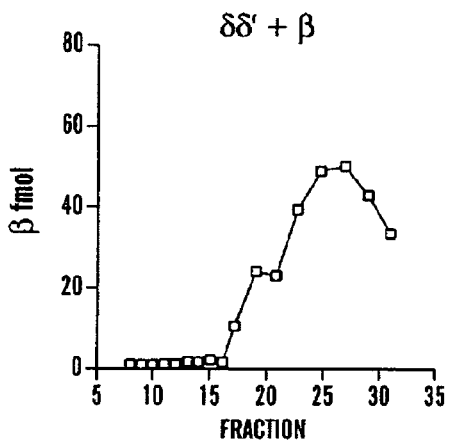
Figure 16D:
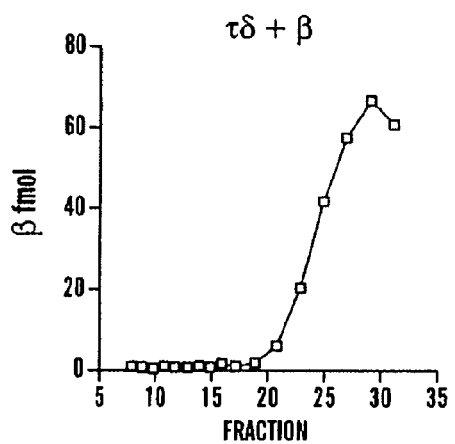
Figure 16E:
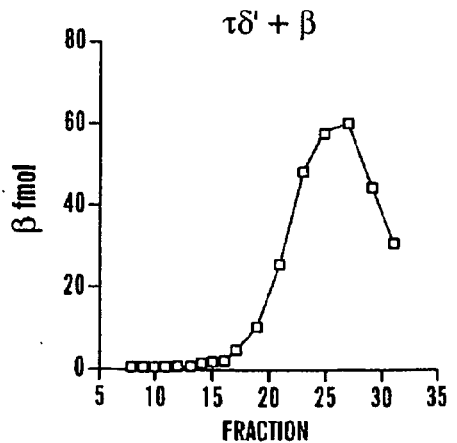

The results, in FIG. 16, demonstrate that the assembly of the ring onto a circular DNA molecule requires the presence of τ, δ, and δ' proteins (FIG. 16A). In absence of any one of the subunits, loading onto DNA does not occur (FIGS. 16B-E). The clamp loader complex (τδδ') can be supplied as a mixture of τ, δ, δ' subunits or as an assembled complex (purified from unassembled subunits by gel filtration, or by ion exchange chromatography on MonoQ). Proteins bound to the large DNA molecule elute in the early fractions (void fr#10-17) and resolve from free proteins that elute in later fractions (fr#18-35).

Example 32

The τ Subunit Product of the dnaX Gene Binds α-Large

The interaction of *S. pyogenes* α and τ proteins was examined by analyzing a mixture of the proteins by gel filtration. Gel filtration of τ, α-large or a mixture of α-large and τ was performed using an HR 10/30 Superose 6 column equilibrated with buffer A containing 100 mM NaCl. Either α-large (400 µg) (200 µM) or a mixture of α-large and t was incubated for 30 min at 15° C. in 100 µl of buffer A containing 100 mM NaCl, and the entire mixture was injected onto the column. The mixture was resolved on the column by collection of 170 µl fractions after the initial void (6.6 ml) volume was collected. Fractions were analyzed by 10% SDS-polyacrylamide gels (30 µl/lane) stained with Coomassie Blue.

Figure 17A:
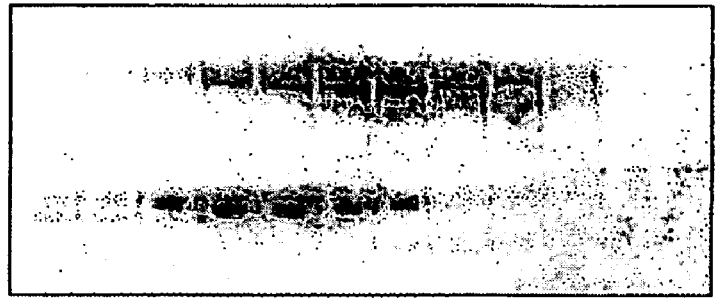
FIGS. 17A-C show that τ and alpha interact.
Figure 17B:
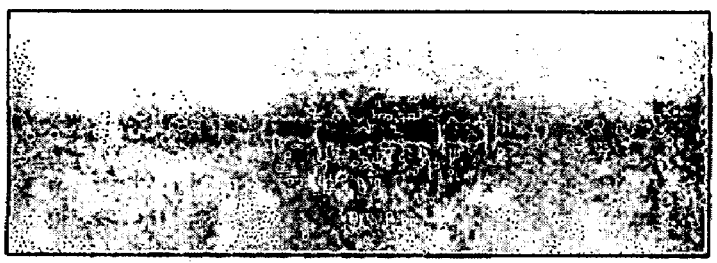
Figure 17C:
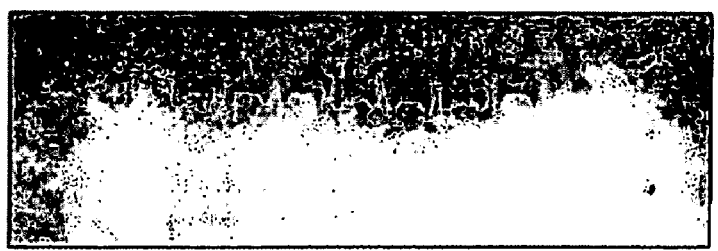

The results show a complex of $α_L τ$ was formed as demonstrated by coelution of α-large and T (fr#30-38) proteins (FIG. 17A) compared to the elution profile of individual proteins (FIGS. 17B-C). Also, the migration of the τ in the $α_L τ$ complex changes significantly to a larger complex (4 fractions, from fr#37 to fr#33).

Example 33

Formation of $α_L τδδ'$ Complex

To determine whether a $α_L τδδ'$ complex could form, the following components were mixed: α-large (400 µg, 2.5 nmol), τ (200 µg, 1.3 nmol), δ (200 µg, 4.8 nmol), δ' (200 µg, 5.75 µmol) in a final volume of 150 µl. The mixture was diluted to 300 ml with buffer A to lower conductivity of the sample to that equivalent of 100 mM NaCl and incubated for 30 min at 15° C. The mixture was injected onto a Superose 6 column (equilibrated with buffer A containing 100 mM NaCl) and fractions (170 µl) were collected after an initial 6.6 ml of void volume was collected. Fractions were analyzed by 10% SDS-polyacrylamide gels (30 µl/lane) stained with Coomassie Blue.

Figure 18:
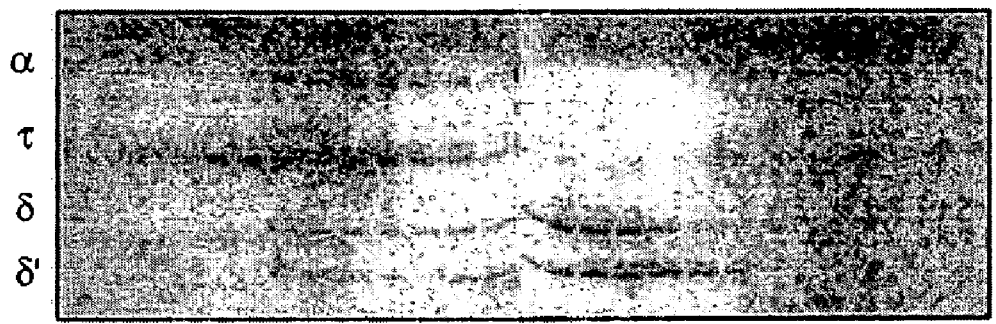
FIGS. 18 documents the ability to reconstitute $α_Lτδδ'$ (pol III*) complex of *S. pyogenes*. Proteins were mixed, preincubated for 20 min at 15° C., gel filtered on Superose 6, followed by analysis of the column fractions in a SDS polyacrylamide gel (FIG. 18). Proteins were loaded on a MonoQ column, then eluted with a linear gradient of 50-500 mM NaCl, followed by analysis of the column fractions in a SDS polyacrylamide gel. The $a_Lτδδ'$ complex migrates early.

A gel filterable complex (FIG. 18) of $α_L τδδ'$ was formed as demonstrated by coelution of τ, δ and δ' with α-large (fr#14-26), whereas excess δδ' complex elutes in later fractions (fr#30-38). The migration of the τδδ' protein complex in the $α_L τδδ'$ complex does not change significantly. The complex might dissociate under the nonequilibrium conditions of gel filtration due to low concentration of proteins, salt concentration and speed of resolution.

Next, ion exchange chromatography was used to analyze the protein mixture to prepare the reconstituted $α_L τδδ'$ complex of *S. pyogenes*. The $α_L τδδ'$ complex was reconstituted upon mixing α-large (10 mg, 62 nmol), T (6 mg, 72 nmol), δ (3.3 mg, 80 nmol), δ' (1.6 mg, 90 nmol). The α, τ, δ, δ' protein mixture was dialyzed for 2 hrs against buffer A containing 50 mM NaCl. The entire mixture was loaded onto a 1 ml MonoQ column equilibrated in buffer A containing 50 mM NaCl. Proteins were eluted with a 20 column volume linear gradient of 50-500 mM NaCl in buffer A and 0.25 ml fractions were collected. Fractions were analyzed by 10% SDS-polyacrylamide gels (20 µl/lane) stained with Coomassie Blue.

Generally, the reconstitution of the $α_L τδδ'$ complex on a MonoQ column results in a tight salt resistant complex which elutes at 500 mM NaCl. The high concentration of the proteins in the eluted fractions contributes to stability of the complex.

Example 34

The *S. pyogenes* Three Component Pol III-L Polymerase is Rapid and Processive In DNA Synthesis It was previously demonstrated (i.e., in Examples 29 and 30) that the putative delta subunit plays an integral part in the assembly of the τδδ' complex (FIG. 15) and that this complex is sufficient to assemble β clamps onto circular primed DNA (FIG. 16). It was also shown that the strong interaction between the α-large and τsubunits (FIG. 17) results in an isolatable $α_L τδδ'$ complex (FIG. 18), similar to that of the *E. coli* DNA polymerase III*.

The MonoQ fractions containing $α_L τδδ'$ complex were then used to assemble β onto primed DNA and determine whether this now resulted in rapid and processive DNA synthesis. Replication reactions contained 70 ng of singly primed M13mp18 ssDNA and 0.82 µg of *S. pyogenes* SSB in 25 µl buffer C (20 mM Tris-HCl (pH 7.5), 4% glycerol, 0.1 mM EDTA, 5 mM DTT, 2 mM ATP, 8 mM MgCl$_2$) with 60 µM each of dGTP, dCTP, and dATP, 30 µM cold TTP and 20 µM [α-$^{32}$P] TTP (specific activity of 2,000-4,000 cpm/pmol). The complex is assembled onto DNA in the following manner: 40 ng (3:1) or 140 ng (10:1) of the $α_L τδδ'$ complex and 60 ng of β protein were preincubated for 2 min at 30° C. in presence of SSB coated primed M13 DNA and two nucleotides (dCTP and dGTP). Reactions were initiated by addition of the two remaining nucleotides dATP and TTP and quenched with an equal volume of 1% SDS/40 mM EDTA. Each time point is a separate reaction.

Figure 19:
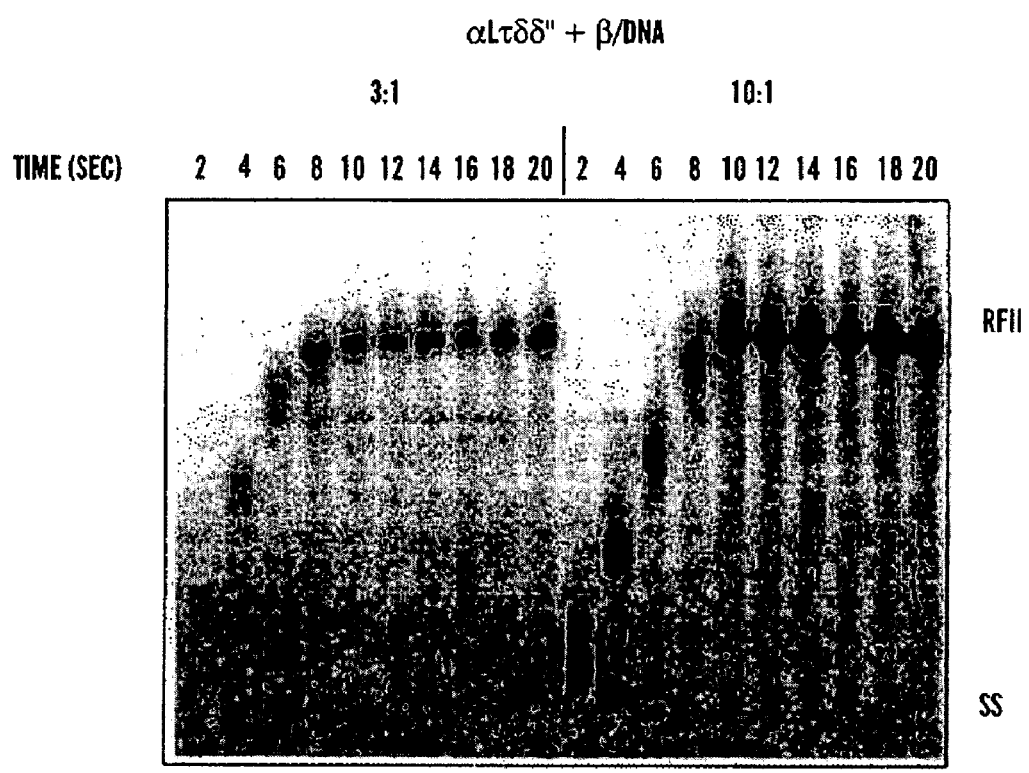
FIG. 19 illustrates the speed and processivity of the *S. pyogenes* $a_Lτδδ'$ (pol III*) complex. The $a_Lτδδ'$ (pol III*) complex was incubated with primed M13pm 18 ssDNA (coated with *S. pyogenes* SSB) and only two dNTPs, then replication was initiated upon adding the remaining two dNTPs. Reactions contained 25 fmol singly primed M13 mp18 ssDNA template, 300 fmol β$_2$, and either 75 fmol or 250 fmol $a_Lτδδ'$. Time points were quenched with SDS/EDTA then analyzed in a neutral agarose gel followed by autoradiography. Each time point is a separate reaction. The time course of polymerization was performed at two different ratios of polymerase/primed template to assess speed and processivity of nucleotide incorporation.
Figure 20A:
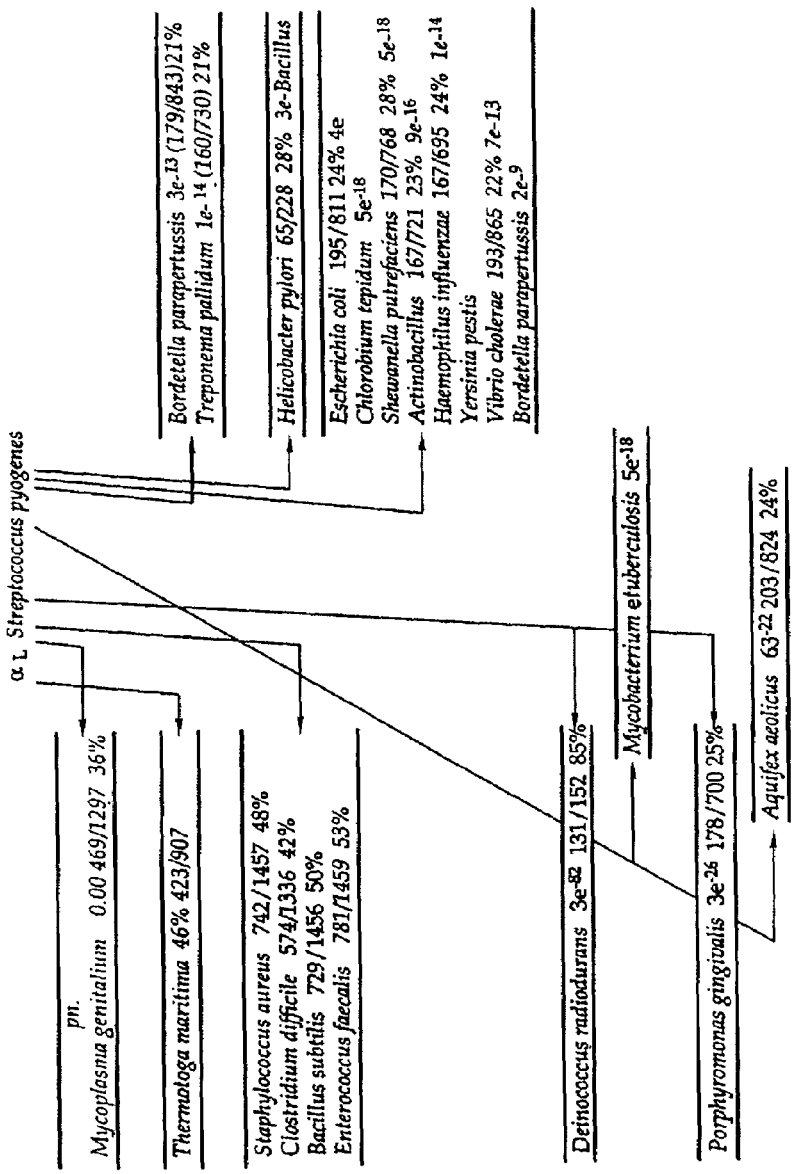
FIGS. 20A-I show the extent of homology between *S. pyogenes* replication genes and other organisms. Due to the low homology of delta (FIG. 20D), one must "walk" from one organism to the next in order to recognize the homologue with high probability. Percent identity over regions of the indicated number of amino acid residues is shown for each match (i.e., the two organisms at the opposite ends of each line). Amino acid sequences were retrieved from either GenBank or individual unfinished genome databases.
Figure 20B:
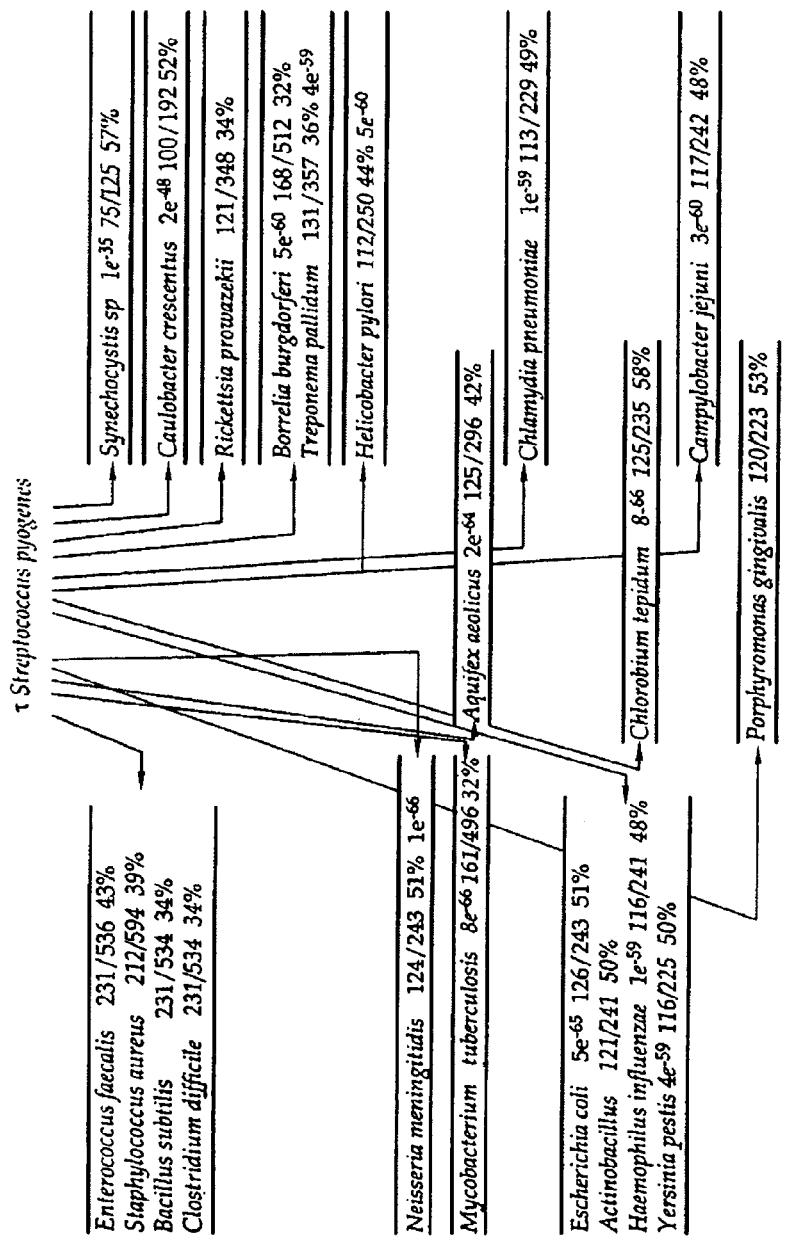
Figure 20C:
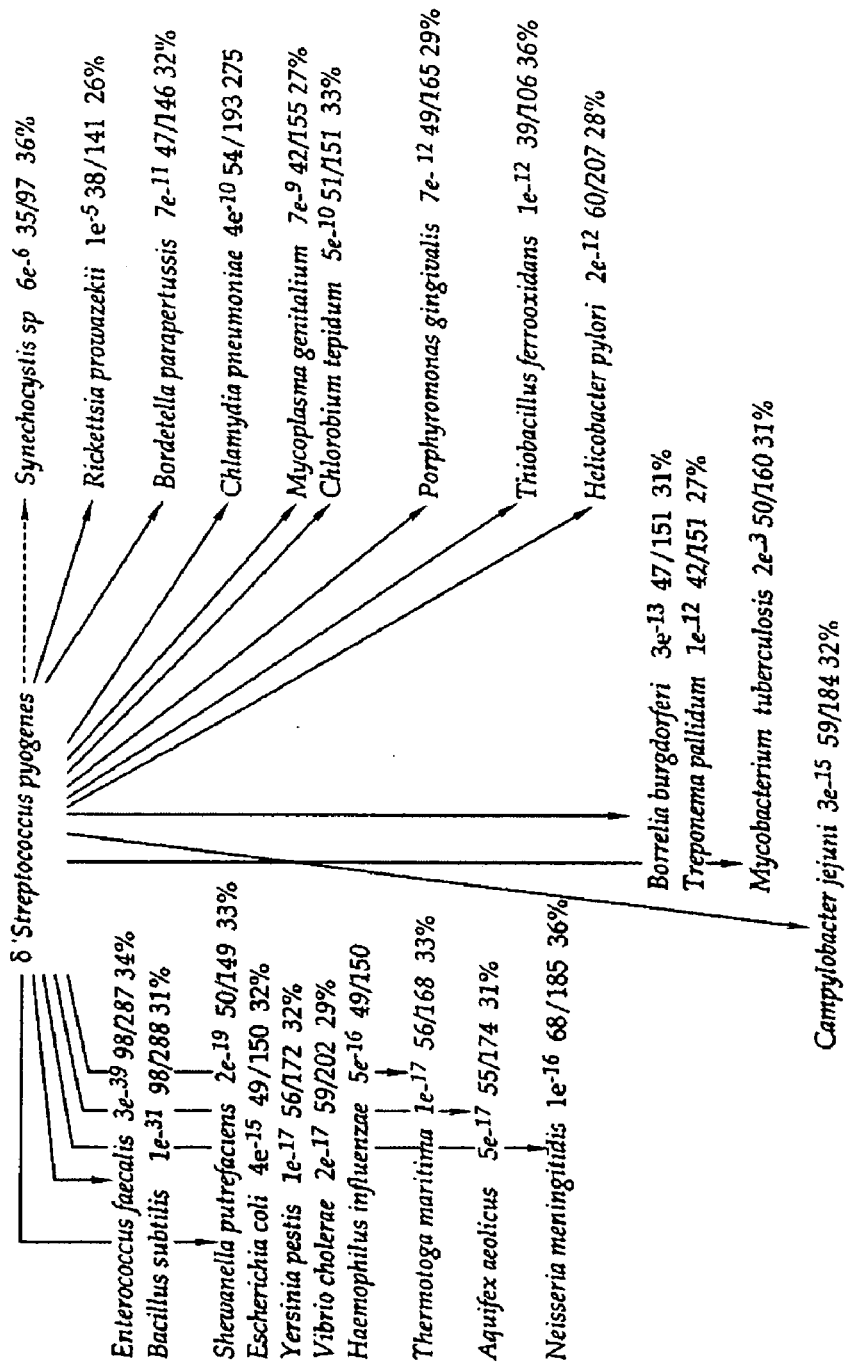
Figure 20D:
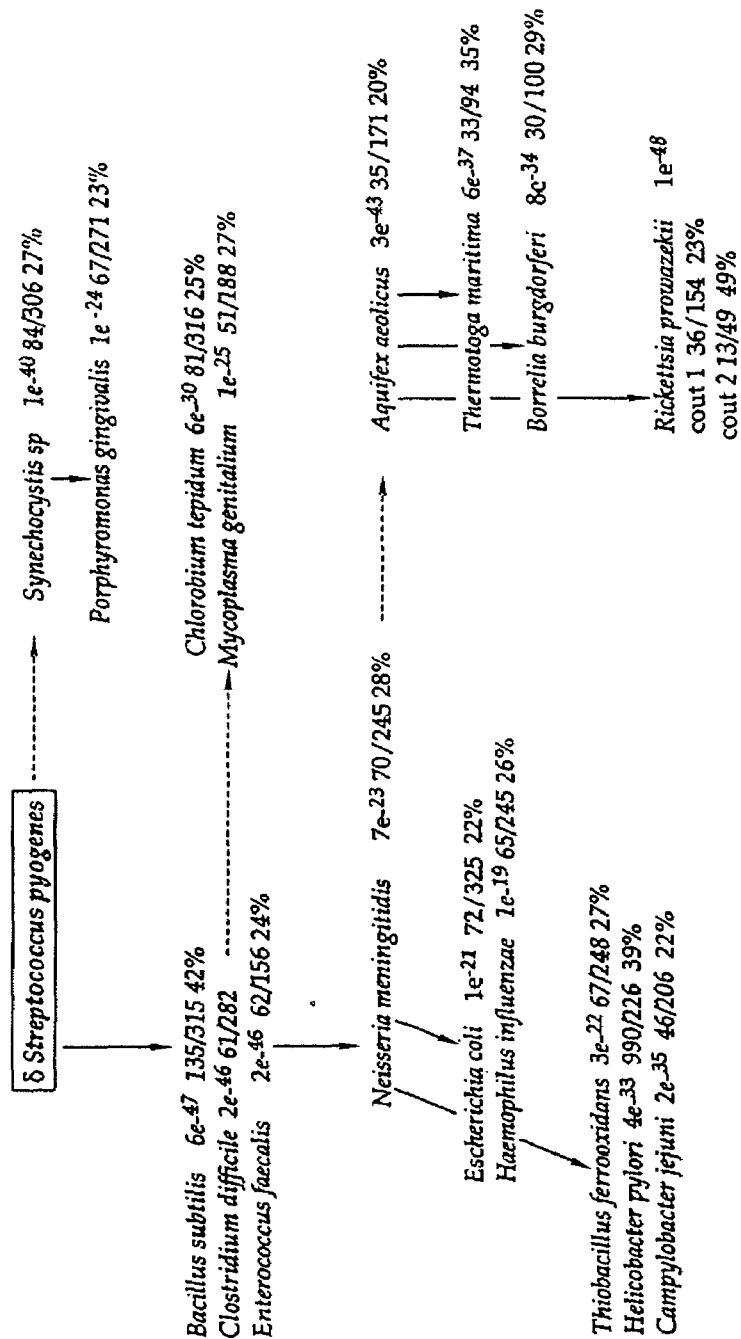
Figure 20E:
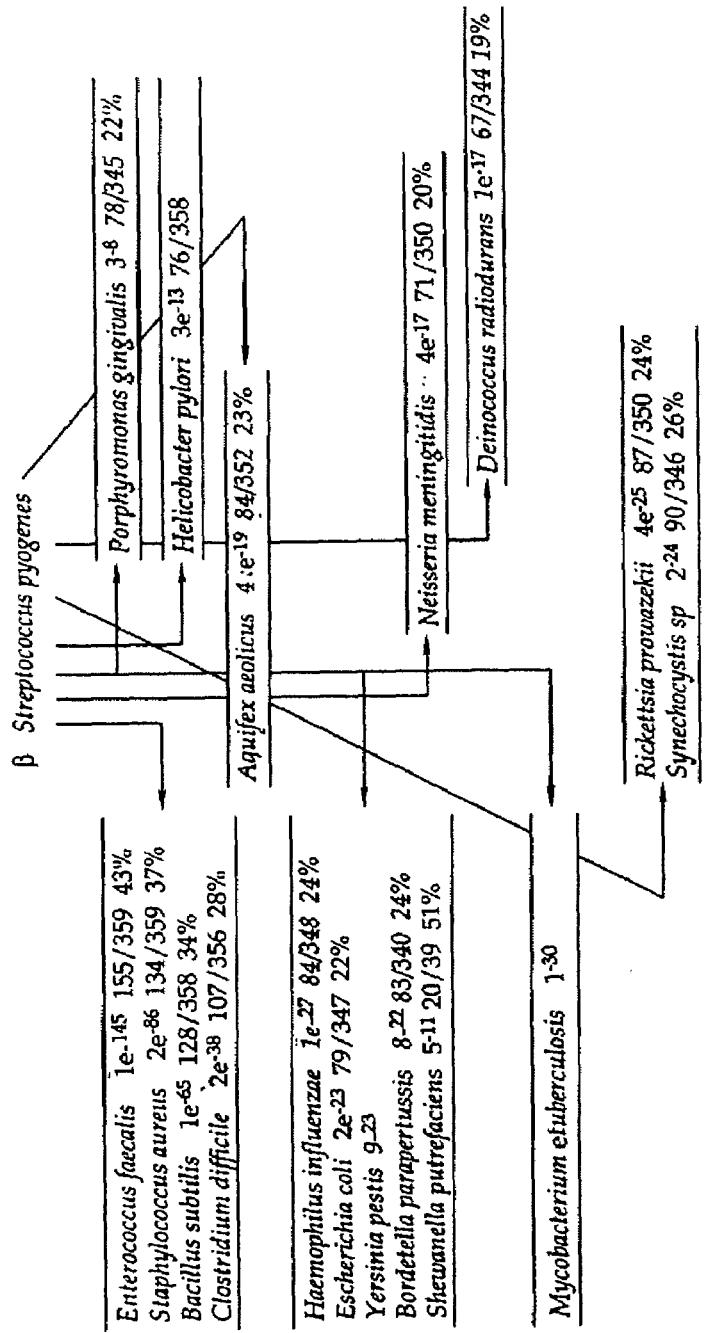
Figure 20F:
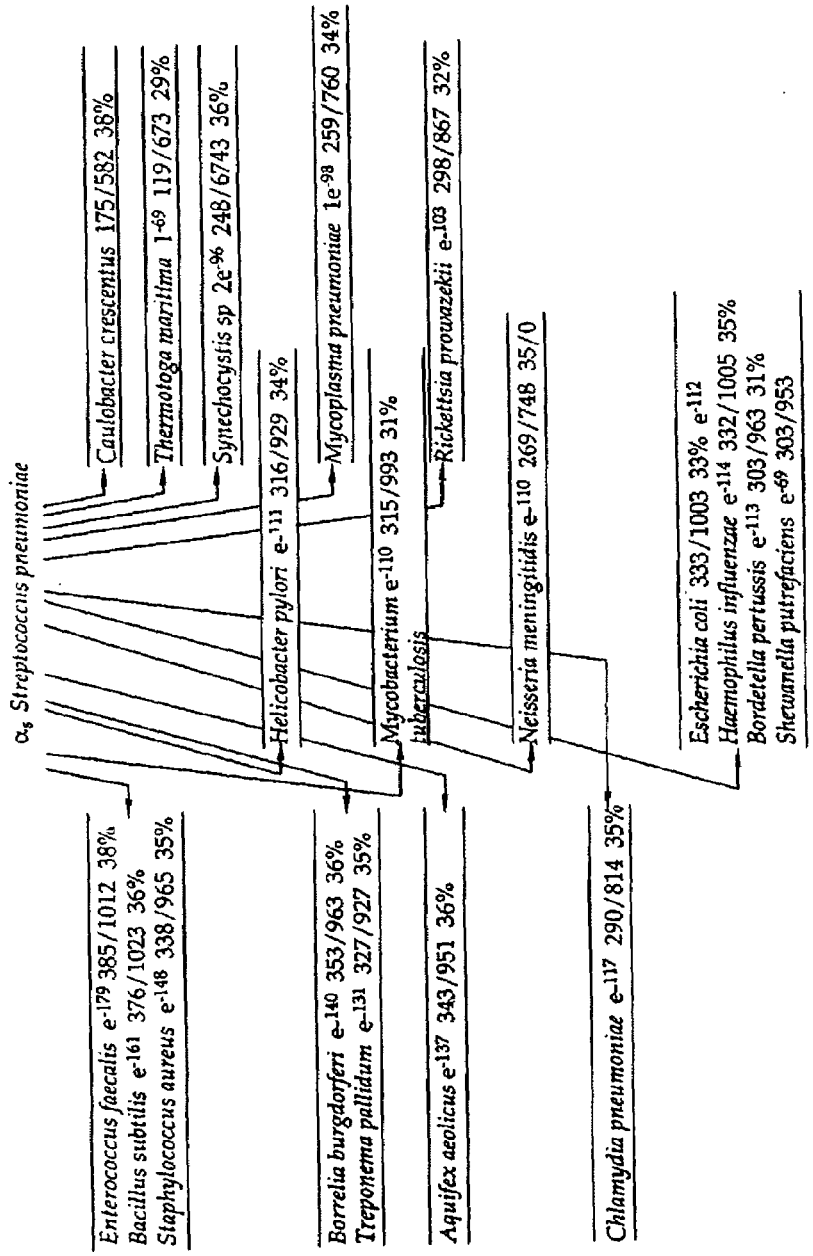
Figure 20G:
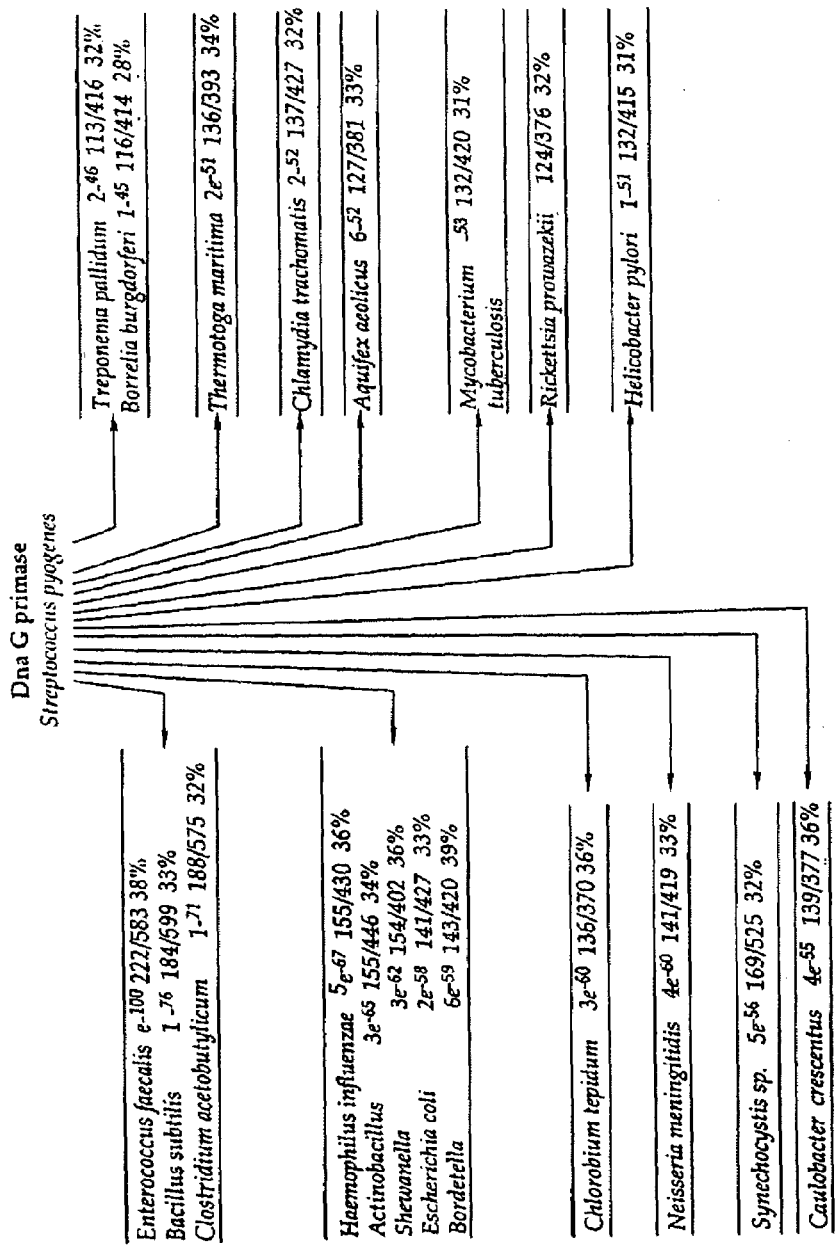
Figure 20H:
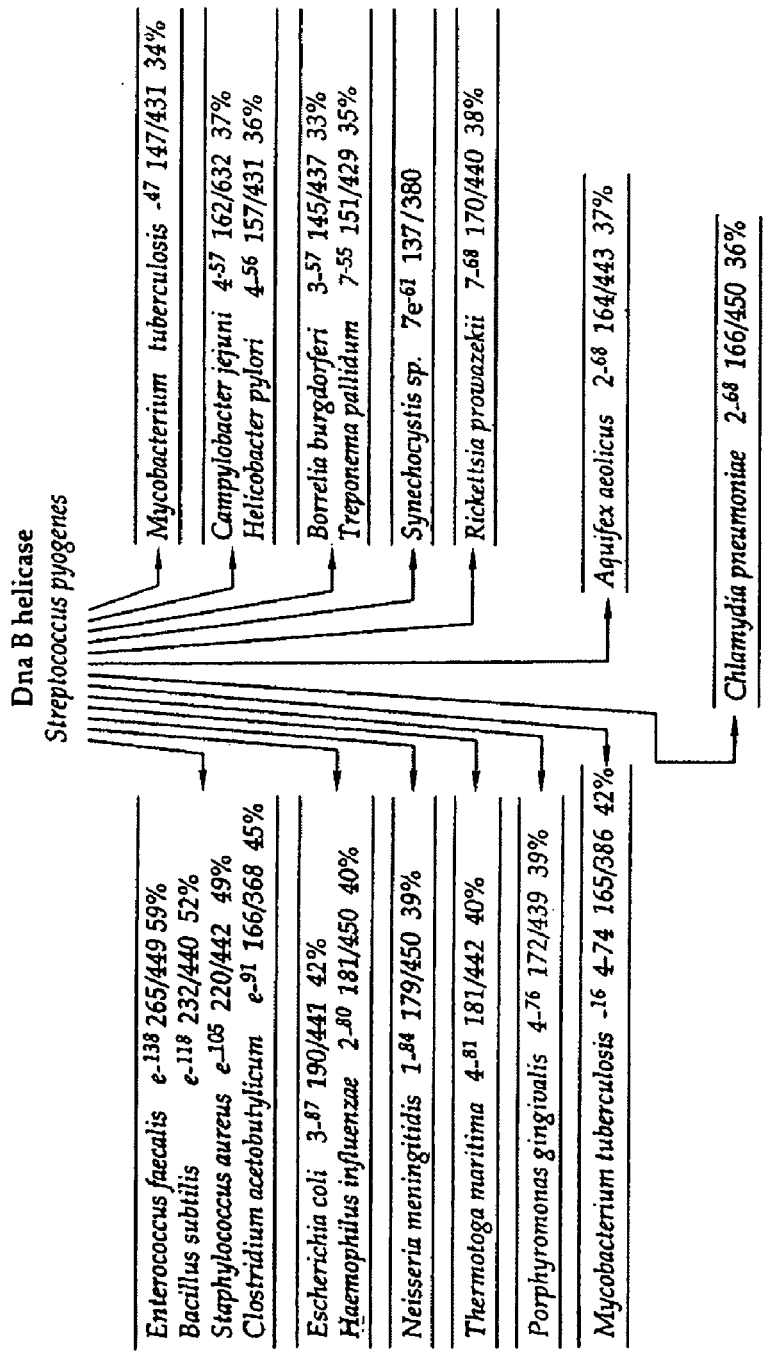
Figure 20I:
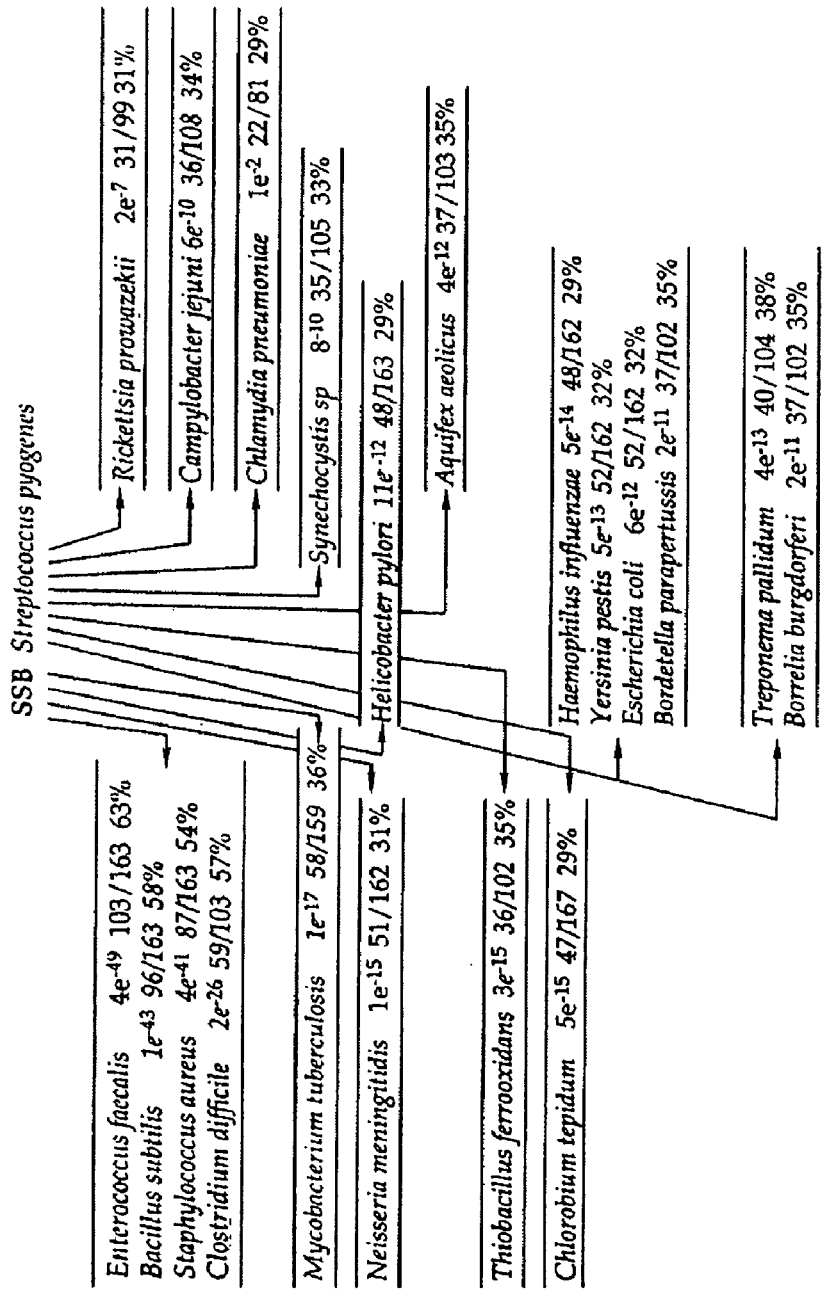

A time course of replication on singly primed circular M13mp18 ssDNA is shown in FIG. 19. The agarose gel analysis shows conversion of the oligonucleotide primed single stranded DNA to the slower migrating replicative form II. The fact that the speed of synthesis is independent of the concentration of polymerase in the reaction indicates that the $α_L τδδ'$ complex synthesizes DNA in a rapid and a highly processive manner. The *S. pyogenes* $α_L τδδ'$ complex in presence of the β clamp, completely replicates (is able to complete replication of) 7250 nt of M13 mp18 ssDNA in 8-9 sec.

Example 35

The *S. pyogenes* DnaE (α-small) Forms a Three-Component Polymerase with τδδ' and β

The *S. pyogenes* DnaE (α-small) polymerase is more homologous to *E. coli* a than *S. pyogenes* PolC. Thus, it seems reasonable to expect that the DnaE polymerase may also function with the β clamp (FIGS. 21A-B). To test DnaE for function with τδδ' and β, replication reactions contained 70 ng (25 fmol) of 30-mer singly primed M13 mp18 ssDNA, 0.82 µg of *S. pyogenes* SSB, and 3.3 ng-300 ng of DnaE (25 fmol –2.3 pmol) in 23.5 µl of 20 mM Tris-HCl (pH 7.5), 4% glycerol, 0.1 mM EDTA, 5 mM dithreitol (DTT), 40 µg/ml BSA, 2 mM ATP, 8 mM MgCl$_2$, and 60 µM each of dGTP and dCTP. When present, reactions included 43.3 ng of β and 10 ng of τδδ'. Reactions were preincubated for 3 min at 37° C., and then NaCl was added to 40 mM followed by another 2 min at 37° C. DNA synthesis was initiated upon addition of 1.5 µl of 1.5 mM dATP, 0.5 mM [$\alpha^{32}$P]-dTTP (specific activity 2,000-4,000 cpm/pmol). Aliquots of 25 µl were removed at the indicated times and quenched with an equal volume (25 µl) of 1% SDS, 40 mM EDTA. One-half of the quenched reaction was analyzed for total deoxynucleotide incorporation using DE81 filter paper and the other half was analyzed on a 0.8% neutral agarose gel. The effect of TMAU was also examined, in which 100 µM TMAU in DMSO (2% DMSO final concentration) was present. In this case, replication was allowed to proceed for 1 min before being quenched with 25 µM of 1% SDS, 40 mM EDTA.

At a saturating concentration of DnaE polymerase, the time course of primer extension shows that it completes an M13mp18 primed ssDNA template within 2 minutes for a speed of at least 60 nucleotides/s (FIG. 21C). This rate of synthesis holds true for the highest amount of DnaE in the rightmost panel of the figure. As the DnaE concentration is decreased, a longer time is required to complete the circular template, indicating that the DnaE polymerase is not processive over the entire length of the M13mp18 template. If the DnaE polymerase were fully processive during synthesis of the 7.2 kb ssDNA circle, the product profile over time would be qualitatively similar at all concentrations of enzyme, but the overall intensity of the profile would be diminished. This particular experiment was performed in the absence of β, but presence of τδδ'. When repeated in the presence of β but without τδδ', and in the absence of both β and τδδ', results similar to those shown in FIG. 21C were observed.

In the presence of β and τδδ', DnaE polymerase is stimulated in synthesis at low concentration, indicating that β increases the processivity and/or speed of DnaE (FIGS. 21C-D). At higher concentrations of DnaE, the presence of P/τδδ' has no effect on the rate of synthesis, and thus β does not increase the intrinsic speed of the enzyme (i.e., panels 3 and 4 of FIG. 21D). Hence, the effect of the β clamp on DnaE is primarily due to an increase in processivity. The profile of product length over time remains essentially unchanged at the different DnaE concentrations, and therefore the processivity of DnaE, with β is at least equal to the 7.2 kb length of the M13mp18 substrate.

The DnaE sequence does not show homology to an exonuclease, implying that it may have no associated nuclease activity. The DnaE preparation was examined for the presence of a 3'-5' exonuclease (FIG. 21E). The DnaE and PolC polymerases were each incubated with a 5' 32P-labeled oligonucleotide, followed by analysis in a sequencing gel. The result showed no degradation of the oligonucleotide by DnaE. PolC is a known 3'-5' exonuclease and it digests the end-labeled oligonucleotide as expected.

Gram positive PolC is known to be inhibited by the antibiotic hydroxyphenylaza-uracil ("HPUra") and its derivatives. In FIG. 21F, the PolC·τδδ', β and DnaE were tested for inhibition of synthesis on SSB coated primed M13mp18 ssDNA by an HPUra derivative, trimethylanilino-uracil ("TMAU"). The PolC·τδδ' β enzyme was prevented from forming the RFII product by TMAU. In contrast, the DnaE polymerase was not affected by TMAU in the presence of τδδ'/β (nor in the absence of τδδ'/β, not shown).

Although the invention has been described in detail for the purpose of illustration, it is understood that such detail is solely for that purpose, and variations can be made therein by those skilled in the art without departing from the spirit and scope of the invention which is defined by the following claims.

The invention claimed is:

1. An isolated DNA molecule that encodes the amino acid sequence comprising SEQ ID NO:28.

2. The isolated DNA molecule according to claim 1, wherein the DNA molecule comprises the nucleotide sequence of SEQ ID NO:27.

3. An expression system comprising an expression vector into which is inserted a heterologous DNA molecule according to claim 1.

4. The expression system according to claim 3, wherein the heterologous DNA molecule is in sense orientation and correct reading frame relative to a promoter.

5. A host cell comprising a heterologous DNA molecule according to claim 1.

* * * * *

SEQUENCE LISTING

<160> NUMBER OF SEQ ID NOS: 84

<210> SEQ ID NO 1
<211> LENGTH: 3195
<212> TYPE: DNA
<213> ORGANISM: Staphylococcus aureus

<400> SEQUENCE: 1

```
atggtggcat atttaaatat tcatacggct tatgatttgt taaattcaag cttaaaaata      60
gaagatgccg taagacttgc tgtgtctgaa aatgttgatg cacttgccat aactgacacc     120
aatgtattgt atggttttcc taaatttat gatgcatgta tagcaaataa cattaaaccg     180
atttttggta tgacaatata tgtgacaaat ggattaaata cagtcgaaac agttgttcta     240
gctaaaaata atgatggatt aaaagatttg tatcaactat catcggaaat aaaaatgaat     300
gcattagaac atgtgtcgtt tgaattatta aaacgatttt ctaacaatat gattatcatt     360
tttaaaaaag tcggtgatca acatcgtgat attgtacaag tgtttgaaac ccataatgac     420
acatatatgg accaccttag tatttcgatt caaggtagaa aacatgtttg gattcaaaat     480
gtttgttacc aaacacgtca agatgccgat acgatttctg cattagcagc tattagagac     540
aatacaaaat tagacttaat tcatgatcaa gaagattttg gtgcacattt tttaactgaa     600
aaggaaatta atcaattaga tattaaccaa gaatatttaa cgcaggttga tgttatagct     660
caaaagtgtg atgcagaatt aaaatatcat caatctctac ttcctcaata tgagacacct     720
aatgatgaat cagctaaaaa atatttgtgg cgtgtcttag ttacacaatt gaaaaaatta     780
```

```
gaacttaatt atgacgtcta tttagagcga ttgaaatatg agtataaagt tattactaat    840
atgggttttg aagattattt cttaatagta agtgatttaa tccattatgc gaaaacgaat    900
gatgtgatgg taggtcctgg tcgtggttct tcagctggct cactggtcag ttatttattg    960
ggaattacaa cgattgatcc tattaaattc aatctattat ttgaacgttt tttaaaccca   1020
gaacgtgtaa caatgcctga tattgatatt gactttgaag atacacgccg agaaagggtc   1080
attcagtacg tccaagaaaa atatggcgag ctacatgtat ctggaattgt gactttcggt   1140
catctgcttg caagagcagt tgctagagat gttggaagaa ttatgggggtt tgatgaagtt   1200 acattaaatg aaatttcaag tttaatccca cataaattag gaattacact tgatgaagca   1260
tatcaaattg acgattttaa agagtttgta catcgaaacc atcgacatga acgctggttc   1320
agtatttgta aaaagttaga aggtttacca agacatacat ctacacatgc ggcaggaatt   1380
attattaatg accatccatt atatgaatat gcccctttaa cgaaagggga tacaggatta   1440
ttaacgcaat ggacaatgac tgaagccgaa cgtattgggt tattaaaaat agattttcta   1500
gggttgagaa acttatcgat tattcatcaa atcttaacac aagtcaaaaa agatttaggt   1560
attaatattg atatcgaaaa agattccgttt gatgatcaaa aagtgtttga attgttgtcg   1620
caaggagata cgactggcat attccaatta gagtctgacg gtgtaagaag tgtattaaaa   1680
aaattaaagc cggaacactt tgaagatatt gttgctgtaa cttctttgta tagaccaggt   1740
ccaatggaag aaattccaac ttacattaca agaagacatg atccaagcaa agttcaatat   1800
ttacatccgc atttagaacc tatattaaaa aatacttacg gtgttattat ttatcaagag   1860
caaattatgc aaatagcgag cacatttgca aacttcagtt atggtgaagc ggatatttta   1920
agaagagcaa tgagtaaaaa aaatagagct gttcttgaaa gtgagcgtca acattttata   1980
gaaggtgcaa agcaaaatgg ttatcacgaa gacattagta agcaaatatt tgatttgatt   2040
ctgaaatttg ctgattatgg ttttcctaga gcacatgctg tcagctattc taaaattgca   2100
tacattatga gcttttttaaa agtccattat ccaaattatt tttacgcaaa tattttaagt   2160
aatgttattg gaagtgagaa gaaaactgct caaatgatag aagaagcaaa aaaacaaggt   2220
atcactatat tgccaccgaa cattaacgaa agtcattggt tttataaacc ttcccaagaa   2280
ggcatttatt tatcaattgg tacaattaaa ggtgttggtt atcaaagtgt gaaagtgatt   2340
gttgatgaac gttatcagaa cggcaaattt aaagattttct ttgattttgc tagacgtata   2400
ccgaagagag tcaaaacgag aaagttactt gaagcactga ttttagtggg agcgtttgat   2460
gcttttggta aaacacgttc aacgttgttg caagctattg atcaagtgtt ggatggcgat   2520
ttaaacattg aacaagatgg ttttttattt gatattttaa cgccaaaaca gatgtatgaa   2580
gataaagaag aattgcctga tgcacttatt agtcagtacg aaaagaata tttaggattt   2640 tatgtttcgc aacacccagt agataaaaag tttgttgcca acaatatttt aacgatattt   2700
aaattgagta acgcgcagaa ttataaacct atattagtac agtttgataa agttaaacaa   2760
attcgaacta aaaatggtca aaatatggca ttcgtcacat taaatgatgg cattgaaact   2820
ttagatggtg tgatttttccc taatcagttt aaaaagtacg aagagttgtt atcacataat   2880
gacttgttta tagttagcgg gaaatttgac catagaaagc aacaacgtca actaattata   2940
aatgagattc agacattagc cacttttgaa gaacaaaaat tagcatttgc caaacaaatt   3000
ataattagaa ataaatcaca aatagatatg tttgaagaga tgattaaagc tacgaaagag   3060
aatgctaatg atgttgtgtt atcctttat gatgaaacga ttaaacaaat gactactta    3120
```
ggctatatta atcaaaaaga tagtatgttt aataatttta tacaatcctt taaccctagt      3180
gatattaggc ttata      3195

<210> SEQ ID NO 2
<211> LENGTH: 1065
<212> TYPE: PRT
<213> ORGANISM: Staphylococcus aureus

<400> SEQUENCE: 2

```
Met Val Ala Tyr Leu Asn Ile His Thr Ala Tyr Asp Leu Leu Asn Ser
  1               5                  10                  15

Ser Leu Lys Ile Glu Asp Ala Val Arg Leu Ala Val Ser Glu Asn Val
             20                  25                  30

Asp Ala Leu Ala Ile Thr Asp Thr Asn Val Leu Tyr Gly Phe Pro Lys
         35                  40                  45

Phe Tyr Asp Ala Cys Ile Ala Asn Asn Ile Lys Pro Ile Phe Gly Met
     50                  55                  60

Thr Ile Tyr Val Thr Asn Gly Leu Asn Thr Val Glu Thr Val Val Leu
 65                  70                  75                  80

Ala Lys Asn Asn Asp Gly Leu Lys Asp Leu Tyr Gln Leu Ser Ser Glu
                 85                  90                  95

Ile Lys Met Asn Ala Leu Glu His Val Ser Phe Glu Leu Leu Lys Arg
            100                 105                 110

Phe Ser Asn Asn Met Ile Ile Ile Phe Lys Lys Val Gly Asp Gln His
        115                 120                 125

Arg Asp Ile Val Gln Val Phe Glu Thr His Asn Asp Thr Tyr Met Asp
    130                 135                 140

His Leu Ser Ile Ser Ile Gln Gly Arg Lys His Val Trp Ile Gln Asn
145                 150                 155                 160

Val Cys Tyr Gln Thr Arg Gln Asp Ala Asp Thr Ile Ser Ala Leu Ala
                165                 170                 175

Ala Ile Arg Asp Asn Thr Lys Leu Asp Leu Ile His Asp Gln Glu Asp
            180                 185                 190

Phe Gly Ala His Phe Leu Thr Glu Lys Glu Ile Asn Gln Leu Asp Ile
        195                 200                 205

Asn Gln Glu Tyr Leu Thr Gln Val Asp Val Ile Ala Gln Lys Cys Asp
    210                 215                 220

Ala Glu Leu Lys Tyr His Gln Ser Leu Leu Pro Gln Tyr Glu Thr Pro
225                 230                 235                 240

Asn Asp Glu Ser Ala Lys Lys Tyr Leu Trp Arg Val Leu Val Thr Gln
                245                 250                 255

Leu Lys Lys Leu Glu Leu Asn Tyr Asp Val Tyr Leu Glu Arg Leu Lys
            260                 265                 270

Tyr Glu Tyr Lys Val Ile Thr Asn Met Gly Phe Glu Asp Tyr Phe Leu
        275                 280                 285

Ile Val Ser Asp Leu Ile His Tyr Ala Lys Thr Asn Asp Val Met Val
    290                 295                 300

Gly Pro Gly Arg Gly Ser Ser Ala Gly Ser Leu Val Ser Tyr Leu Leu
305                 310                 315                 320

Gly Ile Thr Thr Ile Asp Pro Ile Lys Phe Asn Leu Leu Phe Glu Arg
                325                 330                 335

Phe Leu Asn Pro Glu Arg Val Thr Met Pro Asp Ile Asp Ile Asp Phe
            340                 345                 350

Glu Asp Thr Arg Arg Glu Arg Val Ile Gln Tyr Val Gln Glu Lys Tyr
```

-continued

```
            355                 360                 365
Gly Glu Leu His Val Ser Gly Ile Val Thr Phe Gly His Leu Leu Ala
    370                 375                 380
Arg Ala Val Ala Arg Asp Val Gly Arg Ile Met Gly Phe Asp Glu Val
385                 390                 395                 400
Thr Leu Asn Glu Ile Ser Ser Leu Ile Pro His Lys Leu Gly Ile Thr
                405                 410                 415
Leu Asp Glu Ala Tyr Gln Ile Asp Asp Phe Lys Glu Phe Val His Arg
            420                 425                 430
Asn His Arg His Glu Arg Trp Phe Ser Ile Cys Lys Lys Leu Glu Gly
        435                 440                 445
Leu Pro Arg His Thr Ser Thr His Ala Ala Gly Ile Ile Ile Asn Asp
    450                 455                 460
His Pro Leu Tyr Glu Tyr Ala Pro Leu Thr Lys Gly Asp Thr Gly Leu
465                 470                 475                 480
Leu Thr Gln Trp Thr Met Thr Glu Ala Glu Arg Ile Gly Leu Leu Lys
                485                 490                 495
Ile Asp Phe Leu Gly Leu Arg Asn Leu Ser Ile Ile His Gln Ile Leu
            500                 505                 510
Thr Gln Val Lys Lys Asp Leu Gly Ile Asn Ile Asp Ile Glu Lys Ile
        515                 520                 525
Pro Phe Asp Asp Gln Lys Val Phe Glu Leu Leu Ser Gln Gly Asp Thr
    530                 535                 540
Thr Gly Ile Phe Gln Leu Glu Ser Asp Gly Val Arg Ser Val Leu Lys
545                 550                 555                 560
Lys Leu Lys Pro Glu His Phe Glu Asp Ile Val Ala Val Thr Ser Leu
                565                 570                 575
Tyr Arg Pro Gly Pro Met Glu Glu Ile Pro Thr Tyr Ile Thr Arg Arg
            580                 585                 590
His Asp Pro Ser Lys Val Gln Tyr Leu His Pro His Leu Glu Pro Ile
        595                 600                 605
Leu Lys Asn Thr Tyr Gly Val Ile Ile Tyr Gln Glu Gln Ile Met Gln
    610                 615                 620
Ile Ala Ser Thr Phe Ala Asn Phe Ser Tyr Gly Glu Ala Asp Ile Leu
625                 630                 635                 640
Arg Arg Ala Met Ser Lys Lys Asn Arg Ala Val Leu Glu Ser Glu Arg
                645                 650                 655
Gln His Phe Ile Glu Gly Ala Lys Gln Asn Gly Tyr His Glu Asp Ile
            660                 665                 670
Ser Lys Gln Ile Phe Asp Leu Ile Leu Lys Phe Ala Asp Tyr Gly Phe
        675                 680                 685
Pro Arg Ala His Ala Val Ser Tyr Ser Lys Ile Ala Tyr Ile Met Ser
    690                 695                 700
Phe Leu Lys Val His Tyr Pro Asn Tyr Phe Tyr Ala Asn Ile Leu Ser
705                 710                 715                 720
Asn Val Ile Gly Ser Glu Lys Lys Thr Ala Gln Met Ile Glu Glu Ala
                725                 730                 735
Lys Lys Gln Gly Ile Thr Ile Leu Pro Pro Asn Ile Asn Glu Ser His
            740                 745                 750
Trp Phe Tyr Lys Pro Ser Gln Glu Gly Ile Tyr Leu Ser Ile Gly Thr
        755                 760                 765
Ile Lys Gly Val Gly Tyr Gln Ser Val Lys Val Ile Val Asp Glu Arg
    770                 775                 780
```

Tyr Gln Asn Gly Lys Phe Lys Asp Phe Phe Asp Phe Ala Arg Arg Ile
785                 790                 795                 800

Pro Lys Arg Val Lys Thr Arg Lys Leu Leu Glu Ala Leu Ile Leu Val
            805                 810                 815

Gly Ala Phe Asp Ala Phe Gly Lys Thr Arg Ser Thr Leu Leu Gln Ala
        820                 825                 830

Ile Asp Gln Val Leu Asp Gly Asp Leu Asn Ile Glu Gln Asp Gly Phe
    835                 840                 845

Leu Phe Asp Ile Leu Thr Pro Lys Gln Met Tyr Glu Asp Lys Glu Glu
850                 855                 860

Leu Pro Asp Ala Leu Ile Ser Gln Tyr Glu Lys Glu Tyr Leu Gly Phe
865                 870                 875                 880

Tyr Val Ser Gln His Pro Val Asp Lys Lys Phe Val Ala Lys Gln Tyr
            885                 890                 895

Leu Thr Ile Phe Lys Leu Ser Asn Ala Gln Asn Tyr Lys Pro Ile Leu
        900                 905                 910

Val Gln Phe Asp Lys Val Lys Gln Ile Arg Thr Lys Asn Gly Gln Asn
    915                 920                 925

Met Ala Phe Val Thr Leu Asn Asp Gly Ile Glu Thr Leu Asp Gly Val
930                 935                 940

Ile Phe Pro Asn Gln Phe Lys Lys Tyr Glu Glu Leu Leu Ser His Asn
945                 950                 955                 960

Asp Leu Phe Ile Val Ser Gly Lys Phe Asp His Arg Lys Gln Gln Arg
            965                 970                 975

Gln Leu Ile Ile Asn Glu Ile Gln Thr Leu Ala Thr Phe Glu Glu Gln
        980                 985                 990

Lys Leu Ala Phe Ala Lys Gln Ile Ile Ile Arg Asn Lys Ser Gln Ile
    995                 1000                1005

Asp Met Phe Glu Glu Met Ile Lys Ala Thr Lys Glu Asn Ala Asn Asp
    1010                1015                1020

Val Val Leu Ser Phe Tyr Asp Glu Thr Ile Lys Gln Met Thr Thr Leu
1025                1030                1035                1040

Gly Tyr Ile Asn Gln Lys Asp Ser Met Phe Asn Asn Phe Ile Gln Ser
            1045                1050                1055

Phe Asn Pro Ser Asp Ile Arg Leu Ile
        1060                1065

<210> SEQ ID NO 3
<211> LENGTH: 1698
<212> TYPE: DNA
<213> ORGANISM: Staphylococcus aureus

<400> SEQUENCE: 3
ttgaattatc aagccttata tcgtatgtac agaccccaaa gtttcgagga tgtcgtcgga      60
caagaacatg tcacgaagac attgcgcaat gcgatttcga agaaaaaaca gtcgcatgca     120
tatattttta gtggtccgag aggtacgggg aaaacgagta ttgccaaagt gtttgctaaa     180
gcaatcaact gtttaaatag cactgatgga gaaccttgta atgaatgtca tatttgtaaa     240
ggcattacgc aggggactaa ttcagatgtg atagaaattg atgctgctag taataatggc     300
gttgatgaaa taagaaatat tagagacaaa gttaaatatg caccaagtga atcgaaatat     360
aaagtttata ttatagatga ggtgcacatg ctaacaacag gtgcttttaa tgcccttta     420 aagacgttag aagaacctcc agcacacgct atttttatat tggcaacgac agaaccacat     480

-continued

```
aaaatccctc caacaatcat ttctagggca caacgttttg attttaaagc aattagccta    540
gatcaaattg ttgaacgttt aaaatttgta gcagatgcac aacaaattga atgtgaagat    600
gaagccttgg catttatcgc taaagcgtct gaaggggggta tgcgtgatgc attaagtatt    660
atggatcagg ctattgcttt cggcgatggc acattgacat tacaagatgc cctaaatgtt    720
acgggtagcg ttcatgatga agcgttggat cacttgtttg atgatattgt acaaggtgac    780
gtacaagcat cttttaaaaa ataccatcag tttataacag aaggtaaaga agtgaatcgc    840
ctaataaatg atatgattta ttttgtcaga gatacgatta tgaataaaac atctgagaaa    900
gatactgagt atcgagcact gatgaactta gaattagata tgttatatca atgattgat    960 cttattaatg atacattagt gtcgattcgt tttagtgtga atcaaaacgt tcattttgaa   1020
gtattgttag taaaattagc tgagcagatt aagggtcaac cacaagtgat tgcgaatgta   1080
gctgaaccag cacaaattgc ttcatcgcca aacacagatg tattgttgca acgtatggaa   1140
cagttagagc aagaactaaa aacactaaaa gcacaaggag tgagtgttgc tcctactcaa   1200
aaatcttcga aaaagcctgc gagaggtata caaaaatcta aaaatgcatt ttcaatgcaa   1260
caaattgcaa aagtgctaga taaagcgaat aaggcagata tcaaattgtt gaaagatcat   1320
tggcaagaag tgattgacca tgcccaaaac aatgataaaa aatcactcgt tagtttattg   1380
caaaattcgg aacctgtggc ggcaagtgaa gatcacgtcc ttgtgaaatt tgaggaagag   1440
atccattgtg aaatcgtcaa taaagacgac gagaaacgta gtagtataga aagtgttgta   1500
tgtaatatcg ttaataaaaa cgttaaagtt gttggtgtac catcagatca atggcaaaga   1560
gttcgaacgg agtatttaca aaatcgtaaa aacgaaggcg atgatatgcc aaagcaacaa   1620
gcacaacaaa cagatattgc tcaaaaagca aaagatcttt tcggtgaaga aactgtacat   1680
gtgatagatg aagagtga                                                 1698
```

<210> SEQ ID NO 4
<211> LENGTH: 566
<212> TYPE: PRT
<213> ORGANISM: Staphylococcus aureus

<400> SEQUENCE: 4

```
Leu Asn Tyr Gln Ala Leu Tyr Arg Met Tyr Arg Pro Gln Ser Phe Glu
  1               5                  10                  15

Asp Val Val Gly Gln Glu His Val Thr Lys Thr Leu Arg Asn Ala Ile
             20                  25                  30

Ser Lys Glu Lys Gln Ser His Ala Tyr Ile Phe Ser Gly Pro Arg Gly
         35                  40                  45

Thr Gly Lys Thr Ser Ile Ala Lys Val Phe Ala Lys Ala Ile Asn Cys
     50                  55                  60

Leu Asn Ser Thr Asp Gly Glu Pro Cys Asn Glu Cys His Ile Cys Lys
 65                  70                  75                  80

Gly Ile Thr Gln Gly Thr Asn Ser Asp Val Ile Glu Ile Asp Ala Ala
                 85                  90                  95

Ser Asn Asn Gly Val Asp Glu Ile Arg Asn Ile Arg Asp Lys Val Lys
            100                 105                 110

Tyr Ala Pro Ser Glu Ser Lys Tyr Lys Val Tyr Ile Ile Asp Glu Val
        115                 120                 125

His Met Leu Thr Thr Gly Ala Phe Asn Ala Leu Leu Lys Thr Leu Glu
    130                 135                 140

Glu Pro Pro Ala His Ala Ile Phe Ile Leu Ala Thr Thr Glu Pro His
145                 150                 155                 160
```

```
Lys Ile Pro Pro Thr Ile Ile Ser Arg Ala Gln Arg Phe Asp Phe Lys
            165                 170                 175

Ala Ile Ser Leu Asp Gln Ile Val Glu Arg Leu Lys Phe Val Ala Asp
            180                 185                 190

Ala Gln Gln Ile Glu Cys Glu Asp Glu Ala Leu Ala Phe Ile Ala Lys
            195                 200                 205

Ala Ser Glu Gly Gly Met Arg Asp Ala Leu Ser Ile Met Asp Gln Ala
        210                 215                 220

Ile Ala Phe Gly Asp Gly Thr Leu Thr Leu Gln Asp Ala Leu Asn Val
225                 230                 235                 240

Thr Gly Ser Val His Asp Glu Ala Leu Asp His Leu Phe Asp Asp Ile
                245                 250                 255

Val Gln Gly Asp Val Gln Ala Ser Phe Lys Lys Tyr His Gln Phe Ile
                260                 265                 270

Thr Glu Gly Lys Glu Val Asn Arg Leu Ile Asn Asp Met Ile Tyr Phe
            275                 280                 285

Val Arg Asp Thr Ile Met Asn Lys Thr Ser Glu Lys Asp Thr Glu Tyr
290                 295                 300

Arg Ala Leu Met Asn Leu Glu Leu Asp Met Leu Tyr Gln Met Ile Asp
305                 310                 315                 320

Leu Ile Asn Asp Thr Leu Val Ser Ile Arg Phe Ser Val Asn Gln Asn
                325                 330                 335

Val His Phe Glu Val Leu Leu Val Lys Leu Ala Glu Gln Ile Lys Gly
                340                 345                 350

Gln Pro Gln Val Ile Ala Asn Val Ala Glu Pro Ala Gln Ile Ala Ser
            355                 360                 365

Ser Pro Asn Thr Asp Val Leu Leu Gln Arg Met Glu Gln Leu Glu Gln
        370                 375                 380

Glu Leu Lys Thr Leu Lys Ala Gln Gly Val Ser Val Ala Pro Thr Gln
385                 390                 395                 400

Lys Ser Ser Lys Lys Pro Ala Arg Gly Ile Gln Lys Ser Lys Asn Ala
                405                 410                 415

Phe Ser Met Gln Gln Ile Ala Lys Val Leu Asp Lys Ala Asn Lys Ala
            420                 425                 430

Asp Ile Lys Leu Leu Lys Asp His Trp Gln Glu Val Ile Asp His Ala
            435                 440                 445

Gln Asn Asn Asp Lys Lys Ser Leu Val Ser Leu Leu Gln Asn Ser Glu
        450                 455                 460

Pro Val Ala Ala Ser Glu Asp His Val Leu Val Lys Phe Glu Glu Glu
465                 470                 475                 480

Ile His Cys Glu Ile Val Asn Lys Asp Asp Glu Lys Arg Ser Ser Ile
                485                 490                 495

Glu Ser Val Val Cys Asn Ile Val Asn Lys Asn Val Lys Val Val Gly
            500                 505                 510

Val Pro Ser Asp Gln Trp Gln Arg Val Arg Thr Glu Tyr Leu Gln Asn
            515                 520                 525

Arg Lys Asn Glu Gly Asp Asp Met Pro Lys Gln Gln Ala Gln Gln Thr
        530                 535                 540

Asp Ile Ala Gln Lys Ala Lys Asp Leu Phe Gly Glu Glu Thr Val His
545                 550                 555                 560

Val Ile Asp Glu Glu Glx
                565
```

<210> SEQ ID NO 5
<211> LENGTH: 1398
<212> TYPE: DNA
<213> ORGANISM: Staphylococcus aureus

<400> SEQUENCE: 5

| | | | | | |
|---|---|---|---|---|---|
| atggatagaa | tgtatgagca | aaatcaaatg | ccgcataaca | atgaagctga | acagtctgtc | 60 |
| ttaggttcaa | ttattataga | tccagaattg | attaatacta | ctcaggaagt | tttgcttcct | 120 |
| gagtcgtttt | ataggggtgc | ccatcaacat | attttccgtg | caatgatgca | cttaaatgaa | 180 |
| gataataaag | aaattgatgt | tgtaacattg | atggatcaat | tatcgacgga | aggtacgttg | 240 |
| aatgaagcgg | gtggcccgca | atatcttgca | gagttatcta | caaatgtacc | aacgacgcga | 300 |
| aatgttcagt | attatactga | tatcgtttct | aagcatgcat | taaaacgtag | attgattcaa | 360 |
| actgcagata | gtattgccaa | tgatggatat | aatgatgaac | ttgaactaga | tgcgatttta | 420 |
| agtgatgcag | aacgtcgaat | tttagagcta | tcatcttctc | gtgaaagcga | tggctttaaa | 480 |
| gacattcgag | acgtcttagg | acaagtgtat | gaaacagctg | aagagcttga | tcaaaatagt | 540 |
| ggtcaaacac | caggtatacc | tacaggatat | cgagatttag | accaaatgac | agcagggttc | 600 |
| aaccgaaatg | atttaattat | ccttgcagcg | cgtccatctg | taggtaagac | tgcgttcgca | 660 |
| cttaatattg | cacaaaaagt | tgcaacgcat | gaagatatgt | atacagttgg | tattttctcg | 720 |
| ctagagatgg | gtgctgatca | gttagccaca | cgtatgattt | gtagttctgg | aaatgttgac | 780 |
| tcaaaccgct | taagaacggg | tactatgact | gaggaagatt | ggagtcgttt | tactatagcg | 840 |
| gtaggtaaat | tatcacgtac | gaagattttt | attgatgata | caccgggtat | tcgaattaat | 900 |
| gatttacgtt | ctaaatgtcg | tcgattaaag | caagaacatg | gcttagacat | gattgtgatt | 960 |
| gactacttac | agttgattca | aggtagtggt | tcacgtgcgt | ccgataacag | acaacaggaa | 1020 |
| gtttctgaaa | tctctcgtac | attaaaagca | ttagcccgtg | aattaaaatg | tccagttatc | 1080 |
| gcattaagtc | agttatctcg | tggtgttgaa | caacgacaag | ataaacgtcc | aatgatgagt | 1140 |
| gatattcgtg | aatctggttc | gattgagcaa | gatgccgata | tcgttgcatt | cttataccgt | 1200 |
| gatgattact | ataaccgtgg | cggcgatgaa | gatgatgacg | atgatggtgg | tttcgagcca | 1260 |
| caaacgaatg | atgaaaacgg | tgaaattgaa | attatcattg | ctaagcaacg | taacggtcca | 1320 |
| acaggcacag | ttaagttaca | ttttatgaaa | caatataata | aatttaccga | tatcgattat | 1380 |
| gcacatgcag | atatgatg | | | | | 1398 |

<210> SEQ ID NO 6
<211> LENGTH: 466
<212> TYPE: PRT
<213> ORGANISM: Staphylococcus aureus

<400> SEQUENCE: 6

Met Asp Arg Met Tyr Glu Gln Asn Gln Met Pro His Asn Asn Glu Ala
1               5                   10                  15

Glu Gln Ser Val Leu Gly Ser Ile Ile Ile Asp Pro Glu Leu Ile Asn
            20                  25                  30

Thr Thr Gln Glu Val Leu Leu Pro Glu Ser Phe Tyr Arg Gly Ala His
        35                  40                  45

Gln His Ile Phe Arg Ala Met Met His Leu Asn Glu Asp Asn Lys Glu
    50                  55                  60

Ile Asp Val Val Thr Leu Met Asp Gln Leu Ser Thr Glu Gly Thr Leu
65                  70                  75                  80

```
Asn Glu Ala Gly Gly Pro Gln Tyr Leu Ala Glu Leu Ser Thr Asn Val
             85                  90                  95

Pro Thr Thr Arg Asn Val Gln Tyr Tyr Thr Asp Ile Val Ser Lys His
            100                 105                 110

Ala Leu Lys Arg Arg Leu Ile Gln Thr Ala Asp Ser Ile Ala Asn Asp
        115                 120                 125

Gly Tyr Asn Asp Glu Leu Glu Leu Asp Ala Ile Leu Ser Asp Ala Glu
    130                 135                 140

Arg Arg Ile Leu Glu Leu Ser Ser Arg Glu Ser Asp Gly Phe Lys
145                 150                 155                 160

Asp Ile Arg Asp Val Leu Gly Gln Val Tyr Glu Thr Ala Glu Glu Leu
                165                 170                 175

Asp Gln Asn Ser Gly Gln Thr Pro Gly Ile Pro Thr Gly Tyr Arg Asp
            180                 185                 190

Leu Asp Gln Met Thr Ala Gly Phe Asn Arg Asn Asp Leu Ile Ile Leu
        195                 200                 205

Ala Ala Arg Pro Ser Val Gly Lys Thr Ala Phe Ala Leu Asn Ile Ala
    210                 215                 220

Gln Lys Val Ala Thr His Glu Asp Met Tyr Thr Val Gly Ile Phe Ser
225                 230                 235                 240

Leu Glu Met Gly Ala Asp Gln Leu Ala Thr Arg Met Ile Cys Ser Ser
                245                 250                 255

Gly Asn Val Asp Ser Asn Arg Leu Arg Thr Gly Thr Met Thr Glu Glu
            260                 265                 270

Asp Trp Ser Arg Phe Thr Ile Ala Val Gly Lys Leu Ser Arg Thr Lys
        275                 280                 285

Ile Phe Ile Asp Asp Thr Pro Gly Ile Arg Ile Asn Asp Leu Arg Ser
    290                 295                 300

Lys Cys Arg Arg Leu Lys Gln Glu His Gly Leu Asp Met Ile Val Ile
305                 310                 315                 320

Asp Tyr Leu Gln Leu Ile Gln Gly Ser Gly Ser Arg Ala Ser Asp Asn
                325                 330                 335

Arg Gln Gln Glu Val Ser Glu Ile Ser Arg Thr Leu Lys Ala Leu Ala
            340                 345                 350

Arg Glu Leu Lys Cys Pro Val Ile Ala Leu Ser Gln Leu Ser Arg Gly
        355                 360                 365

Val Glu Gln Arg Gln Asp Lys Arg Pro Met Met Ser Asp Ile Arg Glu
    370                 375                 380

Ser Gly Ser Ile Glu Gln Asp Ala Asp Ile Val Ala Phe Leu Tyr Arg
385                 390                 395                 400

Asp Asp Tyr Tyr Asn Arg Gly Asp Glu Asp Asp Asp Asp Gly
                405                 410                 415

Gly Phe Glu Pro Gln Thr Asn Asp Glu Asn Gly Glu Ile Glu Ile Ile
            420                 425                 430

Ile Ala Lys Gln Arg Asn Gly Pro Thr Gly Thr Val Lys Leu His Phe
        435                 440                 445

Met Lys Gln Tyr Asn Lys Phe Thr Asp Ile Asp Tyr Ala His Ala Asp
    450                 455                 460

Met Met
465

<210> SEQ ID NO 7
<211> LENGTH: 4308
<212> TYPE: DNA
```

<213> ORGANISM: Staphylococcus aureus

<400> SEQUENCE: 7

```
atgacagagc aacaaaaatt taaagtgctt gctgatcaaa ttaaaatttc aaatcaatta      60
gatgctgaaa ttttaaattc aggtgaactg acacgtatag atgtttctaa caaaaacaga    120
acatgggaat tcatattac attaccacaa ttcttagctc atgaagatta tttattattt     180
ataaatgcaa tagagcaaga gtttaaagat atcgccaacg ttacatgtcg ttttacggta    240
acaaatggca cgaatcaaga tgaacatgca attaaatact ttgggcactg tattgaccaa    300
acagctttat ctccaaaagt taaggtcaa ttgaaacaga aaaagcttat tatgtctgga     360
aaagtattaa aagtaatggt atcaaatgac attgaacgta atcattttga taaggcatgt    420
aatggaagtc ttatcaaagc gtttagaaat tgtggttttg atatcgataa aatcatattc    480
gaaacaaatg ataatgatca agaacaaaac ttagcttctt tagaagcaca tattcaagaa    540
gaagacgaac aaagtgcacg attggcaaca gagaaacttg aaaaaatgaa agctgaaaaa    600
gcgaaacaac aagataacaa cgaaagtgct gtcgataagt gtcaaattgg taagccgatt    660
caaattgaaa atattaaacc aattgaatct attattgagg aagagtttaa agttgcaata    720
gagggtgtca ttttgatat aaacttaaaa gaacttaaaa gtggtcgcca tatcgtagaa     780
attaaagtga ctgactatac ggactctta gttttaaaaa tgtttactcg taaaaacaaa     840
gatgatttag aacattttaa agcgctaagt gttggtaaat gggttagggc tcaaggtcgt    900
attgaagaag atacatttat tagagattta gttatgatga tgtctgatat tgaagagatt    960
aaaaaagcga caaaaaaga taaggctgaa gaaaagcgtg tagaattcca cttgcatact   1020
gcaatgagcc aaatggatgg tatacccaat attggtgcgt atgttaaaca ggcagcagac   1080
tggggacatc cagccattgc ggttacagac cataatgttg tgcaagcatt tccagatgct   1140
cacgcagcag cggaaaaaca tggcattaaa atgatatacg gtatggaagg tatgttagtt   1200
gatgatggtg ttccgattgc atacaaacca caagatgtcg tattaaaaga tgctacttat   1260
gttgtgttcg acgttgagac aactggttta tcaaatcagt atgataaaat catcgagctt   1320
gcagctgtga agttcataa cggtgaaatc atcgataagt ttgaaaggtt tagtaatccg   1380
catgaacgat tatcggaaac gattatcaat ttgacgcata ttactgatga tatgttagta   1440
gatgcccctg agattgaaga agtacttaca gagtttaaag aatgggttgg cgatgcgata   1500
ttcgtagcgc ataatgcttc gtttgatatg ggcttcatcg atacgggata tgaacgtctt   1560
gggtttggac catcaacgaa tggtgttatc gatactttag aattatctcg tacgattaat   1620
actgaatatg gtaaacatgg tttgaatttc ttggctaaaa aatatggcgt agaattaacg   1680
caacatcacc gtgccattta tgatacagaa gcaacagctt acatttcat aaaaatggtt    1740
caacaaatga agaattagg cgtattaaat cataacgaaa tcaacaaaaa actcagtaat    1800
gaagatgcat ataaacgtgc aagacctagt catgtcacat taattgtaca aaaccaacaa    1860
ggtcttaaaa atctatttaa aattgtaagt gcatcattgg tgaagtattt ctaccgtaca    1920
cctcgaattc cacgttcatt gttagatgaa tatcgtgagg gattattggt aggtacagcg    1980
tgtgatgaag gtgaattatt tacggcagtt atgcagaagg accagagtca agttgaaaaa    2040
attgccaaat attatgattt tattgaaatt caaccaccgg cactttatca agatttaatt    2100
gatagagagc ttattagaga tactgaaaca ttacatgaaa tttatcaacg tttaatacat    2160
gcaggtgaca cagcgggtat acctgttatt gcgacaggaa atgcacacta tttgtttgaa    2220
catgatggta tcgcacgtaa aattttaata gcatcacaac ccggcaatcc acttaatcgc    2280
```

-continued

```
tcaactttac cggaagcaca ttttagaact acagatgaaa tgttaaacga gtttcatttt    2340
ttaggtgaag aaaaagcgca tgaaattgtt gtgaaaaata caaacgaatt agcagatcga    2400
attgaacgtg ttgttcctat taaagatgaa ttatacacac cgcgtatgga aggtgctaac    2460
gaagaaatta gagaactaag ttatgcaaat gcgcgtaaac tgtatggtga agacctgcct    2520
caaatcgtaa ttgatcgatt agaaaaagaa ttaaaaagta ttatcggtaa tggatttgcg    2580
gtaatttact taatttcgca acgtttagtt aaaaaatcat tagatgatgg atacttagtt    2640
ggttcccgtg gttcagtagg ttctagtttt gtagcgacaa tgactgagat tactgaagta    2700
aacccgttac cgccacacta tatttgtccg aactgtaaaa cgagtgaatt tttcaatgat    2760
ggttcagtag gatcaggatt tgatttacct gataagacgt gtgaaacttg tggagcgcca    2820
cttattaaag aaggacaaga tattccgttt gaaacatttt taggatttaa gggagataaa    2880
gttcctgata tcgacttaaa ctttagtggt gaatatcaac cgaatgccca taactacaca    2940
aaagtattat ttggtgagga taaagtattc cgtgcaggta caattggtac tgttgctgaa    3000
aagactgctt ttggttatgt taaaggttat ttgaatgatc aaggtatcca caaaagaggt    3060
gctgaaatag atcgactcgt taaaggatgt acaggtgtta acgtacaac tggacagcat    3120 ccaggggta ttattgtagt acctgattac atggatattt tgattttac gccgatacaa    3180 tatcctgccg atgatcaaaa ttcagcatgg atgacgacac attttgattt ccattctatt    3240
catgataatg tattaaaact tgatatactt ggacacgatg atccaacaat gattcgtatg    3300
cttcaagatt tatcaggaat tgatccaaaa acaatacctg tagatgataa agaagttatg    3360
cagatattta gtacacctga aagtttgggt gttactgaag atgaaatttt atgtaaaaca    3420
ggtacatttg gggtaccaga attcggtaca ggattcgtgc gtcaaatgtt agaagataca    3480
aagccaacaa cattttctga attagttcaa atctcaggat tatctcatgg tacagatgtg    3540
tggttaggca atgctcaaga attaattaaa accggtatat gtgatttatc aagtgtaatt    3600
ggttgtcgtg atgatatcat ggtttattta atgtatgctg gtttagaacc atcaatggct    3660
tttaaaataa tggagtcagt acgtaaaggt aaaggtttaa ctgaagaaat gattgaaacg    3720
atgaaagaaa atgaagtgcc agattggtat ttagattcat gtcttaaaat taagtacatg    3780
ttccctaaag cccatgcagc agcatacgtt ttaatggcag tacgtatcgc atatttcaaa    3840
gtacatcatc cactttatta ctatgcatct tactttacaa ttcgtgcgtc agactttgat    3900
ttaatcacga tgattaaaga taaacaagc attcgaaata ctgtaaaaga catgtattct    3960
cgctatatgg atctaggtaa aaaagaaaaa gacgtattaa cagtcttgga aattatgaat    4020
gaaatggcgc atcgaggtta tcgaatgcaa ccgattagtt tagaaaagag tcaggcgttc    4080
gaatttatca ttgaaggcga tacacttatt ccgccgttca tatcagtgcc tgggcttggc    4140
gaaaacgttg cgaaacgaat tgttgaagct cgtgacgatg gcccattttt atcaaaagaa    4200
gatttaaaca aaaaagctgg attatctcag aaaattattg agtatttaga tgagttaggc    4260
tcattaccga atttaccaga taaagctcaa ctttcgatat ttgatatg               4308
```

<210> SEQ ID NO 8
<211> LENGTH: 1435
<212> TYPE: PRT
<213> ORGANISM: Staphylococcus aureus

<400> SEQUENCE: 8

```
Met Thr Glu Gln Gln Lys Phe Lys Val Leu Ala Asp Gln Ile Lys Ile
 1               5                  10                  15
```

```
Ser Asn Gln Leu Asp Ala Glu Ile Leu Asn Ser Gly Glu Leu Thr Arg
         20                  25                  30

Ile Asp Val Ser Asn Lys Asn Arg Thr Trp Glu Phe His Ile Thr Leu
         35                  40                  45

Pro Gln Phe Leu Ala His Glu Asp Tyr Leu Leu Phe Ile Asn Ala Ile
         50                  55                  60

Glu Gln Glu Phe Lys Asp Ile Ala Asn Val Thr Cys Arg Phe Thr Val
 65                  70                  75                  80

Thr Asn Gly Thr Asn Gln Asp Glu His Ala Ile Lys Tyr Phe Gly His
                 85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
            115                 120                 125

Asn Asp Ile Glu Arg Asn His Phe Asp Lys Ala Cys Asn Gly Ser Leu
130                 135                 140

Ile Lys Ala Phe Arg Asn Cys Gly Phe Asp Ile Asp Lys Ile Ile Phe
145                 150                 155                 160

Glu Thr Asn Asp Asn Asp Gln Glu Gln Asn Leu Ala Ser Leu Glu Ala
                165                 170                 175

His Ile Gln Glu Glu Asp Glu Gln Ser Ala Arg Leu Ala Thr Glu Lys
            180                 185                 190

Leu Glu Lys Met Lys Ala Glu Lys Ala Lys Gln Gln Asp Asn Lys Gln
            195                 200                 205

Ser Ala Val Asp Lys Cys Gln Ile Gly Lys Pro Ile Gln Ile Glu Asn
210                 215                 220

Ile Lys Pro Ile Glu Ser Ile Ile Glu Glu Phe Lys Val Ala Ile
225                 230                 235                 240

Glu Gly Val Ile Phe Asp Ile Asn Leu Lys Glu Leu Lys Ser Gly Arg
                245                 250                 255

His Ile Val Glu Ile Lys Val Thr Asp Tyr Thr Asp Ser Leu Val Leu
            260                 265                 270

Lys Met Phe Thr Arg Lys Asn Lys Asp Asp Leu Glu His Phe Lys Ala
            275                 280                 285

Leu Ser Val Gly Lys Trp Val Arg Ala Gln Gly Arg Ile Glu Glu Asp
            290                 295                 300

Thr Phe Ile Arg Asp Leu Val Met Met Met Ser Asp Ile Glu Glu Ile
305                 310                 315                 320

Lys Lys Ala Thr Lys Lys Asp Lys Ala Glu Glu Lys Arg Val Glu Phe
                325                 330                 335

His Leu His Thr Ala Met Ser Gln Met Asp Gly Ile Pro Asn Ile Gly
            340                 345                 350

Ala Tyr Val Lys Gln Ala Ala Asp Trp Gly His Pro Ala Ile Ala Val
            355                 360                 365

Thr Asp His Asn Val Val Gln Ala Phe Pro Asp Ala His Ala Ala Ala
            370                 375                 380

Glu Lys His Gly Ile Lys Met Ile Tyr Gly Met Glu Gly Met Leu Val
385                 390                 395                 400

Asp Asp Gly Val Pro Ile Ala Tyr Lys Pro Gln Asp Val Val Leu Lys
                405                 410                 415

Asp Ala Thr Tyr Val Val Phe Asp Val Glu Thr Thr Gly Leu Ser Asn
            420                 425                 430
```

-continued

```
Gln Tyr Asp Lys Ile Ile Glu Leu Ala Ala Val Lys Val His Asn Gly
            435                 440                 445
Glu Ile Ile Asp Lys Phe Glu Arg Phe Ser Asn Pro His Glu Arg Leu
        450                 455                 460
Ser Glu Thr Ile Ile Asn Leu Thr His Ile Thr Asp Asp Met Leu Val
465                 470                 475                 480
Asp Ala Pro Glu Ile Glu Val Leu Thr Glu Phe Lys Glu Trp Val
                485                 490                 495
Gly Asp Ala Ile Phe Val Ala His Asn Ala Ser Phe Asp Met Gly Phe
                500                 505                 510
Ile Asp Thr Gly Tyr Glu Arg Leu Gly Phe Gly Pro Ser Thr Asn Gly
            515                 520                 525
Val Ile Asp Thr Leu Glu Leu Ser Arg Thr Ile Asn Thr Glu Tyr Gly
        530                 535                 540
Lys His Gly Leu Asn Phe Leu Ala Lys Lys Tyr Gly Val Glu Leu Thr
545                 550                 555                 560
Gln His His Arg Ala Ile Tyr Asp Thr Glu Ala Thr Ala Tyr Ile Phe
                565                 570                 575
Ile Lys Met Val Gln Gln Met Lys Glu Leu Gly Val Leu Asn His Asn
                580                 585                 590
Glu Ile Asn Lys Lys Leu Ser Asn Glu Asp Ala Tyr Lys Arg Ala Arg
            595                 600                 605
Pro Ser His Val Thr Leu Ile Val Gln Asn Gln Gln Gly Leu Lys Asn
        610                 615                 620
Leu Phe Lys Ile Val Ser Ala Ser Leu Val Lys Tyr Phe Tyr Arg Thr
625                 630                 635                 640
Pro Arg Ile Pro Arg Ser Leu Leu Asp Glu Tyr Arg Glu Gly Leu Leu
                645                 650                 655
Val Gly Thr Ala Cys Asp Glu Gly Leu Phe Thr Ala Val Met Gln
                660                 665                 670
Lys Asp Gln Ser Gln Val Glu Lys Ile Ala Lys Tyr Asp Phe Ile
            675                 680                 685
Glu Ile Gln Pro Pro Ala Leu Tyr Gln Asp Leu Ile Asp Arg Glu Leu
        690                 695                 700
Ile Arg Asp Thr Glu Thr Leu His Glu Ile Tyr Gln Arg Leu Ile His
705                 710                 715                 720
Ala Gly Asp Thr Ala Gly Ile Pro Val Ile Ala Thr Gly Asn Ala His
                725                 730                 735
Tyr Leu Phe Glu His Asp Gly Ile Ala Arg Lys Ile Leu Ile Ala Ser
                740                 745                 750
Gln Pro Gly Asn Pro Leu Asn Arg Ser Thr Leu Pro Glu Ala His Phe
            755                 760                 765
Arg Thr Thr Asp Glu Met Leu Asn Glu Phe His Phe Leu Gly Glu Glu
        770                 775                 780
Lys Ala His Glu Ile Val Val Lys Asn Thr Asn Glu Leu Ala Asp Arg
785                 790                 795                 800
Ile Glu Arg Val Val Pro Ile Lys Asp Glu Leu Tyr Thr Pro Arg Met
                805                 810                 815
Glu Gly Ala Asn Glu Glu Ile Arg Glu Leu Ser Tyr Ala Asn Ala Arg
                820                 825                 830
Lys Leu Tyr Gly Glu Asp Leu Pro Gln Ile Val Ile Asp Arg Leu Glu
            835                 840                 845
Lys Glu Leu Lys Ser Ile Ile Gly Asn Gly Phe Ala Val Ile Tyr Leu
```

-continued

```
                    850                 855                 860
Ile Ser Gln Arg Leu Val Lys Lys Ser Leu Asp Asp Gly Tyr Leu Val
865                 870                 875                 880

Gly Ser Arg Gly Ser Val Gly Ser Ser Phe Val Ala Thr Met Thr Glu
                    885                 890                 895

Ile Thr Glu Val Asn Pro Leu Pro Pro His Tyr Ile Cys Pro Asn Cys
                    900                 905                 910

Lys Thr Ser Glu Phe Phe Asn Asp Gly Ser Val Gly Ser Gly Phe Asp
                    915                 920                 925

Leu Pro Asp Lys Thr Cys Glu Thr Cys Gly Ala Pro Leu Ile Lys Glu
930                 935                 940

Gly Gln Asp Ile Pro Phe Glu Lys Phe Leu Gly Phe Lys Gly Asp Lys
945                 950                 955                 960

Val Pro Asp Ile Asp Leu Asn Phe Ser Gly Glu Tyr Gln Pro Asn Ala
                    965                 970                 975

His Asn Tyr Thr Lys Val Leu Phe Gly Glu Asp Lys Val Phe Arg Ala
                    980                 985                 990

Gly Thr Ile Gly Thr Val Ala Glu Lys Thr Ala Phe Gly Tyr Val Lys
                    995                 1000                1005

Gly Tyr Leu Asn Asp Gln Gly Ile His Lys Arg Gly Ala Glu Ile Asp
    1010                1015                1020

Arg Leu Val Lys Gly Cys Thr Gly Val Lys Ala Thr Thr Gly Gln His
1025                1030                1035                1040

Pro Gly Gly Ile Ile Val Val Pro Asp Tyr Met Asp Ile Tyr Asp Phe
                    1045                1050                1055

Thr Pro Ile Gln Tyr Pro Ala Asp Asp Gln Asn Ser Ala Trp Met Thr
                    1060                1065                1070

Thr His Phe Asp Phe His Ser Ile His Asp Asn Val Leu Lys Leu Asp
                    1075                1080                1085

Ile Leu Gly His Asp Asp Pro Thr Met Ile Arg Met Leu Gln Asp Leu
                    1090                1095                1100

Ser Gly Ile Asp Pro Lys Thr Ile Pro Val Asp Asp Lys Glu Val Met
1105                1110                1115                1120

Gln Ile Phe Ser Thr Pro Glu Ser Leu Gly Val Thr Glu Asp Glu Ile
                    1125                1130                1135

Leu Cys Lys Thr Gly Thr Phe Gly Val Pro Asn Ser Asp Arg Ile Arg
                    1140                1145                1150

Arg Gln Met Leu Glu Asp Thr Lys Pro Thr Thr Phe Ser Glu Leu Val
                    1155                1160                1165

Gln Ile Ser Gly Leu Ser His Gly Thr Asp Val Trp Leu Gly Asn Ala
                    1170                1175                1180

Gln Glu Leu Ile Lys Thr Gly Ile Cys Asp Leu Ser Ser Val Ile Gly
1185                1190                1195                1200

Cys Arg Asp Asp Ile Met Val Tyr Leu Met Tyr Ala Gly Leu Glu Pro
                    1205                1210                1215

Ser Met Ala Phe Lys Ile Met Glu Ser Val Arg Lys Gly Lys Gly Leu
                    1220                1225                1230

Thr Glu Glu Met Ile Glu Thr Met Lys Glu Asn Glu Val Pro Asp Trp
                    1235                1240                1245

Tyr Leu Asp Ser Cys Leu Lys Ile Lys Tyr Ile Phe Pro Lys Ala His
    1250                1255                1260

Ala Ala Ala Tyr Val Leu Met Ala Val Arg Ile Ala Tyr Phe Lys Val
1265                1270                1275                1280
```

His His Pro Leu Tyr Tyr Tyr Ala Ser Tyr Phe Thr Ile Arg Ala Ser
                1285                1290                1295

Asp Phe Asp Leu Ile Thr Met Ile Lys Asp Lys Thr Ser Ile Arg Asn
            1300                1305                1310

Thr Val Lys Asp Met Tyr Ser Arg Tyr Met Asp Leu Gly Lys Lys Glu
        1315                1320                1325

Lys Asp Val Leu Thr Val Leu Glu Ile Met Asn Glu Met Ala His Arg
    1330                1335                1340

Gly Tyr Arg Met Gln Pro Ile Ser Leu Glu Lys Ser Gln Ala Phe Glu
1345                1350                1355                1360

Phe Ile Ile Glu Gly Asp Thr Leu Ile Pro Pro Phe Ile Ser Val Pro
                1365                1370                1375

Gly Leu Gly Glu Asn Val Ala Lys Arg Ile Val Glu Ala Arg Asp Asp
            1380                1385                1390

Gly Pro Phe Leu Ser Lys Glu Asp Leu Asn Lys Lys Ala Gly Leu Tyr
        1395                1400                1405

Gln Lys Ile Ile Glu Tyr Leu Asp Glu Leu Gly Ser Leu Pro Asn Leu
    1410                1415                1420

Pro Asp Lys Ala Gln Leu Ser Ile Phe Asp Met
1425                1430                1435

<210> SEQ ID NO 9
<211> LENGTH: 1134
<212> TYPE: DNA
<213> ORGANISM: Staphylococcus aureus

<400> SEQUENCE: 9
atgatggaat tcactattaa aagagattat tttattacac aattaaatga cacattaaaa      60
gctatttcac caagaacaac attacctata ttaactggta tcaaaatcga tgcgaaagaa     120
catgaagtta tattaactgg ttcagactct gaaatttcaa tagaaatcac tattcctaaa     180
actgtagatg gcgaagatat tgtcaatatt tcagaaacag gctcagtagt acttcctgga     240
cgattctttg ttgatattat aaaaaaatta cctggtaaag atgttaaatt atctacaaat     300
gaacaattcc agacattaat tacatcaggt cattctgaat ttaatttgag tggcttagat     360
ccagatcaat atcctttatt acctcaagtt tctagagatg acgcaattca attgtcggta     420
aaagtactta aaaacgtgat tgcacaaacg aattttgcag tgtccacctc agaaacacgc     480
ccagtactaa ctggtgtgaa ctggcttata caagaaaatg aattaatatg cacagcgact     540
gattcacacc gcttggctgt aagaaagttg cagttagaag atgtttctga aacaaaaat      600
gtcatcattc caggtaaggc tttagctgaa ttaaataaaa ttatgtctga caatgaagaa     660
gacattgata tcttctttgc ttcaaaccaa gttttattta agttggaaa tgtgaacttt       720
atttctcgat tattagaagg acattatcct gatacaacac gtttattccc tgaaaactat     780
gaaattaaat taagtataga caatgggag ttttatcatg cgattgatcg tgcctcttta       840
ttagcacgtg aaggtggtaa taacgttatt aaattaagta caggtgatga cgttgttgaa     900
ttatcttcta catcaccaga aattggtact gtaaaagaag aagttgatgc aaacgatgtt     960
gaaggtggta gcctgaaaat ttcattcaac tctaaatata tgatggatgc tttaaaagca    1020
atcgataatg atgaggttga agttgaattc ttcggtacaa tgaaaccatt tattctaaaa    1080
ccaaaaggtg acgactcggt aacgcaatta attttaccaa tcagaactta ctaa          1134

<210> SEQ ID NO 10

```
<211> LENGTH: 377
<212> TYPE: PRT
<213> ORGANISM: Staphylococcus aureus

<400> SEQUENCE: 10

Met Met Glu Phe Thr Ile Lys Arg Asp Tyr Phe Ile Thr Gln Leu Asn
 1               5                  10                  15

Asp Thr Leu Lys Ala Ile Ser Pro Arg Thr Thr Leu Pro Ile Leu Thr
                20                  25                  30

Gly Ile Lys Ile Asp Ala Lys Glu His Glu Val Ile Leu Thr Gly Ser
            35                  40                  45

Asp Ser Glu Ile Ser Ile Glu Ile Thr Ile Pro Lys Thr Val Asp Gly
    50                  55                  60

Glu Asp Ile Val Asn Ile Ser Glu Thr Gly Ser Val Val Leu Pro Gly
65                  70                  75                  80

Arg Phe Phe Val Asp Ile Ile Lys Lys Leu Pro Gly Lys Asp Val Lys
                85                  90                  95

Leu Ser Thr Asn Glu Gln Phe Gln Thr Leu Ile Thr Ser Gly His Ser
            100                 105                 110

Glu Phe Asn Leu Ser Gly Leu Asp Pro Asp Gln Tyr Pro Leu Leu Pro
    115                 120                 125

Gln Val Ser Arg Asp Asp Ala Ile Gln Leu Ser Val Lys Val Leu Lys
130                 135                 140

Asn Val Ile Ala Gln Thr Asn Phe Ala Val Ser Thr Ser Glu Thr Arg
145                 150                 155                 160

Pro Val Leu Thr Gly Val Asn Trp Leu Ile Gln Glu Asn Glu Leu Ile
                165                 170                 175

Cys Thr Ala Thr Asp Ser His Arg Leu Ala Val Arg Lys Leu Gln Leu
            180                 185                 190

Glu Asp Val Ser Glu Asn Lys Asn Val Ile Ile Pro Gly Lys Ala Leu
    195                 200                 205

Ala Glu Leu Asn Lys Ile Met Ser Asp Asn Glu Glu Asp Ile Asp Ile
210                 215                 220

Phe Phe Ala Ser Asn Gln Val Leu Phe Lys Val Gly Asn Val Asn Phe
225                 230                 235                 240

Ile Ser Arg Leu Leu Glu Gly His Tyr Pro Asp Thr Thr Arg Leu Phe
                245                 250                 255

Pro Glu Asn Tyr Glu Ile Lys Leu Ser Ile Asp Asn Gly Glu Phe Tyr
            260                 265                 270

His Ala Ile Asp Arg Ala Ser Leu Leu Ala Arg Glu Gly Gly Asn Asn
    275                 280                 285

Val Ile Lys Leu Ser Thr Gly Asp Asp Val Val Glu Leu Ser Ser Thr
290                 295                 300

Ser Pro Glu Ile Gly Thr Val Lys Glu Val Asp Ala Asn Asp Val
305                 310                 315                 320

Glu Gly Gly Ser Leu Lys Ile Ser Phe Asn Ser Lys Tyr Met Met Asp
                325                 330                 335

Ala Leu Lys Ala Ile Asp Asn Asp Val Glu Val Glu Phe Phe Gly
            340                 345                 350

Thr Met Lys Pro Phe Ile Leu Lys Pro Lys Gly Asp Asp Ser Val Thr
    355                 360                 365

Gln Leu Ile Leu Pro Ile Arg Thr Tyr
370                 375
```

-continued

<210> SEQ ID NO 11
<211> LENGTH: 930
<212> TYPE: DNA
<213> ORGANISM: Staphylococcus aureus

<400> SEQUENCE: 11

```
atggatgaac agcaacaatt gacgaatgca tatcattcaa ataaattatc gcatgcctat      60
ttatttgaag gtgatgatgc acaaacgatg aaacaagttg cgattaattt tgcaaagctt     120
attttatgtc aaacagatag tcaatgtgaa acaaaggtta gtacatataa tcatccagac     180
tttatgtata tatcaacaac tgagaatgca attaagaaag aacaagttga acaacttgtg     240
cgtcatatga atcaacttcc tatagaaagc acaaataaag tgtacatcat cgaagacttt     300
gaagactttg aaaagttaac tgttcaaggg aaaacagta tcttgaaatt tcttgaagaa      360
ccaccggaca atacgattgc tatttttattg tctacaaaac ctgagcaaat tttagacaca     420
atccattcaa ggtgtcagca tgtatatttc aagcctattg ataaagaaaa gtttataaat     480
agattagttg aacaaaacat gtctaagcca gtagctgaaa tgattagtac ttatactacg     540
caaatagata atgcaatggc tttaaatgaa gaatttgatt tattagcatt aaggaaatca     600
gttatacgtt gggaattgtt gcttactaat aagccaatgg cacttatagg tattattgat     660
ttattgaaac aggctaaaaa taaaaaactg caatctttaa ctattgcagc tgtgaatggt     720
ttcttcgaag atatcataca tacaaaggta aatgtagagg ataaacaaat atatagtgat     780
ttaaaaaatg atattgatca atatgcgcaa aagttgtcgt ttaatcaatt aattttgatg     840
tttgatcaac tgacggaagc acataagaaa ttgaatcaaa atgtaaatcc aacgcttgta     900
tttgaacaaa tcgtaattaa gggtgtgagt                                       930
```

<210> SEQ ID NO 12
<211> LENGTH: 310
<212> TYPE: PRT
<213> ORGANISM: Staphylococcus aureus

<400> SEQUENCE: 12

```
Met Asp Glu Gln Gln Gln Leu Thr Asn Ala Tyr His Ser Asn Lys Leu
  1               5                  10                  15

Ser His Ala Tyr Leu Phe Glu Gly Asp Asp Ala Gln Thr Met Lys Gln
             20                  25                  30

Val Ala Ile Asn Phe Ala Lys Leu Ile Leu Cys Gln Thr Asp Ser Gln
         35                  40                  45

Cys Glu Thr Lys Val Ser Thr Tyr Asn His Pro Asp Phe Met Tyr Ile
     50                  55                  60

Ser Thr Thr Glu Asn Ala Ile Lys Lys Glu Gln Val Glu Gln Leu Val
 65                  70                  75                  80

Arg His Met Asn Gln Leu Pro Ile Glu Ser Thr Asn Lys Val Tyr Ile
                 85                  90                  95

Ile Glu Asp Phe Glu Asp Phe Glu Lys Leu Thr Val Gln Gly Glu Asn
            100                 105                 110

Ser Ile Leu Lys Phe Leu Glu Glu Pro Pro Asp Asn Thr Ile Ala Ile
        115                 120                 125

Leu Leu Ser Thr Lys Pro Glu Gln Ile Leu Asp Thr Ile His Ser Arg
    130                 135                 140

Cys Gln His Val Tyr Phe Lys Pro Ile Asp Lys Glu Lys Phe Ile Asn
145                 150                 155                 160

Arg Leu Val Glu Gln Asn Met Ser Lys Pro Val Ala Glu Met Ile Ser
                165                 170                 175
```

Thr Tyr Thr Thr Gln Ile Asp Asn Ala Met Ala Leu Asn Glu Glu Phe
            180                 185                 190

Asp Leu Leu Ala Leu Arg Lys Ser Val Ile Arg Trp Glu Leu Leu Leu
        195                 200                 205

Thr Asn Lys Pro Met Ala Leu Ile Gly Ile Ile Asp Leu Leu Lys Gln
    210                 215                 220

Ala Lys Asn Lys Lys Leu Gln Ser Leu Thr Ile Ala Ala Val Asn Gly
225                 230                 235                 240

Phe Phe Glu Asp Ile Ile His Thr Lys Val Asn Val Glu Asp Lys Gln
                245                 250                 255

Ile Tyr Ser Asp Leu Lys Asn Asp Ile Asp Gln Tyr Ala Gln Lys Leu
            260                 265                 270

Ser Phe Asn Gln Leu Ile Leu Met Phe Asp Gln Leu Thr Glu Ala His
        275                 280                 285

Lys Lys Leu Asn Gln Asn Val Asn Pro Thr Leu Val Phe Glu Gln Ile
    290                 295                 300

Val Ile Lys Gly Val Ser
305                 310

<210> SEQ ID NO 13
<211> LENGTH: 744
<212> TYPE: DNA
<213> ORGANISM: Staphylococcus aureus

<400> SEQUENCE: 13
atgagcgaca atattgtagc tatttatgga gatgtgcctg aattggttga aaacaaagt      60 gcagaaatca tatcacaatt tttgaaaagt gatagagatg actttaactt tgtgaaatat    120
aatttatacg aaacagagat tgcaccaatt gttgaagaaa cattaacatt gcctttcttt    180
tcagataaaa aagcaatttt ggttaaaaat gcatatatat ttacaggtga aaaagcgcca    240
aaagatatgg ctcataatgt agaccaatta atagaattta ttgaaaaata tgatggcgaa    300
aatttgattg tctttgagat atatcaaaat aaacttgatg aaagaaaaaa gttaactaaa    360
actctaaaaa agcatgcaag gcttaaaaaa atagagcaga tgtcggagga gatcaagtgg    420
attcaaaaaa aagaacaagc gattgatttt gtaaaagatc ttataacaat gaaagaagaa    480
ccaattaaac ttcttgcact acatcaaat tatagacttt tttatcaatg taaaattctt      540
tcacaaaaag gttatagtgg tcaacaaatt gcaaaaacaa taggtgttca tccatataga    600
gtgaaacttg cacttggtca agtgagacat tatcaacttg atgaacttct taatattatt    660
gatgcatgtg cagaaacaga ttataaactt aaatcatcat atatggataa acaacttatt    720
cttgaacttt ttattctttc actt                                           744

<210> SEQ ID NO 14
<211> LENGTH: 248
<212> TYPE: PRT
<213> ORGANISM: Staphylococcus aureus

<400> SEQUENCE: 14

Met Ser Asp Asn Ile Val Ala Ile Tyr Gly Asp Val Pro Glu Leu Val
1               5                   10                  15

Glu Lys Gln Ser Ala Glu Ile Ile Ser Gln Phe Leu Lys Ser Asp Arg
            20                  25                  30

Asp Asp Phe Asn Phe Val Lys Tyr Asn Leu Tyr Glu Thr Glu Ile Ala
        35                  40                  45

```
Pro Ile Val Glu Glu Thr Leu Thr Leu Pro Phe Phe Ser Asp Lys Lys
        50                  55                  60

Ala Ile Leu Val Lys Asn Ala Tyr Ile Phe Thr Gly Glu Lys Ala Pro
 65                  70                  75                  80

Lys Asp Met Ala His Asn Val Asp Gln Leu Ile Glu Phe Ile Glu Lys
                 85                  90                  95

Tyr Asp Gly Glu Asn Leu Ile Val Phe Glu Ile Tyr Gln Asn Lys Leu
                100                 105                 110

Asp Glu Arg Lys Lys Leu Thr Lys Thr Leu Lys Lys His Ala Arg Leu
            115                 120                 125

Lys Lys Ile Glu Gln Met Ser Glu Glu Ile Lys Trp Ile Gln Lys Lys
130                 135                 140

Glu Gln Ala Ile Asp Phe Val Lys Asp Leu Ile Thr Met Lys Glu Glu
145                 150                 155                 160

Pro Ile Lys Leu Leu Ala Leu Thr Ser Asn Tyr Arg Leu Phe Tyr Gln
                165                 170                 175

Cys Lys Ile Leu Ser Gln Lys Gly Tyr Ser Gly Gln Gln Ile Ala Lys
                180                 185                 190

Thr Ile Gly Val His Pro Tyr Arg Val Lys Leu Ala Leu Gly Gln Val
            195                 200                 205

Arg His Tyr Gln Leu Asp Glu Leu Leu Asn Ile Ile Asp Ala Cys Ala
210                 215                 220

Glu Thr Asp Tyr Lys Leu Lys Ser Ser Tyr Met Asp Lys Gln Leu Ile
225                 230                 235                 240

Leu Glu Leu Phe Ile Leu Ser Leu
                245

<210> SEQ ID NO 15
<211> LENGTH: 1719
<212> TYPE: DNA
<213> ORGANISM: Staphylococcus aureus

<400> SEQUENCE: 15
atgataggtt tgtgtccttt tcatgatgaa aagacaccct catttacagt ttctgaagat      60
aaacaaatct gtcattgttt tggttgtaaa aaaggtggca atgttttca atttactcaa      120 gaaattaaag acatatcatt tgttgaagcg gttaaagaat taggtgatag agttaatgtt      180
gctgtagata ttgaggcaac acaatctaac tcaaatgttc aaattgcttc tgatgattta      240
caaatgattg aaatgcatga gttaatacaa gaatttttat tattacgcttt aacaaagaca      300 gtcgaaggcg aacaagcatt aacatactta caagaacgtg gttttacaga tgcgcttatt      360
aaagagcgag gcattggctt tgcacccgat agctcacatt tttgtcatga tttctcttcaa     420 aaaaagggtt acgatattga attagcatat gaagccggat tattatcacg taacgaagaa      480
aatttcagtt attacgatag atttcgaaat cgtattatgt ttcctttgaa aaatgcgcaa      540
ggaagaattg ttggatattc aggtcgaaca tataccggtc aagaaccaaa ataacctaaa       600
agtcctgaaa cgcctatctt tcaaaaaaga aagttgttat ataacttaga taagcacgt       660 aaatcaatta gaaaattaga tgaaattgta ttactagaag gttttatgga tgttataaaa      720
tctgatactg ctggcttgaa aaacgttgtt gcaacaatgg gtacacagtt gtcgatgaa       780 catattaccct ttatacgaaa gttaacatca aatataacat taatgtttga tggggatttt     840
gcgggtagtg aagcaacact taaacaggt caacatttgt tacagcaagg gctaaatgta       900
tttgttatac aattgccatc tggcatggat ccggatgaat acattggtaa gtatggcaac      960
```

-continued

```
gacgcattta ctactttgt aaaaaatgac aaaaagtcat ttgcacatta taaagtaagt    1020
atattaaaag atgaaattgc acataatgac ctttcatatg aacgttattt gaaagaactg    1080
agtcatgaca tttcacttat gaagtcatca attctgcaac aaaaggctat aaatgatgtt    1140
gcgccatttt tcaatgttag tcctgagcag ttagctaacg aaatacaatt caatcaagca    1200
ccagccaatt attatccaga agatgagtat ggcggttatg atgagtatgg cggttatatt    1260
gaacctgagc caattggtat ggcacaattt gacaatttga gccgtcgaga aaaagcggag    1320
cgagcatttt taaaacattt aatgagagat aaagatacat ttttaaatta ttatgaaagt    1380
gttgataagg ataacttcac aaatcagcat tttaaatatg tattcgaagt cttacatgat    1440
ttttatgcgg aaaatgatca atataatatc agtgatgctg tgcagtatgt taattcaaat    1500
gagttgagag aaacactaat tagcttagaa caatataatt tgaatggcga accatatgaa    1560
aatgaaattg atgattatgt caatgttatt aatgaaaaag gacaagaaac aattgagtca    1620
ttgaatcata aattaaggga agctacaagg attggcgatg tagaattaca aaatactat     1680 ttacagcaaa ttgttgctaa gaataaagaa cgcatgtag                           1719
```

<210> SEQ ID NO 16
<211> LENGTH: 572
<212> TYPE: PRT
<213> ORGANISM: Staphylococcus aureus

<400> SEQUENCE: 16

```
Met Ile Gly Leu Cys Pro Phe His Asp Glu Lys Thr Pro Ser Phe Thr
  1               5                  10                  15

Val Ser Glu Asp Lys Gln Ile Cys His Cys Phe Gly Cys Lys Lys Gly
             20                  25                  30

Gly Asn Val Phe Gln Phe Thr Gln Glu Ile Lys Asp Ile Ser Phe Val
         35                  40                  45

Glu Ala Val Lys Glu Leu Gly Asp Arg Val Asn Val Ala Val Asp Ile
     50                  55                  60

Glu Ala Thr Gln Ser Asn Ser Asn Val Gln Ile Ala Ser Asp Asp Leu
 65                  70                  75                  80

Gln Met Ile Glu Met His Glu Leu Ile Gln Glu Phe Tyr Tyr Tyr Ala
                 85                  90                  95

Leu Thr Lys Thr Val Glu Gly Glu Gln Ala Leu Thr Tyr Leu Gln Glu
            100                 105                 110

Arg Gly Phe Thr Asp Ala Leu Ile Lys Glu Arg Gly Ile Gly Phe Ala
        115                 120                 125

Pro Asp Ser Ser His Phe Cys His Asp Phe Leu Gln Lys Lys Gly Tyr
    130                 135                 140

Asp Ile Glu Leu Ala Tyr Glu Ala Gly Leu Leu Ser Arg Asn Glu Glu
145                 150                 155                 160

Asn Phe Ser Tyr Tyr Asp Arg Phe Arg Asn Arg Ile Met Phe Pro Leu
                165                 170                 175

Lys Asn Ala Gln Gly Arg Ile Val Gly Tyr Ser Gly Arg Thr Tyr Thr
            180                 185                 190

Gly Gln Glu Pro Lys Tyr Leu Asn Ser Pro Glu Thr Pro Ile Phe Gln
        195                 200                 205

Lys Arg Lys Leu Leu Tyr Asn Leu Asp Lys Ala Arg Lys Ser Ile Arg
    210                 215                 220

Lys Leu Asp Glu Ile Val Leu Leu Glu Gly Phe Met Asp Val Ile Lys
225                 230                 235                 240
```

-continued

```
Ser Asp Thr Ala Gly Leu Lys Asn Val Val Ala Thr Met Gly Thr Gln
            245                 250                 255

Leu Ser Asp Glu His Ile Thr Phe Ile Arg Lys Leu Thr Ser Asn Ile
        260                 265                 270

Thr Leu Met Phe Asp Gly Asp Phe Ala Gly Ser Glu Ala Thr Leu Lys
    275                 280                 285

Thr Gly Gln His Leu Leu Gln Gln Gly Leu Asn Val Phe Val Ile Gln
290                 295                 300

Leu Pro Ser Gly Met Asp Pro Asp Glu Tyr Ile Gly Lys Tyr Gly Asn
305                 310                 315                 320

Asp Ala Phe Thr Thr Phe Val Lys Asn Asp Lys Lys Ser Phe Ala His
            325                 330                 335

Tyr Lys Val Ser Ile Leu Lys Asp Glu Ile Ala His Asn Asp Leu Ser
        340                 345                 350

Tyr Glu Arg Tyr Leu Lys Glu Leu Ser His Asp Ile Ser Leu Met Lys
    355                 360                 365

Ser Ser Ile Leu Gln Gln Lys Ala Ile Asn Asp Val Ala Pro Phe Phe
370                 375                 380

Asn Val Ser Pro Glu Gln Leu Ala Asn Glu Ile Gln Phe Asn Gln Ala
385                 390                 395                 400

Pro Ala Asn Tyr Tyr Pro Glu Asp Glu Tyr Gly Gly Tyr Asp Glu Tyr
            405                 410                 415

Gly Gly Tyr Ile Glu Pro Glu Pro Ile Gly Met Ala Gln Phe Asp Asn
        420                 425                 430

Leu Ser Arg Arg Glu Lys Ala Glu Arg Ala Phe Leu Lys His Leu Met
    435                 440                 445

Arg Asp Lys Asp Thr Phe Leu Asn Tyr Tyr Glu Ser Val Asp Lys Asp
450                 455                 460

Asn Phe Thr Asn Gln His Phe Lys Tyr Val Phe Glu Val Leu His Asp
465                 470                 475                 480

Phe Tyr Ala Glu Asn Asp Gln Tyr Asn Ile Ser Asp Ala Val Gln Tyr
            485                 490                 495

Val Asn Ser Asn Glu Leu Arg Glu Thr Leu Ile Ser Leu Glu Gln Tyr
        500                 505                 510

Asn Leu Asn Gly Glu Pro Tyr Glu Asn Glu Ile Asp Asp Tyr Val Asn
    515                 520                 525

Val Ile Asn Glu Lys Gly Gln Glu Thr Ile Glu Ser Leu Asn His Lys
530                 535                 540

Leu Arg Glu Ala Thr Arg Ile Gly Asp Val Glu Leu Gln Lys Tyr Tyr
545                 550                 555                 560

Leu Gln Gln Ile Val Ala Lys Asn Lys Glu Arg Met
            565                 570
```

<210> SEQ ID NO 17
<211> LENGTH: 4395
<212> TYPE: DNA
<213> ORGANISM: Streptococcus pyogenes

<400> SEQUENCE: 17

```
atgtcagatt tattcgctaa attgatggac cagatagaaa tgccacttga catgagacgt    60
tcaagtgcct tttcatctgc tgatattatc gaggtaaagg tacattcggt gtcacgcttg   120
tgggaatttc attttgcctt tgcagcggtt ttaccgattg caacttatcg tgaattgcat   180
gatcgtttga taagaacttt tgaggcggct gacattaagg taacctttga catccaagct   240
```

```
gctcaggtgg attattcaga tgatctgctt caagcttatt accaagaagc ttttgagcat    300
gcaccgtgta atagtgctag ttttaaatct tctttctcaa agctcaaagt gacttatgag    360
gatgacaaac tcattattgc agcgccaggt tttgtgaata acgatcattt tagaaacaat    420
catctgccta atctggtcaa gcaattagaa gcctttggct ttggcatctt gaccatagat    480
atggtgtcag atcaggaaat gactgagcat ttgaccaaga attttgtttc cagtcgtcag    540
gctcttgtga aaaggctgt gcaggataat ttggaagccc aaaaatctct tgaagccatg    600
atgccaccag ttgaggaagc cacacctgct cctaagtttg actacaagga acgagcagct    660
aagcgtcagg cagggtttga aaaagcaacc atcacaccaa tgattgagat tgagaccgaa    720
gaaaaccgga ttgtctttga gggtatggtt tttgacgtgg agcgtaaaac gactaggaca    780
ggtcgccata tcatcaactt taaaatgaca gactatacct cctcgtttgc tctccaaaaa    840
tgggctaaag acgatgagga gctccgtaaa tttgatatga ttgctaaggg agcttggtta    900
cgggtacaag ggaatattga gaccaatcct tttacgaaga gtctcaccat gaatgtccag    960
caggtcaaag aaattgtccg tcatgagcgc aaagacctga tgccagaagg gcaaaagcgg   1020
gtcgaacttc atgcccacac caatatgtct accatggatg ccttaccgac agtagaaagc   1080
ttgattgata cggcagccaa gtggggacac aaggcgattg ctatcaccga ccatgctaat   1140
gtgcaaagtt ttcctcatgg ctaccatagg gctcgcaaag ctgggattaa ggctattttt   1200
ggcctagaag ccaatattgt tgaggacaag gtgcctattt cttatgaacc tgttgatatg   1260
gatttgcacg aagccaccta tgtggtcttt gacgtggaaa ccacaggtct atctgctatg   1320
aataatgacc tgattcagat tgcggcttcc aaaatgttta aggaaatat tgtagagcag    1380
tttgatgaat tcattgatcc tgggcatcct ctttcagcct ttaccaccga attgacagga   1440
attaccgata agcatttgca gggcgccaag ccattggtta ctgtcctaaa agcttttcag   1500
gacttttgca agatagtat cttggttgcc cacaacgcca gttttgacgt gggctttatg   1560
aacgccaatt atgaacgcca cgacttgccc aaaatcacac agcctgtgat tgatacctta   1620
gaatttgcta gaaacttgta tcctgagtac aagcgtcacg gtttgggacc gctcaccaag   1680
cgtttccaag tgagtctaga ccaccatcat atggccaatt acgacgcgga agccacagga   1740
cgtcttttgt ttattttct aaaagatgcc agagaaaagc atggcatcaa aaatctttg    1800
caactcaata cagatttggt ggctgaggat tcttacaaaa aagcgcggat taagcatgcg   1860
actatctatg tgcaaaatca ggttggtctt aaaaatatgt ttaagttggt cagcctttcc   1920
aatatcaaat attttgaagg ggtgccgcgt attccaagaa ccgtcttaga tgctcacaga   1980
gagggtttgt tacttggtac agcttgttct gacggcgagg ttttttgatgc cgttctgact   2040
aaaggaattg atgcagcggt tgatttggct aggtattatg attttatcga aatcatgcca   2100
ccagccattt accagccatt ggttgtccgt gaattaatca agatcaagc aggtattgag    2160
caggtgattc gtgacctcat tgaagtaggg aaacgagcta agaaacctgt gcttgccact   2220
gggaatgtgc attatctaga gcctgaagaa gagatttacc gtgaaattat tgtgcgtagt   2280
cttggtcagg gtgccatgat taatagaaca atcggccgtg ggaaggggc acagcctgct    2340
cctctaccta agcgcactt tagaacaacc aatgaaatgc tggatgagtt tgcctttctt   2400
ggaaaagacc tcgcttatca agtagttgtg caaaatactc aggattttgc ggaccgtatt   2460
gaggaagtgg aagtggttaa gggcgatctt tacaccccgt atattgataa ggccgaagag   2520
acggttgccg aattaaccta tcaaaaagcc tttgaaattt atggtaatcc tctcccagat   2580
attattgatt tacgcattga aaaagagtta acctctatct tggggaacgg ttttgctgtg   2640
```

-continued

```
atttatctcg cttcccaaat gcttgttaac cggtcaaatg agcgaggcta cctagttggt    2700 tctagggggat ctgtagggtc tagctttgtc gccaccatga ttgggattac tgaggttaat   2760
cctatgccgc ctcactacgt ttgcccgtcc tgccaacatt ctgaatttat cacagatggg    2820
tcagttggat ctggctatga tttgcctaat aaaccctgtc cgaaatgtgg caccccttat    2880
caaaaagatg gcaagacat tcccttttgag acctttcttg ggtttgatgg ggataaggtg    2940
cccgatattg atttgaactt ctctggtgat gaccagccca gtgcccattt ggatgtccga    3000 gatattttg gtgacgaata cgcctttcgt gctggaacag ttggtaccgt agcagaaaaa    3060
acagcttatg gatttgtcaa aggctatgaa cgcgactatg gcaagttcta tcgtgatgct    3120
gaggtggatc gtctagcagc aggtgctgct ggtgtgaaac gaacgactgg gcagcaccct    3180 gggggggattg ttgttattcc taattacatg gatgtttatg atttttacccc cgtgcaatat   3240 ccagccgatg atgtaacggc ttcttggcag acaactcact ttaacttcca tgatattgat    3300
gaaaacgtct tgaaacttga tatcctaggg catgatgatc cgaccatgat tcgtaaactt    3360
caggatttat cgggcattga tcctattact attcctgctg atgatccggg agttatggct    3420
ctcttttctg ggacagaggt ttttgggcgtt accccggaac aaaattggga ccgactggt    3480 atgctaggca ttccagaatt tggaaccaac tttgttcgcg gcatggttaa tgagacgcat    3540
ccgaccactt ttgcggagct tttgcagttg tctggactat ctcatggaac cgatgtttgg    3600
cttggtaatg cacaagattt gattaaagaa ggcattgcaa ccctaaaaac cgttatcggt   3660
tgtcgtgacg acatcatggt ttacctcatg cacgcaggct tagaaccaaa aatgcccttt    3720
accattatgg agcgtgtgcg taagggatta tggctaaaaa tttctgagga gaacgtaat    3780 ggctatattg atgccatgcg agaaaacaat gtgcccgact ggtacattga atcgtgtgga    3840
aaaatcaagt acatgttccc taaagcccat gcggcagctt atgtttttgat ggcccttcgg   3900 gtggcttatt tcaaggtgca ccaccccatt atgtattatt gtgcttattt ctctattcgt    3960
gcgaaggctt tgaattaaaa accatgagt ggtggtttag atgctgttaa agcaagaatg    4020
gaagatatta ctataaaacg taaaaataat gaagccacca atgtggaaaa tgacctcttt    4080
acaaccttgg agattgtcaa cgaaatgtta aacgcggct ttaagtttgg caaattagac    4140
ctttacaaaa gtgatgctat agaattccaa atcaaaggag ataccctat ccctccattt    4200 atagcgctag aaggtctggg tgaaaacgtg gccaagcaaa tcgttaaagc tcgtcaagaa    4260
ggcgaattcc tctctaaaat ggaattgcgt aaacgaggcg gggcatcgtc aacgctcgtt    4320
gagaaaatgg atgagatggg tatttttagga aatatgccag aagataatca attaagtctt    4380
tttgatgact ttttc                                                      4395
```

<210> SEQ ID NO 18  
<211> LENGTH: 1465  
<212> TYPE: PRT  
<213> ORGANISM: Streptococcus pyogenes

<400> SEQUENCE: 18

```
Met Ser Asp Leu Phe Ala Lys Leu Met Asp Gln Ile Glu Met Pro Leu
  1               5                  10                  15

Asp Met Arg Arg Ser Ser Ala Phe Ser Ser Ala Asp Ile Ile Glu Val
             20                  25                  30

Lys Val His Ser Val Ser Arg Leu Trp Glu Phe His Phe Ala Phe Ala
         35                  40                  45

Ala Val Leu Pro Ile Ala Thr Tyr Arg Glu Leu His Asp Arg Leu Ile
```

```
            50                  55                  60
Arg Thr Phe Glu Ala Ala Asp Ile Lys Val Thr Phe Asp Ile Gln Ala
 65                  70                  75                  80

Ala Gln Val Asp Tyr Ser Asp Leu Leu Gln Ala Tyr Tyr Gln Glu
                 85                  90                  95

Ala Phe Glu His Ala Pro Cys Asn Ser Ala Ser Phe Lys Ser Ser Phe
                100                 105                 110

Ser Lys Leu Lys Val Thr Tyr Glu Asp Lys Leu Ile Ile Ala Ala
                115                 120                 125

Pro Gly Phe Val Asn Asn Asp His Phe Arg Asn Asn His Leu Pro Asn
130                 135                 140

Leu Val Lys Gln Leu Glu Ala Phe Gly Phe Gly Ile Leu Thr Ile Asp
145                 150                 155                 160

Met Val Ser Asp Gln Glu Met Thr Glu His Leu Thr Lys Asn Phe Val
                165                 170                 175

Ser Ser Arg Gln Ala Leu Val Lys Lys Ala Val Gln Asp Asn Leu Glu
                180                 185                 190

Ala Gln Lys Ser Leu Glu Ala Met Met Pro Val Glu Glu Ala Thr
                195                 200                 205

Pro Ala Pro Lys Phe Asp Tyr Lys Glu Arg Ala Ala Lys Arg Gln Ala
                210                 215                 220

Gly Phe Glu Lys Ala Thr Ile Thr Pro Met Ile Glu Ile Glu Thr Glu
225                 230                 235                 240

Glu Asn Arg Ile Val Phe Glu Gly Met Val Phe Asp Val Glu Arg Lys
                245                 250                 255

Thr Thr Arg Thr Gly Arg His Ile Ile Asn Phe Lys Met Thr Asp Tyr
                260                 265                 270

Thr Ser Ser Phe Ala Leu Gln Lys Trp Ala Lys Asp Glu Glu Leu
                275                 280                 285

Arg Lys Phe Asp Met Ile Ala Lys Gly Ala Trp Leu Arg Val Gln Gly
                290                 295                 300

Asn Ile Glu Thr Asn Pro Phe Thr Lys Ser Leu Thr Met Asn Val Gln
305                 310                 315                 320

Gln Val Lys Glu Ile Val Arg His Glu Arg Lys Asp Leu Met Pro Glu
                325                 330                 335

Gly Gln Lys Arg Val Glu Leu His Ala His Thr Asn Met Ser Thr Met
                340                 345                 350

Asp Ala Leu Pro Thr Val Glu Ser Leu Ile Asp Thr Ala Ala Lys Trp
                355                 360                 365

Gly His Lys Ala Ile Ala Ile Thr Asp His Ala Asn Val Gln Ser Phe
                370                 375                 380

Pro His Gly Tyr His Arg Ala Arg Lys Ala Gly Ile Lys Ala Ile Phe
385                 390                 395                 400

Gly Leu Glu Ala Asn Ile Val Glu Asp Lys Val Pro Ile Ser Tyr Glu
                405                 410                 415

Pro Val Asp Met Asp Leu His Gly Ala Thr Tyr Val Val Phe Asp Val
                420                 425                 430

Glu Thr Thr Gly Leu Ser Ala Met Asn Asn Asp Leu Ile Gln Ile Ala
                435                 440                 445

Ala Ser Lys Met Phe Lys Gly Asn Ile Val Glu Gln Phe Asp Glu Phe
                450                 455                 460

Ile Asp Pro Gly His Pro Leu Ser Ala Phe Thr Thr Glu Leu Thr Gly
465                 470                 475                 480
```

-continued

Ile Thr Asp Lys His Leu Gln Gly Ala Lys Pro Leu Val Thr Val Leu
            485                 490                 495

Lys Ala Phe Gln Asp Phe Cys Lys Asp Ser Ile Leu Val Ala His Asn
        500                 505                 510

Ala Ser Phe Asp Val Gly Phe Met Asn Ala Asn Tyr Glu Arg His Asp
        515                 520                 525

Leu Pro Lys Ile Thr Gln Pro Val Ile Asp Thr Leu Glu Phe Ala Arg
        530                 535                 540

Asn Leu Tyr Pro Glu Tyr Lys Arg His Gly Leu Gly Pro Leu Thr Lys
545                 550                 555                 560

Arg Phe Gln Val Ser Leu Asp His His Met Ala Asn Tyr Asp Ala
            565                 570                 575

Glu Ala Thr Gly Arg Leu Leu Phe Ile Phe Leu Lys Asp Ala Arg Glu
            580                 585                 590

Lys His Gly Ile Lys Asn Leu Leu Gln Leu Asn Thr Asp Leu Val Ala
            595                 600                 605

Glu Asp Ser Tyr Lys Lys Ala Arg Ile Lys His Ala Thr Ile Tyr Val
            610                 615                 620

Gln Asn Gln Val Gly Leu Lys Asn Met Phe Lys Leu Val Ser Leu Ser
625                 630                 635                 640

Asn Ile Lys Tyr Phe Glu Gly Val Pro Arg Ile Pro Arg Thr Val Leu
            645                 650                 655

Asp Ala His Arg Glu Gly Leu Leu Gly Thr Ala Cys Ser Asp Gly
            660                 665                 670

Glu Val Phe Asp Ala Val Leu Thr Lys Gly Ile Asp Ala Ala Val Asp
            675                 680                 685

Leu Ala Arg Tyr Tyr Asp Phe Ile Glu Ile Met Pro Pro Ala Ile Tyr
            690                 695                 700

Gln Pro Leu Val Val Arg Glu Leu Ile Lys Asp Gln Ala Gly Ile Glu
705                 710                 715                 720

Gln Val Ile Arg Asp Leu Ile Glu Val Gly Lys Arg Ala Lys Lys Pro
            725                 730                 735

Val Leu Ala Thr Gly Asn Val His Tyr Leu Glu Pro Glu Glu Glu Ile
            740                 745                 750

Tyr Arg Glu Ile Ile Val Arg Ser Leu Gly Gln Gly Ala Met Ile Asn
            755                 760                 765

Arg Thr Ile Gly Arg Gly Glu Gly Ala Gln Pro Ala Pro Leu Pro Lys
770                 775                 780

Ala His Phe Arg Thr Thr Asn Glu Met Leu Asp Glu Phe Ala Phe Leu
785                 790                 795                 800

Gly Lys Asp Leu Ala Tyr Gln Val Val Gln Asn Thr Gln Asp Phe
            805                 810                 815

Ala Asp Arg Ile Glu Glu Val Val Val Lys Gly Asp Leu Tyr Thr
            820                 825                 830

Pro Tyr Ile Asp Lys Ala Glu Thr Val Ala Glu Leu Thr Tyr Gln
            835                 840                 845

Lys Ala Phe Glu Ile Tyr Gly Asn Pro Leu Pro Asp Ile Ile Asp Leu
850                 855                 860

Arg Ile Glu Lys Glu Leu Thr Ser Ile Leu Gly Asn Gly Phe Ala Val
865                 870                 875                 880

Ile Tyr Leu Ala Ser Gln Met Leu Val Asn Arg Ser Asn Glu Arg Gly
            885                 890                 895

-continued

Tyr Leu Val Gly Ser Arg Gly Ser Val Gly Ser Ser Phe Val Ala Thr
            900                 905                 910

Met Ile Gly Ile Thr Glu Val Asn Pro Met Pro Pro His Tyr Val Cys
            915                 920                 925

Pro Ser Cys Gln His Ser Glu Phe Ile Thr Asp Gly Ser Val Gly Ser
            930                 935                 940

Gly Tyr Asp Leu Pro Asn Lys Pro Cys Pro Lys Cys Gly Thr Pro Tyr
945                 950                 955                 960

Gln Lys Asp Gly Gln Asp Ile Pro Phe Glu Thr Phe Leu Gly Phe Asp
            965                 970                 975

Gly Asp Lys Val Pro Asp Ile Asp Leu Asn Phe Ser Gly Asp Asp Gln
            980                 985                 990

Pro Ser Ala His Leu Asp Val Arg Asp Ile Phe Gly Asp Glu Tyr Ala
            995                 1000                1005

Phe Arg Ala Gly Thr Val Gly Thr Val Ala Glu Lys Thr Ala Tyr Gly
        1010                1015                1020

Phe Val Lys Gly Tyr Glu Arg Asp Tyr Gly Lys Phe Tyr Arg Asp Ala
1025                1030                1035                1040

Glu Val Asp Arg Leu Ala Ala Gly Ala Ala Gly Val Lys Arg Thr Thr
                1045                1050                1055

Gly Gln His Pro Gly Gly Ile Val Val Ile Pro Asn Tyr Met Asp Val
            1060                1065                1070

Tyr Asp Phe Thr Pro Val Gln Tyr Pro Ala Asp Asp Val Thr Ala Ser
            1075                1080                1085

Trp Gln Thr Thr His Phe Asn Phe His Asp Ile Asp Glu Asn Val Leu
            1090                1095                1100

Lys Leu Asp Ile Leu Gly His Asp Asp Pro Thr Met Ile Arg Lys Leu
1105                1110                1115                1120

Gln Asp Leu Ser Gly Ile Asp Pro Ile Thr Ile Pro Ala Asp Asp Pro
                1125                1130                1135

Gly Val Met Ala Leu Phe Ser Gly Thr Glu Val Leu Gly Val Thr Pro
            1140                1145                1150

Glu Gln Ile Gly Thr Pro Thr Gly Met Leu Gly Ile Pro Glu Phe Gly
            1155                1160                1165

Thr Asn Phe Val Arg Gly Met Val Asn Glu Thr His Pro Thr Thr Phe
            1170                1175                1180

Ala Glu Leu Leu Gln Leu Ser Gly Leu Ser His Gly Thr Asp Val Trp
1185                1190                1195                1200

Leu Gly Asn Ala Gln Asp Leu Ile Lys Glu Gly Ile Ala Thr Leu Lys
                1205                1210                1215

Thr Val Ile Gly Cys Arg Asp Asp Ile Met Val Tyr Leu Met His Ala
            1220                1225                1230

Gly Leu Glu Pro Lys Met Ala Phe Thr Ile Met Glu Arg Val Arg Lys
            1235                1240                1245

Gly Leu Trp Leu Lys Ile Ser Glu Glu Glu Arg Asn Gly Tyr Ile Asp
            1250                1255                1260

Ala Met Arg Glu Asn Asn Val Pro Asp Trp Tyr Ile Glu Ser Cys Gly
1265                1270                1275                1280

Lys Ile Lys Tyr Met Phe Pro Lys Ala His Ala Ala Tyr Val Leu
                1285                1290                1295

Met Ala Leu Arg Val Ala Tyr Phe Lys Val His His Pro Ile Met Tyr
            1300                1305                1310

Tyr Cys Ala Tyr Phe Ser Ile Arg Ala Lys Ala Phe Glu Leu Lys Thr

```
                     1315                1320               1325
Met Ser Gly Gly Leu Asp Ala Val Lys Ala Arg Met Glu Asp Ile Thr
    1330                1335               1340

Ile Lys Arg Lys Asn Asn Glu Ala Thr Asn Val Glu Asn Asp Leu Phe
1345               1350                1355               1360

Thr Thr Leu Glu Ile Val Asn Glu Met Leu Glu Arg Gly Phe Lys Phe
              1365                1370               1375

Gly Lys Leu Asp Leu Tyr Lys Ser Asp Ala Ile Glu Phe Gln Ile Lys
             1380                1385               1390

Gly Asp Thr Leu Ile Pro Pro Phe Ile Ala Leu Glu Gly Leu Gly Glu
          1395                1400               1405

Asn Val Ala Lys Gln Ile Val Lys Ala Arg Gln Glu Gly Glu Phe Leu
   1410                1415               1420

Ser Lys Met Glu Leu Arg Lys Arg Gly Gly Ala Ser Ser Thr Leu Val
1425                1430               1435               1440

Glu Lys Met Asp Glu Met Gly Ile Leu Gly Asn Met Pro Glu Asp Asn
              1445                1450               1455

Gln Leu Ser Leu Phe Asp Asp Phe Phe
          1460                1465

<210> SEQ ID NO 19
<211> LENGTH: 3102
<212> TYPE: DNA
<213> ORGANISM: Streptococcus pyogenes

<400> SEQUENCE: 19
atgtttgctc aacttgatac taaaactgta tactcattta tggatagttt aattgactta      60
aatcattatt ttgaacgagc aaagcaattt ggttaccaca ccataggaat catggataag     120
gataatcttt atggtgctta ccattttatt aaaggttgtc aaaaaaatgg actgcagcca     180
gttttaggtt tggaaataga gattctctat caagagcggc aggtgctcct taacttaatc     240
gcccagaata cacaaggcta tcatcagctt ttaaaaattt ccacggcaaa atgtctggc      300 aagcttcata tggattactt ctgccaacat tggaaggga tagcggttat tattcctagt      360
aagggttgga gcgatacatt agtggtccct tttgactact atatgggtgt tgatcagtat     420
actgatttat ctcatatgga ttctaagagg cagcttatac ccctaaggac agttcgttat     480
tttgcgcaag atgatatgga aaccctgcac atgttgcatg ccattcgaga taacctcagt     540
ctggcagaga cccctgtggt agaaagtgat caagagttag cagattgtca acaactaacc     600
gccttctatc aaacacactg ccctcaagct ctacagaatt tagaagactt agtgtcagga     660
atctattatg atttcgatac aaatttaaaa ttgcctcatt ttaatagaga taagtctgcc     720
aagcaagaat tgcaagactt gactgaggct ggtttgaagg aaaaaggatt gtggaaagag     780
ccttatcaat cgcgcttact acatgaattg gtcattattt ctgacatggg ctttgatgat     840 tatttttga ttgtgtggga tttacttcgc tttggacgca gtaaaggcta ttatatggga     900
atgggacgtg gctcggcggc aggtagtcta gtggcttatg ctctgaacat tacagggatt     960
gatccagttc aacatgattt gctatttgag cgcttttta acaaagaacg ttatagcatg    1020
cctgatattg atatcgatct tccagatatt taccgttcag aatttctacg gtatgtccga    1080
aatcgttatg gtagcgacca tcggcgcaa attgtgacct tttcaacctt tggccaggct    1140
attcgtgatg tttcaaacg gttcggggtt ccagaatacg aactgactaa tctcactaaa    1200
aaaattggtt taaagatag cttggctact gtctatgaaa agtcaatctc ttttaggcag    1260
```

-continued

```
gttattaata gtagaactga atttcaaaag gctttttgcca ttgccaagcg tatcgaagga    1320
aatccaagac aaacgtccat tcacgcagct ggtattgtga tgagtgatga tgccttgacc    1380
aatcatattc ctctaaaatc gggcgatgac atgatgatca cccagtatga tgctcatgcg    1440
gtcgaagcta atggcctgtt aaaaatggat ttttttggggt taagaaattt gacctttgtt    1500
caaaaaatgc aagagaaggt tgctaaagac tacgggtgtc agattgatat tacagccatt    1560
gatttagaag acccgcaaac gttggcactt tttgctaaag gggataccaa gggaattttc    1620
caatttgaac aaaatggtgc tattaatctt ttaaaacgga ttaagccaca acgttttgaa    1680
gaaattgttg ccactaccag tctaaataga ccaggggcaa gtgactatac cactaatttc    1740
attaaacgaa gagaaggaca agaaaaaatt gatttgattg atcctgtgat tgctcccatt    1800
ttagagccaa cttacggtat tatgctttat caagaacaag ttatgcagat tgcacaggtt    1860
tatgctggtt ttacgttagg caaggccgac ttgttaaggc gtgccatgtc taaaaaaaat    1920
ctacaagaaa tgcaaaaaat ggaagaagac tttattgctt ctgctaagca cctagggaga    1980
gctgaagaaa cagctagagg acttttttaaa cggatggaaa aatttgcagg ttatggtttt    2040
aaccgcagcc atgcctttgc ctattcagct ttagcttttc aattggctta tttcaaagcc    2100
cattacccgg ctgttttttta cgatatcatg atgaattatt ctagcagtga ctatatcaca    2160
gatgctctag aatcagattt tcaagtagcg caagttacca ttaatagtat tccttacact    2220
gataaaattg aagctagcaa gatttacatg gggctgaaaa atattaaggg gttgccaagg    2280
gattttgctt attggattat cgagcaaaga ccatttaata gcgtagagga tttttctcact    2340 agaactccag aaaaatatca aaaaaaggtt ttccttgagc ctctgataaa aataggtctg    2400
tttgattgct ttgagcctaa ccgtaaaaaa attctggaca atttggatgg tttactggta    2460
tttgttaatg agcttggttc tcttttttca gattcttcct ttagttgggt agatacgaaa    2520
gattactcag taactgaaaa atattctttg gaacaggaga tcgttggagt tggcatgagc    2580
aagcatcctt taattgatat tgctgagaaa agtacccaaa ctttttactcc tatttcacag    2640 ttagtcaaag aaagcgaagc agtcgtactg attcaaatag atagcattag gatcattaga    2700
accaaaacaa gtgggcagca aatggctttt ttaagtgtga atgacactaa gaaaaagctc    2760
gatgtcacac ttttttccaca agagtatgcc atttataaag accaattaaa agaaggagaa    2820
ttctattact taaaaggtag aataaaagaa agagaccatc gactgcagat ggtgtgtcag    2880
caagtgcaaa tggctattag tcaaaaatat tggttattag ttgaaaacca tcagtttgat    2940 tcccaaatttt ctgagatttt aggtgccttt ccaggaacga ctccagttgt tattcactat    3000
caaaaaaata aggaaacaat tgcattaact aagattcagg ttcatgtaac agagaattta    3060
aaggaaaaac ttcgtccttt tgttctgaaa acggttttttc ga                      3102
```

<210> SEQ ID NO 20
<211> LENGTH: 1034
<212> TYPE: PRT
<213> ORGANISM: Streptococcus pyogenes

<400> SEQUENCE: 20

Met Phe Ala Gln Leu Asp Thr Lys Thr Val Tyr Ser Phe Met Asp Ser
 1               5                  10                  15

Leu Ile Asp Leu Asn His Tyr Phe Glu Arg Ala Lys Gln Phe Gly Tyr
            20                  25                  30

His Thr Ile Gly Ile Met Asp Lys Asp Asn Leu Tyr Gly Ala Tyr His
        35                  40                  45

-continued

```
Phe Ile Lys Gly Cys Gln Lys Asn Gly Leu Gln Pro Val Leu Gly Leu
     50                  55                  60

Glu Ile Glu Ile Leu Tyr Gln Glu Arg Gln Val Leu Leu Asn Leu Ile
 65                  70                  75                  80

Ala Gln Asn Thr Gln Gly Tyr His Gln Leu Leu Lys Ile Ser Thr Ala
                 85                  90                  95

Lys Met Ser Gly Lys Leu His Met Asp Tyr Phe Cys Gln His Leu Glu
                100                 105                 110

Gly Ile Ala Val Ile Ile Pro Ser Lys Gly Trp Ser Asp Thr Leu Val
            115                 120                 125

Val Pro Phe Asp Tyr Tyr Met Gly Val Asp Gln Tyr Thr Asp Leu Ser
    130                 135                 140

His Met Asp Ser Lys Arg Gln Leu Ile Pro Leu Arg Thr Val Arg Tyr
145                 150                 155                 160

Phe Ala Gln Asp Met Glu Thr Leu His Met Leu His Ala Ile Arg
                165                 170                 175

Asp Asn Leu Ser Leu Ala Glu Thr Pro Val Val Glu Ser Asp Gln Glu
            180                 185                 190

Leu Ala Asp Cys Gln Gln Leu Thr Ala Phe Tyr Gln Thr His Cys Pro
        195                 200                 205

Gln Ala Leu Gln Asn Leu Glu Asp Leu Val Ser Gly Ile Tyr Tyr Asp
    210                 215                 220

Phe Asp Thr Asn Leu Lys Leu Pro His Phe Asn Arg Asp Lys Ser Ala
225                 230                 235                 240

Lys Gln Glu Leu Gln Asp Leu Thr Glu Ala Gly Leu Lys Glu Lys Gly
                245                 250                 255

Leu Trp Lys Glu Pro Tyr Gln Ser Arg Leu Leu His Glu Leu Val Ile
            260                 265                 270

Ile Ser Asp Met Gly Phe Asp Asp Tyr Phe Leu Ile Val Trp Asp Leu
        275                 280                 285

Leu Arg Phe Gly Arg Ser Lys Gly Tyr Tyr Met Gly Met Gly Arg Gly
    290                 295                 300

Ser Ala Ala Gly Ser Leu Val Ala Tyr Ala Leu Asn Ile Thr Gly Ile
305                 310                 315                 320

Asp Pro Val Gln His Asp Leu Leu Phe Glu Arg Phe Leu Asn Lys Glu
                325                 330                 335

Arg Tyr Ser Met Pro Asp Ile Asp Ile Asp Leu Pro Asp Ile Tyr Arg
            340                 345                 350

Ser Glu Phe Leu Arg Tyr Val Arg Asn Arg Tyr Gly Ser Asp His Ser
        355                 360                 365

Ala Gln Ile Val Thr Phe Ser Thr Phe Gly Pro Lys Gln Ala Ile Arg
    370                 375                 380

Asp Val Phe Lys Arg Phe Gly Val Pro Glu Tyr Glu Leu Thr Asn Leu
385                 390                 395                 400

Thr Lys Lys Ile Gly Phe Lys Asp Ser Leu Ala Thr Val Tyr Glu Lys
                405                 410                 415

Ser Ile Ser Phe Arg Gln Val Ile Asn Ser Arg Thr Glu Phe Gln Lys
            420                 425                 430

Ala Phe Ala Ile Ala Lys Arg Ile Glu Gly Asn Pro Arg Gln Thr Ser
        435                 440                 445

Ile His Ala Ala Gly Ile Val Met Ser Asp Ala Leu Thr Asn His
    450                 455                 460

Ile Pro Leu Lys Ser Gly Asp Asp Met Met Ile Thr Gln Tyr Asp Ala
```

```
                465                 470                 475                 480
           His Ala Val Glu Ala Asn Gly Leu Leu Lys Met Asp Phe Leu Gly Leu
                           485                 490                 495

Arg Asn Leu Thr Phe Val Gln Lys Met Gln Glu Lys Val Ala Lys Asp
                           500                 505                 510

Tyr Gly Cys Gln Ile Asp Ile Thr Ala Ile Asp Leu Glu Asp Pro Gln
                           515                 520                 525

Thr Leu Ala Leu Phe Ala Lys Gly Asp Thr Lys Gly Ile Phe Gln Phe
                           530                 535                 540

Glu Gln Asn Gly Ala Ile Asn Leu Leu Lys Arg Ile Lys Pro Gln Arg
           545                 550                 555                 560

Phe Glu Glu Ile Val Ala Thr Thr Ser Leu Asn Arg Pro Gly Ala Ser
                           565                 570                 575

Asp Tyr Thr Thr Asn Phe Ile Lys Arg Arg Glu Gly Gln Glu Lys Ile
                           580                 585                 590

Asp Leu Ile Asp Pro Val Ile Ala Pro Ile Leu Glu Pro Thr Tyr Gly
                           595                 600                 605

Ile Met Leu Tyr Gln Glu Gln Val Met Gln Ile Ala Gln Val Tyr Ala
                           610                 615                 620

Gly Phe Thr Leu Gly Lys Ala Asp Leu Leu Arg Arg Ala Met Ser Lys
           625                 630                 635                 640

Lys Asn Leu Gln Glu Met Gln Lys Met Glu Glu Asp Phe Ile Ala Ser
                           645                 650                 655

Ala Lys His Leu Gly Arg Ala Glu Glu Thr Ala Arg Gly Leu Phe Lys
                           660                 665                 670

Arg Met Glu Lys Phe Ala Gly Tyr Gly Phe Asn Arg Ser His Ala Phe
                           675                 680                 685

Ala Tyr Ser Ala Leu Ala Phe Gln Leu Ala Tyr Phe Lys Ala His Tyr
                           690                 695                 700

Pro Ala Val Phe Tyr Asp Ile Met Met Asn Tyr Ser Ser Ser Asp Tyr
           705                 710                 715                 720

Ile Thr Asp Ala Leu Glu Ser Asp Phe Gln Val Ala Gln Val Thr Ile
                           725                 730                 735

Asn Ser Ile Pro Tyr Thr Asp Lys Ile Glu Ala Ser Lys Ile Tyr Met
                           740                 745                 750

Gly Leu Lys Asn Ile Lys Gly Leu Pro Arg Asp Phe Ala Tyr Trp Ile
                           755                 760                 765

Ile Glu Gln Arg Pro Phe Asn Ser Val Glu Asp Phe Leu Thr Arg Thr
                           770                 775                 780

Pro Glu Lys Tyr Gln Lys Lys Val Phe Leu Glu Pro Leu Ile Lys Ile
           785                 790                 795                 800

Gly Leu Phe Asp Cys Phe Glu Pro Asn Arg Lys Lys Ile Leu Asp Asn
                           805                 810                 815

Leu Asp Gly Leu Leu Val Phe Val Asn Glu Leu Gly Ser Leu Phe Ser
                           820                 825                 830

Asp Ser Ser Phe Ser Trp Val Asp Thr Lys Asp Tyr Ser Val Thr Glu
                           835                 840                 845

Lys Tyr Ser Leu Glu Gln Glu Ile Val Gly Val Gly Met Ser Lys His
                           850                 855                 860

Pro Leu Ile Asp Ile Ala Glu Lys Ser Thr Gln Thr Phe Thr Pro Ile
           865                 870                 875                 880

Ser Gln Leu Val Lys Glu Ser Glu Ala Val Val Leu Ile Gln Ile Asp
                           885                 890                 895
```

Ser Ile Arg Ile Ile Arg Thr Lys Thr Ser Gly Gln Gln Met Ala Phe
         900                 905                 910

Leu Ser Val Asn Asp Thr Lys Lys Lys Leu Asp Val Thr Leu Phe Pro
         915                 920                 925

Gln Glu Tyr Ala Ile Tyr Lys Asp Gln Leu Lys Glu Gly Glu Phe Tyr
         930                 935                 940

Tyr Leu Lys Gly Arg Ile Lys Glu Arg Asp His Arg Leu Gln Met Val
945                 950                 955                 960

Cys Gln Gln Val Gln Met Ala Ile Ser Gln Lys Tyr Trp Leu Leu Val
                 965                 970                 975

Glu Asn His Gln Phe Asp Ser Gln Ile Ser Glu Ile Leu Gly Ala Phe
         980                 985                 990

Pro Gly Thr Thr Pro Val Val Ile His Tyr Gln Lys Asn Lys Glu Thr
         995                 1000                1005

Ile Ala Leu Thr Lys Ile Gln Val Thr Glu Asn Leu Lys Glu Lys Leu
    1010                1015                1020

Arg Pro Phe Val Leu Lys Thr Val Phe Arg
1025                1030

<210> SEQ ID NO 21
<211> LENGTH: 1038
<212> TYPE: DNA
<213> ORGANISM: Streptococcus pyogenes

<400> SEQUENCE: 21
atgattgcga tagaaaagat tgaaaaactg agtaaagaaa atttgggtct tataacccTT    60
gtcacaggag atgacattgg tcagtatagc cagttgaaat cccgcttaat ggagcagatt   120
gcttttgata aggatgattt ggcctattct tactttgata tgtctgaggc cgcttatcag   180
gatgcagaaa tggatctagt gagcctaccc ttctttgctg agcagaaggt ggttattttt   240
gaccatttgt tagatatcac gaccaataaa aaaagtttct taaagaaaaa agacctaaag   300
gcctttgaag cctatttaga aaatccctta gagactactc gactaattat ctttgctcca   360
ggtaaattgg atagtaagag acggcttgtt aagcttttga acgtgatgc ccttgtttta   420 gaagccaacc tctgaaaga agcagagcta agaacttatt tcaaaaata cagtcatcaa   480 ctgggtttag gtttcgagag tggtgccttt gaccaattac ttttgaaatc aaacgatgat   540
tttagtcaaa tcatgaaaaa catggccttt ttaaaagcct ataaaaaaac gggaaatatt   600
agcctaactg atattgagca agccattcct aaaagtttac aagataatat tttcgatctg   660
actagacttg tcctaggagg taaaattgat gcggctagag atttgattca tgatttacgg   720
ttatctggag aagatgacat taaattaatc gctatcatgc taggccaatt tcgcttattt   780
ttgcagctga ctattcttgc tagagatgta aaaaacgagc aacaactagt gattagttta   840
tcagatattc ttgggcggcg ggttaatcct taccaggtca agtatgcgtt aaaggattct   900
aggaccttat ctcttgcctt tctaacagga gcggtgaaaa ccttgattga cagattac    960 cagataaaaa caggacttta tgagaagagt tatctagttg atattgctct cttaaaaatc  1020
atgactcact ctcaaaaa                                                 1038

<210> SEQ ID NO 22
<211> LENGTH: 346
<212> TYPE: PRT
<213> ORGANISM: Streptococcus pyogenes

<400> SEQUENCE: 22

```
Met Ile Ala Ile Glu Lys Ile Glu Lys Leu Ser Lys Glu Asn Leu Gly
  1               5                  10                  15

Leu Ile Thr Leu Val Thr Gly Asp Asp Ile Gly Gln Tyr Ser Gln Leu
             20                  25                  30

Lys Ser Arg Leu Met Glu Gln Ile Ala Phe Asp Lys Asp Leu Ala
         35                  40                  45

Tyr Ser Tyr Phe Asp Met Ser Glu Ala Ala Tyr Gln Asp Ala Glu Met
         50                  55                  60

Asp Leu Val Ser Leu Pro Phe Phe Ala Glu Gln Lys Val Val Ile Phe
 65                  70                  75                  80

Asp His Leu Leu Asp Ile Thr Thr Asn Lys Lys Ser Phe Leu Lys Glu
                 85                  90                  95

Lys Asp Leu Lys Ala Phe Glu Ala Tyr Leu Glu Asn Pro Leu Glu Thr
                100                 105                 110

Thr Arg Leu Ile Ile Phe Ala Pro Gly Lys Leu Asp Ser Lys Arg Arg
                115                 120                 125

Leu Val Lys Leu Leu Lys Arg Asp Ala Leu Val Leu Glu Ala Asn Pro
130                 135                 140

Leu Lys Glu Ala Glu Leu Arg Thr Tyr Phe Gln Lys Tyr Ser His Gln
145                 150                 155                 160

Leu Gly Leu Gly Phe Glu Ser Gly Ala Phe Asp Gln Leu Leu Leu Lys
                165                 170                 175

Ser Asn Asp Asp Phe Ser Gln Ile Met Lys Asn Met Ala Phe Leu Lys
                180                 185                 190

Ala Tyr Lys Lys Thr Gly Asn Ile Ser Leu Thr Asp Ile Glu Gln Ala
                195                 200                 205

Ile Pro Lys Ser Leu Gln Asp Asn Ile Phe Asp Leu Thr Arg Leu Val
                210                 215                 220

Leu Gly Gly Lys Ile Asp Ala Ala Arg Asp Leu Ile His Asp Leu Arg
225                 230                 235                 240

Leu Ser Gly Glu Asp Asp Ile Lys Leu Ile Ala Ile Met Leu Gly Gln
                245                 250                 255

Phe Arg Leu Phe Leu Gln Leu Thr Ile Leu Ala Arg Asp Val Lys Asn
                260                 265                 270

Glu Gln Gln Leu Val Ile Ser Leu Ser Asp Ile Leu Gly Arg Arg Val
                275                 280                 285

Asn Pro Tyr Gln Val Lys Tyr Ala Leu Lys Asp Ser Arg Thr Leu Ser
                290                 295                 300

Leu Ala Phe Leu Thr Gly Ala Val Lys Thr Leu Ile Glu Thr Asp Tyr
305                 310                 315                 320

Gln Ile Lys Thr Gly Leu Tyr Glu Lys Ser Tyr Leu Val Asp Ile Ala
                325                 330                 335

Leu Leu Lys Ile Met Thr His Ser Gln Lys
                340                 345

<210> SEQ ID NO 23
<211> LENGTH: 873
<212> TYPE: DNA
<213> ORGANISM: Streptococcus pyogenes

<400> SEQUENCE: 23
atggatttag cgcaaaaagc tcctaacgtt tatcaagctt ttcagacaat tttaaagaaa      60
gaccgtctga atcatgctta tcttttttcg ggtgattttg ctaatgaaga aatggctctt     120
```

```
tttttagcta aggtcatctt ttgtgaacag aaaaaggatc agacgccctg cgggcattgt    180
cgctcttgtc aattgattga acaaggagat tttgccgatg tgacggtatt ggaaccaaca    240
gggcaagtga ttaaaacgga tgtggtcaaa gaaatgatgg ctaacttttc tcagacagga    300
tatgaaaaca aacgacaagt ttttattatc aaagattgtg acaaaatgca tatcaatgcc    360
gctaatagct tgctaaaata cattgaggag cctcagggag aagcttacat attttttattg   420
accaatgatg ataacaaagt gcttccgacc attaaaagtc ggacacaggt ttttcagttt    480
cctaaaaacg aagcctatct ttaccaattg gcacaagaaa agggattatt aaaccatcag    540
gctaagctag tagccaaact tgccacaaac accagtcatc tagaacgtct gttgcaaacg    600
agcaagcttt tagaactgat aactcaagca gagcgttttg tatctatttg gctgaaagat    660
cagttgcagg catatttagc gttgaaccgt ctggtacagt tagcaactga aaaagaagaa    720
caagatttag ttttgaccct tttgaccttg ctcttggcaa gagagcgtgc gcaaacgcct    780
ttgacacaat tggaggctgt ctatcaggct aggctcatgt ggcagagcaa tgttaatttt    840
caaaacacat tagaatatat ggtgatgtca gaa                                 873

<210> SEQ ID NO 24
<211> LENGTH: 291
<212> TYPE: PRT
<213> ORGANISM: Streptococcus pyogenes

<400> SEQUENCE: 24

Met Asp Leu Ala Gln Lys Ala Pro Asn Val Tyr Gln Ala Phe Gln Thr
1               5                   10                  15

Ile Leu Lys Lys Asp Arg Leu Asn His Ala Tyr Leu Phe Ser Gly Asp
                20                  25                  30

Phe Ala Asn Glu Glu Met Ala Leu Phe Leu Ala Lys Val Ile Phe Cys
            35                  40                  45

Glu Gln Lys Lys Asp Gln Thr Pro Cys Gly His Cys Arg Ser Cys Gln
        50                  55                  60

Leu Ile Glu Gln Gly Asp Phe Ala Asp Val Thr Val Leu Glu Pro Thr
65                  70                  75                  80

Gly Gln Val Ile Lys Thr Asp Val Val Lys Glu Met Met Ala Asn Phe
                85                  90                  95

Ser Gln Thr Gly Tyr Glu Asn Lys Arg Gln Val Phe Ile Ile Lys Asp
            100                 105                 110

Cys Asp Lys Met His Ile Asn Ala Ala Asn Ser Leu Leu Lys Tyr Ile
        115                 120                 125

Glu Glu Pro Gln Gly Glu Ala Tyr Ile Phe Leu Leu Thr Asn Asp Asp
    130                 135                 140

Asn Lys Val Leu Pro Thr Ile Lys Ser Arg Thr Gln Val Phe Gln Phe
145                 150                 155                 160

Pro Lys Asn Glu Ala Tyr Leu Tyr Gln Leu Ala Gln Glu Lys Gly Leu
                165                 170                 175

Leu Asn His Gln Ala Lys Leu Val Ala Lys Leu Ala Thr Asn Thr Ser
            180                 185                 190

His Leu Glu Arg Leu Leu Gln Thr Ser Lys Leu Leu Glu Leu Ile Thr
        195                 200                 205

Gln Ala Glu Arg Phe Val Ser Ile Trp Leu Lys Asp Gln Leu Gln Ala
    210                 215                 220

Tyr Leu Ala Leu Asn Arg Leu Val Gln Leu Ala Thr Glu Lys Glu Glu
225                 230                 235                 240
```

-continued

```
Gln Asp Leu Val Leu Thr Leu Thr Leu Leu Leu Ala Arg Glu Arg
                245                 250                 255

Ala Gln Thr Pro Leu Thr Gln Leu Glu Ala Val Tyr Gln Ala Arg Leu
            260                 265                 270

Met Trp Gln Ser Asn Val Asn Phe Gln Asn Thr Leu Glu Tyr Met Val
        275                 280                 285

Met Ser Glu
    290

<210> SEQ ID NO 25
<211> LENGTH: 1665
<212> TYPE: DNA
<213> ORGANISM: Streptococcus pyogenes

<400> SEQUENCE: 25
atgtatcaag ctctttatcg gaaataccgg agccaaacgt ttgacgaaat ggtgggacaa      60
tcggttattt ccacaacttt aaagcaggca gttgaatctg caagattag ccatgcttat     120 cttttttcag gtcctagagg gactgggaaa acaagtgcgg caaagatttt tgcaaaggcc    180
atgaattgtc ctaaccaagt cgatggtgaa ccctgtaatc aatgcgatat tgccgagat    240 atcacgaatg gaagcttgga agatgtgatt gaaattgatg ctgcctcgaa taatggtgtt     300
gatgaaattc gtgacattcg agacaaatca acctatgcgc caagtcgtgc gacttacaag    360
gtttatatta ttgatgaggt tcacatgtta tcaacagggg cttttaatgc gcttttgaaa    420
actttggaag aaccgacaga atgttgtctt tatcttggca caacggaat gcataaaatt     480 ccagccacta ttttatctcg tgtgcaacgc tttgaattca aagctattaa gcaaaaagct    540
attcgagagc atttagcctg ggttttggac aaagaaggta ttgcctatga ggtggatgct    600
ttaaatctca ttgcaaggcg agcagaagga ggcatgcgtg atgctttatc tattttagat    660
caggctttga gcttgtcacc agataatcag gtcgccattg caattgccga gaaaattaca     720
ggttctattt ccatacttgc tctgggtgac tatgttcgat atgtctccca gaacaggct     780 acgcaagctc tggcagcctt agagaccatt tatgatagtg ggaagagcat gagccgcttt    840
gcgacagatt tattgaccta tctgcgtgat ttattggtgg ttaaagctgg cggcgacaat    900
caacgtcagt cagctgtttt tgataccaat ttgtctctct cgatagatcg tatattccaa    960
atgataacag ttgttactag tcatctccct gaaatcaaaa agggaaccca tcctcggatt   1020
tatgccgaaa tgatgactat ccaattagct cagaaagagc agattttgtc ccaagtaaac   1080
ttgtcaggag agttaatctc agagattgaa acgctcaaaa atgagttggc acaacttaaa   1140
caacaattgt cgcagctcca atcgcgtcct gattcactgg caagatctga taaaacgaaa   1200
cctaaaacca aagctacag ggttgatcgg gttaccattt tgaaaatcat ggaagaaacg    1260
gttcgaaata gccaacaatc tcgacaatat ctagatgctc taaaaaatgc ttggaatgaa   1320
attctagata catttctgc caagacaga gccttattga tgggctctga gcctgtctta    1380
gcaaatagtg agaatgcgat tttggctttc gaggctgcct ttaatgcaga acaagtcatg   1440
agccgaaata atcttaatga tatgtttggt aacattatga gtaaagctgc tggttttct    1500 cccaatattc tggcagtacc aaggacagat tttcagcata ttcgtaagga atttgctcag   1560
caaatgaaat cgcaaaaaga cagtgttcaa gaagaacaag aagtagcgct tgatattcca   1620 gaagggttg attttttgct cgataaaata aatactattg acgac                    1665

<210> SEQ ID NO 26
<211> LENGTH: 555
```

-continued

```
<212> TYPE: PRT
<213> ORGANISM: Streptococcus pyogenes

<400> SEQUENCE: 26

Met Tyr Gln Ala Leu Tyr Arg Lys Tyr Arg Ser Gln Thr Phe Asp Glu
  1               5                  10                  15

Met Val Gly Gln Ser Val Ile Ser Thr Thr Leu Lys Gln Ala Val Glu
                 20                  25                  30

Ser Gly Lys Ile Ser His Ala Tyr Leu Phe Ser Gly Pro Arg Gly Thr
             35                  40                  45

Gly Lys Thr Ser Ala Ala Lys Ile Phe Ala Lys Ala Met Asn Cys Pro
         50                  55                  60

Asn Gln Val Asp Gly Glu Pro Cys Asn Gln Cys Asp Ile Cys Arg Asp
 65                  70                  75                  80

Ile Thr Asn Gly Ser Leu Glu Asp Val Ile Glu Ile Asp Ala Ala Ser
                 85                  90                  95

Asn Asn Gly Val Asp Glu Ile Arg Asp Ile Arg Asp Lys Ser Thr Tyr
                100                 105                 110

Ala Pro Ser Arg Ala Thr Tyr Lys Val Tyr Ile Ile Asp Glu Val His
            115                 120                 125

Met Leu Ser Thr Gly Ala Phe Asn Ala Leu Leu Lys Thr Leu Glu Glu
        130                 135                 140

Pro Thr Glu Asn Val Phe Ile Leu Ala Thr Thr Glu Leu His Lys Ile
145                 150                 155                 160

Pro Ala Thr Ile Leu Ser Arg Val Gln Arg Phe Glu Phe Lys Ala Ile
                165                 170                 175

Lys Gln Lys Ala Ile Arg Glu His Leu Ala Trp Val Leu Asp Lys Glu
            180                 185                 190

Gly Ile Ala Tyr Glu Val Asp Ala Leu Asn Leu Ile Ala Arg Arg Ala
        195                 200                 205

Glu Gly Gly Met Arg Asp Ala Leu Ser Ile Leu Asp Gln Ala Leu Ser
    210                 215                 220

Leu Ser Pro Asp Asn Gln Val Ala Ile Ala Ile Ala Glu Glu Ile Thr
225                 230                 235                 240

Gly Ser Ile Ser Ile Leu Ala Leu Gly Asp Tyr Val Arg Tyr Val Ser
                245                 250                 255

Gln Glu Gln Ala Thr Gln Ala Leu Ala Ala Leu Glu Thr Ile Tyr Asp
            260                 265                 270

Ser Gly Lys Ser Met Ser Arg Phe Ala Thr Asp Leu Leu Thr Tyr Leu
        275                 280                 285

Arg Asp Leu Leu Val Val Lys Ala Gly Gly Asp Asn Gln Arg Gln Ser
    290                 295                 300

Ala Val Phe Asp Thr Asn Leu Ser Leu Ser Ile Asp Arg Ile Phe Gln
305                 310                 315                 320

Met Ile Thr Val Val Thr Ser His Leu Pro Glu Ile Lys Lys Gly Thr
                325                 330                 335

His Pro Arg Ile Tyr Ala Glu Met Met Thr Ile Gln Leu Ala Gln Lys
            340                 345                 350

Glu Gln Ile Leu Ser Gln Val Asn Leu Ser Gly Glu Leu Ile Ser Glu
        355                 360                 365

Ile Glu Thr Leu Lys Asn Glu Leu Ala Gln Leu Lys Gln Gln Leu Ser
    370                 375                 380

Gln Leu Gln Ser Arg Pro Asp Ser Leu Ala Arg Ser Asp Lys Thr Lys
385                 390                 395                 400
```

```
Pro Lys Thr Thr Ser Tyr Arg Val Asp Arg Val Thr Ile Leu Lys Ile
            405                 410                 415
Met Glu Glu Thr Val Arg Asn Ser Gln Gln Ser Arg Gln Tyr Leu Asp
            420                 425                 430
Ala Leu Lys Asn Ala Trp Asn Glu Ile Leu Asp Asn Ile Ser Ala Gln
            435                 440                 445
Asp Arg Ala Leu Leu Met Gly Ser Glu Pro Val Leu Ala Asn Ser Glu
            450                 455                 460
Asn Ala Ile Leu Ala Phe Glu Ala Ala Phe Asn Ala Glu Gln Val Met
465                 470                 475                 480
Ser Arg Asn Asn Leu Asn Asp Met Phe Gly Asn Ile Met Ser Lys Ala
            485                 490                 495
Ala Gly Phe Ser Pro Asn Ile Leu Ala Val Pro Arg Thr Asp Phe Gln
            500                 505                 510
His Ile Arg Lys Glu Phe Ala Gln Gln Met Lys Ser Gln Lys Asp Ser
            515                 520                 525
Val Gln Glu Glu Gln Glu Val Ala Leu Asp Ile Pro Glu Gly Phe Asp
            530                 535                 540
Phe Leu Leu Asp Lys Ile Asn Thr Ile Asp Asp
545                 550                 555

<210> SEQ ID NO 27
<211> LENGTH: 1134
<212> TYPE: DNA
<213> ORGANISM: Streptococcus pyogenes

<400> SEQUENCE: 27
atgattcaat tttcaattaa tcgcacatta tttattcatg ctttaaatac aactaaacgt     60
gctattagca ctaaaaatgc cattcctatt ctttcatcaa taaaaattga agtcacttct    120
acaggagtaa ctttaacagg gtctaacggt caaatatcaa ttgaaaacac tattcctgta    180
agtaatgaaa atgctggttt gctaattacc tctccaggag ctatttttatt agaagctagt    240
ttttttatta atattattc aagtttgcca gatattagta taaatgttaa agaaattgaa    300
caacaccaag ttgttttaac cagtggtaaa tcagagatta ccttaaaagg aaaagatgtt    360
gaccagtatc ctcgtctaca agaagtatca acagaaaatc ctttgatttt aaaaacaaaa    420
ttattgaagt ctattattgc tgaaacagct tttgcagcca gtttacaaga aagtcgtcct    480
atttttaacag gagttcatat tgtattaagt aatcataaag attttaaagc agtagcgact    540
gactctcatc gtatgagcca acgtttaatc actttggaca atacttcagc agatttgatg    600
gtagttcttc caagtaaatc tttgagagaa tttttcagcag tatttacaga tgatattgag    660
accgttgagg tattttctc accaagccaa atcttgttca gaagtgaaca catttctttt    720
tatacacgcc tcttagaagg aaattatccc gatacagacc gttattaat gacagaattt    780
gagacggagg ttgttttcaa tacccaatcc cttcgccacg ctatggaacg tgccttcttg    840
atttctaatg ctactcaaaa tggtactgtt aagcttgaga ttactcaaaa tcatatttca    900
gctcatgtta actcacctga ggttggtaag gtaaacgagg atttagatat tgttagtcag    960
tctggtagtg atttaactat cagcttcaat ccaacttacc ttattgagtc tttaaaagct   1020
attaaaagtg aaacagtaaa aattcatttc ttatcaccag ttcgaccatt caccctaaca   1080
ccaggcgatg aggaagaaag ttttatccaa ttaattacac cagtacgaac aaac           1134

<210> SEQ ID NO 28
```

```
<211> LENGTH: 378
<212> TYPE: PRT
<213> ORGANISM: Streptococcus pyogenes

<400> SEQUENCE: 28
```

| Met | Ile | Gln | Phe | Ser | Ile | Asn | Arg | Thr | Leu | Phe | Ile | His | Ala | Leu | Asn |
|---|---|---|---|---|---|---|---|---|---|---|---|---|---|---|---|
| 1 | | | | 5 | | | | | 10 | | | | | 15 | |

| Thr | Thr | Lys | Arg | Ala | Ile | Ser | Thr | Lys | Asn | Ala | Ile | Pro | Ile | Leu | Ser |
|---|---|---|---|---|---|---|---|---|---|---|---|---|---|---|---|
| | | | 20 | | | | | 25 | | | | | 30 | | |

| Ser | Ile | Lys | Ile | Glu | Val | Thr | Ser | Thr | Gly | Val | Thr | Leu | Thr | Gly | Ser |
|---|---|---|---|---|---|---|---|---|---|---|---|---|---|---|---|
| | | | 35 | | | | | 40 | | | | | 45 | | |

| Asn | Gly | Gln | Ile | Ser | Ile | Glu | Asn | Thr | Ile | Pro | Val | Ser | Asn | Glu | Asn |
|---|---|---|---|---|---|---|---|---|---|---|---|---|---|---|---|
| | 50 | | | | | 55 | | | | | 60 | | | | |

| Ala | Gly | Leu | Leu | Ile | Thr | Ser | Pro | Gly | Ala | Ile | Leu | Leu | Glu | Ala | Ser |
|---|---|---|---|---|---|---|---|---|---|---|---|---|---|---|---|
| 65 | | | | | 70 | | | | | 75 | | | | | 80 |

| Phe | Phe | Ile | Asn | Ile | Ile | Ser | Ser | Leu | Pro | Asp | Ile | Ser | Ile | Asn | Val |
|---|---|---|---|---|---|---|---|---|---|---|---|---|---|---|---|
| | | | | 85 | | | | | 90 | | | | | 95 | |

| Lys | Glu | Ile | Glu | Gln | His | Gln | Val | Val | Leu | Thr | Ser | Gly | Lys | Ser | Glu |
|---|---|---|---|---|---|---|---|---|---|---|---|---|---|---|---|
| | | | 100 | | | | | 105 | | | | | 110 | | |

| Ile | Thr | Leu | Lys | Gly | Lys | Asp | Val | Asp | Gln | Tyr | Pro | Arg | Leu | Gln | Glu |
|---|---|---|---|---|---|---|---|---|---|---|---|---|---|---|---|
| | | | 115 | | | | | 120 | | | | | 125 | | |

| Val | Ser | Thr | Glu | Asn | Pro | Leu | Ile | Leu | Lys | Thr | Lys | Leu | Leu | Lys | Ser |
|---|---|---|---|---|---|---|---|---|---|---|---|---|---|---|---|
| | 130 | | | | | 135 | | | | | 140 | | | | |

| Ile | Ile | Ala | Glu | Thr | Ala | Phe | Ala | Ala | Ser | Leu | Gln | Glu | Ser | Arg | Pro |
|---|---|---|---|---|---|---|---|---|---|---|---|---|---|---|---|
| 145 | | | | | 150 | | | | | 155 | | | | | 160 |

| Ile | Leu | Thr | Gly | Val | His | Ile | Val | Leu | Ser | Asn | His | Lys | Asp | Phe | Lys |
|---|---|---|---|---|---|---|---|---|---|---|---|---|---|---|---|
| | | | | 165 | | | | | 170 | | | | | 175 | |

| Ala | Val | Ala | Thr | Asp | Ser | His | Arg | Met | Ser | Gln | Arg | Leu | Ile | Thr | Leu |
|---|---|---|---|---|---|---|---|---|---|---|---|---|---|---|---|
| | | | 180 | | | | | 185 | | | | | 190 | | |

| Asp | Asn | Thr | Ser | Ala | Asp | Leu | Met | Val | Val | Leu | Pro | Ser | Lys | Ser | Leu |
|---|---|---|---|---|---|---|---|---|---|---|---|---|---|---|---|
| | | | 195 | | | | | 200 | | | | | 205 | | |

| Arg | Glu | Phe | Ser | Ala | Val | Phe | Thr | Asp | Asp | Ile | Glu | Thr | Val | Glu | Val |
|---|---|---|---|---|---|---|---|---|---|---|---|---|---|---|---|
| | 210 | | | | | 215 | | | | | 220 | | | | |

| Phe | Phe | Ser | Pro | Ser | Gln | Ile | Leu | Phe | Arg | Ser | Glu | His | Ile | Ser | Phe |
|---|---|---|---|---|---|---|---|---|---|---|---|---|---|---|---|
| 225 | | | | | 230 | | | | | 235 | | | | | 240 |

| Tyr | Thr | Arg | Leu | Leu | Glu | Gly | Asn | Tyr | Pro | Asp | Thr | Asp | Arg | Leu | Leu |
|---|---|---|---|---|---|---|---|---|---|---|---|---|---|---|---|
| | | | | 245 | | | | | 250 | | | | | 255 | |

| Met | Thr | Glu | Phe | Glu | Thr | Glu | Val | Val | Phe | Asn | Thr | Gln | Ser | Leu | Arg |
|---|---|---|---|---|---|---|---|---|---|---|---|---|---|---|---|
| | | | 260 | | | | | 265 | | | | | 270 | | |

| His | Ala | Met | Glu | Arg | Ala | Phe | Leu | Ile | Ser | Asn | Ala | Thr | Gln | Asn | Gly |
|---|---|---|---|---|---|---|---|---|---|---|---|---|---|---|---|
| | | 275 | | | | | 280 | | | | | 285 | | | |

| Thr | Val | Lys | Leu | Glu | Ile | Thr | Gln | Asn | His | Ile | Ser | Ala | His | Val | Asn |
|---|---|---|---|---|---|---|---|---|---|---|---|---|---|---|---|
| | 290 | | | | | 295 | | | | | 300 | | | | |

| Ser | Pro | Glu | Val | Gly | Lys | Val | Asn | Glu | Asp | Leu | Asp | Ile | Val | Ser | Gln |
|---|---|---|---|---|---|---|---|---|---|---|---|---|---|---|---|
| 305 | | | | | 310 | | | | | 315 | | | | | 320 |

| Ser | Gly | Ser | Asp | Leu | Thr | Ile | Ser | Phe | Asn | Pro | Thr | Tyr | Leu | Ile | Glu |
|---|---|---|---|---|---|---|---|---|---|---|---|---|---|---|---|
| | | | 325 | | | | | 330 | | | | | 335 | | |

| Ser | Leu | Lys | Ala | Ile | Lys | Ser | Glu | Thr | Val | Lys | Ile | His | Phe | Leu | Ser |
|---|---|---|---|---|---|---|---|---|---|---|---|---|---|---|---|
| | | | 340 | | | | | 345 | | | | | 350 | | |

| Pro | Val | Arg | Pro | Phe | Thr | Leu | Thr | Pro | Gly | Asp | Glu | Glu | Glu | Ser | Phe |
|---|---|---|---|---|---|---|---|---|---|---|---|---|---|---|---|
| | | 355 | | | | | 360 | | | | | 365 | | | |

| Ile | Gln | Leu | Ile | Thr | Pro | Val | Arg | Thr | Asn |
|---|---|---|---|---|---|---|---|---|---|
| | 370 | | | | | 375 | | | |

<210> SEQ ID NO 29
<211> LENGTH: 492
<212> TYPE: DNA
<213> ORGANISM: Streptococcus pyogenes

<400> SEQUENCE: 29

```
atgattaata atgtagtact agttggtcgc atgaccaagg atgcagaact tcgttacaca     60
ccaagtcaag tagctgtggc taccttcaca cttgctgtta accgtacctt taaaagccaa    120
aatggtgaac gcgaggcaga tttcattaac tgtgtgatct ggcgtcaacc ggctgaaaat    180
ttagcgaact gggctaaaaa aggtgctttg atcggagtta cgggtcgtat tcatacacgt    240
aactacgaaa accaacaagg acaacgtgtc tatgtaacag aagttgttgc agataatttc    300
caaatgttgg aaagtcgtgc tacacgtgaa ggtggctcaa ctggctcatt taatggtggt    360
tttaacaata acacttcatc atcaaacagt tactcagcgc ctgcacaaca aacgcctaac    420
tttggaagag atgatagccc atttgggaac tcaaacccga tggatatctc agatgacgat    480
cttccattct ag                                                        492
```

<210> SEQ ID NO 30
<211> LENGTH: 163
<212> TYPE: PRT
<213> ORGANISM: Streptococcus pyogenes

<400> SEQUENCE: 30

```
Met Ile Asn Asn Val Val Leu Val Gly Arg Met Thr Lys Asp Ala Glu
  1               5                  10                  15

Leu Arg Tyr Thr Pro Ser Gln Val Ala Val Ala Thr Phe Thr Leu Ala
             20                  25                  30

Val Asn Arg Thr Phe Lys Ser Gln Asn Gly Glu Arg Glu Ala Asp Phe
         35                  40                  45

Ile Asn Cys Val Ile Trp Arg Gln Pro Ala Glu Asn Leu Ala Asn Trp
     50                  55                  60

Ala Lys Lys Gly Ala Leu Ile Gly Val Thr Gly Arg Ile Gln Thr Arg
 65                  70                  75                  80

Asn Tyr Glu Asn Gln Gln Gly Gln Arg Val Tyr Val Thr Glu Val Val
                 85                  90                  95

Ala Asp Asn Phe Gln Met Leu Glu Ser Arg Ala Thr Arg Glu Gly Gly
            100                 105                 110

Ser Thr Gly Ser Phe Asn Gly Gly Phe Asn Asn Asn Thr Ser Ser Ser
        115                 120                 125

Asn Ser Tyr Ser Ala Pro Ala Gln Gln Thr Pro Asn Phe Gly Arg Asp
    130                 135                 140

Asp Ser Pro Phe Gly Asn Ser Asn Pro Met Asp Ile Ser Asp Asp Asp
145                 150                 155                 160

Leu Pro Phe
```

<210> SEQ ID NO 31
<211> LENGTH: 1815
<212> TYPE: DNA
<213> ORGANISM: Streptococcus pyogenes

<400> SEQUENCE: 31

```
atgggatttt tatggggagg tgacgatttg gcaattgaca agaaaatgat ttcccaagta     60
aaaaatagcg ttaatattgt cgatgtcatt ggagaagtgg tcaaactttc ccgatcaggg    120
cggcattacc tcgggctttg cccatttcat aaggaaaaga caccctcttt taatgttgtt    180
```

```
gaagacagac aatttttca ctgctttggc tgtggaaaat cagggatgt ttttaaattt      240 attgaggaat accgccaagt ccccttctta gaaagtgttc agattattgc cgataagact      300
ggtatgtcgc ttaatatacc gccaagtcag gcagtacttg ctagccaaca caagcaccct      360
aatcacgctt tgatgacact tcatgaggat gctgctaaat tttaccatgc agttttgatg      420
accactacca ttggtcaaga agctaggaag tacctttacc agagaggctt ggatgaccaa      480
ttaattgagc atttcaatat tggtttagcc ccagatgagt cagattatct ttatcaagct      540 cttctaaaa aatacgagga aggtcaattg gttgcttcag gattgtttca cttgtccgat      600
caatccaata ccatttacga cgcctttcga atcgtatca tgtttccctt atcagatgac      660
cgagggcata ttattgcctt ttcaggacgt atctggacgg cagctgatat ggaaaagaga      720
caggcaaagt ataaaaattc aagaggaaca gttctttta acaaatctta tgaattgtat      780
catctggaca aggcaaggcc tgttattgcc aaaacccatg aagtgtttct aatggaaggg      840
tttatggacg tgattgccgc ttaccgttcc ggctatgaaa atgctgttgc ttcaatgggg      900
acggcattga ctcaagaaca tgtcaatcac cttaagcaag tcactaaaaa agttgttttg      960
atttatgatg tgacgatgc tggacaacat gctattgcaa atcactaga attgcttaaa     1020 gattttgttg tcgaaattgt cagaatcccc aataaaatgg atcctgacga atttgtacaa     1080
cggcattccc cagaagcatt tgcagatttg cttaagcagt cacggatcag tagtgttgaa     1140 tttttattg attacctaaa acctactaat gtagacaatt gcaatcaca aattgtttat     1200 gtggagaaaa tggcaccatt gattgctcaa tcaccatcca tcacagctca acattcgtat     1260
attaacaaga ttgctgattt gttgccaaac tttgactatt ttcaagtaga acaatcagta     1320
aatgcattaa ggattcaaga taggcaaaaa catcaaggtc aaatagctca agccgtcagc     1380
aatcttgtga ccttaccaat gccaaaaagt ttgacagcta ttgctaagac agaaagtcat     1440
ctcatgcatc ggctcttaca tcatgactat ttattaaatg aatttcgaca tcgtgatgat     1500 tttatttg atacctctac cttagaatta ctttatcaac ggctgaagca acaaggacac     1560
attacatctt atgatttgtc agagatgtca gaggaagtta accgtgctta ttacaatgtt     1620
ttagaagaaa accttcccaa agaagtagct cttggtgaga ttgatgatat tttatccaaa     1680
cgtgccaaac ttttagcaga gcgcgatctt cacaaacaag ggaaaaaagt tagagaatct     1740
agtaacaaag gcgatcatca gcggctcta gaagtactag aacattttat tgcgcagaaa     1800
cgaaaaatgg aatag                                                     1815
```

<210> SEQ ID NO 32
<211> LENGTH: 600
<212> TYPE: PRT
<213> ORGANISM: Streptococcus pyogenes

<400> SEQUENCE: 32

```
Met Gly Phe Leu Trp Gly Gly Asp Asp Leu Ala Ile Asp Lys Glu Met
  1               5                  10                  15

Ile Ser Gln Val Lys Asn Ser Val Asn Ile Val Asp Val Ile Gly Glu
                 20                  25                  30

Val Val Lys Leu Ser Arg Ser Gly Arg His Tyr Leu Gly Leu Cys Pro
             35                  40                  45

Phe His Lys Glu Lys Thr Pro Ser Phe Asn Val Val Glu Asp Arg Gln
         50                  55                  60

Phe Phe His Cys Phe Gly Cys Gly Lys Ser Gly Asp Val Phe Lys Phe
  65                  70                  75                  80
```

-continued

```
Ile Glu Glu Tyr Arg Gln Val Pro Phe Leu Glu Ser Val Gln Ile Ile
             85                  90                  95

Ala Asp Lys Thr Gly Met Ser Leu Asn Ile Pro Pro Ser Gln Ala Val
            100                 105                 110

Leu Ala Ser Gln His Lys His Pro Asn His Ala Leu Met Thr Leu His
            115                 120                 125

Glu Asp Ala Ala Lys Phe Tyr His Ala Val Leu Met Thr Thr Thr Ile
130                 135                 140

Gly Gln Glu Ala Arg Lys Tyr Leu Tyr Gln Arg Gly Leu Asp Asp Gln
145                 150                 155                 160

Leu Ile Glu His Phe Asn Ile Gly Leu Ala Pro Asp Glu Ser Asp Tyr
                165                 170                 175

Leu Tyr Gln Ala Leu Ser Lys Lys Tyr Glu Glu Gly Gln Leu Val Ala
            180                 185                 190

Ser Gly Leu Phe His Leu Ser Asp Gln Ser Asn Thr Ile Tyr Asp Ala
            195                 200                 205

Phe Arg Asn Arg Ile Met Phe Pro Leu Ser Asp Asp Arg Gly His Ile
210                 215                 220

Ile Ala Phe Ser Gly Arg Ile Trp Thr Ala Ala Asp Met Glu Lys Arg
225                 230                 235                 240

Gln Ala Lys Tyr Lys Asn Ser Arg Gly Thr Val Leu Phe Asn Lys Ser
                245                 250                 255

Tyr Glu Leu Tyr His Leu Asp Lys Ala Arg Pro Val Ile Ala Lys Thr
            260                 265                 270

His Glu Val Phe Leu Met Glu Gly Phe Met Asp Val Ile Ala Ala Tyr
            275                 280                 285

Arg Ser Gly Tyr Glu Asn Ala Val Ala Ser Met Gly Thr Ala Leu Thr
290                 295                 300

Gln Glu His Val Asn His Leu Lys Gln Val Thr Lys Lys Val Val Leu
305                 310                 315                 320

Ile Tyr Asp Gly Asp Asp Ala Gly Gln His Ala Ile Ala Lys Ser Leu
                325                 330                 335

Glu Leu Leu Lys Asp Phe Val Val Glu Ile Val Arg Ile Pro Asn Lys
            340                 345                 350

Met Asp Pro Asp Glu Phe Val Gln Arg His Ser Pro Glu Ala Phe Ala
            355                 360                 365

Asp Leu Leu Lys Gln Ser Arg Ile Ser Ser Val Glu Phe Phe Ile Asp
370                 375                 380

Tyr Leu Lys Pro Thr Asn Val Asp Asn Leu Gln Ser Gln Ile Val Tyr
385                 390                 395                 400

Val Glu Lys Met Ala Pro Leu Ile Ala Gln Ser Pro Ser Ile Thr Ala
                405                 410                 415

Gln His Ser Tyr Ile Asn Lys Ile Ala Asp Leu Leu Pro Asn Phe Asp
            420                 425                 430

Tyr Phe Gln Val Glu Gln Ser Val Asn Ala Leu Arg Ile Gln Asp Arg
            435                 440                 445

Gln Lys His Gln Gly Gln Ile Ala Gln Ala Val Ser Asn Leu Val Thr
450                 455                 460

Leu Pro Met Pro Lys Ser Leu Thr Ala Ile Ala Lys Thr Glu Ser His
465                 470                 475                 480

Leu Met His Arg Leu Leu His His Asp Tyr Leu Leu Asn Glu Phe Arg
                485                 490                 495

His Arg Asp Asp Phe Tyr Phe Asp Thr Ser Thr Leu Glu Leu Leu Tyr
```

```
             500             505             510
Gln Arg Leu Lys Gln Gln Gly His Ile Thr Ser Tyr Asp Leu Ser Glu
            515                 520                 525

Met Ser Glu Glu Val Asn Arg Ala Tyr Tyr Asn Val Leu Glu Glu Asn
        530                 535                 540

Leu Pro Lys Glu Val Ala Leu Gly Glu Ile Asp Asp Ile Leu Ser Lys
545                 550                 555                 560

Arg Ala Lys Leu Leu Ala Glu Arg Asp Leu His Lys Gln Gly Lys Lys
                565                 570                 575

Val Arg Glu Ser Ser Asn Lys Gly Asp His Gln Ala Ala Leu Glu Val
            580                 585                 590

Leu Glu His Phe Ile Ala Gln Lys
        595                 600

<210> SEQ ID NO 33
<211> LENGTH: 1368
<212> TYPE: DNA
<213> ORGANISM: Streptococcus pyogenes

<400> SEQUENCE: 33
atgaggttgc ctgaagtagc tgaattacga gttcaacccc aagatttact agcagagcaa      60
tctgttcttg ggtcaatctt tatctcacct gataagctga ttgcagtgag agaatttatc     120
agtccagacg attttttataa gtacgctcat aaaattatct ttcgggcaat gattacccctc    180 agcgatcgta tgatgccat tgatgcaacc actataagaa caatcctaga tgatcaagat     240
gatctgcaaa gtattggtgg cttatcctat attgttgaac tagttaatag tgtcccaact     300
agtgctaatg cagaatatta tgctaaaatt gtagctgaga agctatgtt gcgtgatatt     360 attgctaggt tgacagaatc tgtcaaccta gcttatgatg aaattttaaa accagaagag    420
gttatcgctg gagttgagag agctttaatt gaactcaatg aacatagtaa tcgtagtggg    480
tttcgcaaaa tttcagatgt gctaaaagtt aattacgagg ctttagaagc acgttctaag    540
cagacttcaa atgttacagg tttaccaact ggttttagag accttgacaa gattacaaca    600
ggtttacacc cagatcaatt agttatttta gctgctcggc agcagtgggg aagactgcc     660 tttgttctta atattgcgca aaatgtgggg actaagcaaa aaaagactgt tgctattttt    720
tctttggaaa tgggtgctga agtttagta gatcgtatgc ttgcagcaga aggaatggtt    780
gattcgcaca gtttaagaac agggcaactc acagatcagg attggaataa tgtaacaatt    840
gctcagggag ctttggcaga agcaccgatt tatattgacg atacgcccgg gattaaaatt    900
actgaaatcc gcgcaagatc acggaaattg tctcaagaag tggatggtgg tttaggtctc    960
attgtaattg actacttaca gttgattaca ggaactaaac ccgaaaatcg tcagcaagag   1020
gtttcagata tttcaagaca gcttaaaatc ctagctaaag aattgaaagt accagttatt   1080
gccctaagtc agctttctcg tggcgttgag caaaggcaag ataaacgacc agttttatca   1140
gatattcgtg aatcaggatc tattgagcag gatgccgata ttgtagcctt cttataccgg   1200
gacgattatt accgtaaaga atgtgatgat gctgaagaag ctgttgaaga taacacaatt   1260
gaagttatcc tcgagaaaaa tagagctggg gcgcgtggaa cagtcaaact gatgttccaa   1320
aaagaataca caaattctc aagtatagcc cagtttgaag aaagataa                 1368

<210> SEQ ID NO 34
<211> LENGTH: 455
<212> TYPE: PRT
<213> ORGANISM: Streptococcus pyogenes
```

```
<400> SEQUENCE: 34

Met Arg Leu Pro Glu Val Ala Glu Leu Arg Val Gln Pro Gln Asp Leu
 1               5                  10                  15

Leu Ala Glu Gln Ser Val Leu Gly Ser Ile Phe Ile Ser Pro Asp Lys
             20                  25                  30

Leu Ile Ala Val Arg Glu Phe Ile Ser Pro Asp Asp Phe Tyr Lys Tyr
         35                  40                  45

Ala His Lys Ile Ile Phe Arg Ala Met Ile Thr Leu Ser Asp Arg Asn
     50                  55                  60

Asp Ala Ile Asp Ala Thr Thr Ile Arg Thr Ile Leu Asp Asp Gln Asp
 65                  70                  75                  80

Asp Leu Gln Ser Ile Gly Gly Leu Ser Tyr Ile Val Glu Leu Val Asn
             85                  90                  95

Ser Val Pro Thr Ser Ala Asn Ala Glu Tyr Tyr Ala Lys Ile Val Ala
            100                 105                 110

Glu Lys Ala Met Leu Arg Asp Ile Ile Ala Arg Leu Thr Glu Ser Val
        115                 120                 125

Asn Leu Ala Tyr Asp Glu Ile Leu Lys Pro Glu Glu Val Ile Ala Gly
130                 135                 140

Val Glu Arg Ala Gln Gly Ala Leu Ala Glu Ala Pro Ile Tyr Ile Asp
145                 150                 155                 160

Asp Thr Pro Gly Ile Lys Ile Ala Leu Ile Glu Leu Asn Glu His Ser
                165                 170                 175

Asn Arg Ser Gly Phe Arg Lys Ile Ser Asp Val Leu Lys Val Asn Tyr
            180                 185                 190

Glu Ala Leu Glu Ala Arg Ser Lys Gln Thr Ser Asn Val Thr Gly Leu
        195                 200                 205

Pro Thr Gly Phe Arg Asp Leu Asp Lys Ile Thr Thr Gly Leu His Pro
210                 215                 220

Asp Gln Leu Val Ile Leu Ala Ala Arg Pro Ala Val Gly Lys Thr Ala
225                 230                 235                 240

Phe Val Leu Asn Ile Ala Gln Asn Val Gly Thr Lys Gln Lys Lys Thr
                245                 250                 255

Val Ala Ile Phe Ser Leu Glu Met Gly Ala Glu Ser Leu Val Asp Arg
            260                 265                 270

Met Leu Ala Ala Glu Gly Met Val Asp Ser His Ser Leu Arg Thr Gly
        275                 280                 285

Gln Leu Thr Asp Gln Asp Trp Asn Asn Val Thr Ile Thr Glu Ile Arg
290                 295                 300

Ala Arg Ser Arg Lys Leu Ser Gln Glu Val Asp Gly Gly Leu Gly Leu
305                 310                 315                 320

Ile Val Ile Asp Tyr Leu Gln Leu Ile Thr Gly Thr Lys Pro Glu Asn
                325                 330                 335

Arg Gln Gln Glu Val Ser Asp Ile Ser Arg Gln Leu Lys Ile Leu Ala
            340                 345                 350

Lys Glu Leu Lys Val Pro Val Ile Ala Leu Ser Gln Leu Ser Arg Gly
        355                 360                 365

Val Glu Gln Arg Gln Asp Lys Arg Pro Val Leu Ser Asp Ile Arg Glu
370                 375                 380

Ser Gly Ser Ile Glu Gln Asp Ala Asp Ile Val Ala Phe Leu Tyr Arg
385                 390                 395                 400

Asp Asp Tyr Tyr Arg Lys Glu Cys Asp Asp Ala Glu Glu Ala Val Glu
```

```
                    405                 410                 415
Asp Asn Thr Ile Glu Val Ile Leu Glu Lys Asn Arg Ala Gly Ala Arg
        420                 425                 430

Gly Thr Val Lys Leu Met Phe Gln Lys Glu Tyr Asn Lys Phe Ser Ser
    435                 440                 445

Ile Ala Gln Phe Glu Glu Arg
    450                 455
```

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 35
ggtggtaatt gtcttgcata tgacagagc                                    29

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 36
agcgattaag tggattgccg ggttgtgatg c                                  31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 37
agcatcacaa cccggcaatc cacttaatcg c                                  31

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 38
gactacgcca tgggcattaa ataaatacc                                    29

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 39
gaagatgcat ataaacgtgc aagacctagt                                   30

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: primer -continued

<400> SEQUENCE: 40
gtctgacgca cgaattgtaa agtaagatgc atag					34

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 41
cgactggaag gagttttaac atatgatgga attcac					36

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 42
ttatatggat ccttagtaag ttctgattgg					30

<210> SEQ ID NO 43
<211> LENGTH: 15
<212> TYPE: PRT
<213> ORGANISM: Escherichia coli

<400> SEQUENCE: 43

Leu Leu Phe Glu Arg Phe Leu Asn Pro Glu Arg Val Ser Met Pro
 1               5                  10                  15

<210> SEQ ID NO 44
<211> LENGTH: 15
<212> TYPE: PRT
<213> ORGANISM: Escherichia coli

<400> SEQUENCE: 44

Lys Phe Ala Gly Tyr Gly Phe Asn Lys Ser His Ser Ala Ala Tyr
 1               5                  10                  15

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 45 cttcttttg aaagatttct aaataaagaa cgttattcaa tgcc					44

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 46
ataagctgca gcatgacttt tattaaaacc ataacctgca aattt					45

<210> SEQ ID NO 47
<211> LENGTH: 39
<212> TYPE: DNA
<213> ORGANISM: Artificial Sequence

```
<220> FEATURE:
<223> OTHER INFORMATION: Description of Artificial Sequence:  primer

<400> SEQUENCE: 47
agttaaaaat gccatatttt gacgtgtttt agttctaat                                39

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence:  primer

<400> SEQUENCE: 48
cttgcaaaag cggttgctaa agatgttgga cgaattatgg gg                            42

<210> SEQ ID NO 49
<211> LENGTH: 10
<212> TYPE: PRT
<213> ORGANISM: Escherichia coli

<400> SEQUENCE: 49

His Ala Tyr Leu Phe Ser Gly Pro Arg Gly
  1               5                  10

<210> SEQ ID NO 50
<211> LENGTH: 10
<212> TYPE: PRT
<213> ORGANISM: Escherichia coli

<400> SEQUENCE: 50

His Ala Tyr Leu Phe Ser Gly Pro Arg Gly
  1               5                  10

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence:  primer

<400> SEQUENCE: 51
cgcggatccc atgcatattt attttcaggt ccaagagg                                 38

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence:  primer

<400> SEQUENCE: 52
ccggaattct ggtggttctt ctaatgtttt taataatgc                                39

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence:  primer

<400> SEQUENCE: 53
tttgtaaagg cattacgcag gggactaatt cagatgtg                                 38

<210> SEQ ID NO 54
```

```
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 54
tatgacattc attacaaggt tctccatcag tgc                                33

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 55
gagcactgat gaacttagaa ttagatatg                                    29

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 56
gatactcagt atctttctca gatgttttat tc                                32

<210> SEQ ID NO 57
<211> LENGTH: 14
<212> TYPE: PRT
<213> ORGANISM: Escherichia coli

<400> SEQUENCE: 57

Asp Leu Ile Ile Val Ala Ala Arg Pro Ser Met Gly Lys Thr
 1               5                  10

<210> SEQ ID NO 58
<211> LENGTH: 15
<212> TYPE: PRT
<213> ORGANISM: Escherichia coli

<400> SEQUENCE: 58

Glu Ile Ile Ile Gly Lys Gln Arg Asn Gly Pro Ile Gly Thr Val
 1               5                  10                  15

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 59
gaccttataa ttgtagctgc acgtccttct atgggaaaaa c                      41

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 60
aacattatta agtcagcatc ttgttctatt gatccagatt caacgaag               48
```

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 61
gatttgtagt tctggtaatg ttgactcaaa ccgcttaaga accgg          45

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 62
atacgtgtgg ttaactgatc agcaacccat ctctagtgag aaaatacc       48

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 63
cgttttaatg catgcttaga aacgatatca g                          31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 64
cattgctaag caacgttacg gtccaacagg c                          31

<210> SEQ ID NO 65
<211> LENGTH: 69
<212> TYPE: DNA
<213> ORGANISM: Artificial Sequence
<220> FEATURE:
<223> OTHER INFORMATION: Description of Artificial Sequence: primer

<400> SEQUENCE: 65
ggataacaat tccccgctag caataatttt gtttaacttt aagaaggaga tatacccatg    60
gatgaacag                                                             69

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 66
aattttaaag gatccgtgta taatattcta attttcccg                  39

<210> SEQ ID NO 67
<211> LENGTH: 28
<212> TYPE: DNA

```
<213> ORGANISM: Artificial Sequence
<220> FEATURE:
<223> OTHER INFORMATION: Description of Artificial Sequence: primer

<400> SEQUENCE: 67
gggagtttgt aatccatgga tgaacagc                                         28

<210> SEQ ID NO 68
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 68
ctgaacacct attaccctag gcatctaact cacaccc                               37

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 69
ggagcagatt gcttttgata catatgattg gcctattc                              38

<210> SEQ ID NO 70
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 70
ttgtctccgc atcaaactgg gatccaagag catcatacgc gtatgg                     46

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 71
gcctaggata agggagggta catatggatt tagcgc                                36

<210> SEQ ID NO 72
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 72
cgggcaagtc ttttgacaag cttcggatcc ccataacgaa ttcc                       44

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 73
ggagttaaaa acatatgtat caagctcttt atc                                   33
```

<210> SEQ ID NO 74
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 74
cgtgggtaag ggcaaaacgg atcccttatg tatttcag                       38

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 75
ggagttcata tgattcaatt ttcaaattaa tcgc                           34

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 76
tatcagctcc tggatccagt accttccatt gattagcc                       38

<210> SEQ ID NO 77
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 77
ggataacaat tccccgctag caataatttt gtttaacttt aagaaggaga tacccatg   60 tcagatttat tcgc                                                  74

<210> SEQ ID NO 78
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 78
cggtgtctct atctaaatga ctcatttggg atcctcgctt tatacggtat gtcacag   57

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 79
gggaacaaga taaccaagga ggaacccatg gttgctcaac ttg                 43

<210> SEQ ID NO 80
<211> LENGTH: 40
<212> TYPE: DNA

```
<213> ORGANISM: Artificial Sequence
<220> FEATURE:
<223> OTHER INFORMATION: Description of Artificial Sequence: primer

<400> SEQUENCE: 80
cgaatagcag cgttcatacc aggatcctcg ccgccactgg                                40

<210> SEQ ID NO 81
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 81
accattttgg cttttaaagg tacggttaac agcaagtgtg aaggtagcc                      49

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 82
gaacgcgagg cagatttcat taactgtgtg atctggcg                                 38

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 83
tttaaaagag ggtagcatat gattaataat gtagtactag ttggtcgc                      48

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 84
tttaaattta aacctaggtt caatccattc tgactagaat ggaagatcgt c                  51
```